(12) United States Patent
Baumann et al.

(10) Patent No.: US 10,604,517 B2
(45) Date of Patent: Mar. 31, 2020

(54) BRIDGED PIPERIDINE DERIVATIVES

(71) Applicant: Hoffmann-La Roche Inc., Little Falls, NJ (US)

(72) Inventors: Karlheinz Baumann, Efringen-Kirchen (DE); Guido Galley, Rheinfelden (DE); Roland Jakob-Roetne, Inzlingen (DE); Anja Limberg, Basel (CH); Werner Neidhart, Basel (CH); Rosa Maria Rodriguez Sarmiento, Basel (CH); Björn Bartels, Schopfheim (DE); Hasane Ratni, Habsheim (FR)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/913,087

(22) Filed: Mar. 6, 2018

(65) Prior Publication Data
US 2018/0237432 A1    Aug. 23, 2018

Related U.S. Application Data

(63) Continuation of application No. PCT/EP2016/070800, filed on Sep. 5, 2016.

(30) Foreign Application Priority Data

Sep. 9, 2015 (EP) .................................. 15184480

(51) Int. Cl.
| | | |
|---|---|---|
| *C07D 417/14* | (2006.01) | |
| *C07D 519/00* | (2006.01) | |
| *A61P 25/28* | (2006.01) | |
| *C07D 413/14* | (2006.01) | |

(52) U.S. Cl.
CPC ............ *C07D 417/14* (2013.01); *A61P 25/28* (2018.01); *C07D 413/14* (2013.01); *C07D 519/00* (2013.01)

(58) Field of Classification Search
None
See application file for complete search history.

(56) References Cited

U.S. PATENT DOCUMENTS

| | | | |
|---|---|---|---|
| 2011/0190269 A1 | 4/2011 | Baumann et al. | |
| 2011/0201605 A1* | 8/2011 | Baumann ............ | C07D 401/14 514/230.5 |
| 2012/0225884 A1 | 6/2012 | Baumann et al. | |

FOREIGN PATENT DOCUMENTS

| | | | |
|---|---|---|---|
| WO | 2011/092272 A1 | 8/2011 | |
| WO | WO-2011101304 A2 * | 8/2011 | ........... C07D 401/14 |
| WO | WO-2012116965 A1 * | 9/2012 | ........... C07D 451/04 |
| WO | 2017/042114 A1 | 3/2017 | |

OTHER PUBLICATIONS

International Preliminary Report on Patentabliity for PCT/EP2016/070800, pp. 1-28, Nov. (Year: 2017).*
International Search Report and Written Opinion for PCT/EP2016/070800 (dated Nov. 17, 2016).
International Preliminary Report on Patentability (IPRP) for PCT/EP2016/070800 completed on Nov. 24, 2017.

* cited by examiner

*Primary Examiner* — Zinna Northington Davis
(74) *Attorney, Agent, or Firm* — Genentech Inc.; Richard G. A. Bone

(57) ABSTRACT

The present invention relates to compounds of formula

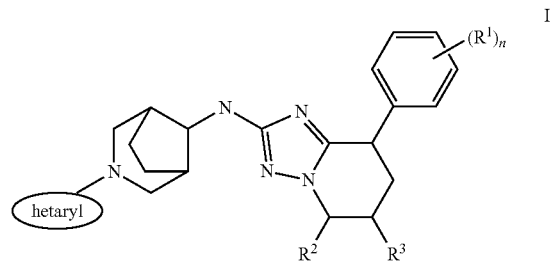

I hetaryl is a five membered heteroaryl group, containing 1 to 3 heteroatoms, selected from O, S or N;
$R^1$ is hydrogen, halogen, lower alkyl, lower alkoxy, lower alkyl substituted by halogen, S-lower alkyl substituted by halogen or lower alkoxy substituted by halogen,
or two neighboring carbon atoms may form on phenyl an additional ring containing —O—$CH_2$—O—;
n is 1 to 5;
$R^2$ is hydrogen or lower alkyl substituted by halogen;
$R^3$ is hydrogen or lower alkyl substituted by halogen;
or to pharmaceutically active acid addition salts thereof, to racemic mixtures or to its corresponding enantiomers or optical isomers or stereoisomers thereof.
The compounds may be used for the treatment of Alzheimer's disease, cerebral amyloid angiopathy, hereditary cerebral hemorrhage with amyloidosis, Dutch-type (HCHWA-D), multi-infarct dementia, dementia pugilistica or Down syndrome.

13 Claims, No Drawings

BRIDGED PIPERIDINE DERIVATIVES

CROSS-REFERENCE TO RELATED APPLICATIONS

This application is a continuation of, and claims priority to, International Patent Application No. PCT/EP2016/070800, filed on Sep. 5, 2016. This application also claims priority to European Patent Application No. 15184480.0, filed on Sep. 9, 2015. The entire contents of each of the above patent applications are hereby incorporated by reference.

The present invention relates to compounds of formula I

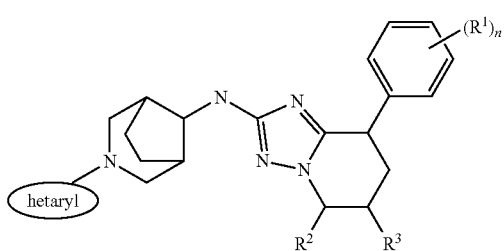

hetaryl is a five membered heteroaryl group, containing 1 to 3 heteroatoms, selected from O, S or N;
$R^1$ is hydrogen, halogen, lower alkyl, lower alkoxy, lower alkyl substituted by halogen, S-lower alkyl substituted by halogen or lower alkoxy substituted by halogen,
or two neighboring carbon atoms may form on phenyl an additional ring containing —O—CH$_2$—O—;
n is 1 to 5;
$R^2$ is hydrogen or lower alkyl substituted by halogen;
$R^3$ is hydrogen or lower alkyl substituted by halogen;
or to pharmaceutically active acid addition salts thereof, to racemic mixtures or to its corresponding enantiomers or optical isomers or stereoisomers thereof.

Now it has been found that the present compounds of formula I are modulators of γ-secretase, they may be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHW A-D), multi-infarct dementia, dementia pugilistica and Down syndrome.

Alzheimer's disease (AD) is the most common cause of dementia in later life. Pathologically, AD is characterized by the deposition of amyloid in extracellular plaques and intracellular neurofibrillary tangles in the brain. The amyloid plaques are mainly composed of amyloid peptides (Aβ peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Aβ peptides are derived from the same domain of the APP.

Aβ peptides are produced from APP through the sequential action of two proteolytic enzymes termed β- and γ-secretase. β-Secretase cleaves first in the extracellular domain of APP just outside of the trans-membrane domain (TM) to produce a C-terminal fragment of APP (CTFβ) containing the TM- and cytoplasmatic domain. CTFβ is the substrate for γ-secretase which cleaves at several adjacent positions within the TM to produce the Aβ peptides and the cytoplasmic fragment. Various proteolytic cleavages mediated by γ-secretase result in Aβ peptides of different chain length, e.g. Aβ38, Aβ40 and Aβ42. The latter one is regarded to be the more pathogenic amyloid peptide because of its strong tendency to form neurotoxic aggregates.

The β-secretase is a typical aspartyl protease. The γ-secretase is a high molecular weight complex that consists of four essential subunits: Presenilin (PS, including PS1 and PS2), nicastrin, anterior pharynx defective 1 (APH-1), and presenilin enhancer 2 (PEN-2). The atomic structure of human γ-secretase at 3.4 Å resolution has been published (X. Bai, C. Yan, G. Yang, P. Lu, D. Ma, L. Sun, R. Zhou, S. H. W. Scheres, Y. Shi, Nature 2015, doi: 10.1038/nature14892). The presenilins are bearing the catalytic site and represent a group of atypical aspartyl proteases which cleave their substrates within the TM of and which are themselves polytopic membrane proteins. The other essential components of γ-secretase, nicastrin and the products of the aph1 and pen-2 genes are believed to be responsible for substrate recognition and recruitment. Proven substrates for γ-secretase are APP and the proteins of the Notch receptor family, however, γ-secretase has a loose substrate specificity and many further membrane proteins unrelated to APP and Notch have been reported to be cleaved by the γ-secretase in vitro.

The γ-secretase activity is absolutely required for the production of Aβ peptides. This has been shown both by genetic means, i.e., ablation of the presenilin genes and by low-molecular-weight inhibitory compounds. According to the amyloid cascade hypothesis for AD the production and deposition of Aβ is the ultimate cause for the disease. Therefore, it was believed that selective and potent inhibition of γ-secretase might be useful for the prevention and treatment of AD.

An alternative mode of treatment is the modulation of the γ-secretase activity which results in a selective reduction of the Aβ42 production. This will lead in an increase of shorter Aβ isoforms, such as Aβ338, Aβ337 or others, which have no or reduced capability for aggregation and plaque formation, and are not or less neurotoxic. Compounds which show this effect on modulating γ-secretase activity include certain non-steroidal anti-inflammatory drugs (NSAIDs) and related analogues (Weggen et al. Nature, 414 (2001) 212-16).

Thus, the compounds of this invention will be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

Numerous documents describe the current knowledge on γ-secretase modulation, for example the following publications:

Morihara et al, J. Neurochem., 83 (2002) 1009-12
Jantzen et al, J. Neuroscience, 22 (2002) 226-54
Takahashi et al, J. Biol. Chem., 278 (2003) 18644-70
Beher et al, J. Biol. Chem. 279 (2004) 43419-26
Lleo et al, Nature Med. 10 (2004) 1065-6
Kukar et al, Nature Med. 11 (2005) 545-50
Perretto et al, J. Med. Chem. 48 (2005) 5705-20
Clarke et al, J. Biol. Chem. 281 (2006) 31279-89
Stock et al, Bioorg. Med. Chem. Lett. 16 (2006) 2219-2223
Narlawar et al, J. Med. Chem. 49 (2006) 7588-91
Ebke et al, J. Biol. Chem., 286 (2011) 37181-86
Hall et al, Progress in Med. Chem., 53 (2014) 101-145

The following definitions for compounds of formula I are used:

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkyl substituted by halogen" denotes an alkyl group as defined above, wherein at least one hydrogen atom is replaced by halogen, for example $CF_3$, $CHF_2$, $CH_2F$, $CH_2CHF_2$, $CH_2CF_3$, $CH_2CH_2CF_3CH_2CF_2CF_3$ and the like.

As used herein, the term "lower alkoxy" denotes an alkyl group as defined above, which is bonded via an O-atom.

The term "halogen" denotes chlorine, iodine, fluorine and bromine.

As used herein, the term "lower alkoxy substituted by halogen" denotes an alkyl group substituted by halogen as defined above, which is connected via an oxygen atom.

As used herein, the term "S-lower alkyl substituted by halogen" denotes an alkyl group substituted by halogen as defined above, which is connected via a sulfur atom.

The term "a five membered heteroaryl group, containing 1 to 3 heteroatoms, selected from O, S or N" is selected from the group consisting of

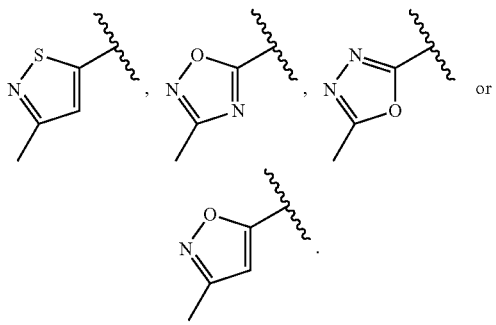

or

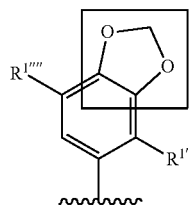

The term "or two neighboring carbon atoms may form on phenyl an additional ring containing —O—CH$_2$—O—" means

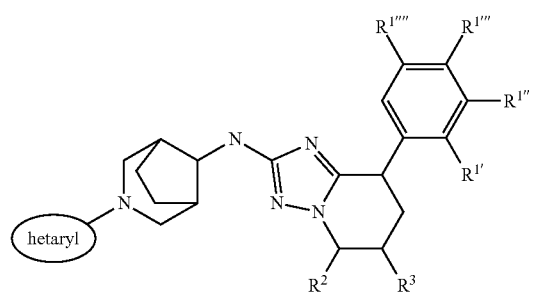

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Objects of the present invention are compounds of formula I, the use of such compounds for the preparation of medicaments for the treatment of Alzheimer's disease, cerebral amyloid angiopathy, hereditary cerebral hemorrhage with amyloidosis, Dutch-type (HCHWA-D), multi-infarct dementia, dementia pugilistica or Down syndrome, their manufacture and medicaments based on a compound of formula I in accordance with the invention.

Further objects of the invention are all forms of optically pure enantiomers, racemates or diastereomeric mixtures for compounds of formula I.

One object of the invention is a compound of formula I-1

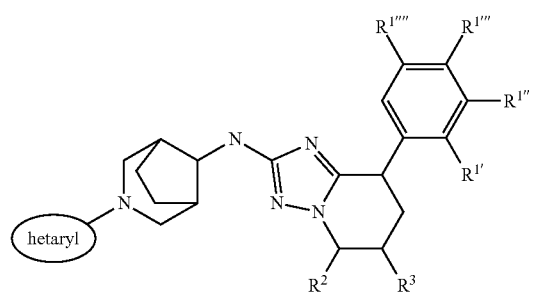

I-1 wherein hetaryl is a five membered heteroaryl group, containing 1 to 3 heteroatoms, selected from O, S or N;

$R^{1'}$ is hydrogen, halogen, lower alkyl, lower alkoxy, lower alkyl substituted by halogen or lower alkoxy substituted by halogen;

$R^{1''}$ is hydrogen, halogen, lower alkyl substituted by halogen or lower alkoxy substituted by halogen;

$R^{1'''}$ is hydrogen, halogen, lower alkyl, lower alkyl substituted by halogen, lower alkoxy, lower alkoxy substituted by halogen, S-lower alkyl substituted by halogen;

or $R^2$ and $R^3$ form together with the carbon atoms, to which they are attached a ring, containing —O—CH$_2$—O—;

$R^{1''''}$ is hydrogen or halogen;

$R^2$ is hydrogen or lower alkyl substituted by halogen;

$R^3$ is hydrogen or lower alkyl substituted by halogen;

or a pharmaceutically active acid addition salts thereof, a racemic mixtures or its corresponding enantiomers or optical isomers or stereoisomers thereof.

An embodiment of the invention are compounds of formula Ia,

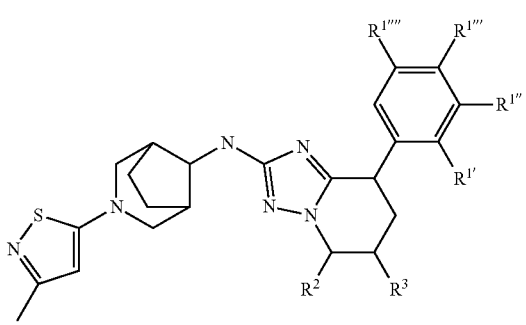

Ia wherein $R^{1'}$ is hydrogen, halogen, lower alkyl, lower alkoxy, lower alkyl substituted by halogen or lower alkoxy substituted by halogen;

$R^{1''}$ is hydrogen, halogen, lower alkyl substituted by halogen or lower alkoxy substituted by halogen;

R¹''' is hydrogen, halogen, lower alkyl, lower alkyl substituted by halogen, lower alkoxy, lower alkoxy substituted by halogen, S-lower alkyl substituted by halogen;
or R² and R³ form together with the carbon atoms, to which they are attached a ring, containing —O—CH₂—O—;
R¹'''' is hydrogen or halogen;
R² is hydrogen or lower alkyl substituted by halogen;
R³ is hydrogen or lower alkyl substituted by halogen;
or a pharmaceutically active acid addition salts thereof, a racemic mixtures or its corresponding enantiomers or optical isomers or stereoisomers thereof, for example the compounds N-((8-endo)-3-(3-Methylisothiazol-5-yl)-3-azabicyclo[3.2.1]octan-8-yl)-8-(4-(trifluoromethyl)phenyl)-5,6,7,8-tetrahydro-[1,2,4]triazolo[1,5-a]pyridin-2-amine (+)-N-((8-endo)-3-(3-Methylisothiazol-5-yl)-3-azabicyclo[3.2.1]octan-8-yl)-8-(4-(trifluoromethyl)phenyl)-5,6,7,8-tetrahydro-[1,2,4]triazolo[1,5-a]pyridin-2-amine (−)-N-((8-endo)-3-(3-Methylisothiazol-5-yl)-3-azabicyclo[3.2.1]octan-8-yl)-8-(4-(trifluoromethyl)phenyl)-5,6,7,8-tetrahydro-[1,2,4]triazolo[1,5-a]pyridin-2-amine (−)-N-[(8-endo)-3-(3-Methyl-1,2-thiazol-5-yl)-3-azabicyclo[3.2.1]octan-8-yl]-8-(2,3,4-trifluorophenyl)-5,6,7,8-tetrahydro-[1,2,4]triazolo[1,5-a]pyridin-2-amine (+)-N-[(8-endo)-3-(3-Methyl-1,2-thiazol-5-yl)-3-azabicyclo[3.2.1]octan-8-yl]-8-(2,3,4-trifluorophenyl)-5,6,7,8-tetrahydro-[1,2,4]triazolo[1,5-a]pyridin-2-amine N-((8-endo)-3-(3-Methylisothiazol-5-yl)-3-azabicyclo[3.2.1]octan-8-yl)-8-(4-(trifluoromethoxy)phenyl)-5,6,7,8-tetrahydro-[1,2,4]triazolo[1,5-a]pyridin-2-amine (+)-N-[(8-endo)-3-(3-Methyl-1,2-thiazol-5-yl)-3-azabicyclo[3.2.1]octan-8-yl]-8-[4-(trifluoromethoxy)phenyl]-5,6,7,8-tetrahydro-[1,2,4]triazolo[1,5-a]pyridin-2-amine (−)-N-[(8-endo)-3-(3-Methyl-1,2-thiazol-5-yl)-3-azabicyclo[3.2.1]octan-8-yl]-8-[4-(trifluoromethoxy)phenyl]-5,6,7,8-tetrahydro-[1,2,4]triazolo[1,5-a]pyridin-2-amine 8-(2-Chloro-4-fluorophenyl)-N-[(8-endo)-3-(3-methyl-1,2-thiazol-5-yl)-3-azabicyclo[3.2.1]octan-8-yl]-5,6,7,8-tetrahydro-[1,2,4]triazolo[1,5-a]pyridin-2-amine N-[(8-endo)-3-(3-Methyl-1,2-thiazol-5-yl)-3-azabicyclo[3.2.1]octan-8-yl]-8-[4-(trifluoromethylsulfanyl)phenyl]-5,6,7,8-tetrahydro-[1,2,4]triazolo[1,5-a]pyridin-2-amine (+)-N-((8-endo)-3-(3-Methylisothiazol-5-yl)-3-azabicyclo[3.2.1]octan-8-yl)-8-(4-((trifluoromethyl)thio)phenyl)-5,6,7,8-tetrahydro-[1,2,4]triazolo[1,5-a]pyridin-2-amine (−)-N-((8-endo)-3-(3-Methylisothiazol-5-yl)-3-azabicyclo[3.2.1]octan-8-yl)-8-(4-((trifluoromethyl)thio)phenyl)-5,6,7,8-tetrahydro-[1,2,4]triazolo[1,5-a]pyridin-2-amine (+)-N-((8-endo)-3-(3-Methylisothiazol-5-yl)-3-azabicyclo[3.2.1]octan-8-yl)-8-(4-(2,2,2-trifluoroethyl)phenyl)-5,6,7,8-tetrahydro-[1,2,4]triazolo[1,5-a]pyridin-2-amine (−)-N-((8-endo)-3-(3-Methylisothiazol-5-yl)-3-azabicyclo[3.2.1]octan-8-yl)-8-(4-(2,2,2-trifluoroethyl)phenyl)-5,6,7,8-tetrahydro-[1,2,4]triazolo[1,5-a]pyridin-2-amine N-((8-endo)-3-(3-Methylisothiazol-5-yl)-3-azabicyclo[3.2.1]octan-8-yl)-8-(2-(trifluoromethyl)phenyl)-5,6,7,8-tetrahydro-[1,2,4]triazolo[1,2,4]triazolo[1,5-a]pyridin-2-amine N-((8-endo)-3-(3-Methylisothiazol-5-yl)-3-azabicyclo[3.2.1]octan-8-yl)-8-(2-(trifluoromethyl)phenyl)-5,6,7,8-tetrahydro-[1,2,4]triazolo[1,5-a]pyridin-2-amine (enantiomer A)

N-((8-endo)-3-(3-Methylisothiazol-5-yl)-3-azabicyclo[3.2.1]octan-8-yl)-8-(2-(trifluoromethyl)phenyl)-5,6,7,8-tetrahydro-[1,2,4]triazolo[1,5-a]pyridin-2-amine (enantiomer B)

(+)-N-((8-endo)-3-(3-Methylisothiazol-5-yl)-3-azabicyclo[3.2.1]octan-8-yl)-8-(3-(trifluoromethyl)phenyl)-5,6,7,8-tetrahydro-[1,2,4]triazolo[1,5-a]pyridin-2-amine (−)-N-((8-endo)-3-(3-Methylisothiazol-5-yl)-3-azabicyclo[3.2.1]octan-8-yl)-8-(3-(trifluoromethyl)phenyl)-5,6,7,8-tetrahydro-[1,2,4]triazolo[1,5-a]pyridin-2-amine (+)-N-((8-endo)-3-(3-Methylisothiazol-5-yl)-3-azabicyclo[3.2.1]octan-8-yl)-8-(2-(trifluoromethoxy)phenyl)-5,6,7,8-tetrahydro-[1,2,4]triazolo[1,5-a]pyridin-2-amine (−)-N-((8-endo)-3-(3-Methylisothiazol-5-yl)-3-azabicyclo[3.2.1]octan-8-yl)-8-(2-(trifluoromethoxy)phenyl)-5,6,7,8-tetrahydro-[1,2,4]triazolo[1,5-a]pyridin-2-amine (+)-N-((8-endo)-3-(3-Methylisothiazol-5-yl)-3-azabicyclo[3.2.1]octan-8-yl)-8-(3-(trifluoromethoxy)phenyl)-5,6,7,8-tetrahydro-[1,2,4]triazolo[1,5-a]pyridin-2-amine (−)-N-((8-endo)-3-(3-Methylisothiazol-5-yl)-3-azabicyclo[3.2.1]octan-8-yl)-8-(3-(trifluoromethoxy)phenyl)-5,6,7,8-tetrahydro-[1,2,4]triazolo[1,5-a]pyridin-2-amine 8-(4-Methoxyphenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (+)-8-(4-Methoxyphenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (−)-8-(4-Methoxyphenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (+)-8-(4-Fluoro-2-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (−)-8-(4-Fluoro-2-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (−)-N-((8-endo)-3-(3-Methylisothiazol-5-yl)-3-azabicyclo[3.2.1]octan-8-yl)-8-(3,4,5-trifluorophenyl)-5,6,7,8-tetrahydro-[1,2,4]triazolo[1,5-a]pyridin-2-amine (+)-(N-((8-endo)-3-(3-Methylisothiazol-5-yl)-3-azabicyclo[3.2.1]octan-8-yl)-8-(3,4,5-trifluorophenyl)-5,6,7,8-tetrahydro-[1,2,4]triazolo[1,5-a]pyridin-2-amine (+)-8-(4-Fluoro-3-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (−)-8-(4-Fluoro-3-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (+)-8-(Benzo[d][1,3]dioxol-5-yl)-N-((8-endo)-3-(3-methylisothiazol -5-yl)-3-azabicyclo[3.2.1]octan-8-yl)-5,6,7,8-tetrahydro-[1,2,4]triazolo[1,5-a]pyridin-2-amine (−)-8-(Benzo[d][1,3]dioxol-5-yl)-N-((8-endo)-3-(3-methylisothiazol -5-yl)-3-azabicyclo[3.2.1]octan-8-yl)-5,6,7,8-tetrahydro-[1,2,4]triazolo[1,5-a]pyridin-2-amine 8-(3-Fluoro-5-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (+)-8-(3-Fluoro-5-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (−)-8-(3-Fluoro-5-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine N-((8-endo)-3-(3-Methylisothiazol-5-yl)-3-azabicyclo[3.2.1]octan-8-yl)-8-(4-(2,2,2-trifluoroethoxy)phenyl)-5,6,7,8-tetrahydro-[1,2,4]triazolo[1,5-a]pyridin-2-amine 8-(2-Fluoro-4-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (+)-8-(2-Fluoro-4-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (−)-8-(2-Fluoro-4-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (+)-8-(4-(Difluoromethoxy)phenyl)-N-((8-endo)-3-(3-methylisothiazol-5-yl) -3-azabicyclo[3.2.1]octan-8-yl)-5,6,7,8-tetrahydro-[1,2,4]triazolo[1,5-a]pyridin-2-amine (−)-8-(4-(Difluoromethoxy)phenyl)-N-((8-endo)-3-(3-methylisothiazol-5-yl) -3-azabicyclo[3.2.1]octan-8-yl)-5,6,7,8-tetrahydro-[1,2,4]triazolo[1,5-a]pyridin-2-amine (−)-N-((8-endo)-3-(3-Methylisothiazol-5-yl)-3-azabicyclo[3.2.1]octan-8-yl)-8-(p-tolyl)-5,6,7,8-tetrahydro-[1,2,4]triazolo[1,5-a]pyridin-2-amine (+)-N-((8-endo)-3-(3-Methylisothiazol-5-yl)-3-azabicyclo[3.2.1]octan-8-yl)-8-(p-tolyl)-5,6,7,8-tetrahydro-[1,2,4]triazolo[1,5-a]pyridin-2-amine (−)-8-(2-Methoxy-4-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (+)-8-(2-Methoxy-4-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine 8-(5-Fluoro-2-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (+)-8-(5-Fluoro-2-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (−)-8-(5-Fluoro-2-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine 8-(4-Fluoro-2-methylphenyl)-N-[(8-endo)-3-(3-methyl-1,2-thiazol-5-yl)-3-azabicyclo[3.2.1]octan-8-yl]-5,6,7,8-tetrahydro-[1,2,4]triazolo[1,5-a]pyridin-2-amine (−)-8-(4-Fluoro-2-methylphenyl)-N-[(8-endo)-3-(3-methyl-1,2-thiazol-5-yl)-3-azabicyclo[3.2.1]octan-8-yl]-5,6,7,8-tetrahydro-[1,2,4]triazolo[1,5-a]pyridin-2-amine or (+)-8-(4-Fluoro-2-methylphenyl)-N-[(8-endo)-3-(3-methyl-1,2-thiazol-5-yl)-3-azabicyclo[3.2.1]octan-8-yl]-5,6,7,8-tetrahydro-[1,2,4]triazolo[1,5-a]pyridin-2-amine.

One further embodiment of the invention are compounds of formula Ib,

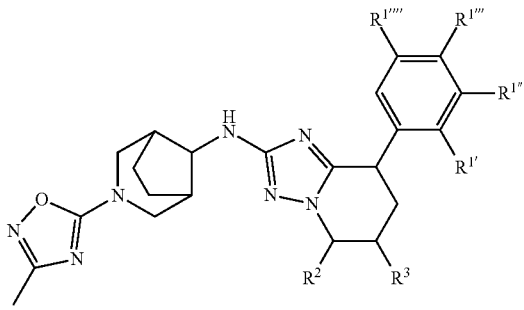

Ib wherein
$R^{1'}$ is hydrogen, halogen, lower alkyl, lower alkoxy, lower alkyl substituted by halogen or lower alkoxy substituted by halogen;

$R^{1''}$ is hydrogen, halogen, lower alkyl substituted by halogen or lower alkoxy substituted by halogen;

$R^{1'''}$ is hydrogen, halogen, lower alkyl, lower alkyl substituted by halogen, lower alkoxy, lower alkoxy substituted by halogen, S-lower alkyl substituted by halogen;
or $R^2$ and $R^3$ form together with the carbon atoms, to which they are attached a ring, containing —O—CH$_2$—O—;

$R^{1''''}$ is hydrogen or halogen;
$R^2$ is hydrogen or lower alkyl substituted by halogen;
$R^3$ is hydrogen or lower alkyl substituted by halogen;
or a pharmaceutically active acid addition salts thereof, a racemic mixtures or its corresponding enantiomers or optical isomers or stereoisomers thereof, for example the compounds (−)-N-((8-endo)-3-(3-Methyl-1,2,4-oxadiazol-5-yl)-3-azabicyclo[3.2.1]octan-8-yl)-8-(2,3,4-trifluorophenyl)-5,6,7,8-tetrahydro-[1,2,4]triazolo[1,5-a]pyridin-2-amine 8-(4-Fluoro-3-(trifluoromethyl)phenyl)-N-((8-endo)-3-(3-methyl-1,2,4-oxadiazol-5-yl)-3-azabicyclo[3.2.1]octan-8-yl)-5,6,7,8-tetrahydro-[1,2,4]triazolo[1,5-a]pyridin-2-amine (−)-8-(4-Fluoro-3-(trifluoromethyl)phenyl)-N-((8-endo)-3-(3-methyl-1,2,4-oxadiazol-5-yl)-3-azabicyclo[3.2.1]octan-8-yl)-5,6,7,8-tetrahydro-[1,2,4]triazolo[1,5-a]pyridin-2-amine N-((8-endo)-3-(3-Methyl-1,2,4-oxadiazol-5-yl)-3-azabicyclo[3.2.1]octan-8-yl)-8-(4-(trifluoromethyl)phenyl)-5,6,7,8-tetrahydro-[1,2,4]triazolo[1,5-a]pyridin-2-amine (−)-N-((8-endo)-3-(3-Methyl-1,2,4-oxadiazol-5-yl)-3-azabicyclo[3.2.1]octan-8-yl)-8-(4-(trifluoromethyl)phenyl)-5,6,7,8-tetrahydro-[1,2,4]triazolo[1,5-a]pyridin-2-amine 8-(2-Fluoro-4-(trifluoromethyl)phenyl)-N-((8-endo)-3-(3-methyl-1,2,4-oxadiazol-5-yl)-3-azabicyclo[3.2.1]octan-8-yl)-5,6,7,8-tetrahydro-[1,2,4]triazolo[1,5-a]pyridin-2-amine (−)-8-(2-Fluoro-4-(trifluoromethyl)phenyl)-N-((8-endo)-3-(3-methyl-1,2,4-oxadiazol-5-yl)-3-azabicyclo[3.2.1]octan-8-yl)-5,6,7,8-tetrahydro-[1,2,4]triazolo[1,5-a]pyridin-2-amine N-((8-endo)-3-(3-Methyl-1,2,4-oxadiazol-5-yl)-3-azabicyclo[3.2.1]octan-8-yl)-8-(4-(trifluoromethoxy)phenyl)-5,6,7,8-tetrahydro-[1,2,4]triazolo[1,5-a]pyridin-2-amine (−)-N-((8-endo)-3-(3-Methyl-1,2,4-oxadiazol-5-yl)-3-azabicyclo[3.2.1]octan-8-yl)-8-(4-(trifluoromethoxy)phenyl)-5,6,7,8-tetrahydro-[1,2,4]triazolo[1,5-a]pyridin-2-amine N-((8-endo)-3-(3-Methyl-1,2,4-oxadiazol-5-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine (−)-N-((8-endo)-3-(3-Methyl-1,2,4-oxadiazol-5-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine (+)-N-((8-endo)-3-(3-Methyl-1,2,4-oxadiazol-5-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine N-((8-endo)-3-(3-Methyl-1,2,4-oxadiazol-5-yl)-3-azabicyclo[3.2.1]octan-8-yl)-5-(trifluoromethyl)-8-(2-(trifluoromethyl)phenyl)-5,6,7,8-tetrahydro-[1,2,4]triazolo[1,5-a]pyridin-2-amine (+)-N-((8-endo)-3-(3-Methyl-1,2,4-oxadiazol-5-yl)-3-azabicyclo[3.2.1]octan-8-yl)-5-(trifluoromethyl)-8-(2-(trifluoromethyl)phenyl)-5,6,7,8-tetrahydro-[1,2,4]triazolo[1,5-a]pyridin-2-amine (−)-N-((8-endo)-3-(3-Methyl-1,2,4-oxadiazol-5-yl)-3-azabicyclo[3.2.1]octan-8-yl)-5-(trifluoromethyl)-8-(2-(trifluoromethyl)phenyl)-5,6,7,8-tetrahydro-[1,2,4]triazolo[1,5-a]pyridin-2-amine N-((8-endo)-3-(3-Methyl-1,2,4-oxadiazol-5-yl)-3-azabicyclo[3.2.1]octan-8-yl)-5-(trifluoromethyl)-8-(3-(trifluoromethyl)phenyl)-5,6,7,8-tetrahydro-[1,2,4]triazolo[1,5-a]pyridin-2-amine (+)-N-((8-endo)-3-(3-Methyl-1,2,4-oxadiazol-5-yl)-3-azabicyclo[3.2.1]octan-8-yl)-5-(trifluoromethyl)-8-(3-(trifluoromethyl)phenyl)-5,6,7,8-tetrahydro-[1,2,4]triazolo[1,5-a]pyridin-2-amine (−)-N-((8-endo)-3-(3-Methyl-1,2,4-oxadiazol-5-yl)-3-azabicyclo[3.2.1]octan-8-yl)-5-(trifluoromethyl)-8-(3-(trifluoromethyl)phenyl)-5,6,7,8-tetrahydro-[1,2,4]triazolo[1,5-a]pyridin-2-amine or (−)-N-((8-endo)-3-(3-Methyl-1,2,4-oxadiazol-5-yl)-3-azabicyclo[3.2.1]octan-8-yl)-6-(trifluoromethyl)-8-(2,3,4-trifluorophenyl)-5,6,7,8-tetrahydro-[1,2,4]triazolo[1,5-a]pyridin-2-amine.

One further embodiment of the invention are compounds of formula Ic,

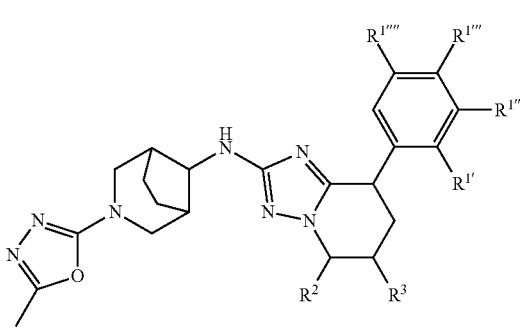

Ic wherein
R$^{1'}$ is hydrogen, halogen, lower alkyl, lower alkoxy, lower alkyl substituted by halogen or lower alkoxy substituted by halogen;
R$^{1''}$ is hydrogen, halogen, lower alkyl substituted by halogen or lower alkoxy substituted by halogen;
R$^{1'''}$ is hydrogen, halogen, lower alkyl, lower alkyl substituted by halogen, lower alkoxy, lower alkoxy substituted by halogen, S-lower alkyl substituted by halogen;
or R$^{2}$ and R$^{3}$ form together with the carbon atoms, to which they are attached a ring, containing —O—CH$_2$—O—;
R$^{1''''}$ is hydrogen or halogen;
R$^{2}$ is hydrogen or lower alkyl substituted by halogen;
R$^{3}$ is hydrogen or lower alkyl substituted by halogen;
or a pharmaceutically active acid addition salts thereof, a racemic mixtures or its corresponding enantiomers or optical isomers or stereoisomers thereof, for example the compounds 8-(2-Fluoro-4-(trifluoromethyl)phenyl)-N-((8-endo)-3-(5-methyl-1,3,4-oxadiazol-2-yl)-3-azabicyclo[3.2.1]octan-8-yl)-5,6,7,8-tetrahydro-[1,2,4]triazolo[1,5-a]pyridin-2-amineN-[(8-endo)-3-(5-Methyl-1,3,4-oxadiazol-2-yl)-3-azabicyclo[3.2.1]octan-8-yl]-5-(trifluoromethyl)-8-(2,3,4-trifluorophenyl)-5,6,7,8-tetrahydro-[1,2,4]triazolo[1,5-a]pyridin-2-amine (diastereomer A)

N-((8-endo)-3-(5-Methyl-1,3,4-oxadiazol-2-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine (diastreomer B)

(+)-N-((8-endo)-3-(5-Methyl-1,3,4-oxadiazol-2-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine N-((8-endo)-3-(5-Methyl-1,3,4-oxadiazol-2-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine (+)-N-((8-endo)-3-(5-Methyl-1,3,4-oxadiazol-2-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine (−)-N-((8-endo)-3-(5-Methyl-1,3,4-oxadiazol-2-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine N-[(8-endo)-3-(5-Methyl-1,3,4-oxadiazol-2-yl)-3-azabicyclo[3.2.1]octan-8-yl]-5-(trifluoromethyl)-8-[4-(trifluoromethyl)phenyl]-5,6,7,8-tetrahydro-[1,2,4]triazolo[1,5-a]pyridin-2-amine (−)-N-((8-endo)-3-(5-Methyl-1,3,4-oxadiazol-2-yl)-3-azabicyclo[3.2.1]octan-8-yl)-5-(trifluoromethyl)-8-(4-(trifluoromethyl)phenyl)-5,6,7,8-tetrahydro-[1,2,4]triazolo[1,5-a]pyridin-2-amine (+)-N-((8-endo)-3-(5-Methyl-1,3,4-oxadiazol-2-yl)-3-azabicyclo[3.2.1]octan-8-yl)-5-(trifluoromethyl)-8-(4-(trifluoromethyl)phenyl)-5,6,7,8-tetrahydro-[1,2,4]triazolo[1,5-a]pyridin-2-amine (−)-8-(3,5-Bis(trifluoromethyl)phenyl)-N-((8-endo)-3-(5-methyl-1,3,4-oxadiazol-2-yl)-3-azabicyclo[3.2.1]octan-8-yl)-5,6,7,8-tetrahydro-[1,2,4]triazolo[1,5-a]pyridin-2-amine N-((8-endo)-3-(5-Methyl-1,3,4-oxadiazol-2-yl)-3-azabicyclo[3.2.1]octan-8-yl)-5-(trifluoromethyl)-8-(3-(trifluoromethyl)phenyl)-5,6,7,8-tetrahydro-[1,2,4]triazolo[1,5-a]pyridin-2-amine (+)-N-((8-endo)-3-(5-Methyl-1,3,4-oxadiazol-2-yl)-3-azabicyclo[3.2.1]octan-8-yl)-5-(trifluoromethyl)-8-(3-(trifluoromethyl)phenyl)-5,6,7,8-tetrahydro-[1,2,4]triazolo[1,5-a]pyridin-2-amine or (−)-N-((8-endo)-3-(5-Methyl-1,3,4-oxadiazol-2-yl)-3-azabicyclo[3.2.1]octan-8-yl)-5-(trifluoromethyl)-8-(3-(trifluoromethyl)phenyl)-5,6,7,8-tetrahydro-[1,2,4]triazolo[1,5-a]pyridin-2-amine.

One further embodiment of the invention are compounds of formula Id,

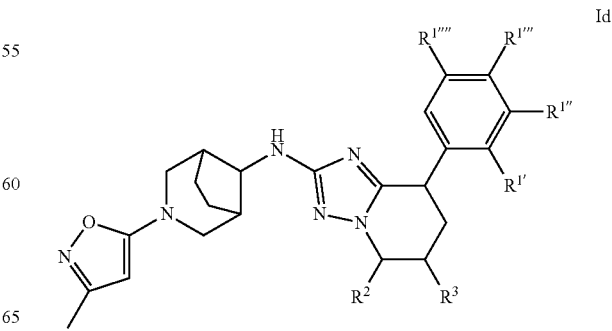

Id wherein

R¹' is hydrogen, halogen, lower alkyl, lower alkoxy, lower alkyl substituted by halogen or lower alkoxy substituted by halogen;

R¹" is hydrogen, halogen, lower alkyl substituted by halogen or lower alkoxy substituted by halogen;

R¹'" is hydrogen, halogen, lower alkyl, lower alkyl substituted by halogen, lower alkoxy, lower alkoxy substituted by halogen, S-lower alkyl substituted by halogen;

or R² and R³ form together with the carbon atoms, to which they are attached a ring, containing —O—CH₂—O—;

R¹"" is hydrogen or halogen;

R² is hydrogen or lower alkyl substituted by halogen;

R³ is hydrogen or lower alkyl substituted by halogen;

or a pharmaceutically active acid addition salts thereof, a racemic mixtures or its corresponding enantiomers or optical isomers or stereoisomers thereof, for example the compound (−)-N-((endo)-3-(3-Methylisoxazol-5-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine.

The present compounds of formula I and their pharmaceutically acceptable salts can be prepared by methods known in the art, for example, by processes described below, which processes comprise a) reducing a compound of formula

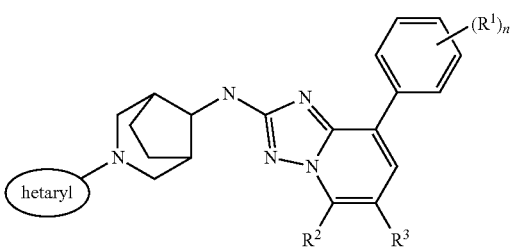

by catalytic hydrogenation or with Mg in methanol in the presence of iodine to a compound of formula

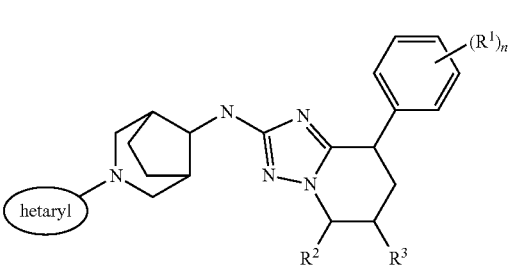

wherein the substituents have the meaning as described above and, if desired, converting the compounds obtained into pharmaceutically acceptable acid addition salts;

or b) reacting a compound of formula

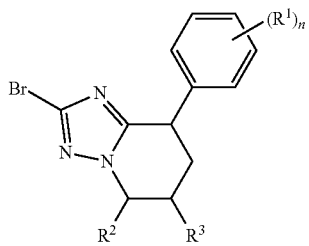

with a compound of formula

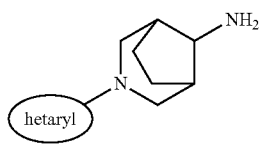

to a compound of formula

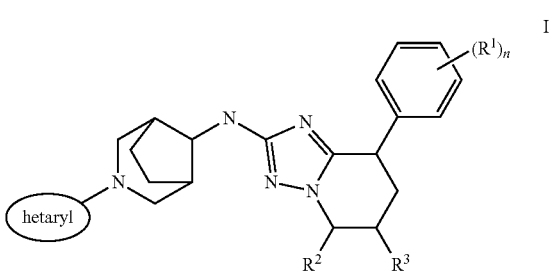

wherein the groups have the meaning as described above, or c) reacting a compound of formula

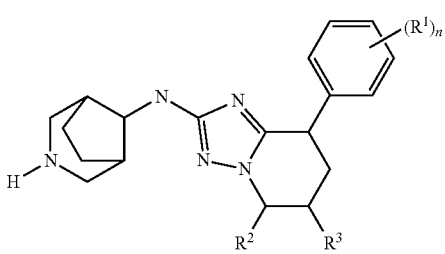

with a compound of formula

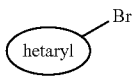

to a compound of formula

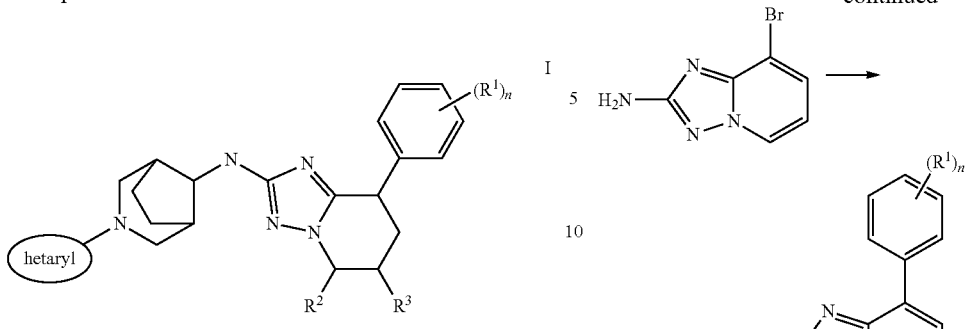

wherein the groups have the meaning as described above, and,
if desired converting the compounds obtained into pharmaceutically acceptable acid addition salts.

The preparation of compounds of formula I of the present invention may be carried out in sequential or convergent synthetic routes. Syntheses of the compounds of the invention are shown in the following schemes. The capability required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in the examples, or by methods known in the art.

Particularly, compounds of formula I can be prepared following standard methods in accordance with any of the Schemes 1 to 9.

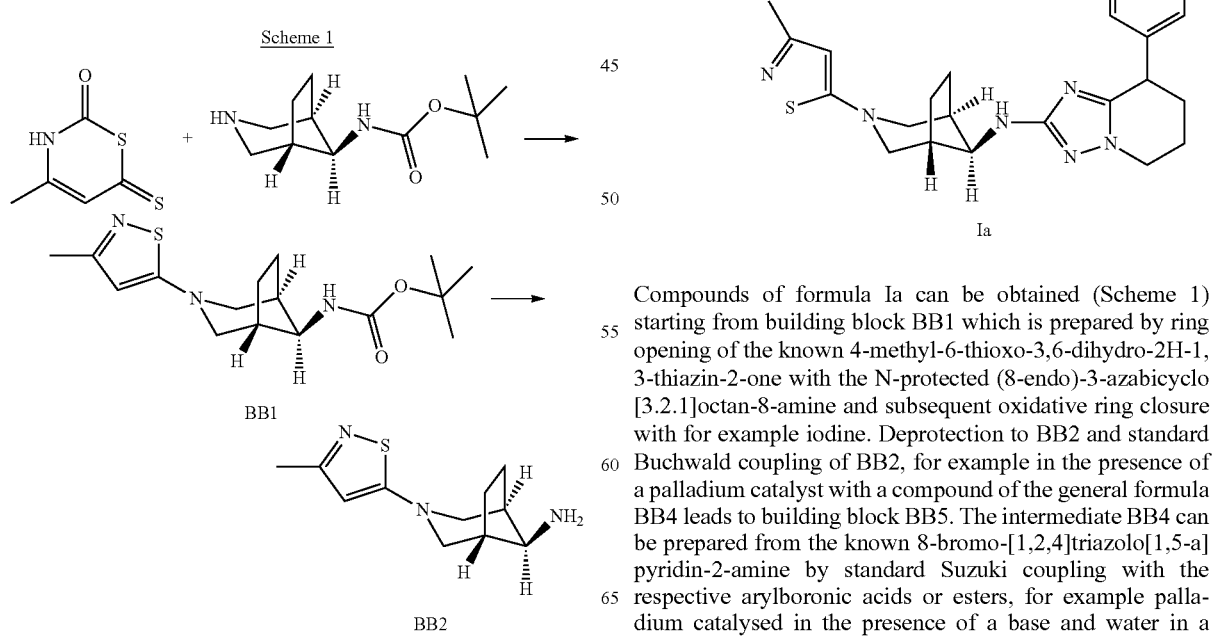

Compounds of formula Ia can be obtained (Scheme 1) starting from building block BB1 which is prepared by ring opening of the known 4-methyl-6-thioxo-3,6-dihydro-2H-1,3-thiazin-2-one with the N-protected (8-endo)-3-azabicyclo[3.2.1]octan-8-amine and subsequent oxidative ring closure with for example iodine. Deprotection to BB2 and standard Buchwald coupling of BB2, for example in the presence of a palladium catalyst with a compound of the general formula BB4 leads to building block BB5. The intermediate BB4 can be prepared from the known 8-bromo-[1,2,4]triazolo[1,5-a]pyridin-2-amine by standard Suzuki coupling with the respective arylboronic acids or esters, for example palladium catalysed in the presence of a base and water in a solvent such as dioxane, to yield intermediate BB3 and subsequent Sandmeyer transformation to bromide BB4. The compounds of formula I are then obtained by reduction of the aromatic ring by standard methods for example by catalytic hydrogenation or with magnesium in methanol in the presence of iodine. Separation of the enantiomers of compounds of formula Ia is achieved by preparative HPLC on chiral columns.

Scheme 2

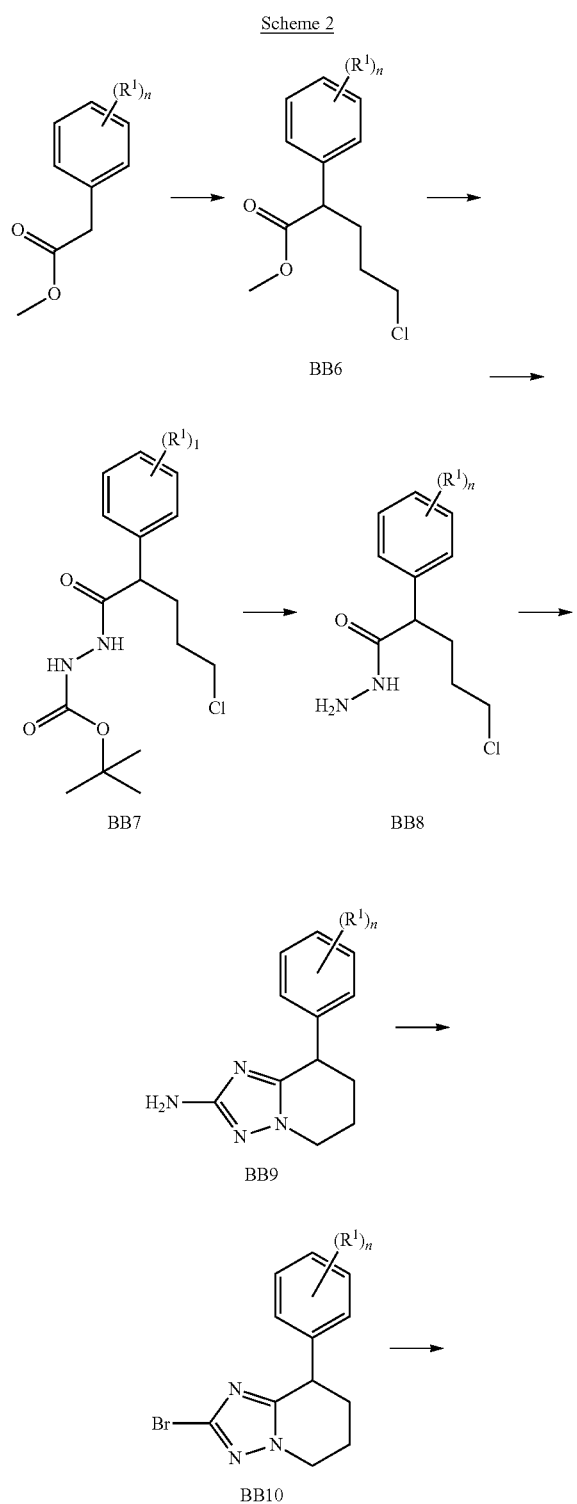

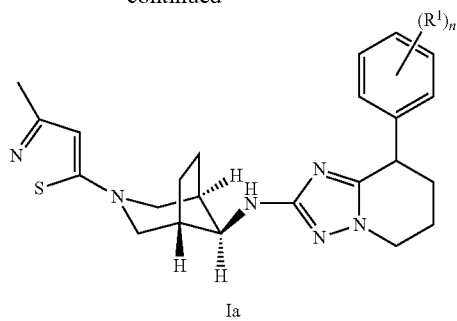

Ia

Alternatively, compounds of formula Ia can be obtained (Scheme 2) by Buchwald coupling of the corresponding 2-bromo-5,6,7,8-tetrahydro-[1,2,4]triazolo[1,5-a]pyridines of the general formula BB10 with amines such as BB2. Alkylation of phenylacetic acid esters by deprotonation with a base such as sodium hydride and reaction with 1,3-dihalopropane (halogen=Br, Cl or I) in a suitable solvent, for example dimethylformamide, leads to intermediate BB6. The ester BB6 is then hydrolysed to the acid, for example under basic conditions and the amide BB7 is prepared under standard conditions with tert-butyl hydrazinecarboxylate. Cleavage of the protecting group under acidic conditions yields the hydrazide BB8 which can be reacted to BB9 with cyanamide under acidic conditions. Subsequent Sandmeyer transformation of BB9 using tert-butylnitrite, copper(II) bromide in solvent such as acetonitrile leads to intermediate BB10. The compounds of formula I are then obtained by Buchwald coupling with the corresponding amines.

Scheme 3

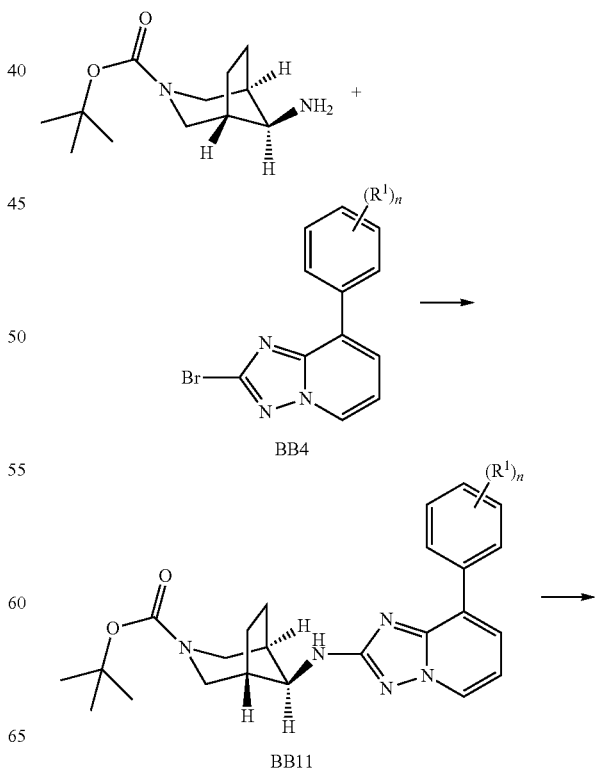

Scheme 4

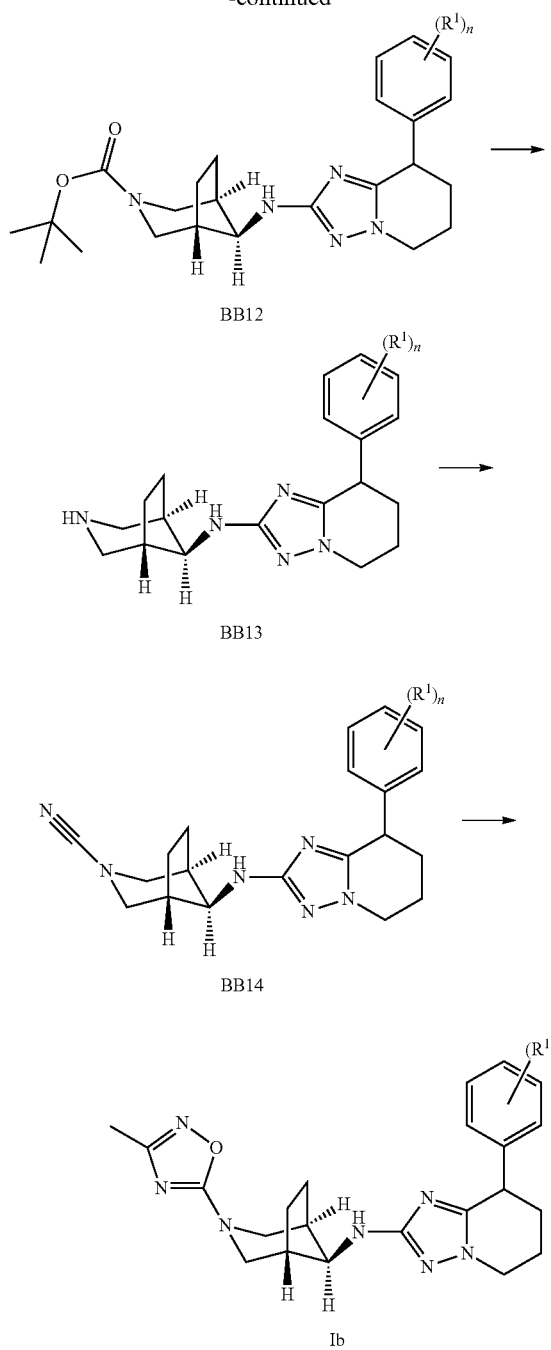

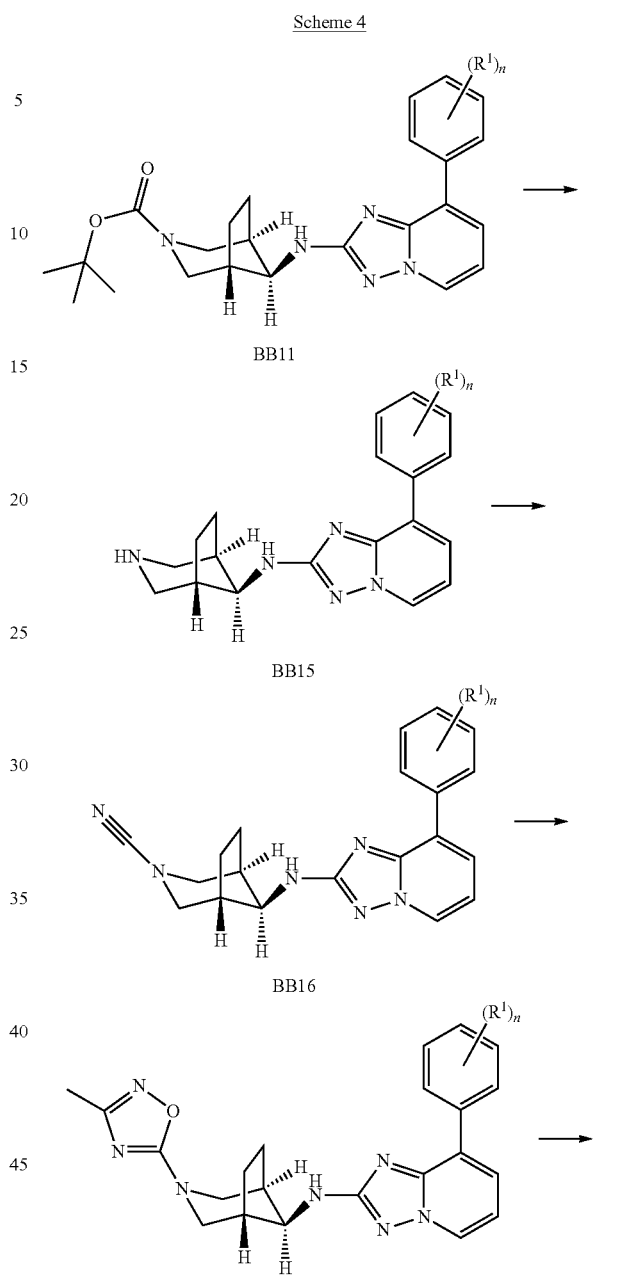

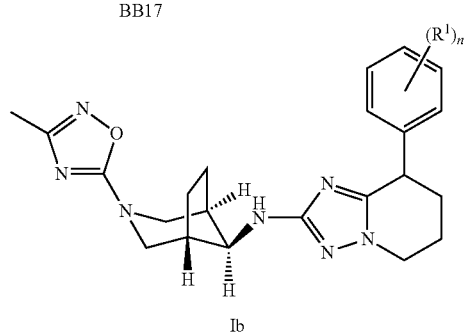

Compounds of formula Ib can be obtained starting from building block BB4 (Scheme 3). Standard Buchwald coupling with the known Boc-protected (8-endo)-tert-butyl-8-amino-3-azabicyclo[3.2.1]octane-3-carboxylate provides BB11 which is saturated under standard conditions by catalytic hydrogenation or with magnesium in methanol in presence of iodine to yield BB12. Deprotection gives the amine BB13 which is then used to introduce the heteroaryl group for example by reaction with cyanic bromide to yield intermediate BB14 followed by ring closure with hydroxy-acetimidamide to a 1,2,4-oxadiazole derivative of the general formula Ib.

Alternatively the order of steps can be changed (Scheme 4). The heteroaryl groups are then introduced after deprotection of BB11 to yield the intermediate BB15, which is for example reacted with cyanic bromide to BB16 followed by ring closure to a 1,2,4-oxadiazole intermediate BB17 with hydroxyacetimidamide. Reduction of the annellated ring under conditions as described above yields compounds of formula Ib.

Scheme 5

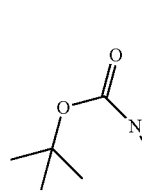

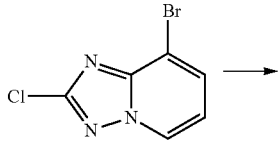

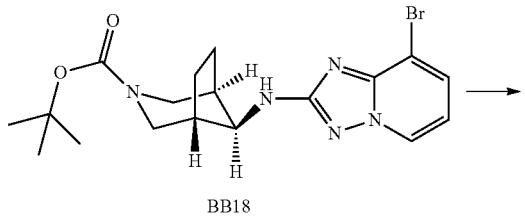

BB18

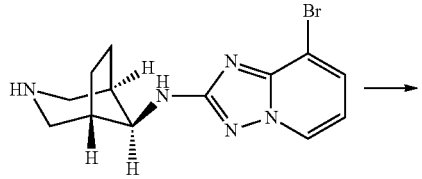

BB19

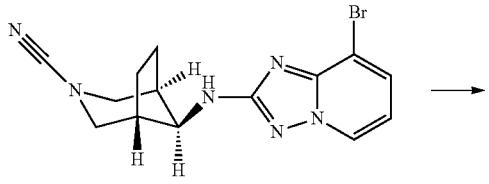

BB20

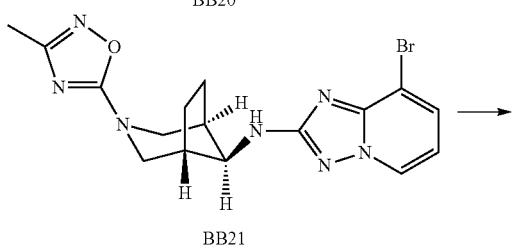

BB21

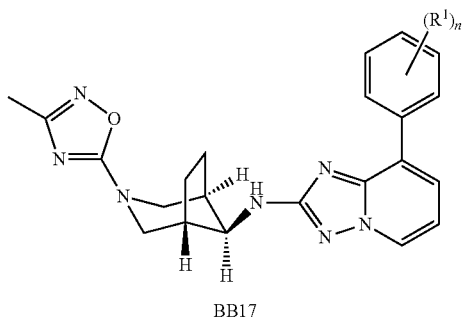

BB17

-continued

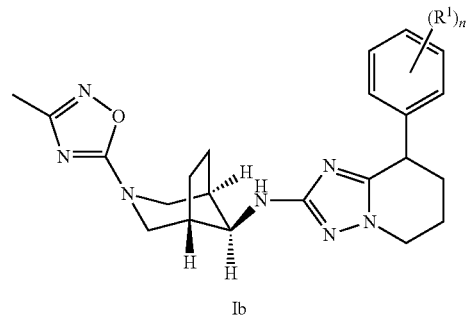

Ib

Another order of steps to prepare compounds of formula Ib starts from bromide BB18 (Scheme 5) which can be obtained from the known 8-bromo-2-chloro-[1,2,4]triazolo[1,5-a]pyridine and (8-endo)-tert-butyl-8-amino-3-azabicyclo[3.2.1]octane-3-carboxylate by substitution reaction in a solvent such as dimethylsulfoxide in the presence of cesium fluoride. Cleavage of the protecting group to BB19 and introduction of the heteroaryl group, for example by reaction with cyanic bromide to BB20 followed by ring closure with hydroxyacetimidamide, leads to a 1,2,4-oxadiazole intermediate BB21. Introduction of the aryl substituent by standard Suzuki reaction with the corresponding arylboronic acids oder esters leads to BB17 which is reduced to the compounds of formula Ib as described in Scheme 4.

Scheme 6

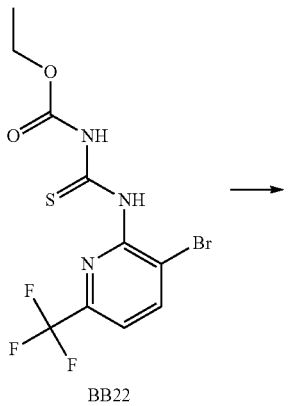

BB22

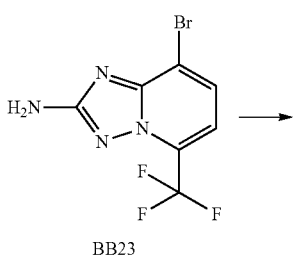

BB23

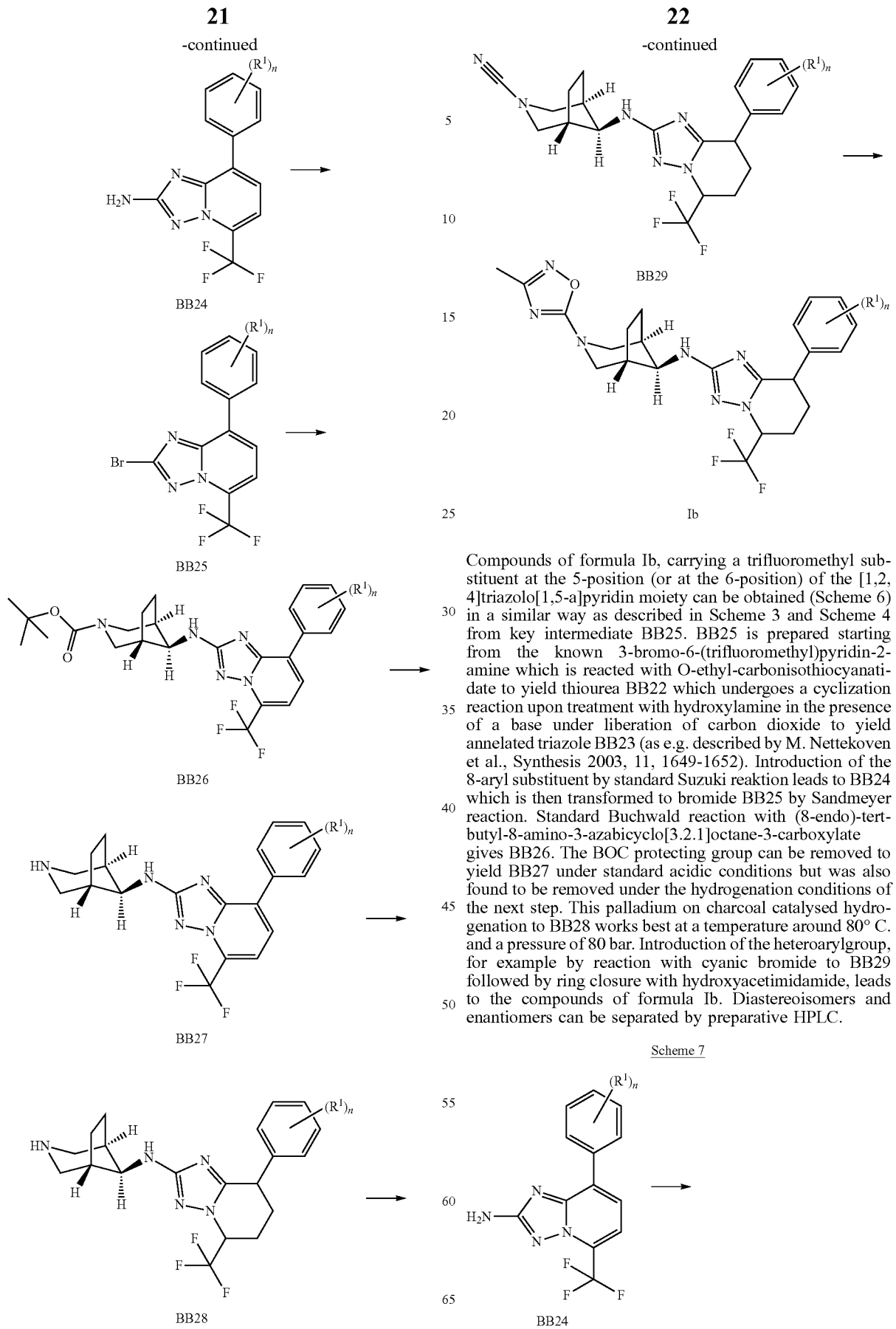

Compounds of formula Ib, carrying a trifluoromethyl substituent at the 5-position (or at the 6-position) of the [1,2,4]triazolo[1,5-a]pyridin moiety can be obtained (Scheme 6) in a similar way as described in Scheme 3 and Scheme 4 from key intermediate BB25. BB25 is prepared starting from the known 3-bromo-6-(trifluoromethyl)pyridin-2-amine which is reacted with O-ethyl-carbonisothiocyanatidate to yield thiourea BB22 which undergoes a cyclization reaction upon treatment with hydroxylamine in the presence of a base under liberation of carbon dioxide to yield annelated triazole BB23 (as e.g. described by M. Nettekoven et al., Synthesis 2003, 11, 1649-1652). Introduction of the 8-aryl substituent by standard Suzuki reaktion leads to BB24 which is then transformed to bromide BB25 by Sandmeyer reaction. Standard Buchwald reaction with (8-endo)-tert-butyl-8-amino-3-azabicyclo[3.2.1]octane-3-carboxylate gives BB26. The BOC protecting group can be removed to yield BB27 under standard acidic conditions but was also found to be removed under the hydrogenation conditions of the next step. This palladium on charcoal catalysed hydrogenation to BB28 works best at a temperature around 80° C. and a pressure of 80 bar. Introduction of the heteroarylgroup, for example by reaction with cyanic bromide to BB29 followed by ring closure with hydroxyacetimidamide, leads to the compounds of formula Ib. Diastereoisomers and enantiomers can be separated by preparative HPLC.

Scheme 7

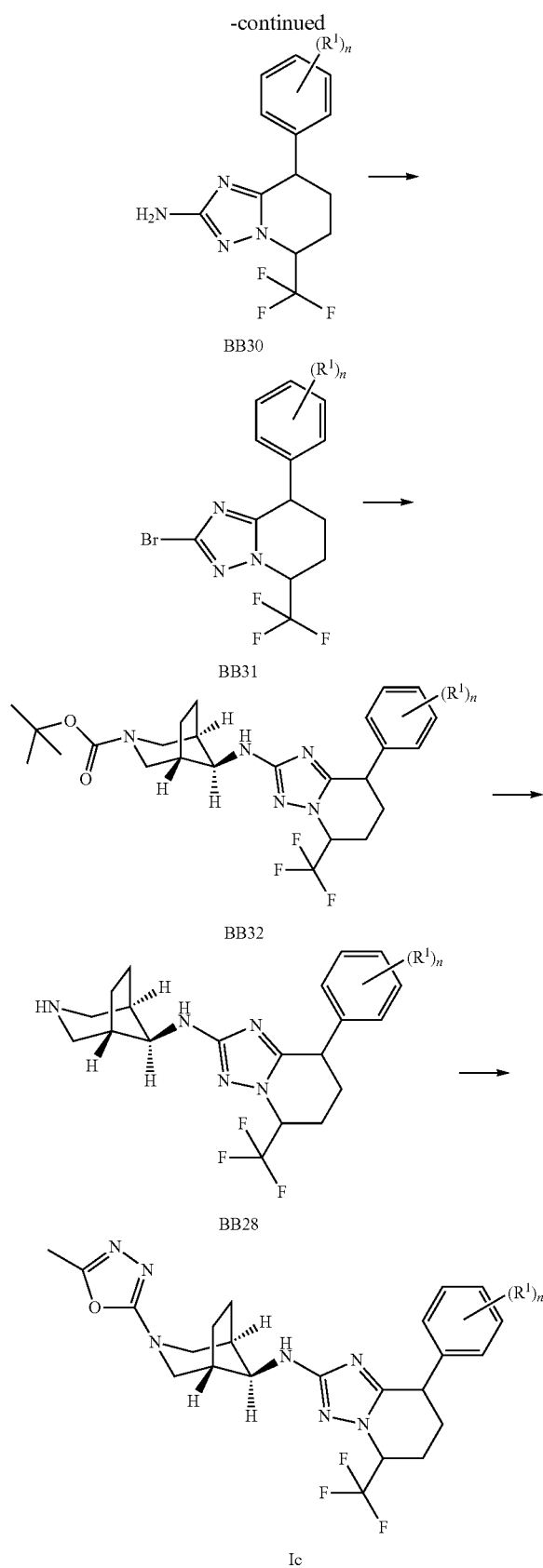

moiety can also be obtained (Scheme 7) by first hydrogenating BB24 to BB30 at a temperature of about 80° C. and a pressure of 80 bar with palladium on carbon followed by Sandmeyer reaction to introduce the bromo substituent of BB31. Buchwald reaction with (8-endo)-tert-butyl-8-amino-3-azabicyclo[3.2.1]octane-3-carboxylate leads to BB32 which is then deprotected under acidic conditions to BB28. Introduction of the heteroarylgroup, for example by reaction with 2-bromo-5-methyl-1,3,4-oxadiazole, leads to the compounds of formula Ic. Diastereoisomers and enantiomers can be separated by preparative HPLC. Compounds, in which $R^3$ is $CF_3$ can be prepared at the same way as described above for $R^2$ is $CF_3$.

Scheme 8

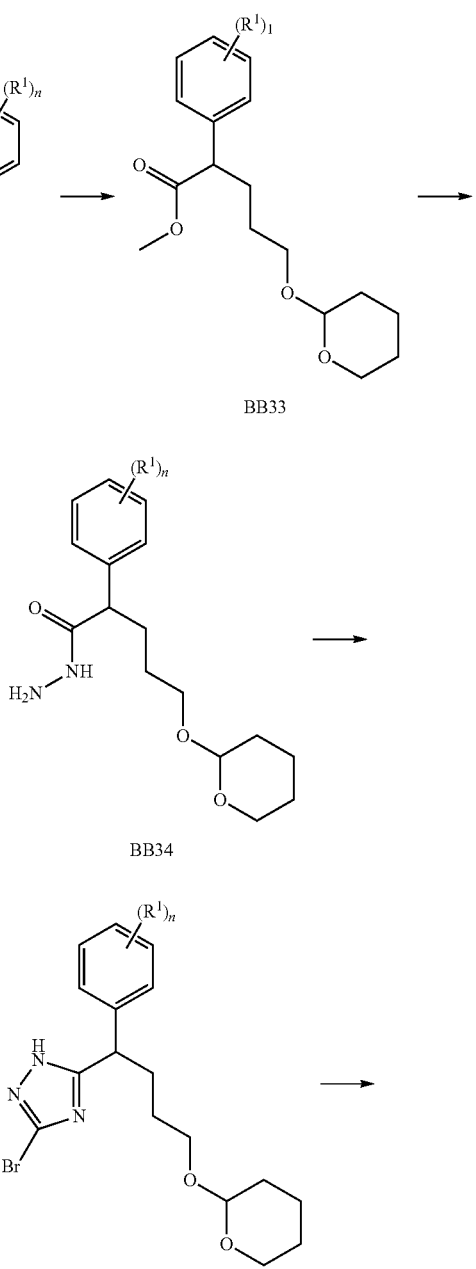

Compounds of formula Ic, carrying a trifluoromethyl substituent at the 5-position of the [1,2,4]triazolo[1,5-a]pyridin

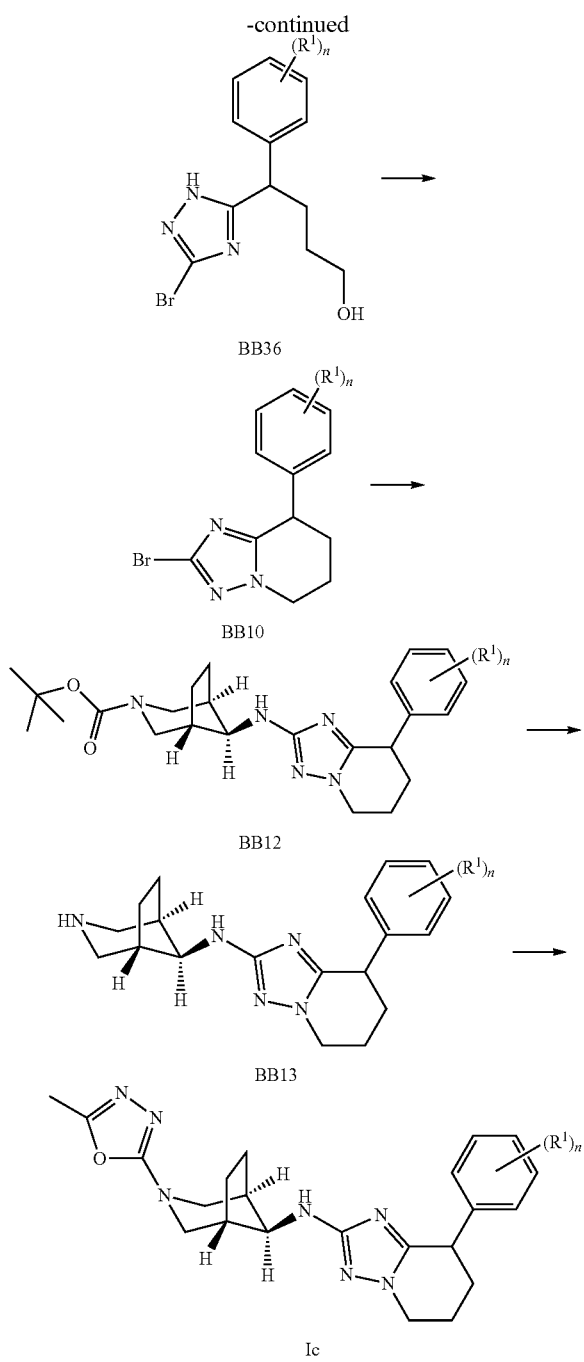

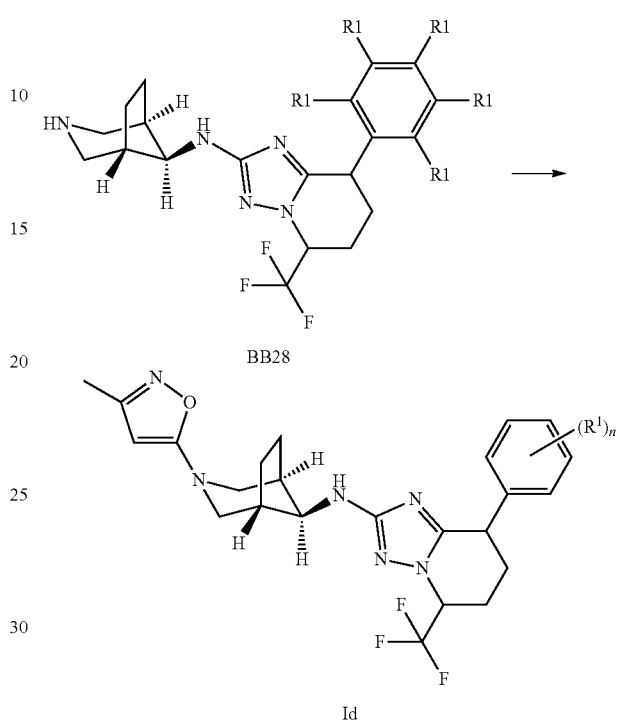

the intermediate BB36 which can be cylised under Mitsunobu conditions with 2-(trimethylphosphoranylidene)acetonitrile to BB10.

Compounds of formula Id can be obtained from BB28 (Scheme 9) for example by reaction with 5-iodo-3-methyl-isoxazole and copper(I)iodide as catalyst in presence of diethylsalicylamide and tripotassium phosphate in a solvent such as dimethylformamide. Enantiomers can be separated by preparative chiral HPLC.

The compounds were investigated in accordance with the test given hereinafter.

DESCRIPTION OF γ-SECRETASE ASSAY

Cellular γ-secretase Assay

Human neuroglioma H4 cells overexpressing human APP695 with the Swedish double mutation (K595N/M596L) were plated at 30,000 cells/well/100 μl in 96-well plates in IMDM media containing 10% FCS, 0.2 mg/l Hygromycin B and incubated at 37° C., 5% $CO_2$.

3-4 hr post plating, compounds are a diluted in media and 50 μl is added as 1.5-fold concentrate to achieve the final concentration. Compound incubation is performed for 24 hr. Final doses typically range from 4 μM down to 0.0013 μM in half-log steps resulting in a eight point dose response curve.

Appropriate controls using vehicle only and reference compound were applied to this assay. The final concentration of $Me_2SO$ was 0.4%.

After incubation at 37° C., 5% $CO_2$, the supernatant was subjected to quantification of secreted Aβ42 by the means of an AlphaLisa assay kit (Human Amyloid beta 1-42 Kit: Cat#AL203C, Perkin Elmer). 20 μl of the cell culture supernatant was transferred to an assay plate. Then 10 μl of Compounds of formula Ic can also be obtained from BB10 (Scheme 8) by Buchwald reaction with (8-endo)-tert-butyl-8-amino-3-azabicyclo[3.2.1]octane-3-carboxylate to give BB12 and as shown in Scheme 3, followed by cleavage of the BOC protecting group to give BB13, which is then reacted for example with 2-bromo-5-methyl-1,3,4-oxadiazole. The intermediate BB10 can be obtained starting from the corresponding phenylacetic acid esters. Deprotonation for example with sodium hydride in DMF at lower temperature and alkylation with 2-(3-bromopropoxy)tetrahydro-2H-pyran leads to intermediate BB33. Reaction with hydrazine hydrate in methanol leads to the hydrazide BB34, which is cyclised with methyl carbamimidothioate hemisulfate to BB35. Sandmeyer transformation and acidification leads to a mixture of the AlphaLisa coupled capture antibody and the biotinylated detection antibody was added and incubated for 3 hours at room temperature while softly shaking the assay plate. After a further addition of 20 µl of the Donor beads the assay plate was incubated for 30 min at room temperature and constant shaking without exposure to direct light. The assay plate was then read on a Paradigm AlphaLisa Reader using the build-in program with excitation at 680 nm and emission at 570 nm.

The measured signals were then used to calculate $IC_{50}$ values for inhibition of Aβ42 secretion by nonlinear regression fit analysis using XLfit 5.3 software (IDBS).

In the list below are described the data for all compounds to the inhibition of Aβ42 secretion (µM):

| Example No. | $EC_{50}$ Aβ42 (µM) |
|---|---|
| 1a | 0.022 |
| 1b | 0.008 |
| 1c | 0.005 |
| 2a | 0.003 |
| 2b | 0.009 |
| 3a | 0.003 |
| 3b | 0.010 |
| 3c | 0.003 |
| 4 | 0.004 |
| 5a | 0.004 |
| 5b | 0.007 |
| 5c | 0.002 |
| 6a | 0.012 |
| 6b | 0.006 |
| 7a | 0.005 |
| 7b | 0.005 |
| 7c | 0.004 |
| 8a | 0.007 |
| 8b | 0.004 |
| 9a | 0.005 |
| 9b | 0.006 |
| 10a | 0.018 |
| 10b | 0.003 |
| 11a | 0.010 |
| 11b | 0.013 |
| 11c | 0.020 |
| 12a | 0.003 |
| 12b | 0.004 |
| 13a | 0.003 |
| 13b | 0.006 |
| 14a | 0.002 |
| 14b | 0.004 |
| 15a | 0.005 |
| 15b | 0.007 |
| 16a | 0.003 |
| 16b | 0.003 |
| 16c | 0.003 |
| 17 | 0.019 |
| 18a | 0.010 |
| 18b | 0.009 |
| 18c | 0.003 |
| 19a | 0.015 |
| 19b | 0.007 |
| 20a | 0.006 |
| 20b | 0.008 |
| 21a | 0.007 |
| 21b | 0.026 |
| 22a | 0.003 |
| 22b | 0.008 |
| 22c | 0.004 |
| 23a | 0.011 |
| 23b | 0.003 |
| 23c | 0.011 |
| 24 | 0.034 |
| 25a | 0.029 |
| 25b | 0.021 |
| 26a | 0.026 |
| 26b | 0.020 |
| 27a | 0.062 |
| 27b | 0.015 |
| 28a | 0.022 |
| 28b | 0.035 |
| 29a | 0.016 |
| 29b | 0.017 |
| 29c | 0.053 |
| 30 | 0.028 |
| 31a | 0.051 |
| 31b | 0.029 |
| 31c | 0.026 |
| 31d | 0.011 |
| 32a | 0.026 |
| 32b | 0.022 |
| 32c | 0.040 |
| 33 | 0.045 |
| 34a | 0.041 |
| 34b | 0.047 |
| 34c | 0.013 |
| 35a | 0.047 |
| 35b | 0.050 |
| 35c | 0.032 |
| 36a | 0.021 |
| 36b | 0.030 |
| 36c | 0.010 |
| 37 | 0.032 |
| 38 | 0.010 |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, parenterally, e.g. in the form of injection solutions. The administration can also be effected topically, e.g. transdermal administration, or in form of eye drops or ear drops.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the inhibition of Aβ42 secretion, such as of Alzheimer's disease.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

| Item | Ingredients | mg/tablet | | | |
|---|---|---|---|---|---|
| | | 5 | 25 | 100 | 500 |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| Item | Ingredients | mg/capsule | | | |
|---|---|---|---|---|---|
| | | 5 | 25 | 100 | 500 |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

EXAMPLE 1a

N-((8-endo)-3-(3-Methylisothiazol-5-yl)-3-azabicyclo[3.2.1]octan-8-yl)-8-(4-(trifluoromethyl)phenyl)-5,6,7,8-tetrahydro-[1,2,4]triazolo[1,5-a]pyridin-2-amine

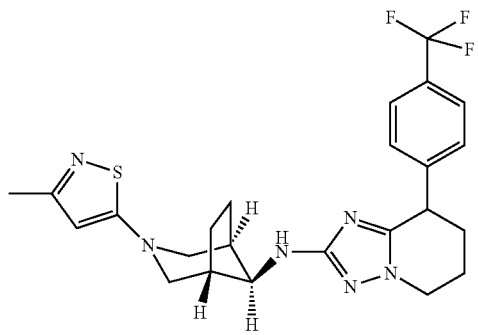 [SMILES: Cc1cc(N2C[C@H]3CC[C@@H](C2)[C@@H]3Nc2nc3n(n2)CCCC3c2ccc(C(F)(F)F)cc2)sn1]

a) tert-Butyl ((8-endo)-3-(3-Methylisothiazol-5-yl)-3-azabicyclo[3.2.1]octan-8-yl)carbamate

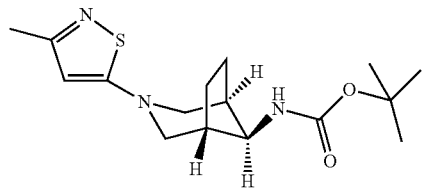 [SMILES: Cc1cc(N2C[C@H]3CC[C@@H](C2)[C@@H]3NC(=O)OC(C)(C)C)sn1]

In a 250 ml round-bottomed flask, 4-methyl-6-thioxo-3,6-dihydro-2H-1,3-thiazin-2-one (CAS 97309-82-5, 1.50 g, 9.42 mmol), tert-butyl (8-endo)-3-azabicyclo[3.2.1]octan-8-ylcarbamate (CAS 847862-26-4, 2.13 g, 9.42 mmol), 4-methylmorpholine (2.86 g, 3.11 ml, 28.3 mmol) and 4-dimethylaminopyridine (11.5 mg, 94.2 μmol) were combined with dioxane (150 ml) to give a light brown solution. The reaction mixture was heated to 80° C. and stirred overnight. Diisopropylethylamine (4.87 g, 6.58 ml, 37.7 mmol) was added and the mixture was cooled in an icebath. Iodine (4.78 g, 18.8 mmol) in dioxane (10 ml) was added and the reaction mixture was stirred overnight while warming to room temperature. The crude reaction mixture was concentrated in vacuo and purified by chromatography (silica gel-NH2, 40 g, ethyl acetate/heptane=50:50 to 100:0) to yield the title compound as light brown solid (1.09 g, 36%). MS: m/z=324.2 [M+H]$^+$.

b) (8-endo)-3-(3-Methylisothiazol-5-yl)-3-azabicyclo[3.2.1]octan-8-amine

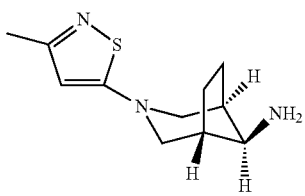

In a 250 ml round-bottomed flask, tert-butyl ((8-endo)-3-(3-methylisothiazol-5-yl)-3-azabicyclo[3.2.1]octan-8-yl)carbamate (2.99 g, 9.24 mmol) was combined with dichloromethane (180 ml) to give a brown solution. Hydrochloric acid (25%, 10 ml) was added and the reaction mixture was stirred at room temperature for 2 hours. The reaction mixture was cooled in an icebath, water (50 ml) was added and the mixture was basified with aqueous sodium hydroxide (4N). Extraction with dichloromethane and chromatography (silica gel-NH2, 40 g, ethyl acetate/heptane=50:50 to 100:0) yielded the title compound as light brown solid (1.64 g, 80%). MS: m/z=224.2 [M+H]$^+$.

c) 2-Bromo-8-(4-(trifluoromethyl)phenyl)-[1,2,4]triazolo[1,5-a]pyridine

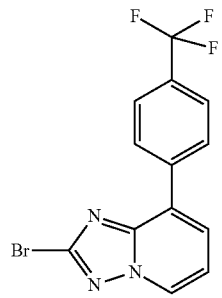 [SMILES: FC(F)(F)c1ccc(-c2cccn3nc(Br)nc23)cc1]

To a dark brown solution of tert-butyl nitrite (1.67 g, 1.92 ml, 16.2 mmol) and copper (II) bromide (3.61 g, 16.2 mmol) in acetonitrile (38 ml) at 60° C. was added in portions 8-(4-(trifluoromethyl)phenyl)-[1,2,4]triazolo[1,5-a]pyridin-2-amine (CAS 1257704-98-5, 3.00 g, 10.8 mmol). After addition the mixture was heated at 75° C. for 2 hours. The reaction mixture was quenched with hydrochloric acid (1 M, 50 ml) and extracted with ethyl acetate (3×100 ml). The organic layers were dried over magnesium sulfate, concentrated in vacuo and purified by chromatography (silica gel, 40 g, ethyl acetate/heptane=0:100 to 50:50). The fractions were concentrated and dried in vacuo to yield the title compound as off-white solid (3.15 g, 85%). MS: m/z=342.0, 344.0 [M+H]$^+$.

d) N-((8-endo)-3-(3-Methylisothiazol-5-yl)-3-azabicyclo[3.2.1]octan-8-yl)-8-(4-(trifluoromethyl)phenyl)-[1,2,4]triazolo[1,5-a]pyridin-2-amine

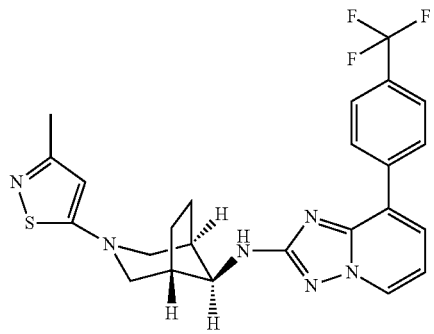 [SMILES: Cc1cc(N2C[C@H]3CC[C@@H](C2)[C@@H]3Nc2nc3c(-c4ccc(C(F)(F)F)cc4)cccn3n2)sn1]

A suspension of 2-bromo-8-(4-(trifluoromethyl)phenyl)-[1,2,4]triazolo[1,5-a]pyridine (460 mg, 1.34 mmol), (8-endo)-3-(3-methylisothiazol-5-yl)-3-azabicyclo[3.2.1]octan-8-amine (300 mg, 1.34 mmol), sodium tert-butoxide (271 mg, 2.82 mmol), xantphos (127 mg, 215 µmol) and tris(dibenzylideneacetone)dipalladium (0) chloroform adduct (115 mg, 107 µmol) in dioxane (15 ml) was heated in the microwave at 150° C. for 30 minutes. The crude reaction mixture was concentrated in vacuo and purified by chromatography (silica gel, 50 g, ethyl acetate/heptane=40:60 to 100:0) to yield the title compound as dark brown solid (545 mg, 84%). MS: m/z=485.2 [M+H]$^+$.

e) N-((8-endo)-3-(3-Methylisothiazol-5-yl)-3-azabicyclo[3.2.1]octan-8-yl)-8-(4-(trifluoromethyl)phenyl)-5,6,7,8-tetrahydro-[1,2,4]triazolo[1,5-a]pyridin-2-amine

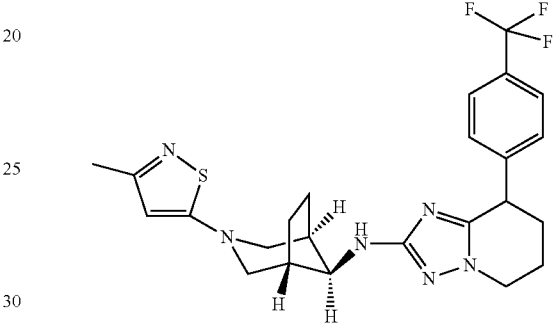

A solution of N-((8-endo)-3-(3-methylisothiazol-5-yl)-3-azabicyclo[3.2.1]octan-8-yl)-8-(4-(trifluoromethyl)phenyl)-[1,2,4]triazolo[1,5-a]pyridin-2-amine (545 mg, 1.12 mmol), iodine (2.85 mg, 11.2 µmol) and magnesium (219 mg, 9 mmol) in methanol (20 ml) and tetrahydrofuran (10 ml) was heated at 80° C. for 24 hours. The reaction mixture was cooled to room temperature, filtered through sintered glass and purified by chromatography (silica gel, 50 g, ethyl acetate/methanol=100:0 to 70:30) to yield the title compound as brown solid (320 mg, 58%). MS: m/z=489.2 [M+H]$^+$.

EXAMPLE 1b (+)-N-((8-endo)-3-(3-Methylisothiazol-5-yl)-3-azabicyclo[3.2.1]octan-8-yl)-8-(4-(trifluoromethyl)phenyl)-5,6,7,8-tetrahydro-[1,2,4]triazolo[1,5-a]pyridin-2-amine

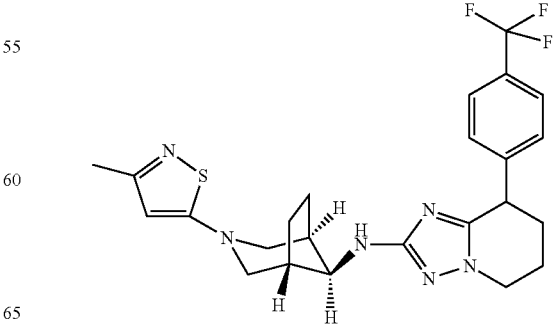

Chromatography of the racemic N-((8-endo)-3-(3-methylisothiazol-5-yl)-3-azabicyclo[3.2.1]octan-8-yl)-8-(4-(trifluoromethyl)phenyl)-5,6,7,8-tetrahydro-[1,2,4]triazolo[1,5-a]pyridin-2-amine (example 1a) on Reprosil Chiral NR (ethanol/heptane=40:60) yielded the title compound as off-white solid (84 mg, 29%). MS: m/z=489.3 [M+H]+.

EXAMPLE 1c (−)-N-((8-endo)-3-(3-Methylisothiazol-5-yl)-3-azabicyclo[3.2.1]octan-8-yl)-8-(4-(trifluoromethyl)phenyl)-5,6,7,8-tetrahydro-[1,2,4]triazolo[1,5-a]pyridin-2-amine

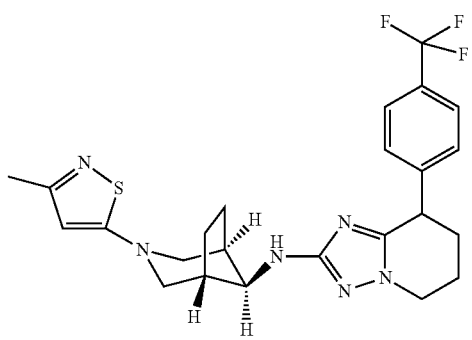 [SMILES: Cc1cc(N2C[C@H]3CC[C@@H](C2)[C@@H]3Nc2nc3n(n2)CCCC3c2ccc(C(F)(F)F)cc2)sn1]

Chromatography of the racemic N-((8-endo)-3-(3-methylisothiazol-5-yl)-3-azabicyclo[3.2.1]octan-8-yl)-8-(4-(trifluoromethyl)phenyl)-5,6,7,8-tetrahydro-[1,2,4]triazolo[1,5-a]pyridin-2-amine (example 1a) on Reprosil Chiral NR (ethanol/heptane=40:60) yielded the title compound as off-white solid (108 mg, 38%). MS: m/z=489.3 [M+H]+.

EXAMPLE 2a (−)-N-[(8-endo)-3-(3-Methyl-1,2-thiazol-5-yl)-3-azabicyclo[33.2.1]octan-8-yl]-8-(2,3,4-trifluorophenyl)-5,6,7,8-tetrahydro-[1,2,4]triazolo[1,5-a]pyridin-2-amine

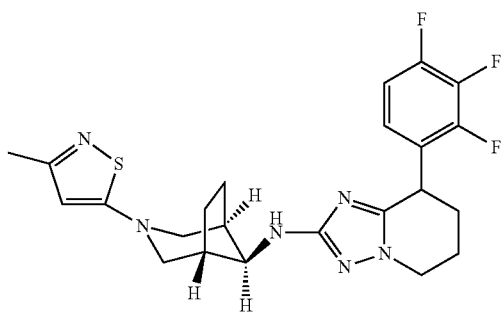 [SMILES: Cc1cc(N2C[C@H]3CC[C@@H](C2)[C@@H]3Nc2nc3n(n2)CCCC3c2ccc(F)c(F)c2F)sn1]

a) N-((8-endo)-3-(3-Methylisothiazol-5-yl)-3-azabicyclo[3.2.1]octan-8-yl)-8-(2,3,4-trifluorophenyl)-[1,2,4]triazolo[1,5-a]pyridin-2-amine

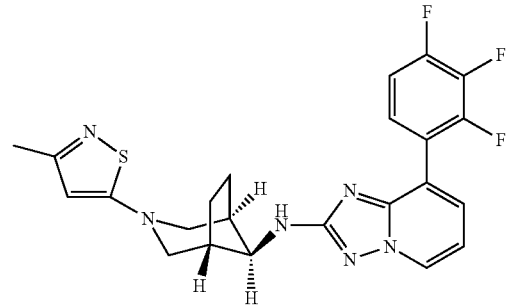 [SMILES: Cc1cc(N2C[C@H]3CC[C@@H](C2)[C@@H]3Nc2nc3c(-c4ccc(F)c(F)c4F)cccn3n2)sn1]

A suspension of (8-endo)-3-(3-methylisothiazol-5-yl)-3-azabicyclo[3.2.1]octan-8-amine (55 mg, 246 µmol), 2-bromo-8-(2,3,4-trifluorophenyl)-[1,2,4]triazolo[1,5-a]pyridine (CAS1329673-61-1, 80.8 mg, 246 µmol), xantphos (22.8 mg, 39.4 µmol), tris(dibenzylideneacetone)dipalladium (0) chloroform adduct (20.4 mg, 19.7 µmol) and sodium tert-butoxide (49.7 mg, 517 µmol) in dioxane (4 ml) was heated in the microwave at 150° C. for 30 minutes. The crude reaction mixture was concentrated in vacuo and purified by chromatography (silica gel, 12 g, ethyl acetate/heptane=20:80 to 100:0). The product fractions were concentrated in vacuo and triturated with diethyl ether (0.5 ml)/pentane (1 ml) to yield the title compound as off-white solid (87 mg, 75%). MS: m/z=471.3 [M+H]+.

b) (−)-N-[(8-endo)-3-(3-Methyl-1,2-thiazol-5-yl)-3-azabicyclo[3.2.1]octan-8-yl]-8-(2,3,4-trifluorophenyl)-5,6,7,8-tetrahydro-[1,2,4]triazolo[1,5-a]pyridin-2-amine

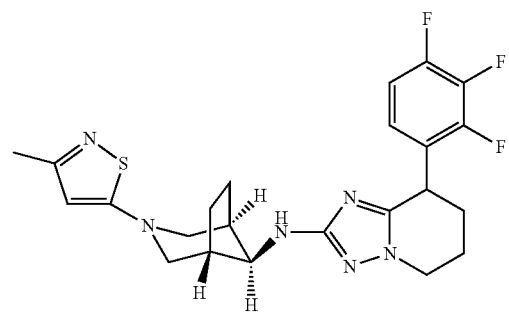 [SMILES: Cc1cc(N2C[C@H]3CC[C@@H](C2)[C@@H]3Nc2nc3n(n2)CCCC3c2ccc(F)c(F)c2F)sn1]

In a 10 ml microwave vial were combined N-((8-endo)-3-(3-methylisothiazol-5-yl)-3-azabicyclo[3.2.1]octan-8-yl)-8-(2,3,4-trifluorophenyl)-[1,2,4]triazolo[1,5-a]pyridin-2-amine (85.0 mg, 0.18 mmol), magnesium (35.1 mg, 1.45 mmol) and iodine (459 µg, 1.81 µmol) in methanol (4.44 ml) and tetrahydrofuran (2.22 ml). The vial was capped and heated in the oilbath at 70° C. for 3 hours. The reaction mixture was cooled to RT and filtered through sintered glass. Purification by chromatography (silica gel, 12 g, ethyl acetate/methanol=100:0 to 80:20) gave N-[(8-endo)-3-(3-Methyl-1,2-thiazol-5-yl)-3-azabicyclo[3.2.1]octan-8-yl]-8-(2,3,4-trifluorophenyl)-5,6,7,8-tetrahydro-[1,2,4]triazolo[1,5-a]pyridin-2-amine as racemate. Separation of the enantiomers on Reprosil Chiral-AM (ethanol/heptane=40:60) yielded the title compound as off-white solid (10.9 mg, 13%). MS: m/z=475.3 [M+H]$^+$.

EXAMPLE 2b (+)-N-[(8-endo)-3-(3-Methyl-1,2-thiazol-5-yl)-3-azabicyclo[3.2.1]octan-8-yl]-8-(2,3,4-trifluorophenyl)-5,6,7,8-tetrahydro-[1,2,4]triazolo[1,5-a]pyridin-2-amine

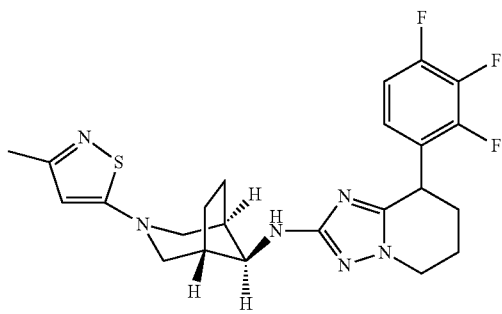 [SMILES: Cc1cc(N2C[C@H]3CC[C@@H](C2)[C@@H]3Nc2nc3n(n2)CCCC3c2ccc(F)c(F)c2F)sn1]

Separation of the enantiomers of the racemic N-[(8-endo)-3-(3-Methyl-1,2-thiazol-5-yl)-3-azabicyclo[3.2.1]octan-8-yl]-8-(2,3,4-trifluorophenyl)-5,6,7,8-tetrahydro-[1,2,4]triazolo[1,5-a]pyridin-2-amine (previous example) on Reprosil Chiral-AM (ethanol/heptane=40:60) yielded the title compound as off-white solid (9.6 mg, 11%). MS: m/z=475.3 [M+H]$^+$.

EXAMPLE 3a

N-((8-endo)-3-(3-Methylisothiazol-5-yl)-3-azabicyclo[3.2.1]octan-8-yl)-8-(4-(trifluoromethoxy)phenyl)-5,6,7,8-tetrahydro-[1,2,4]triazolo[1,5-a]pyridin-2-amine

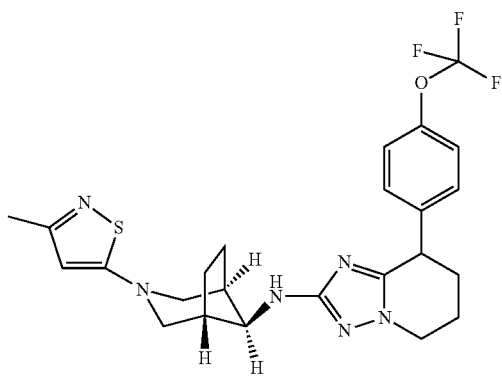 [SMILES: Cc1cc(N2C[C@H]3CC[C@@H](C2)[C@@H]3Nc2nc3n(n2)CCCC3c2ccc(OC(F)(F)F)cc2)sn1]

a) 8-(4-(Trifluoromethoxy)phenyl)-[1,2,4]triazolo[1,5-a]pyridin-2-amine

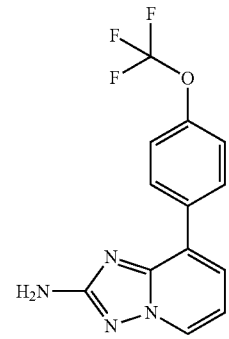

In a 500 ml round-bottomed flask were combined 8-bromo-[1,2,4]triazolo[1,5-a]pyridin-2-amine (CAS1124382-72-4, 6.00 g, 28.2 mmol), (4-(trifluoromethoxy)phenyl)boronic acid (11.6 g, 56.3 mmol) and cesium carbonate (18.4 g, 56.3 mmol) in dioxane (300 ml) and water (30 ml) to give a light brown solution. 1,1'-Bis(diphenylphosphino)ferrocene-palladium(II)dichloride dichloromethane complex (2.06 g, 2.82 mmol) was added. The reaction mixture was stirred for 2 hours at 100° C. Chromatography (silica gel, 330 g, ethyl acetate/heptane=40:60 to 100:0) yielded the title compound as light brown solid (7.64 g, 92%). MS: m/z=295.2 [M+H]$^+$.

b) 2-Bromo-8-(4-(trifluoromethoxy)phenyl)-[1,2,4]triazolo[1,5-a]pyridine

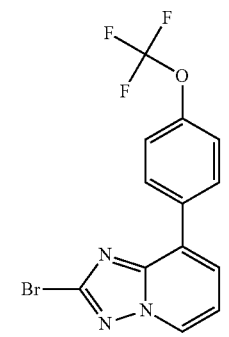 [SMILES: FC(F)(F)Oc1ccc(-c2cccn3nc(Br)nc23)cc1]

In a 150 ml round-bottomed flask, tert-butyl nitrite (3.47 g, 4 ml, 33.6 mmol) and copper (II) bromide (7.52 g, 33.6 mmol) were combined with acetonitrile (120 ml) to give a black solution. The reaction mixture was heated to 60° C., then 8-(4-(trifluoromethoxy)phenyl)-[1,2,4]triazolo[1,5-a]pyridin-2-amine (6.60 g, 22.4 mmol) was added. The temperature was raised to 80° C. and stirring was continued for 2 hours. The mixture was cooled to room temperature and was concentrated in vacuo. Hydrochloric acid (1N, 25 ml) was added followed by extraction with ethyl acetate (3×150 ml). Purification by chromatography (silica gel, 330 g, ethyl acetate/heptane=0:100 to 40:60) yielded the title compound as white solid (7.25 g, 90%). MS: m/z=358.1 and 360.0 [M+H]$^+$.

c) N-((8-endo)-3-(3-Methylisothiazol-5-yl)-3-azabicyclo[3.2.1]octan-8-yl)-8-(4-(trifluoromethoxy)phenyl)-[1,2,4]triazolo[1,5-a]pyridin-2-amine

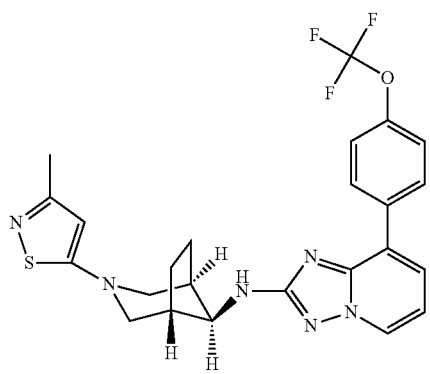 [SMILES: Cc1cc(N2C[C@H]3CC[C@@H](C2)[C@@H]3Nc2nc3c(-c4ccc(OC(F)(F)F)cc4)cccn3n2)sn1]

In a microwave vial were combined 2-bromo-8-(4-(triflu2-bromo-8-(4-(trifluoromethoxy)phenyl)-[1,2,4]triazolo[1,5-a]pyridine (497 mg, 1.39 mmol), (8-endo)-3-(3-methylisothiazol-5-yl)-3-azabicyclo[3.2.1]octan-8-amine (310 mg, 1.39 mmol), sodium tert-butoxide (280 mg, 2.91 mmol), xantphos (132 mg, 222 µmol) and tris(dibenzylideneacetone)dipalladium (0) chloroform adduct (117 mg, 111 µmol) in dioxane (16 ml). The vial was capped and heated in the microwave at 150° C. for 30 minutes. Purification by chromatography (silica gel, 20 g, ethyl acetate/heptane=10:90 to 100:0) yielded the title compound as light brown foam (460 mg, 66%). MS: m/z=501.2 [M+H]$^+$.

d) N-((8-endo)-3-(3-Methylisothiazol-5-yl)-3-azabicyclo[3.2.1]octan-8-yl)-8-(4-(trifluoromethoxy)phenyl)-5,6,7,8-tetrahydro-[1,2,4]triazolo[1,5-a]pyridin-2-amine

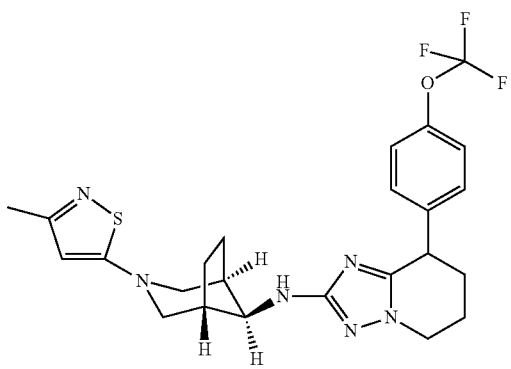 [SMILES: Cc1cc(N2C[C@H]3CC[C@@H](C2)[C@@H]3Nc2nc3n(n2)CCCC3c2ccc(OC(F)(F)F)cc2)sn1]

In a 100 ml round-bottomed flask, N-((8-endo)-3-(3-methylisothiazol-5-yl)-3-azabicyclo[3.2.1]octan-8-yl)-8-(4-(trifluoromethoxy)phenyl)-[1,2,4]triazolo[1,5-a]pyridin-2-amine (460 mg, 919 µmol), magnesium (179 mg, 7.35 mmol) and iodine (2.33 mg, 9.19 µmol) were combined with methanol (30 ml) and tetrahydrofuran (15 ml) to give a light brown solution. The reaction mixture was heated to 80° C. and stirred for 4 hours. The mixture was cooled to room temperature and filtered through sintered glass. Chromatography (silica gel, 20 g, ethyl acetate/heptane=20:80 to 100:0) yielded the title compound as a brown oil (360 mg, 78%). MS: m/z=505.3 [M+H]$^+$.

EXAMPLE 3b (+)-N-[(8-endo)-3-(3-Methyl-1,2-thiazol-5-yl)-3-azabicyclo[3.2.1]octan-8-yl]-8-[4-(trifluoromethoxy)phenyl]-5,6,7,8-tetrahydro-[1,2,4]triazolo[1,5-a]pyridin-2-amine

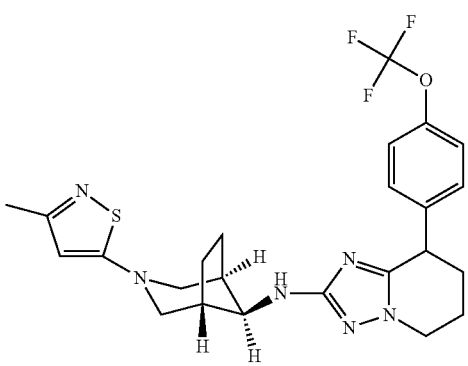 [SMILES: Cc1cc(N2C[C@H]3CC[C@@H](C2)[C@@H]3Nc2nc3n(n2)CCCC3c2ccc(OC(F)(F)F)cc2)sn1]

Chromatography of the racemic N-((8-endo)-3-(3-methylisothiazol-5-yl)-3-azabicyclo[3.2.1]octan-8-yl)-8-(4-(trifluoromethoxy)phenyl)-5,6,7,8-tetrahydro-[1,2,4]triazolo[1,5-a]pyridin-2-amine (example 3a) on Reprosil Chiral NR (ethanol/heptane=40:60) yielded the title compound as off-white solid (164 mg, 46%). MS: m/z=503.3 [M+H]$^+$.

EXAMPLE 3c (−)-N-[(8-endo)-3-(3-Methyl-1,2-thiazol-5-yl)-3-azabicyclo[3.2.1]octan-8-yl]-8-[4-(trifluoromethoxy)phenyl]-5,6,7,8-tetrahydro-[1,2,4]triazolo[1,5-a]pyridin-2-amine

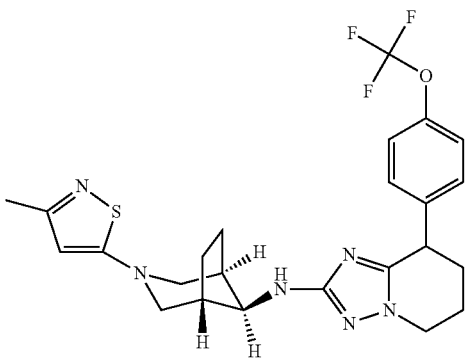 [SMILES: Cc1cc(N2C[C@H]3CC[C@@H](C2)[C@@H]3Nc2nc3n(n2)CCCC3c2ccc(OC(F)(F)F)cc2)sn1]

Chromatography of the racemic N-((8-endo)-3-(3-methylisothiazol-5-yl)-3-azabicyclo[3.2.1]octan-8-yl)-8-(4-(trifluoromethoxy)phenyl)-5,6,7,8-tetrahydro-[1,2,4]triazolo[1,5-a]pyridin-2-amine (example 3a) on Reprosil Chiral NR (ethanol/heptane=40:60) yielded the title compound as off-white solid (140 mg, 39%). MS: m/z=503.5 [M+H]$^+$.

EXAMPLE 4

8-(2-Chloro-4-fluorophenyl)-N-[(8-endo)-3-(3-methyl-1,2-thiazol-5-yl)-3-azabicyclo[3.2.1]octan-8-yl]-5,6,7,8-tetrahydro-[1,2,4]triazolo[1,5-a]pyridin-2-amine

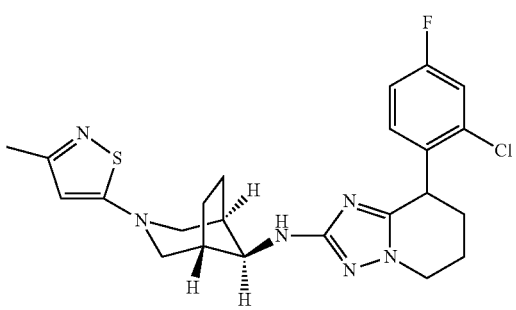 [SMILES: Cc1cc(N2C[C@H]3CC[C@@H](C2)[C@@H]3Nc2nc3n(n2)CCCC3c2ccc(F)cc2Cl)sn1]

a) Methyl-5-chloro-2-(2-chloro-4-fluorophenyl)pentanoate

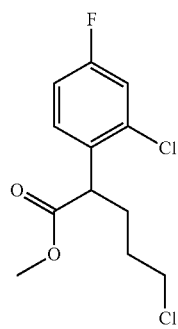 [SMILES: COC(=O)C(CCCCl)c1ccc(F)cc1Cl]

In a 250 ml three-necked flask, methyl 2-(2-chloro-4-fluorophenyl)acetate (3.98 g, 19.6 mmol) was combined with dimethylformamide (70 ml) to give a colorless solution. At 0° C. sodium hydride (943 mg, 21.6 mmol) was added slowly in small portions. Stirring was continued for 10 minutes at 0° C. and then for 30 minutes at room temperature. The reaction mixture was then cooled again to 0° C. and 1-chloro-3-iodopropane (4.30 g, 2.26 ml, 21.0 mmol) was added dropwise under stirring (temperature <5° C.). Stirring was continued at 0° C. for 1 hour and then at room temperature overnight. The reaction mixture was slowly poured into 100 ml water and extracted with ethyl acetate (4×150 ml). The organic layers were combined and washed with saturated brine (2×100 ml). The organic layers were dried over magnesium sulfate, concentrated in vacuo and purified by chromatography (silica gel, 40 g, ethyl acetate/heptane=0:100 to 50:50) to yield the title compound as colorless liquid (4.63 g, 84%). MS: m/z=279.2 [M+H]$^+$.

b) tert-Butyl-2-(5-chloro-2-(2-chloro-4-fluorophenyl)pentanoyl)hydrazinecarboxylate

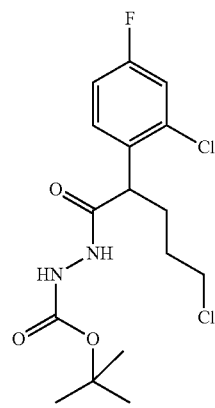 [SMILES: CC(C)(C)OC(=O)NNC(=O)C(CCCCl)c1ccc(F)cc1Cl]

In a 10 ml round-bottomed flask, methyl 5-chloro-2-(2-chloro-4-fluorophenyl)pentanoate (1.2 g, 4.3 mmol) was combined with methanol (3 ml) to give a light yellow solution. Aqueous sodium hydroxide (5M, 4 ml, 20.0 mmol) was added and stirring was continued at room temperature overnight. The crude reaction mixture was concentrated in vacuo, poured into 10 ml water, acidified with hydrochloric acid (5M) and extracted with ethyl acetate (5×50 ml). The organic layers were dried over magnesium sulfate and concentrated in vacuo. The residue was taken up in dichloromethane (20 ml) and tert-butyl hydrazinecarboxylate (739 mg, 5.59 mmol) and diisopropylethylamine (1.17 g, 1.58 ml, 9.03 mmol) were added. The mixture was cooled to 0° C. and then bis(2-oxo-3-oxazolidinyl)phosphinic chloride (1.64 g, 6.45 mmol) was added and stirring was continued for 1 hour at 0° C. and then for 3 hours at room temperature. The crude reaction mixture was concentrated in vacuo, poured into 25 ml saturated aqueous sodium bicarbonate. Extraction with ethyl acetate (3×75 ml) and chromatography (silica gel, 40 g, ethyl acetate/heptane=10/90 to 50:50) yielded the title compound as off-white solid (672 mg, 41%). MS: m/z=377.3 and 379.3 [M−H]$^-$.

c) 5-Chloro-2-(2-chloro-4-fluorophenyl)pentanehydrazide

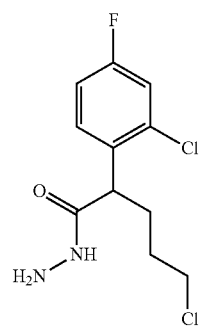 [SMILES: NNC(=O)C(CCCCl)c1ccc(F)cc1Cl]

In a 25 ml round-bottomed flask, tert-butyl 2-(5-chloro-2-(2-chloro-4-fluorophenyl)pentanoyl)hydrazinecarboxylate (660 mg, 1.74 mmol) was combined with ethyl acetate (5 ml) to give a light yellow solution. Hydrogen chloride (4N in ethyl acetate, 6.00 g, 5 ml, 20.0 mmol) was added and stirring was continued at room temperature overnight. The mixture was cooled in an ice bath and made alkaline with aqueous sodium hydroxide (4 N). The reaction mixture was extracted with ethyl acetate (3×50 ml) to yield the title compound as light yellow oil (486 mg, quant.). MS: m/z=279.2 and 281.1 [M+H]$^+$.

d) 8-(2-Chloro-4-fluorophenyl)-5,6,7,8-tetrahydro-[1,2,4]triazolo[1,5-a]pyridin-2-amine

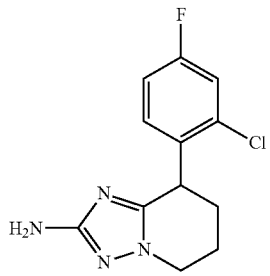 [SMILES: Nc1nc2n(n1)CCCC2c1ccc(F)cc1Cl]

In a 50 ml round-bottomed flask, 5-chloro-2-(2-chloro-4-fluorophenyl)pentanehydrazide (1.50 g, 5.37 mmol), p-toluenesulfonic acid monohydrate (971 mg, 5.1 mmol) and cyanamide (1.22 g, 29.0 mmol) were combined with ethanol (30 ml) to give a light yellow solution. The reaction mixture was heated at 90° C. for 2 hours. The reaction mixture was then cooled to room temperature and trietylamine (2.28 g, 3.15 ml, 22.6 mmol) was added. The mixture was stirred at 90° C. overnight. The crude reaction mixture was concentrated in vacuo, poured into 25 ml saturated aqueous sodium bicarbonate and extracted with ethyl acetate (5×50 ml). Chromatography (silica gel, 40 g, ethyl acetate/heptane=0:100 to 10:90) yielded the title compound as off-white solid (0.98 g, 69%). MS: m/z=267.1 [M+H]$^+$.

e) 2-Bromo-8-(2-chloro-4-fluorophenyl)-5,6,7,8-tetrahydro-[1,2,4]triazolo[1,5-a]pyridine

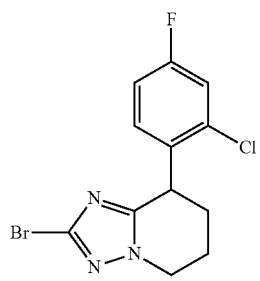 [SMILES: Fc1ccc(C2CCCn3nc(Br)nc32)c(Cl)c1]

To a dark brown solution of tert-butyl nitrite (174 mg, 200 μl, 1.69 mmol) and copper (11) bromide (377 mg, 1.69 mmol) in acetonitrile (6 ml) at 60-C was added 8-(2-chloro-4-fluorophenyl)-5,6,7,8-tetrahydro-[1,2,4]triazolo[1,5-a]pyridin-2-amine (300 mg, 1.12 mmol) in portions. After addition the mixture was heated at 75° C. for 2 hours. The reaction mixture was quenched with 10 ml hydrochloric acid (1M) and extracted with ethyl acetate (3×25 ml). Chromatography (silica gel, 12 g, ethyl acetate/heptane=0:100 to 50:50) yielded the title compound as colorless viscous oil (191 mg, 51%). MS: m/z=330.0 and 332.0 [M+H]$^+$.

f) 8-(2-Chloro-4-fluorophenyl)-N-[(8-endo)-3-(3-methyl-1,2-thiazol-5-yl)-3-azabicyclo[3.2.1]octan-8-yl]-5,6,7,8-tetrahydro-[1,2,4]triazolo[1,5-a]pyridin-2-amine

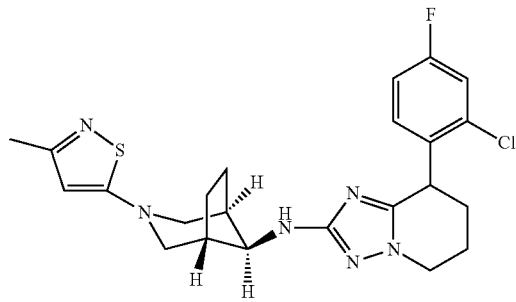 [SMILES: Cc1cc(N2C[C@H]3CC[C@@H](C2)[C@@H]3Nc2nc3n(n2)CCCC3c2ccc(F)cc2Cl)sn1]

In a 10 ml microwave vial were combined (8-endo)-3-(3-methylisothiazol-5-yl)-3-azabicyclo[3.2.1]octan-8-amine (20 mg, 89.6 μmol), 2-bromo-8-(2-chloro-4-fluorophenyl)-5,6,7,8-tetrahydro-[1,2,4]triazolo[1,5-a]pyridine (29.6 mg, 89.6 μmol), xantphos (8.29 mg, 14.3 mol), tris(dibenzylideneacetone)dipalladium (0) chloroform adduct (7.42 mg, 7.16 μmol) and sodium tert-butoxide (18.1 mg, 188 μmol) in dioxane (1.4 ml). The vial was capped and heated in the microwave at 150° C. for 30 minutes. Purification by chromatography (silica gel, 12 g, ethyl acetate/heptane=20:80 to 100:0) and trituration with diethyl ether/pentane (0.5 ml/1 ml) yielded the title compound as off-white solid (7.8 mg, 18%). MS: m/z=472.1 [M–H]$^-$.

EXAMPLE 5a

N-[(8-endo)-3-(3-Methyl-1,2-thiazol-5-yl)-3-azabicyclo[3.2.1]octan-8-yl]-8-[4-(trifluoromethylsulfanyl)phenyl]-5,6,7,8-tetrahydro-[1,2,4]triazolo[1,5-a]pyridin-2-amine

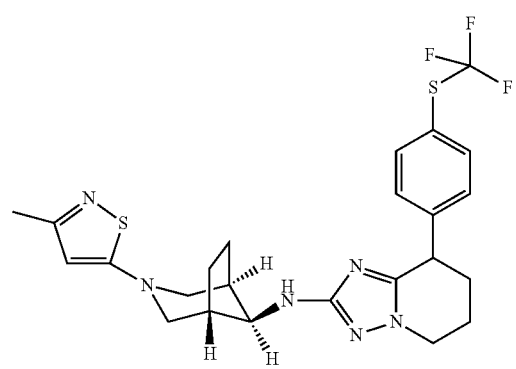 [SMILES: Cc1cc(N2C[C@H]3CC[C@@H](C2)[C@@H]3Nc2nc3n(n2)CCCC3c2ccc(SC(F)(F)F)cc2)sn1]

a) 8-(4-(Trifluoromethylthio)phenyl)-[1,2,4]triazolo[1,5-a]pyridin-2-amine

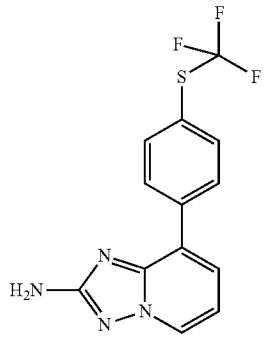 [SMILES: Nc1nc2c(-c3ccc(SC(F)(F)F)cc3)cccn2n1]

In a 150 ml round-bottomed flask, 8-bromo-[1,2,4]triazolo[1,5-a]pyridin-2-amine (1.40 g, 6.58 mmol), 4,4,5,5-tetramethyl-2-(4-(trifluoromethylthio)phenyl)-1,3,2-dioxaborolane (2.00 g, 6.58 mmol) and cesium carbonate (4.29 g, 13.2 mmol) were combined with dioxane (80 ml) and water (8.00 ml) to give a white suspension. 1,1'-Bis(diphenylphosphino)ferrocene-palladium(II)dichloride dichloromethane complex (481 mg, 658 µmol) was added. The reaction mixture was heated to 100° C. and stirred overnight. Chromatography (silica gel, 70 g, ethyl acetate/heptane=30:70 to 100:0) yielded the title compound as a light brown solid (1.77 g, 87%). MS: m/z=311.0 [M+H]$^+$.

b) 2-Bromo-8-(4-((trifluoromethyl)thio)phenyl)-[1,2,4]triazolo[1,5-a]pyridine

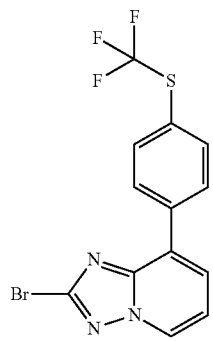 [SMILES: FC(F)(F)Sc1ccc(-c2cccn3nc(Br)nc23)cc1]

In a 25 ml round-bottomed flask, tert-butyl nitrite (245 mg, 282 µl, 2.37 mmol) and copper (II) bromide (530 mg, 2.37 mmol) were combined with acetonitrile (10 ml) to give a black solution. The reaction mixture was heated to 60° C., then 8-(4-((trifluoromethyl)thio)phenyl)-[1,2,4]triazolo[1,5-a]pyridin-2-amine (491 mg, 1.58 mmol) was added. The reaction mixture was heated at 80° C. for 1 hour. The mixture was then cooled to room temperature, hydrochloric acid (1 N, 25 ml) was added and the reaction mixture was extracted with ethyl acetate (3×100 ml). Chromatography (silica gel, 12 g, ethyl acetate/heptane=0:100 to 70:30) yielded the title compound as off-white solid (472 mg, 80%). MS: m/z=374.1 and 376.1 [M+H]$^+$.

c) N-((8-endo)-3-(3-Methylisothiazol-5-yl)-3-azabicyclo[3.2.1]octan-8-yl)-8-(4-((trifluoromethyl)thio)phenyl)-[1,2,4]triazolo[1,5-a]pyridin-2-amine

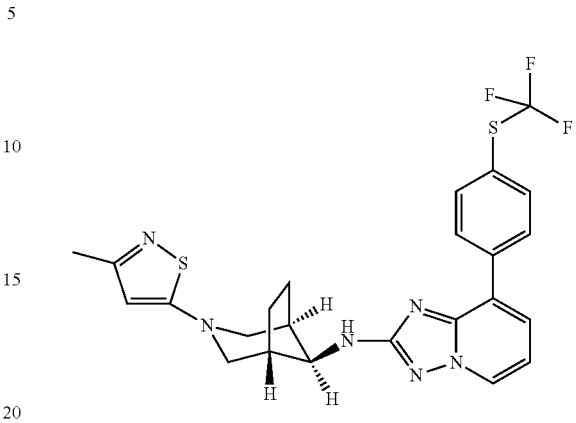

A suspension of (8-endo)-3-(3-methylisothiazol-5-yl)-3-azabicyclo[3.2.1]octan-8-amine (269 mg, 1.2 mmol), 2-bromo-8-(4-((trifluoromethyl)thio)phenyl)-[1,2,4]triazolo[1,5-a]pyridine (450 mg, 1.2 mmol), xantphos (111 mg, 192 µmol), tris(dibenzylideneacetone)dipalladium (0) chloroform adduct (99.6 mg, 96.2 µmol) and sodium tert-butoxide (243 mg, 2.53 mmol) in dioxane (16 ml) was heated in the microwave at 150° C. for 30 minutes. Chromatography (silica gel, 40 g, ethyl acetate/heptane=20:80 to 100:0) yield the title compound as light brown foam (389 mg, 63%). MS: m/z=517.3 [M+H]$^+$.

d) N-[(8-endo)-3-(3-Methyl-1,2-thiazol-5-yl)-3-azabicyclo[3.2.1]octan-8-yl]-8-[4-(trifluoromethylsulfanyl)phenyl]-5,6,7,8-tetrahydro-[1,2,4]triazolo[1,5-a]pyridin-2-amine

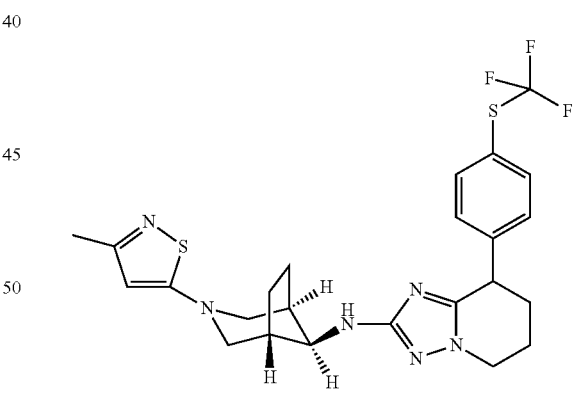

In a 50 ml round-bottomed flask, N-((8-endo)-3-(3-methylisothiazol-5-yl)-3-azabicyclo[3.2.1]octan-8-yl)-8-(4-((trifluoromethyl)thio)phenyl)-[1,2,4]triazolo[1,5-a]pyridin-2-amine (310 mg, 600 µmol), magnesium (117 mg, 4.8 mmol) and iodine (1.52 mg, 6 µmol) were combined with methanol (16 ml) and tetrahydrofurane (8 ml) to give a light brown solution. The reaction mixture was heated at 80° C. for 4 hours. The mixture was cooled to room temperature and filtered through sintered glass. Chromatography (silica gel, 12 g, ethyl acetate/heptane=30:70 to 100:0) yielded the title compound as off-white solid (197 mg, 63%). MS: m/z=519.5 [M−H]$^-$.

EXAMPLE 5b (+)-N-((8-endo)-3-(3-Methylisothiazol-5-yl)-3-azabicyclo[3.2.1]octan-8-yl)-8-(4-((trifluoromethyl)thio)phenyl)-5,6,7,8-tetrahydro-[1,2,4]triazolo[1,5-a]pyridin-2-amine

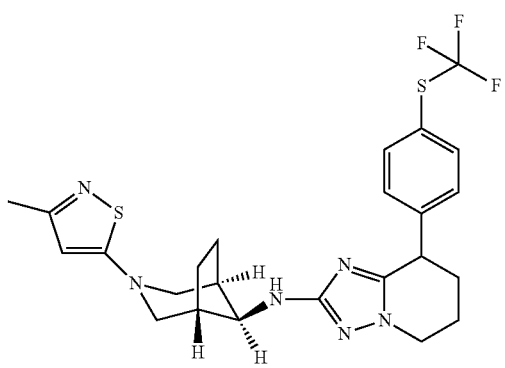 [SMILES: Cc1cc(N2C[C@H]3CC[C@@H](C2)[C@@H]3Nc2nc3n(n2)CCCC3c2ccc(SC(F)(F)F)cc2)sn1]

Chromatography of the racemic N-[(8-endo)-3-(3-methyl-1,2-thiazol-5-yl)-3-azabicyclo[3.2.1]octan-8-yl]-8-[4-(trifluoromethylsulfanyl)phenyl]-5,6,7,8-tetrahydro-[1,2,4]triazolo[1,5-a]pyridin-2-amine (example 5a) on Reprosil Chiral NR (ethanol/heptane=40:60) yielded the title compound as light brown solid (68 mg, 41%). MS: m/z=519.4 [M−H]⁻.

EXAMPLE 5c (−)-N-((8-endo)-3-(3-Methylisothiazol-5-yl)-3-azabicyclo[3.2.1]octan-8-yl)-8-(4-((trifluoromethyl)thio)phenyl)-5,6,7,8-tetrahydro-[1,2,4]triazolo[1,5-a]pyridin-2-amine

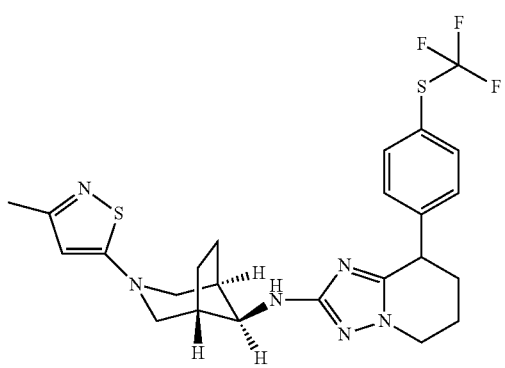 [SMILES: Cc1cc(N2C[C@H]3CC[C@@H](C2)[C@@H]3Nc2nc3n(n2)CCCC3c2ccc(SC(F)(F)F)cc2)sn1]

Chromatography of the racemic N-[(8-endo)-3-(3-methyl-1,2-thiazol-5-yl)-3-azabicyclo[3.2.1]octan-8-yl]-8-[4-(trifluoromethylsulfanyl)phenyl]-5,6,7,8-tetrahydro-[1,2,4]triazolo[1,5-a]pyridin-2-amine (example 5a) on Reprosil Chiral NR (ethanol/heptane=40:60) yielded the title compound as off-white solid (61 mg, 37%). MS: m/z=519.4 [M−H]⁻.

EXAMPLE 6a (+)-N-((8-endo)-3-(3-Methylisothiazol-5-yl)-3-azabicyclo[3.2.1]octan-8-yl)-8-(4-(2,2,2-trifluoroethyl)phenyl)-5,6,7,8-tetrahydro-[1,2,4]triazolo[1,5-a]pyridin-2-amine

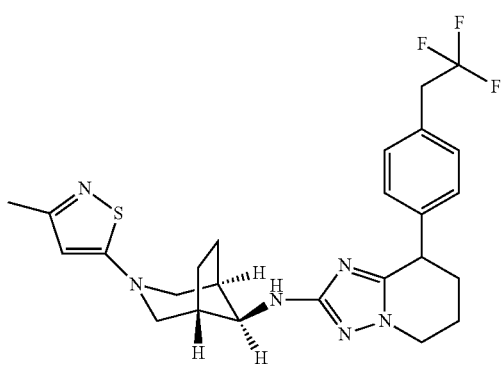 [SMILES: Cc1cc(N2C[C@H]3CC[C@@H](C2)[C@@H]3Nc2nc3n(n2)CCCC3c2ccc(CC(F)(F)F)cc2)sn1]

a) 4,4,5,5-Tetramethyl-2-(4-(perfluoroethyl)phenyl)-1,3,2-dioxaborolane

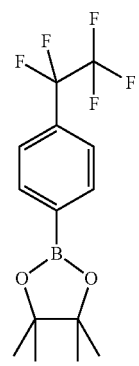 [SMILES: CC1(C)OB(c2ccc(C(F)(F)C(F)(F)F)cc2)OC1(C)C]

In a 100 ml round-bottomed flask, 1-bromo-4-(perfluoroethyl)benzene (2 g, 7.27 mmol), 4,4,4',4',5,5,5',5'-octamethyl-2,2'-bis(1,3,2-dioxaborolane) (2.22 g, 8.73 mmol) and potassium acetate (2.14 g, 21.8 mmol) were combined with dioxane (50 ml) and argon was bubbled through the reaction mixture for 10 minutes. Then 1,1'-bis(diphenylphosphino)ferrocene-palladium(II)dichloride dichloromethane complex (266 mg, 364 μmol) was added and the reaction mixture was heated to 80° C. for 2 hours. Chromatography (silica gel, 40 g, ethyl acetate/heptane=10:90 to 100:0) yielded the title compound as dark brown solid (2.05 g, 79%). MS: m/z (%)=322.1 (10), 307.1 (100), 279.1 (10), 253.1 (10), 236.1 (88), 223 (88), 203.0 (2), 153 (23).

b) 8-(4-(Perfluoroethyl)phenyl)-[1,2,4]triazolo[1,5-a]pyridin-2-amine

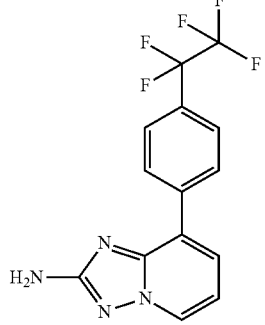

In a 250 ml round-bottomed flask, 8-bromo-[1,2,4]triazolo[1,5-a]pyridin-2-amine (1.5 g, 7.04 mmol), 4,4,5,5-tetramethyl-2-(4-(perfluoroethyl)phenyl)-1,3,2-dioxaborolane (2.27 g, 7.04 mmol) and cesium carbonate (4.59 g, 14.1 mmol) were combined with dioxane (100 ml) and water (10 ml) to give a dark brown solution. 1,1'-Bis(diphenylphosphino)ferrocene-palladium(II)dichloride dichloromethane complex (515 mg, 704 µmol) was added. The reaction mixture was heated at 80° C. for 2 hours. The crude reaction mixture was purified by chromatography (silica gel, 40 g, ethyl acetate/heptane=50:50 to 100:0) to yield the title compound as light brown viscous oil (1.53 g, 66%). MS: m/z=329.2 [M+H]$^+$.

c) 2-Bromo-8-(4-(perfluoroethyl)phenyl)-[1,2,4]triazolo[1,5-a]pyridine

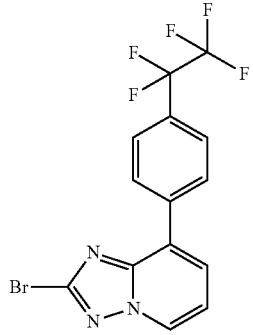 [SMILES: FC(F)(F)C(F)(F)c1ccc(-c2cccn3nc(Br)nc23)cc1]

In a 50 ml round-bottomed flask, tert-butyl nitrite (330 mg, 380 µl, 3.2 mmol) and copper (II) bromide (714 mg, 3.2 mmol) were combined with acetonitrile (30 ml) to give a black solution. The reaction mixture was heated to 60° C. and 8-(4-(perfluoroethyl)phenyl)-[1,2,4]triazolo[1,5-a]pyridin-2-amine (700 mg, 2.13 mmol) in acetonitrile (2 ml) was added slowly. The reaction mixture was heated at 80° C. for 2 hours. The reaction mixture was cooled to room temperature and hydrochloric acid (1N, 20 ml) was added slowly. The reaction mixture was poured into 20 ml water and extracted with ethyl acetate (3×100 ml). Chromatography (silica gel, 40 g, ethyl acetate/heptane=15:85 to 100:0) yielded the title compound as off-white solid (461 mg, 55%). MS: m/z=392.1 and 394.1 [M+H]$^+$.

d) N-((8-endo)-3-(3-Methylisothiazol-5-yl)-3-azabicyclo[3.2.1]octan-8-yl)-8-(4-(perfluoroethyl)phenyl)-[1,2,4]triazolo[1,5-a]pyridin-2-amine

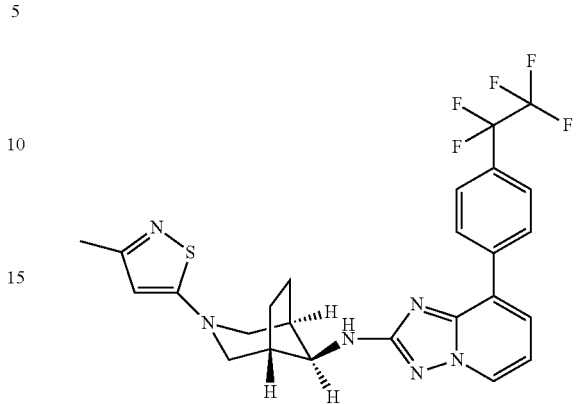

To a 10 ml microwave vial was added (8-endo)-3-(3-methylisothiazol-5-yl)-3-azabicyclo[3.2.1]octan-8-amine (60 mg, 269 µmol), 2-bromo-8-(4-(perfluoroethyl)phenyl)-[1,2,4]triazolo[1,5-a]pyridine (105 mg, 269 µmol), xantphos (24.9 mg, 43 µmol), tris(dibenzylideneacetone)dipalladium (0) chloroform adduct (22.2 mg, 21.5 µmol) and sodium tert-butoxide (54.2 mg, 564 µmol) in dioxane (5 ml). The vial was capped and heated in the microwave at 145° C. for 30 minutes. Chromatography (silica gel, 12 g, ethyl acetate/heptane=30:70 to 100:0) and trituration with diethyl ether/pentane (0.5 ml/1 ml) yielded the title compound as light brown solid (75 mg, 52%). MS: m/z=535.3 [M+H]$^+$.

e) (+)-N-((8-endo)-3-(3-Methylisothiazol-5-yl)-3-azabicyclo[3.2.1]octan-8-yl)-8-(4-(2,2,2-trifluoroethyl)phenyl)-5,6,7,8-tetrahydro-[1,2,4]triazolo[1,5-a]pyridin-2-amine

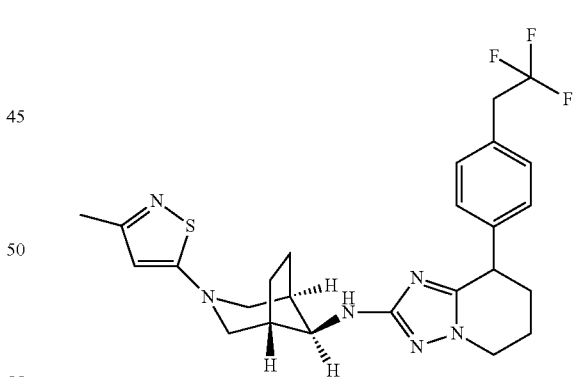

To a solution of N-((8-endo)-3-(3-methylisothiazol-5-yl)-3-azabicyclo[3.2.1]octan-8-yl)-8-(4-(perfluoroethyl)phenyl)-[1,2,4]triazolo[1,5-a]pyridin-2-amine (70 mg, 131 µmol) in methanol (10 ml) and tetrahydrofuran (5 ml) were added magnesium (25.5 mg, 1.05 mmol) and iodine (332 µg, 1.31 µmol) and the reaction mixture was heated at 80° C. for 2 hours. The reaction mixture was cooled to room temperature and diluted with methanol (30 ml). Filtration and chromatography (silica gel, 12 g, ethyl acetate/heptane=50:50 to 100:0) gave 35 mg light yellow solid which was purified by chiral HPLC on Reprosil Chiral NR (ethanol/ heptane=40/60) to yield the title compound as waxy off-white solid (11 mg, 17%). MS: m/z=503.2 [M+H]⁺.

EXAMPLE 6b (−)-N-((8-endo)-3-(3-Methylisothiazol-5-yl)-3-azabicyclo[3.2.1]octan-8-yl)-8-(4-(2,2,2-trifluoroethyl)phenyl)-5,6,7,8-tetrahydro-[1,2,4]triazolo[1,5-a]pyridin-2-amine

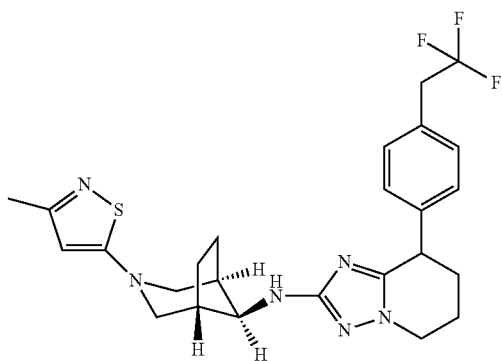 [SMILES: Cc1cc(N2C[C@H]3CC[C@@H](C2)[C@@H]3Nc2nc3n(n2)CCCC3c2ccc(CC(F)(F)F)cc2)sn1]

Chromatography of the racemic N-((8-endo)-3-(3-methylisothiazol-5-yl)-3-azabicyclo[3.2.1]octan-8-yl)-8-(4-(2,2,2-trifluoroethyl)phenyl)-5,6,7,8-tetrahydro-[1,2,4]triazolo[1,5-a]pyridin-2-amine (example 6a) on Reprosil Chiral NR (ethanol/heptane=40:60) yielded the title compound as waxy off-white solid (11 mg, 17%). MS: m/z=503.2 [M+H]⁺.

EXAMPLE 7a

N-((8-endo)-3-(3-Methylisothiazol-5-yl)-3-azabicyclo[3.2.1]octan-8-yl)-8-(2-(trifluoromethyl)phenyl)-5,6,7,8-tetrahydro-[1,2,4]triazolo[1,5-a]pyridin-2-amine

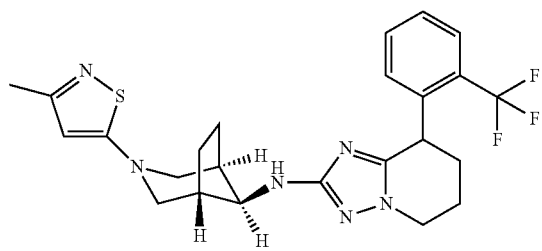 [SMILES: Cc1cc(N2C[C@H]3CC[C@@H](C2)[C@@H]3Nc2nc3n(n2)CCCC3c2ccccc2C(F)(F)F)sn1]

a) 2-Bromo-8-(2-(trifluoromethyl)phenyl)-[1,2,4]triazolo[1,5-a]pyridine

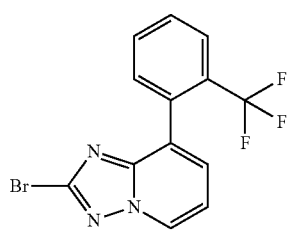 [SMILES: FC(F)(F)c1ccccc1-c1cccn2nc(Br)nc12]

In a 100 ml round-bottomed flask, tert-butyl nitrite (556 mg, 640 μl, 5.39 mmol) and copper (II) bromide (1.2 g, 5.39 mmol) were combined with acetonitrile (25 ml) to give a black solution.

The reaction mixture was heated to 60° C., then 8-(2-(trifluoromethyl)phenyl)-[1,2,4]triazolo[1,5-a]pyridin-2-amine (CAS 1262198-08-2, 1.00 g, 3.59 mmol) was added. The mixture was heated at 80° C. for 2 hours. The reaction mixture was cooled to room temperature, hydrochloric acid (1N, 25 ml) was added, and the reaction mixture was extracted with ethyl acetate (3×100 ml). Chromatography (silica gel, 50 g, ethyl acetate/heptane=0:100 to 70:30) yielded the title compound as a white solid (1.04 g, 84%). MS: m/z=342.0 and 344.0 [M+H]⁺.

b) N-((8-endo)-3-(3-Methylisothiazol-5-yl)-3-azabicyclo[3.2.1]octan-8-yl)-8-(2-(trifluoromethyl)phenyl)-[1,2,4]triazolo[1,5-a]pyridin-2-amine

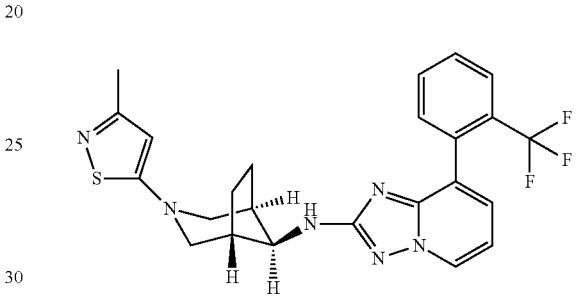

To a microwave vial was added 2-bromo-8-(2-(trifluoromethyl)phenyl)-[1,2,4]triazolo[1,5-a]pyridine (306 mg, 896 μmol), (8-endo)-3-(3-methylisothiazol-5-yl)-3-azabicyclo[3.2.1]octan-8-amine (200 mg, 896 μmol), sodium tert-butoxide (181 mg, 1.88 mmol), xantphos (84.6 mg, 143 μmol) and tris(dibenzylideneacetone)dipalladium (0) chloroform adduct (76.4 mg, 71.6 mol) in dioxane (10 ml). The vial was capped and heated in the microwave at 150° C. for 30 minutes. Chromatography (silica gel, 20 g, ethyl acetate/heptane=0:100 to 70:30) yielded the title compound as light brown solid (370 mg, 85%). MS: m/z=485.3 [M+H]⁺.

c) N-((8-endo)-3-(3-Methylisothiazol-5-yl)-3-azabicyclo[3.2.1]octan-8-yl)-8-(2-(trifluoromethyl)phenyl)-5,6,7,8-tetrahydro-[1,2,4]triazolo[1,5-a]pyridin-2-amine

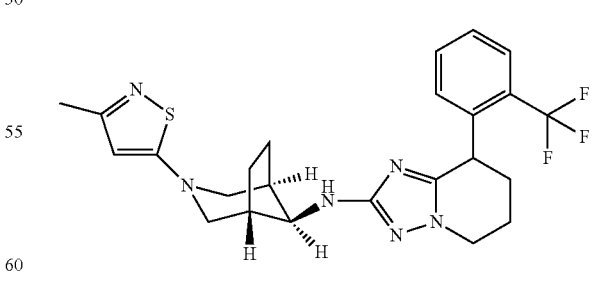

In a 50 ml round-bottomed flask, N-((8-endo)-3-(3-methylisothiazol-5-yl)-3-azabicyclo[3.2.1]octan-8-yl)-8-(2-(trifluoromethyl)phenyl)-[1,2,4]triazolo[1,5-a]pyridin-2-amine (330 mg, 681 μmol), magnesium (132 mg, 5.45 mmol) and iodine (1.73 mg, 6.81 μmol) were combined with methanol (16 ml) and tetrahydrofuran (8 ml) to give a light brown solution. The reaction mixture was heated at 80° C. for 4 hours. The mixture was cooled to room temperature and filtered through sintered glass. Chromatography (silica gel, 20 g, ethyl acetate/heptane=10:90 to 80:20) yielded the title compound as light yellow solid (265 mg, 80%). MS: m/z=489.4 [M+H]⁺.

EXAMPLE 7b

N-((8-endo)-3-(3-Methylisothiazol-5-yl)-3-azabicyclo[3.2.1]octan-8-yl)-8-(2-(trifluoromethyl)phenyl)-5,6,7,8-tetrahydro-[1,2,4]triazolo[1,5-a]pyridin-2-amine (Enantiomer A)

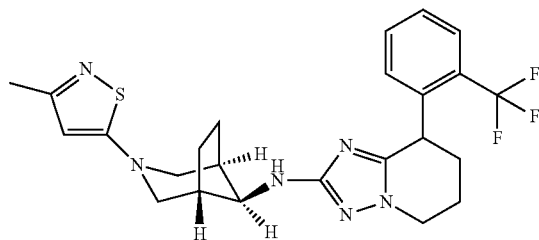 [SMILES: Cc1cc(N2C[C@H]3CC[C@@H](C2)[C@@H]3Nc2nc3n(n2)CCCC3c2ccccc2C(F)(F)F)sn1]

Chromatography of the racemic N-((8-endo)-3-(3-methylisothiazol-5-yl)-3-azabicyclo[3.2.1]octan-8-yl)-8-(2-(trifluoromethyl)phenyl)-5,6,7,8-tetrahydro-[1,2,4]triazolo[1,5-a]pyridin-2-amine (example 7a) on Reprosil Chiral NR (ethanol/heptane=40:60) yielded the title compound as colorless solid (99.4 mg, 42%). MS: m/z=489.3 [M+H]⁺.

EXAMPLE 7c

N-((8-endo)-3-(3-Methylisothiazol-5-yl)-3-azabicyclo[3.2.1]octan-8-yl)-8-(2-(trifluoromethyl)phenyl)-5,6,7,8-tetrahydro-[1,2,4]triazolo[1,5-a]pyridin-2-amine (Enantiomer B)

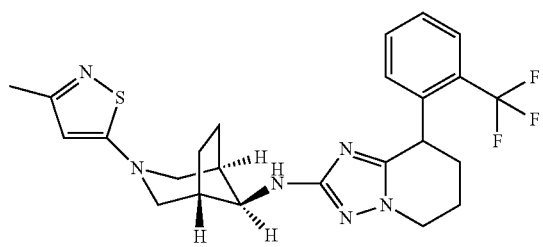 [SMILES: Cc1cc(N2C[C@H]3CC[C@@H](C2)[C@@H]3Nc2nc3n(n2)CCCC3c2ccccc2C(F)(F)F)sn1]

Chromatography of the racemic N-((8-endo)-3-(3-methylisothiazol-5-yl)-3-azabicyclo[3.2.1]octan-8-yl)-8-(2-(trifluoromethyl)phenyl)-5,6,7,8-tetrahydro-[1,2,4]triazolo[1,5-a]pyridin-2-amine (example 7a) on Reprosil Chiral NR (ethanol/heptane=40:60) yielded the title compound as colorless solid (100 mg, 43%). MS: m/z=489.3 [M+H]⁺.

EXAMPLE 8a (+)-N-((8-endo)-3-(3-Methylisothiazol-5-yl)-3-azabicyclo[3.2.1]octan-8-yl)-8-(3-(trifluoromethyl)phenyl)-5,6,7,8-tetrahydro-[1,2,4]triazolo[1,5-a]pyridin-2-amine

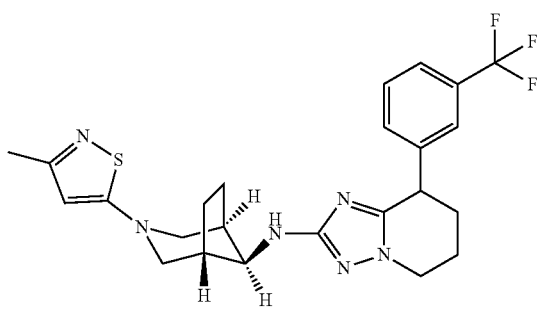 [SMILES: Cc1cc(N2C[C@H]3CC[C@@H](C2)[C@@H]3Nc2nc3n(n2)CCCC3c2cccc(C(F)(F)F)c2)sn1]

a) 2-Bromo-8-(3-(trifluoromethyl)phenyl)-[1,2,4]triazolo[1,5-a]pyridine

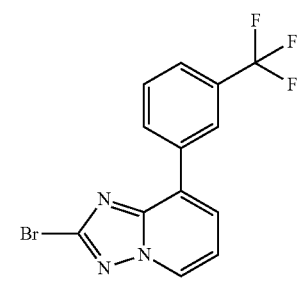 [SMILES: FC(F)(F)c1cccc(-c2cccn3nc(Br)nc23)c1]

In a 25 mL round-bottomed flask, tert-butyl nitrite (500 mg, 576 µl, 4.85 mmol) and copper (II) bromide (1.08 g, 4.85 mmol) were combined with acetonitrile (15 ml) to give a black solution.

The reaction mixture was heated to 60° C., then 8-(3-(trifluoromethyl)phenyl)-[1,2,4]triazolo[1,5-a]pyridin-2-amine (CAS 1202616-57-6, 900 mg, 3.23 mmol) was added. The reaction was heated at 80° C. for 1 hour. The mixture was then cooled to room temperature, hydrochloric acid (1N, 30 ml) was added and the reaction mixture was extracted with ethyl acetate (3×100 mL).

Chromatography (silica gel, 40 g, ethyl acetate/heptane=20:80 to 60:40) yielded the title compound as a white solid (974 mg, 88%). MS: m/z=342.0 and 344.0 [M+H]⁺.

b) N-((8-endo)-3-(3-Methylisothiazol-5-yl)-3-azabicyclo[3.2.1]octan-8-yl)-8-(3-(trifluoromethyl)phenyl)-[1,2,4]triazolo[1,5-a]pyridin-2-amine

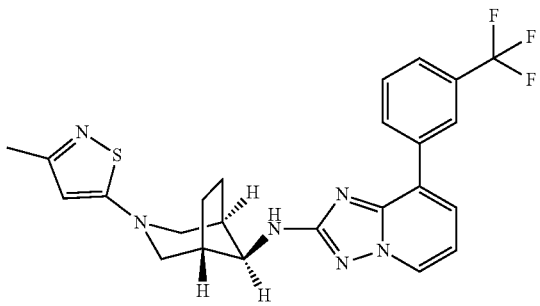 [SMILES: Cc1cc(N2C[C@H]3CC[C@@H](C2)[C@@H]3Nc2nc3c(-c4cccc(C(F)(F)F)c4)cccn3n2)sn1]

To a 10 mL microwave vial (8-endo)-3-(3-methylisothiazol-5-yl)-3-azabicyclo[3.2.1]octan-8-amine (100 mg, 448 µmol), 2-bromo-8-(3-(trifluoromethyl)phenyl)-[1,2,4]triazolo[1,5-a]pyridine (153 mg, 448 µmol), xantphos (41.5 mg, 71.6 µmol), tris(dibenzylideneacetone)dipalladium (0) chloroform adduct (37.1 mg, 35.8 µmol) and sodium tert-butoxide (90.4 mg, 940 µmol) in dioxane (16 ml) were added. The vial was capped and heated in the microwave at 150° C. for 30 minutes. Chromatography (silica gel, 10 g, ethyl acetate/heptane=20:80 to 100:0) yielded the title compound as brown solid (160 mg, 74%). MS: m/z=485.3 [M+H]$^+$.

c) N-((8-endo)-3-(3-Methylisothiazol-5-yl)-3-azabicyclo[3.2.1]octan-8-yl)-8-(3-(trifluoromethyl)phenyl)-5,6,7,8-tetrahydro-[1,2,4]triazolo[1,5-a]pyridin-2-amine

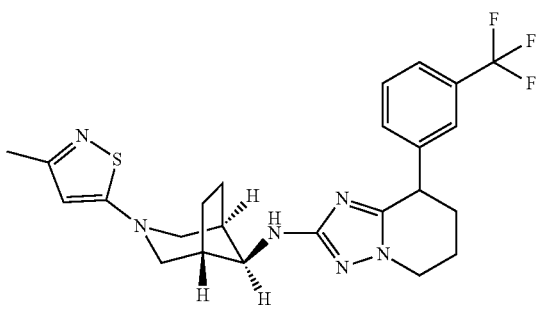 [SMILES: Cc1cc(N2C[C@H]3CC[C@@H](C2)[C@@H]3Nc2nc3n(n2)CCCC3c2cccc(C(F)(F)F)c2)sn1]

In a 50 mL round-bottomed flask, N-((8-endo)-3-(3-methylisothiazol-5-yl)-3-azabicyclo[3.2.1]octan-8-yl)-8-(3-(trifluoromethyl)phenyl)-[1,2,4]triazolo[1,5-a]pyridin-2-amine (145 mg, 299 µmol), magnesium (58.2 mg, 2.39 mmol) and iodine (760 µg, 2.99 µmol) were combined with methanol (8 ml) and tetrahydrofurane (8 ml) to give a light brown solution. The reaction mixture was heated at 80° C. overnight. The mixture was cooled to room temperature and filtered through sintered glass. Chromatography (silica gel, 12 g, ethyl acetate/heptane=30:70 to 100:0) yielded the title compound as colorless solid (85 mg, 58%). MS: m/z=489.4 [M+H]$^+$.

d) (+)-N-((8-endo)-3-(3-Methylisothiazol-5-yl)-3-azabicyclo[3.2.1]octan-8-yl)-8-(3-(trifluoromethyl)phenyl)-5,6,7,8-tetrahydro-[1,2,4]triazolo[1,5-a]pyridin-2-amine

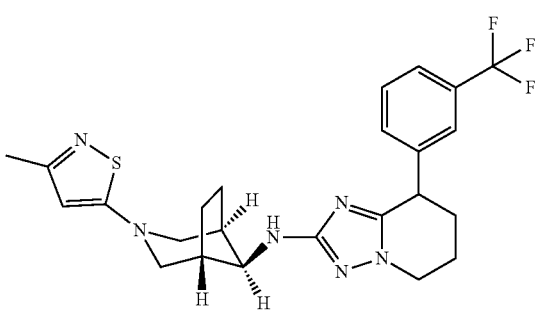 [SMILES: Cc1cc(N2C[C@H]3CC[C@@H](C2)[C@@H]3Nc2nc3n(n2)CCCC3c2cccc(C(F)(F)F)c2)sn1]

Chromatography of the racemic N-((8-endo)-3-(3-methylisothiazol-5-yl)-3-azabicyclo[3.2.1]octan-8-yl)-8-(3-(trifluoromethyl)phenyl)-5,6,7,8-tetrahydro-[1,2,4]triazolo[1,5-a]pyridin-2-amine (example 8a-c) on Reprosil Chiral NR (ethanol/heptane=40:60) yielded the title compound as off-white solid (35.2 mg, 44%). MS: m/z=489.4 [M+H]$^+$.

EXAMPLE 8b (−)-N-((8-endo)-3-(3-Methylisothiazol-5-yl)-3-azabicyclo[3.2.1]octan-8-yl)-8-(3-(trifluoromethyl)phenyl)-5,6,7,8-tetrahydro-[1,2,4]triazolo[1,5-a]pyridin-2-amine

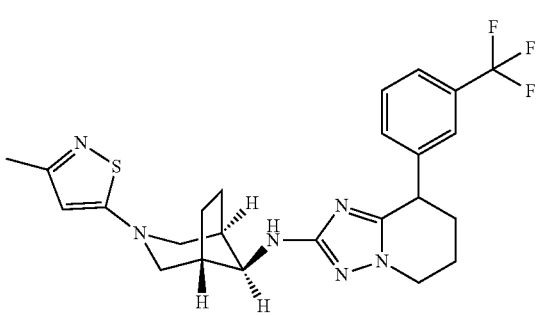 [SMILES: Cc1cc(N2C[C@H]3CC[C@@H](C2)[C@@H]3Nc2nc3n(n2)CCCC3c2cccc(C(F)(F)F)c2)sn1]

Chromatography of the racemic N-((8-endo)-3-(3-methylisothiazol-5-yl)-3-azabicyclo[3.2.1]octan-8-yl)-8-(3-(trifluoromethyl)phenyl)-5,6,7,8-tetrahydro-[1,2,4]triazolo[1,5-a]pyridin-2-amine (example 8a-c) on Reprosil Chiral NR (ethanol/heptane=40:60) yielded the title compound as off-white solid (23.8 mg, 30%). MS: m/z=489.3 [M+H]$^+$.

EXAMPLE 9a (+)-N-((8-endo)-3-(3-Methylisothiazol-5-yl)-3-azabicyclo[3.2.1]octan-8-yl)-8-(2-(trifluoromethoxy)phenyl)-5,6,7,8-tetrahydro-[1,2,4]triazolo[1,5-a]pyridin-2-amine

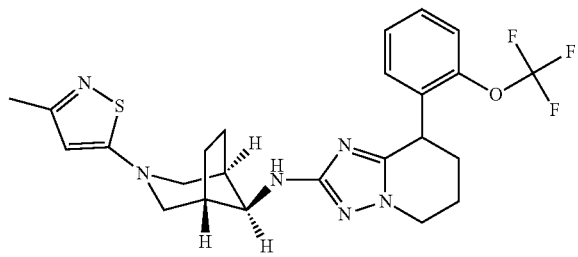 [SMILES: Cc1cc(N2C[C@H]3CC[C@@H](C2)[C@@H]3Nc2nc3n(n2)CCCC3c2ccccc2OC(F)(F)F)sn1]

a) 8-(2-(Trifluoromethoxy)phenyl)-[1,2,4]triazolo[1,5-a]pyridin-2-amine

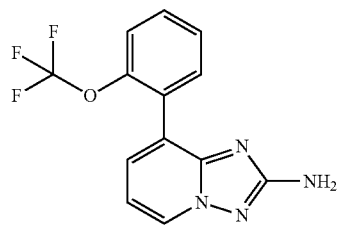 [SMILES: Nc1nc2c(-c3ccccc3OC(F)(F)F)cccn2n1]

In a 150 ml round-bottomed flask were combined 8-bromo-[1,2,4]triazolo[1,5-a]pyridin-2-amine (1.5 g, 7.04 mmol), (2-(trifluoromethoxy)phenyl)boronic acid (2.17 g, 10.6 mmol) and cesium carbonate (4.59 g, 14.1 mmol) in dioxane (60 ml) and water (6 ml) to give a colorless solution. 1,1'-Bis(diphenylphosphino)ferrocene-palladium(II)dichloride dichloromethane complex (515 mg, 704 μmol) was added. The reaction mixture was stirred for 2 hours at 100° C. Chromatography (silica gel, 70 g, ethyl acetate/heptane=40:60 to 100:0) yield the title compound as light brown solid (1.8 g, 87%). MS: m/z=295.2 [M+H]⁺.

b) 2-Bromo-8-(2-(trifluoromethoxy)phenyl)-[1,2,4]triazolo[1,5-a]pyridine

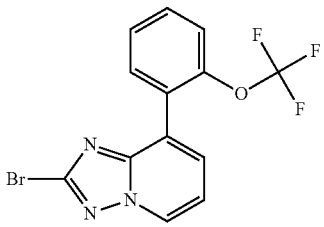 [SMILES: FC(F)(F)Oc1ccccc1-c1cccn2nc(Br)nc12]

In a 100 ml round-bottomed flask, tert-butyl nitrite (526 mg, 606 μl, 5.1 mmol) and copper (II) bromide (1.14 g, 5.1 mmol) were combined with acetonitrile (30 ml) to give a black solution. The reaction mixture was heated to 60° C., then 8-(2-(trifluoromethoxy)phenyl)-[1,2,4]triazolo[1,5-a]pyridin-2-amine (1.00 g, 3.4 mmol) was added. The reaction was heated at 80° C. for 2 hours. The mixture was cooled to room temperature and concentrated in vacuo. Hydrochloric acid (1N, 25 ml) was added and the mixture was extracted with ethyl acetate (3×150 ml). Chromatography (silica gel, 50 g, ethyl acetate/heptane=0:100 to 40:60) yielded the title compound as a white solid (1.10 g, 90%). MS: m/z=358.0 and 361.1 [M+H]⁺.

c) N-((8-endo)-3-(3-Methylisothiazol-5-yl)-3-azabicyclo[3.2.1]octan-8-yl)-8-(2-(trifluoromethoxy)phenyl)-[1,2,4]triazolo[1,5-a]pyridin-2-amine

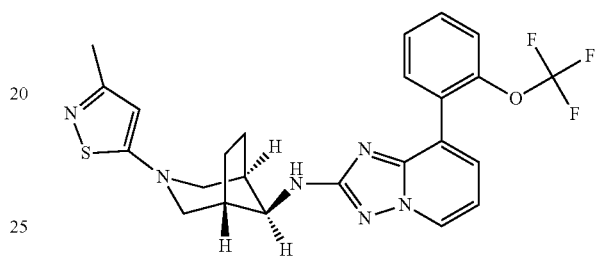

To a microwave vial was added 2-bromo-8-(2-(trifluoromethoxy)phenyl)-[1,2,4]triazolo[1,5-a]pyridine (104 mg, 291 μmol), (8-endo)-3-(3-methylisothiazol-5-yl)-3-azabicyclo[3.2.1]octan-8-amine (65 mg, 291 μmol), sodium tert-butoxide (58.7 mg, 611 μmol), xantphos (27.8 mg, 46.6 mol) and tris(dibenzylideneacetone)dipalladium (0) chloroform adduct (24.6 mg, 23.3 μmol) in dioxane (3 ml). The vial was capped and heated in the microwave at 150° C. for 30 minutes. The crude reaction mixture was concentrated in vacuo and purified by chromatography (silica gel, 20 g, ethyl acetate/heptane=40:60 to 100:0) to yield the title compound as light brown solid (93 mg, 64%). MS: m/z=501.3 [M+H]⁺.

d) N-[(8-endo)-3-(3-Methyl-1,2-thiazol-5-yl)-3-azabicyclo[3.2.1]octan-8-yl]-8-[2-(trifluoromethoxy)phenyl]-5,6,7,8-tetrahydro-[1,2,4]triazolo[1,5-a]pyridin-2-amine

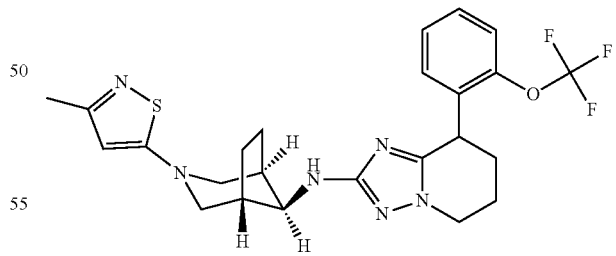

In a 50 ml round-bottomed flask, N-((8-endo)-3-(3-methylisothiazol-5-yl)-3-azabicyclo[3.2.1]octan-8-yl)-8-(2-(trifluoromethoxy)phenyl)-[1,2,4]triazolo[1,5-a]pyridin-2-amine (85 mg, 170 μmol), magnesium (33 mg, 1.36 mmol) and iodine (431 μg, 1.7 μmol) were combined with methanol (8 ml) and tetrahydrofurane (4 ml) to give a light brown solution. The reaction mixture was heated at 80° C. for 4 hours. The mixture was cooled to room temperature and filtered through sintered glass. Chromatography (silica gel, e) (+)-N-((8-endo)-3-(3-Methylisothiazol-5-yl)-3-azabicyclo[3.2.1]octan-8-yl)-8-(2-(trifluoromethoxy)phenyl)-5,6,7,8-tetrahydro-[1,2,4]triazolo[1,5-a]pyridin-2-amine

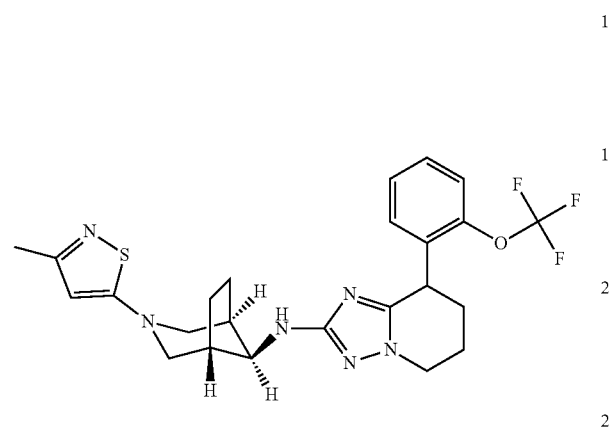

Chromatography of the racemic N-[(8-endo)-3-(3-methyl-1,2-thiazol-5-yl)-3-azabicyclo[3.2.1]octan-8-yl]-8-[2-(trifluoromethoxy)phenyl]-5,6,7,8-tetrahydro-[1,2,4]triazolo[1,5-a]pyridin-2-amine (example 9a-d) on Reprosil Chiral NR (ethanol/heptane=40:60) yielded the title compound as off-white solid (22 mg, 30%). MS: m/z=505.3 [M+H]$^+$.

EXAMPLE 9b (−)-N-((8-endo)-3-(3-Methylisothiazol-5-yl)-3-azabicyclo[3.2.1]octan-8-yl)-8-(2-(trifluoromethoxy)phenyl)-5,6,7,8-tetrahydro-[1,2,4]triazolo[1,5-a]pyridin-2-amine

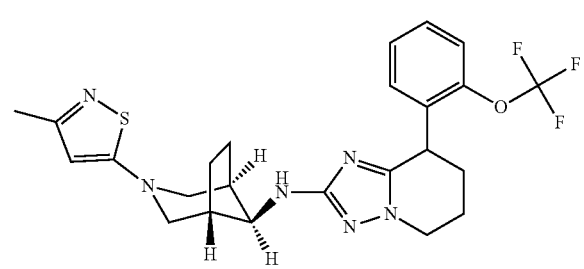 [SMILES: Cc1cc(N2C[C@H]3CC[C@@H](C2)[C@@H]3Nc2nc3n(n2)CCCC3c2ccccc2OC(F)(F)F)sn1]

Chromatography of the racemic N-[(8-endo)-3-(3-methyl-1,2-thiazol-5-yl)-3-azabicyclo[3.2.1]octan-8-yl]-8-[2-(trifluoromethoxy)phenyl]-5,6,7,8-tetrahydro-[1,2,4]triazolo[1,5-a]pyridin-2-amine (example 9a-d) on Reprosil Chiral NR (ethanol/heptane=40:60) yielded the title compound as off-white solid (18 mg, 25%). MS: m/z=505.3 [M+H]$^+$.

EXAMPLE 10a (+)-N-((8-endo)-3-(3-Methylisothiazol-5-yl)-3-azabicyclo[3.2.1]octan-8-yl)-8-(3-(trifluoromethoxy)phenyl)-5,6,7,8-tetrahydro-[1,2,4]triazolo[1,5-a]pyridin-2-amine

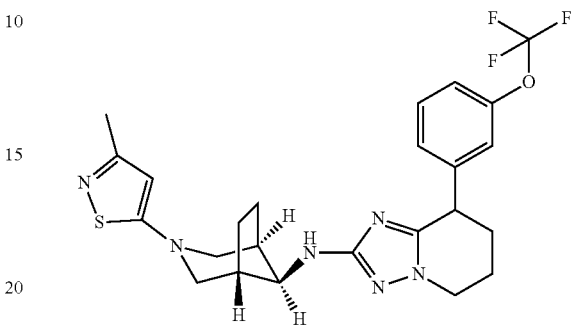

a) 8-(3-(Trifluoromethoxy)phenyl)-[1,2,4]triazolo[1,5-a]pyridin-2-amine

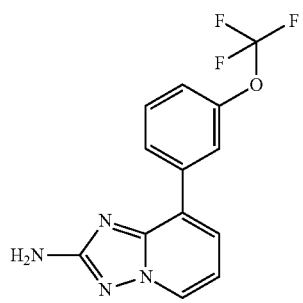 [SMILES: Nc1nc2c(-c3cccc(OC(F)(F)F)c3)cccn2n1]

In a 100 mL round-bottomed flask, 8-bromo-[1,2,4]triazolo[1,5-a]pyridin-2-amine (1.5 g, 7.04 mmol), (3-(trifluoromethoxy)phenyl)boronic acid (1.45 g, 7.04 mmol) and cesium carbonate (4.59 g, 14.1 mmol) were combined with dioxane (50 ml) and water (5 ml) to give a light yellow solution. Under argon 1,1′-Bis(diphenylphosphino)ferrocene-palladium(II)dichloride dichloromethane complex (515 mg, 704 μmol) was added. The reaction mixture was heated at 100° C. for 2 hours. Chromatography (silica gel, 40 g, ethyl acetate/heptane=20:80 to 80:20) yielded the title compound as a white solid (1.82 g, 88%). MS: m/z=295.2 [M+H]$^+$.

b) 2-Bromo-8-(3-(trifluoromethoxy)phenyl)-[1,2,4]triazolo[1,5-a]pyridine

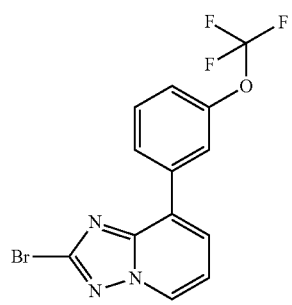 [SMILES: FC(F)(F)Oc1cccc(-c2cccn3nc(Br)nc23)c1]

In a 25 mL round-bottomed flask, tert-butyl nitrite (526 mg, 606 µl, 5.1 mmol) and copper (II) bromide (1.14 g, 5.1 mmol) were combined with acetonitrile (16.7 ml) to give a black solution. The reaction mixture was heated to 60° C., then 8-(3-(trifluoromethoxy)phenyl)-[1,2,4]triazolo[1,5-a] pyridin-2-amine (1 g, 3.4 mmol) was added. The mixture was heated at 80° C. for 1 hour. The mixture was then cooled to room temperature, hydrochloric acid (1N, 30 ml) was added and the reaction mixture was extracted with ethyl acetate (3×100 ml). Chromatography (silica gel, 40 g, ethyl acetate/heptane=20:80 to 50:50) yielded the title compound as white solid (1.15 g, 95%). MS: m/z=358.0 and 360.0 [M+H]+.

c) N-((8-endo)-3-(3-Methylisothiazol-5-yl)-3-azabicyclo[3.2.1]octan-8-yl)-8-(3-(trifluoromethoxy)phenyl)-[1,2,4]triazolo[1,5-a]pyridin-2-amine

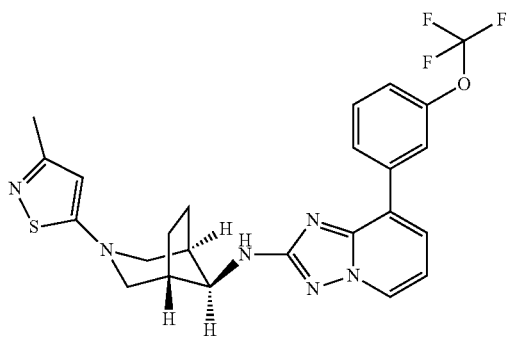 [SMILES: Cc1cc(N2C[C@H]3CC[C@@H](C2)[C@@H]3Nc2nc3c(-c4cccc(OC(F)(F)F)c4)cccn3n2)sn1]

To a microwave vial was added 2-bromo-8-(3-(trifluoromethoxy)phenyl)-[1,2,4]triazolo[1,5-a]pyridine (104 mg, 291 µmol), (8-endo)-3-(3-methylisothiazol-5-yl)-3-azabicyclo[3.2.1]octan-8-amine (65 mg, 291 µmol), sodium tert-butoxide (58.7 mg, 611 µmol), xantphos (27.8 mg, 46.6 mol) and tris(dibenzylideneacetone)dipalladium (0) chloroform adduct (24.6 mg, 23.3 µmol) in dioxane (2.1 ml). The vial was capped and heated in the microwave at 150° C. for 30 minutes. Chromatography (silica gel, 20 g, ethyl acetate/heptane=50:50 to 100:0) yielded the title compound as light yellow solid (72 mg, 49%). MS: m/z=501.3 [M+H]+.

d) (+)-N-((8-endo)-3-(3-Methylisothiazol-5-yl)-3-azabicyclo[3.2.1]octan-8-yl)-8-(3-(trifluoromethoxy)phenyl)-5,6,7,8-tetrahydro-[1,2,4]triazolo[1,5-a]pyridin-2-amine

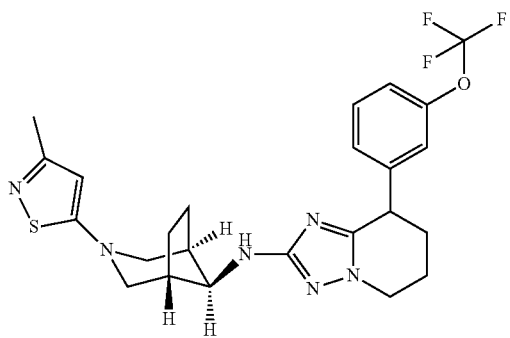 [SMILES: Cc1cc(N2C[C@H]3CC[C@@H](C2)[C@@H]3Nc2nc3n(n2)CCCC3c2cccc(OC(F)(F)F)c2)sn1]

In a 25 mL round-bottomed flask, magnesium (26 mg, 1.07 mmol) and N-((8-endo)-3-(3-methylisothiazol-5-yl)-3-azabicyclo[3.2.1]octan-8-yl)-8-(3-(trifluoromethoxy)phenyl)-[1,2,4]triazolo[1,5-a]pyridin-2-amine (67 mg, 134 µmol) were combined with methanol (10 ml) and tetrahydrofurane (5 ml) to give a grey suspension. Iodine (340 µg, 1.34 µmol) was added and the reaction mixture was heated to 80° C. and stirred for 15 hours. The reaction mixture was diluted with methanol (25 ml) and filtered through sintered glass. Chromatography (silica gel, 12 g, ethyl acetate/heptane=50:50 to 100:0) chromatography (Reprosil Chiral NR, ethanol/heptane=40:60) yielded the title compound as off-white solid (7 mg, 10%). MS: m/z=505.3 [M+H]+.

EXAMPLE 10b (−)-N-((8-endo)-3-(3-Methylisothiazol-5-yl)-3-azabicyclo[3.2.1]octan-8-yl)-8-(3-(trifluoromethoxy)phenyl)-5,6,7,8-tetrahydro-[1,2,4]triazolo[1,5-a]pyridin-2-amine

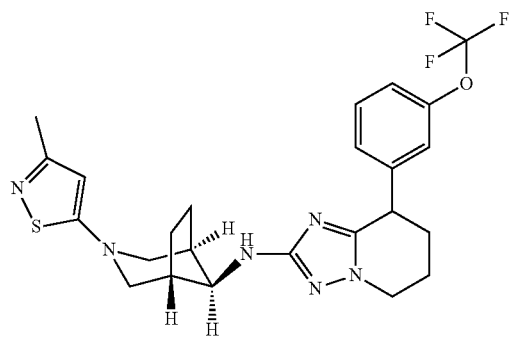 [SMILES: Cc1cc(N2C[C@H]3CC[C@@H](C2)[C@@H]3Nc2nc3n(n2)CCCC3c2cccc(OC(F)(F)F)c2)sn1]

Chromatography of the racemic N-((8-endo)-3-(3-methylisothiazol-5-yl)-3-azabicyclo[3.2.1]octan-8-yl)-8-(3-(trifluoromethoxy)phenyl)-[1,2,4]triazolo[1,5-a]pyridin-2-amine (example 10a) on Reprosil Chiral NR (ethanol/heptane=40:60) yielded the title compound as off-white solid (11 mg, 16%). MS: m/z=505.3 [M+H]+.

EXAMPLE 11a 8-(4-Methoxyphenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

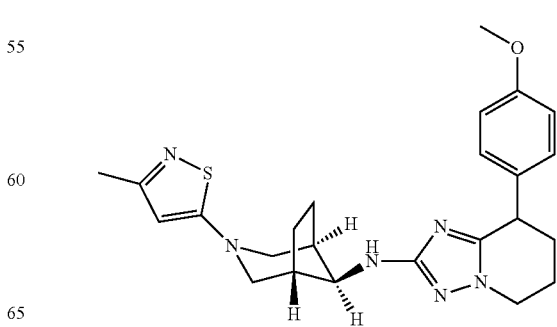

a) 2-Bromo-8-(4-methoxyphenyl)-[1,2,4]triazolo[1,5-a]pyridine

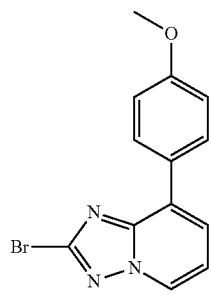 [SMILES: COc1ccc(-c2cccn3nc(Br)nc23)cc1]

In a 100 mL round-bottomed flask, copper (II) bromide (1.8 g, 8.05 mmol, Eq: 1.5) and tert-butyl nitrite (831 mg, 957 µl, 8.05 mmol) were combined with acetonitrile (60 ml) to give a black solution. The reaction mixture was heated to 60° C. and 8-(4-methoxyphenyl)-[1,2,4]triazolo[1,5-a]pyridin-2-amine (CAS1202616-64-5, 1.29 g, 5.37 mmol) was added. The reaction mixture was heated at 80° C. for 2 hours. The reaction mixture was cooled to room temperature and poured into 25 ml water. The mixture was acidified with hydrochloric acid (2N) and extracted with ethyl acetate (5×150 m). Chromatography (silica gel, 40 g, ethyl acetate/heptane=20:80 to 100:0) yielded the title compound as off-white solid (555 mg, 34%). MS: m/z=304.0 and 306.0 [M+H]$^+$.

b) 8-(4-Methoxyphenyl)-N-((8-endo)-3-(3-methyl-isothiazol-5-yl)-3-azabicyclo[3.2.1]octan-8-yl)-[1,2,4]triazolo[1,5-a]pyridin-2-amine

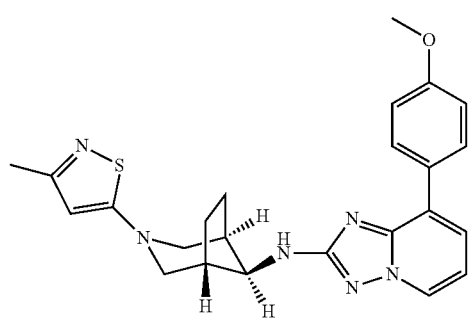 [SMILES: COc1ccc(-c2cccn3nc(N[C@@H]4[C@@H]5CC[C@H]4CN(c4cc(C)ns4)C5)nc23)cc1]

To a 10 mL microwave vial was added (8-endo)-3-(3-methylisothiazol-5-yl)-3-azabicyclo[3.2.1]octan-8-amine (100 mg, 448 µmol), 2-bromo-8-(4-methoxyphenyl)-[1,2,4]triazolo[1,5-a]pyridine (136 mg, 448 µmol), xantphos (41.5 mg, 71.6 µmol), tris(dibenzylideneacetone)dipalladium (0) chloroform adduct (37.1 mg, 35.8 µmol) and sodium tert-butoxide (90.4 mg, 940 µmol) in dioxane (5 ml). The vial was capped and heated in the microwave at 150° C. for 30 minutes. Chromatography (silica gel, 12 g, ethyl acetate/heptane=50:50 to 100:0) and trituration with diethyl ether/pentane (0.5 ml/2 ml) yielded the title compound as a solid (142 mg, 71%). MS: m/z=447.3 [M+H]$^+$.

c) 8-(4-Methoxyphenyl)-N-((8-endo)-3-(3-methyl-isothiazol-5-yl)-3-azabicyclo[3.2.1]octan-8-yl)-5,6,7,8-tetrahydro-[1,2,4]triazolo[1,5-a]pyridin-2-amine

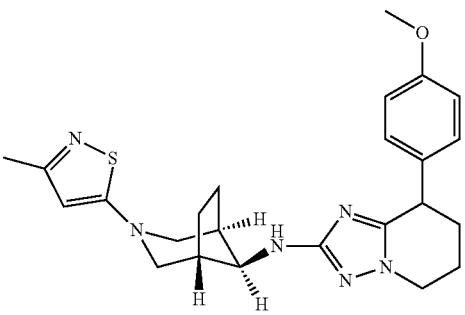 [SMILES: COc1ccc(C2CCCn3nc(N[C@@H]4[C@@H]5CC[C@H]4CN(c4cc(C)ns4)C5)nc32)cc1]

In a 25 mL round-bottomed flask, 8-(4-methoxyphenyl)-N-((8-endo)-3-(3-methylisothiazol-5-yl)-3-azabicyclo[3.2.1]octan-8-yl)-[1,2,4]triazolo[1,5-a]pyridin-2-amine (130 mg, 291 µmol), magnesium (56.6 mg, 2.33 mmol) and iodine (739 µg, 2.91 µmol) were combined with methanol (10 ml) and tetrahydrofurane (5 ml) to give a brown suspension. The reaction mixture was heated at 80° C. for 2 hours. Iodine (739 µg, 2.91 µmol) was added again and stirring was continued at 80° C. for 1 hour. The reaction mixture was cooled to room temperature, methanol (20 ml) was added and the mixture was filtered through sintered glass. Chromatography (silica gel, 12 g, ethyl acetate/heptane=50:50 to 100:0) and trituration with diethyl ether/pentane (0.5 ml/2 ml) yielded the title compound as off-white solid (68 mg, 52%). MS: m/z=451.2 [M+H]$^+$.

EXAMPLE 11b (+)-8-(4-Methoxyphenyl)-N-((8-endo)-3-(3-methyl-isothiazol-5-yl)-3-azabicyclo[3.2.1]octan-8-yl)-5,6,7,8-tetrahydro-[1,2,4]triazolo[1,5-a]pyridin-2-amine

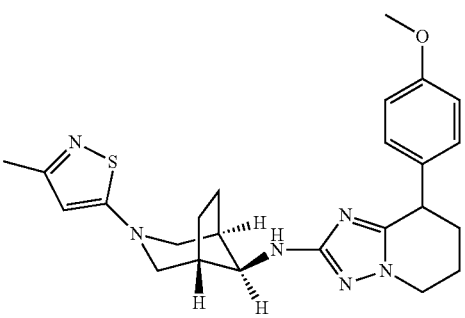 [SMILES: COc1ccc(C2CCCn3nc(N[C@@H]4[C@@H]5CC[C@H]4CN(c4cc(C)ns4)C5)nc32)cc1]

Chromatography of the racemic 8-(4-methoxyphenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin- 2-amine (example 11a) on Reprosil Chiral NR (ethanol/heptane=40:60) and trituration with diethyl ether/pentane (0.5 ml/1 ml) yielded the title compound as off-white solid (27 mg, 46%). MS: m/z=451.3 [M+H]⁺.

EXAMPLE 11c (−)-8-(4-Methoxyphenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

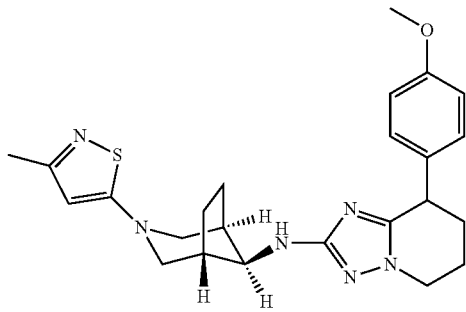 [SMILES: COc1ccc(C2CCCn3nc(N[C@@H]4[C@@H]5CC[C@H]4CN(c4cc(C)ns4)C5)nc32)cc1]

Chromatography of the racemic 8-(4-methoxyphenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (example 11a) on Reprosil Chiral NR (ethanol/heptane=40:60) and trituration with diethyl ether/pentane (0.5 ml/1 ml) yielded the title compound as off-white solid (23 mg, 39%). MS: m/z=451.3 [M+H]⁺.

EXAMPLE 12a (+)-8-(4-Fluoro-2-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

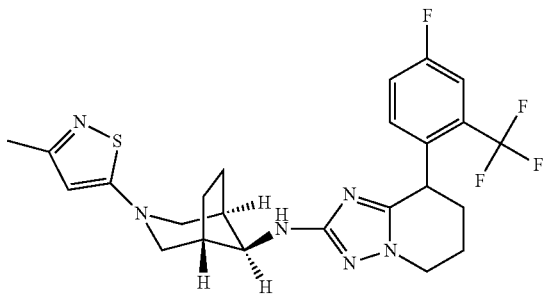 [SMILES: Cc1cc(N2C[C@H]3CC[C@@H](C2)[C@@H]3Nc2nc3n(n2)CCCC3c2ccc(F)cc2C(F)(F)F)sn1]

a) 8-(4-Fluoro-2-(trifluoromethyl)phenyl)-N-((8-endo)-3-(3-methylisothiazol-5-yl)-3-azabicyclo[3.2.1]octan-8-yl)-[1,2,4]triazolo[1,5-a]pyridin-2-amine

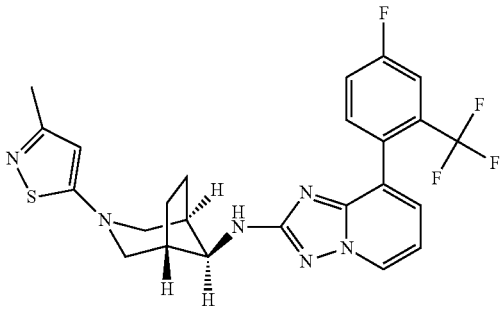 [SMILES: Cc1cc(N2C[C@H]3CC[C@@H](C2)[C@@H]3Nc2nc3c(-c4ccc(F)cc4C(F)(F)F)cccn3n2)sn1]

To a microwave vial was added 2-bromo-8-(4-fluoro-2-(trifluoromethyl)phenyl)-[1,2,4]triazolo[1,5-a]pyridine (CAS1314787-75-1, 677 mg, 1.88 mmol), tert-butyl ((8-endo)-3-(3-methylisothiazol-5-yl)-3-azabicyclo[3.2.1]octan-8-yl)carbamate (420 mg, 1.88 mmol), sodium tert-butoxide (380 mg, 3.95 mmol), xantphos (179 mg, 301 μmol) and tris(dibenzylideneacetone)dipalladium (0) chloroform adduct (159 mg, 150 μmol) in dioxane (16 ml). The vial was capped and heated in the microwave at 150° C. for 30 min. Chromatography (silica gel, 50 g, ethyl acetate/heptane=40:60 to 100:0) yielded the title compound as light brown solid (630 mg, 67%). MS: m/z=503.2 [M+H]⁺.

b) 8-(4-Fluoro-2-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

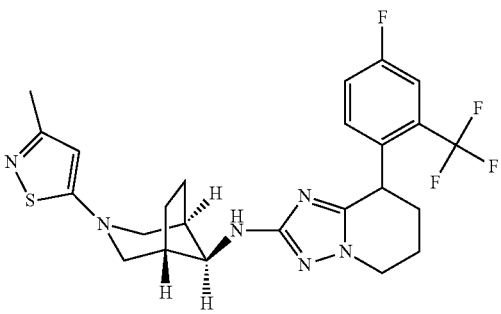 [SMILES: Cc1cc(N2C[C@H]3CC[C@@H](C2)[C@@H]3Nc2nc3n(n2)CCCC3c2ccc(F)cc2C(F)(F)F)sn1]

In a 100 ml round-bottomed flask, 8-(4-fluoro-2-(trifluoromethyl)phenyl)-N-((8-endo)-3-(3-methylisothiazol-5-yl)-3-azabicyclo[3.2.1]octan-8-yl)-[1,2,4]triazolo[1,5-a]pyridin-2-amine (545 mg, 1.08 mmol), iodine (2.75 mg, 10.8 μmol) and magnesium (211 mg, 8.68 mmol) were combined with methanol (30 ml) and tetrahydrofuran (15 ml) to give a light brown solution. The reaction mixture was heated at 80° C. for 24 hours. The mixture was cooled to room temperature and filtered through sintered glass. Chromatography (silica gel, 20 g, ethyl acetate/heptane=60:40 to 100:0) yielded the title compound as light yellow oil (310 mg, 51%). MS: m/z=507.2 [M+H]⁺.

c) (+)-8-(4-Fluoro-2-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

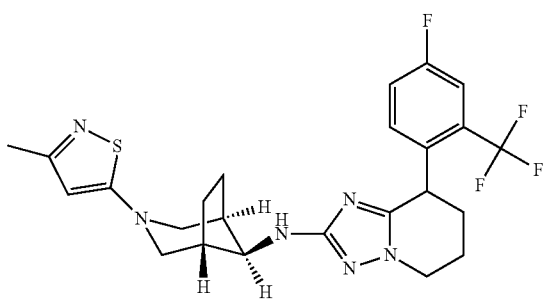 [SMILES: Cc1cc(N2C[C@H]3CC[C@@H](C2)[C@@H]3Nc2nc3n(n2)CCCC3c2ccc(F)cc2C(F)(F)F)sn1]

Chromatography of the racemic 8-(4-fluoro-2-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (example 12a-b) on Reprosil Chiral NR (ethanol/heptane=40:60) yielded the title compound as off-white solid (112 mg, 36%). MS: m/z=507.2 [M+H]$^+$.

EXAMPLE 12b (−)-8-(4-Fluoro-2-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

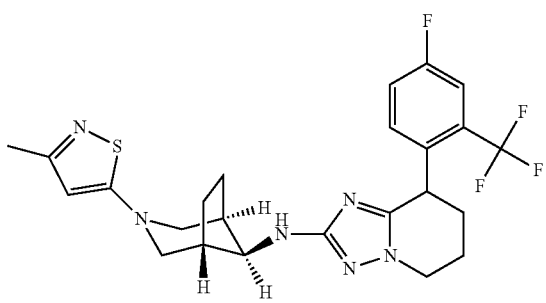 [SMILES: Cc1cc(N2C[C@H]3CC[C@@H](C2)[C@@H]3Nc2nc3n(n2)CCCC3c2ccc(F)cc2C(F)(F)F)sn1]

Chromatography of the racemic 8-(4-fluoro-2-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (example 12a-b) on Reprosil Chiral NR (ethanol/heptane=40:60) yielded the title compound as off-white solid (68 mg, 22%). MS: m/z=507.2 [M+H]$^+$.

EXAMPLE 13a (−)-N-((8-endo)-3-(3-Methylisothiazol-5-yl)-3-azabicyclo[3.2.1]octan-8-yl)-8-(3,4,5-trifluorophenyl)-5,6,7,8-tetrahydro-[1,2,4]triazolo[1,5-a]pyridin-2-amine

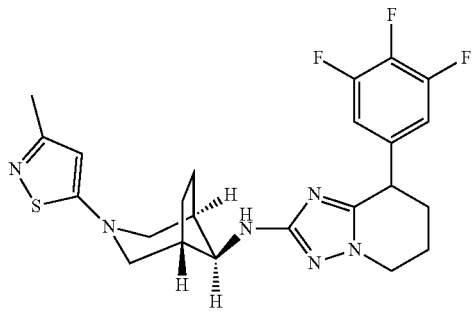 [SMILES: Cc1cc(N2C[C@H]3CC[C@@H](C2)[C@@H]3Nc2nc3n(n2)CCCC3c2cc(F)c(F)c(F)c2)sn1]

a) 8-(3,4,5-Trifluorophenyl)-[1,2,4]triazolo[1,5-a]pyridin-2-amine

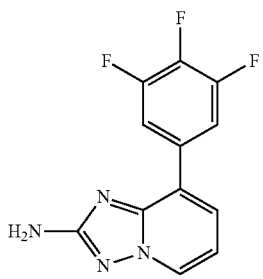 [SMILES: Nc1nc2c(-c3cc(F)c(F)c(F)c3)cccn2n1]

In a 150 ml round-bottomed flask were combined 8-bromo-[1,2,4]triazolo[1,5-a]pyridin-2-amine (1.5 g, 7.04 mmol), (3,4,5-trifluorophenyl)boronic acid (1.24 g, 7.04 mmol) and cesium carbonate (4.59 g, 14.1 mmol). The mixture was dissolved in dioxane (60 ml) and water (6 ml). 1,1'-Bis(diphenylphosphino)ferrocene-palladium(II)dichloride dichloromethane complex (515 mg, 704 μmol) was added and the mixture was stirred for 2 hours at 100° C. Chromatography (silica gel, 50 g, ethyl acetate/heptane=40:60 to 100:0) yielded the title compound as off-white solid (1.2 g, 58%). MS: m/z=265.2 [M+H]$^+$.

b) 2-Bromo-8-(3,4,5-trifluorophenyl)-[1,2,4]triazolo[1,5-a]pyridine

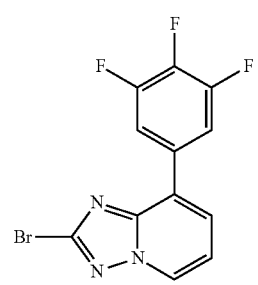 [SMILES: Fc1cc(-c2cccn3nc(Br)nc23)cc(F)c1F]

In a 100 ml round-bottomed flask, tert-butyl nitrite (632 mg, 728 µl, 6.13 mmol) and copper (II) bromide (1.37 g, 6.13 mmol) were combined with acetonitrile (34 ml) to give a black solution. The reaction mixture was heated to 60° C., then 8-(3,4,5-trifluorophenyl)-[1,2,4]triazolo[1,5-a]pyridin-2-amine (1.20 g, 4.09 mmol) was added. The mixture was heated at 80° C. for 2 hours and then cooled to room temperature. The reaction mixture was concentrated in vacuo. Hydrochloric acid (1 N, 25 ml) was added and the mixture was extracted with ethyl acetate (3×150 ml. Chromatography (silica gel, 50 g, ethyl acetate/heptane=0:100 to 50:50) yielded the title compound as white solid (640 mg, 48%). MS: m/z=328.0 and 330.0 [M+H]⁺.

c) N-((8-endo)-3-(3-Methylisothiazol-5-yl)-3-azabicyclo[3.2.1]octan-8-yl)-8-(3,4,5-trifluorophenyl)-[1,2,4]triazolo[1,5-a]pyridin-2-amine

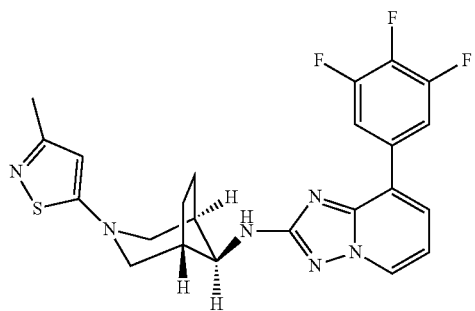 [SMILES: Cc1cc(N2C[C@H]3CC[C@@H](C2)[C@@H]3Nc2nc3c(-c4cc(F)c(F)c(F)c4)cccn3n2)sn1]

To a microwave vial was added 2-bromo-8-(3,4,5-trifluorophenyl)-[1,2,4]triazolo[1,5-a]pyridine (118 mg, 358 µmol), (8-endo)-3-(3-methylisothiazol-5-yl)-3-azabicyclo[3.2.1]octan-8-amine (80 mg, 358 µmol), sodium tert-butoxide (72.3 mg, 752 µmol), xantphos (34.2 mg, 57.3 µmol) and tris(dibenzylideneacetone)dipalladium (0) chloroform adduct (30.3 mg, 28.7 µmol) in dioxane (4 ml). The vial was capped and heated in the microwave at 150° C. for 30 minutes. Chromatography (silica gel, 20 g, ethyl acetate/heptane=40:60 to 100:0) yielded the title compound as light brown solid (125 mg, 73%). MS: m/z=471.3 [M+H]⁺.

d) (−)-N-((8-endo)-3-(3-Methylisothiazol-5-yl)-3-azabicyclo[3.2.1]octan-8-yl)-8-(3,4,5-trifluorophenyl)-5,6,7,8-tetrahydro-[1,2,4]triazolo[1,5-a]pyridin-2-amine

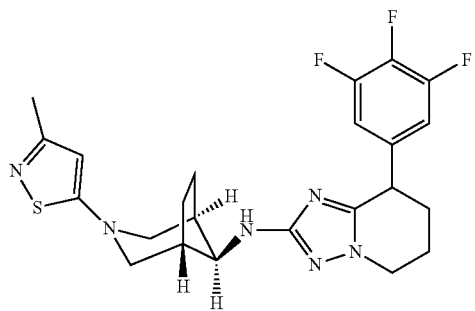 [SMILES: Cc1cc(N2C[C@H]3CC[C@@H](C2)[C@@H]3Nc2nc3n(n2)CCCC3c2cc(F)c(F)c(F)c2)sn1]

In a 50 ml round-bottomed flask, N-((8-endo)-3-(3-methylisothiazol-5-yl)-3-azabicyclo[3.2.1]octan-8-yl)-8-(3,4,5-trifluorophenyl)-[1,2,4]triazolo[1,5-a]pyridin-2-amine (115 mg, 244 µmol), iodine (620 µg, 2.44 µmol) and magnesium (47.5 mg, 1.96 mmol) were combined with methanol (12 ml) and tetrahydrofuran (6 ml) to give a light brown solution. The reaction mixture was heated at 80° C. for 14 hours. The mixture was cooled to room temperature and filtered through sintered glass. The crude material was purified by chromatography (silica gel, 20 g, dichloromethane/methanol=100:0 to 85:0) and the racemic N-((8-endo)-3-(3-methylisothiazol-5-yl)-3-azabicyclo[3.2.1]octan-8-yl)-8-(3,4,5-trifluorophenyl)-5,6,7,8-tetrahydro-[1,2,4]triazolo[1,5-a]pyridin-2-amine was further processed on Reprosil Chiral NR (ethanol/heptane=40:60) to yield the title compound as white solid (25.2 mg, 22%). MS: m/z=475.3 [M+H]⁺.

EXAMPLE 13b (+)-(N-((8-endo)-3-(3-Methylisothiazol-5-yl)-3-azabicyclo[3.2.1]octan-8-yl)-8-(3,4,5-trifluorophenyl)-5,6,7,8-tetrahydro-[1,2,4]triazolo[1,5-a]pyridin-2-amine

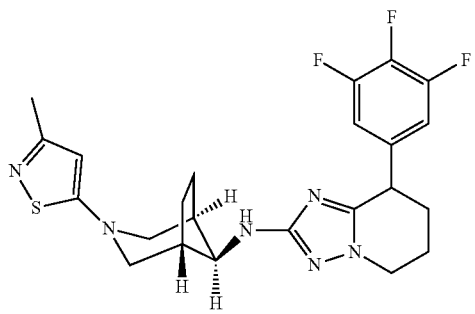 [SMILES: Cc1cc(N2C[C@H]3CC[C@@H](C2)[C@@H]3Nc2nc3n(n2)CCCC3c2cc(F)c(F)c(F)c2)sn1]

Separation of the enatiomers of the racemic N-((8-endo)-3-(3-methylisothiazol-5-yl)-3-azabicyclo[3.2.1]octan-8-yl)-8-(3,4,5-trifluorophenyl)-5,6,7,8-tetrahydro-[1,2,4]triazolo[1,5-a]pyridin-2-amine (example 13a) on Reprosil Chiral NR (ethanol/heptane=40:60) yielded the title compound as white solid (22.2 mg, 19%). MS: m/z=475.3 [M+H]⁺.

EXAMPLE 14a (+)-8-(4-Fluoro-3-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

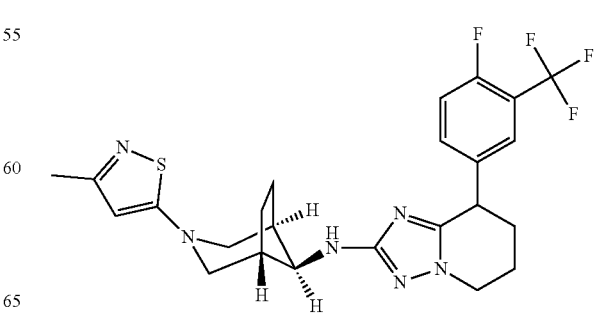

a) 8-(4-Fluoro-3-trifluoromethyl-phenyl)-[1.2.4]triazolo[1,5-a]pyridin-2-ylamine

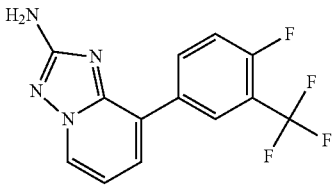 [SMILES: Nc1nc2c(-c3ccc(F)c(C(F)(F)F)c3)cccn2n1]

In a 150 ml round-bottomed flask were combined 8-bromo-[1,2,4]triazolo[1,5-a]pyridin-2-amine (1 g, 4.69 mmol), (4-fluoro-3-(trifluoromethyl)phenyl)boronic acid (976 mg, 4.69 mmol) and cesium carbonate (3.06 g, 9.39 mmol) with dioxane (50 ml) and water (5 ml) to give a colorless solution. 1,1'-Bis(diphenylphosphino)ferrocenepalladium(II)dichloride dichloromethane complex (343 mg, 469 μmol) was added. The reaction mixture was stirred for 3 hours at 100° C. Chromatography (silica gel, 50 g, ethyl acetate/heptane=40:60 to 100:0) yielded the title compound as light brown solid (1.24 g, 89%). MS: m/z=297.1 [M+H]$^+$.

b) 2-Bromo-8-(4-fluoro-3-(trifluoromethyl)phenyl)-[1,2,4]triazolo[1,5-a]pyridine

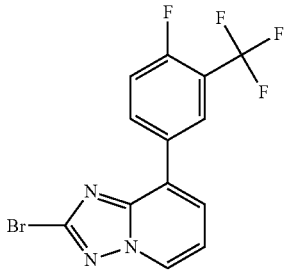 [SMILES: Fc1ccc(-c2cccn3nc(Br)nc23)cc1C(F)(F)F]

In a 100 ml round-bottomed flask, tert-butyl nitrite (647 mg, 746 μl, 6.28 mmol) and copper (II) bromide (1.4 g, 6.28 mmol) were combined with acetonitrile (30 ml) to give a black solution. The reaction mixture was heated to 60° C., then 8-(4-fluoro-3-(trifluoromethyl)phenyl)-[1,2,4]triazolo[1,5-a]pyridin-2-amine (1.24 g, 4.19 mmol) was added. The reaction was heated at 80° C. for 2 hours. The reaction mixture was cooled to room temperature and concentrated in vacuo. Hydrochloric acid (1N, 25 ml) was added and the reaction mixture was extracted with ethyl acetate (3×150 ml). Chromatography (silica gel, 50 g, ethyl acetate/heptane=0:100 to 40:60 yielded the title compound as white solid (1.27 g, 84%). MS: m/z=360.1 and 362.1 [M+H]$^+$.

c) 8-(4-Fluoro-3-(trifluoromethyl)phenyl)-N-((8-endo)-3-(3-methylisothiazol-5-yl)-3-azabicyclo[3.2.1]octan-8-yl)-[1,2,4]triazolo[1,5-a]pyridin-2-amine

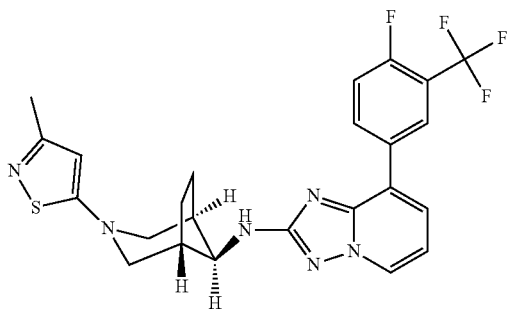 [SMILES: Cc1cc(N2C[C@H]3CC[C@@H](C2)[C@@H]3Nc2nc3c(-c4ccc(F)c(C(F)(F)F)c4)cccn3n2)sn1]

To a microwave vial was added 2-bromo-8-(4-(trifluoro-2-bromo-8-(4-fluoro-3-(trifluoromethyl)phenyl)-[1,2,4]triazolo[1,5-a]pyridine (88.7 mg, 246 μmol), (8-endo)-3-(3-methylisothiazol-5-yl)-3-azabicyclo[3.2.1]octan-8-amine (55 mg, 246 μmol), sodium tert-butoxide (49.7 mg, 517 μmol), xantphos (23.5 mg, 39.4 μmol) and tris(dibenzylideneacetone)dipalladium (0) chloroform adduct (20.8 mg, 19.7 μmol) in dioxane (3 ml). The vial was capped and heated in the microwave at 150° C. for 30 minutes. Chromatography (silica gel, 20 g, ethyl acetate/heptane=40:60 to 100:0) yielded the title compound as yellow solid (88 mg, 71%). MS: m/z=603.3 [M+H]$^+$.

d) 8-(4-Fluoro-3-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

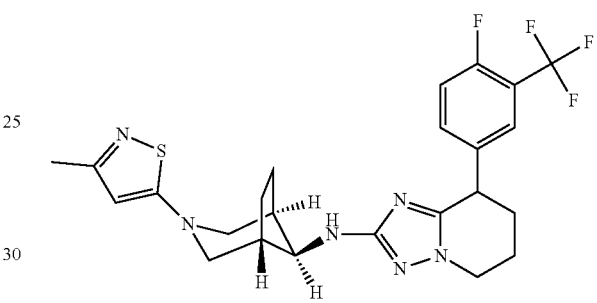

In a 50 ml round-bottomed flask, 8-(4-fluoro-3-(trifluoromethyl)phenyl)-N-((8-endo)-3-(3-methylisothiazol-5-yl)-3-azabicyclo[3.2.1]octan-8-yl)-[1,2,4]triazolo[1,5-a]pyridin-2-amine (82 mg, 163 μmol), magnesium (31.7 mg, 1.31 mmol) and iodine (414 μg, 1.63 μmol) were combined with methanol (8 ml) and tetrahydrofurane (4 ml) to give a light brown solution. The reaction mixture was heated at 80° C. for 4 hours. The mixture was cooled to room temperature and filtered through sintered glass. Chromatography (silica gel, 10 g, ethyl acetate/heptane=50:50 to 100:0) yielded the title compound as light brown solid (82 mg, 99%). MS: m/z=507.3 [M+H]$^+$.

e) (+)-8-(4-Fluoro-3-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

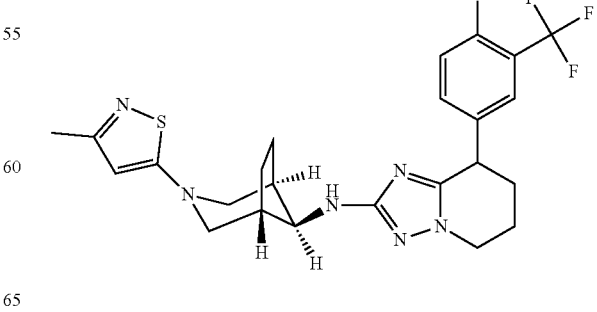

Separation of the enantiomers of the racemic 8-(4-fluoro-3-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (example 14a-d) on Reprosil Chiral-AM (ethanol/heptane=30:70) yielded the title compound as off-white solid (16.3 mg, 20%). MS: m/z=507.3 [M+H]⁺.

EXAMPLE 14b (−)-8-(4-Fluoro-3-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

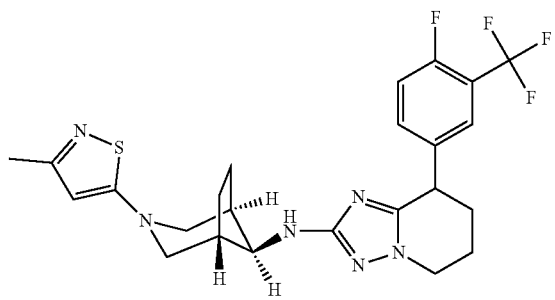 [SMILES: Cc1cc(N2C[C@H]3CC[C@@H](C2)[C@@H]3Nc2nc3n(n2)CCCC3c2ccc(F)c(C(F)(F)F)c2)sn1]

Separation of the enantiomers of the racemic 8-(4-fluoro-3-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (example 14a-d) on Reprosil Chiral-AM (ethanol/heptane=30:70) yielded the title compound as off-white solid (16.4 mg, 20%). MS: m/z=507.3 [M+H]⁺.

EXAMPLE 15a (+)-8-(Benzo[d][1,3]dioxol-5-yl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

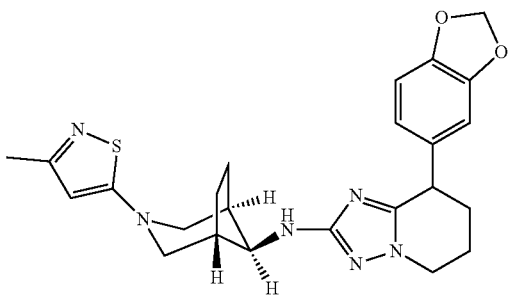 [SMILES: Cc1cc(N2C[C@H]3CC[C@@H](C2)[C@@H]3Nc2nc3n(n2)CCCC3c2ccc3c(c2)OCO3)sn1]

a) 8-(Benzo[d][1,3]dioxol-5-yl)-2-bromo-[1,2,4]triazolo[1,5-a]pyridine

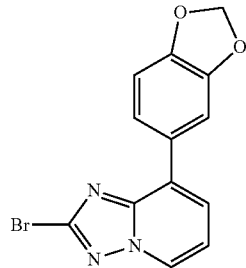 [SMILES: Brc1nc2c(-c3ccc4c(c3)OCO4)cccn2n1]

A solution of copper (II) bromide (406 mg, 1.82 mmol) and tert-butyl nitrite (187 mg, 216 µl, 1.82 mmol) dissolved in acetonitrile (10 ml) was heated to 60° C. and 8-(benzo[d][1,3]dioxol-5-yl)-[1,2,4]triazolo[1,5-a]pyridin-2-amine (CAS1369174-82-2, 420 mg, 1.65 mmol) was added in small portions. After complete addition the reaction mixture was heated at 75° C. for two hours. Again copper (II) bromide (406 mg, 1.82 mmol) and tert-butyl nitrite (187 mg, 216 µl, 1.82 mmol) were added and stirring was continued at 75° C. for 1 hour. Extraction with dichloromethane and chromatography (silica gel, 70 g, methanol (10% ammonia)/dichloromethane=0:100 to 15/85) yielded the title compound as yellow solid (320 mg, 61%). MS: m/z=318.0 and 320.1 [M+H]⁺.

b) 8-(Benzo[d][1,3]dioxol-5-yl)-N-((8-endo)-3-(3-methylisothiazol-5-yl)-3-azabicyclo[3.2.1]octan-8-yl)-[1,2,4]triazolo[1,5-a]pyridin-2-amine

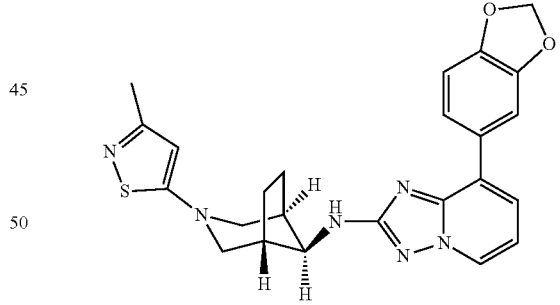

To a microwave vial was added 8-(benzo[d][1,3]dioxol-5-yl)-2-bromo-[1,2,4]triazolo[1,5-a]pyridine a]pyridine (114 mg, 358 µmol), (8-endo)-3-(3-methylisothiazol-5-yl)-3-azabicyclo[3.2.1]octan-8-amine (80 mg, 358 µmol), sodium tert-butoxide (72.3 mg, 752 µmol), xantphos (34.2 mg, 57.3 µmol) and tris(dibenzylideneacetone)dipalladium (0) chloroform adduct (30.3 mg, 28.7 µmol) in dioxane (4 ml). The vial was capped and heated in the microwave at 150° C. for 30 minutes. Chromatography (silica gel, 20 g, ethyl acetate/heptane=40:60 to 100:0) yield the title compound as light brown solid (120 mg, 73%). MS: m/z=461.3 [M+H]⁺.

c) 8-(Benzo[d][1,3]dioxol-5-yl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

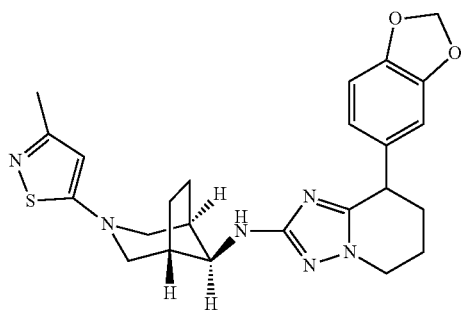 [SMILES: Cc1cc(N2C[C@H]3CC[C@@H](C2)[C@@H]3Nc2nc3n(n2)CCCC3c2ccc3c(c2)OCO3)sn1]

In a 50 ml round-bottomed flask, 8-(benzo[d][1,3]dioxol-5-yl)-N-((8-endo)-3-(3-methylisothiazol-5-yl)-3-azabicyclo[3.2.1]octan-8-yl)-[1,2,4]triazolo[1,5-a]pyridin-2-amine (113 mg, 245 µmol), iodine (623 µg, 2.45 µmol) and magnesium (47.7 mg, 1.96 mmol) were combined with methanol (12 ml) and tetrahydrofuran (6 ml) to give a light brown solution. The reaction mixture was heated at 80° C. for 14 hours. The mixture was cooled to room temperature and filtered through sintered glass. Chromatography (silica gel, 20 g, dichloromethane/methanol=100:0 to 85:15) yielded the title compound as light brown solid (110 mg, 97%). MS: m/z=465.3 [M+H]+.

d) (+)-8-(Benzo[d][1,3]dioxol-5-yl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

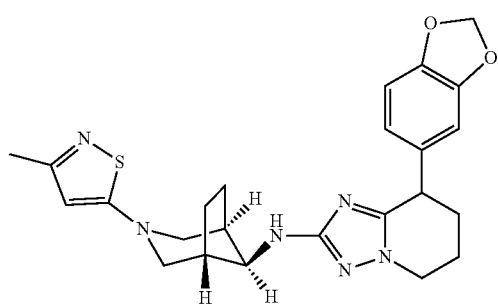 [SMILES: Cc1cc(N2C[C@H]3CC[C@@H](C2)[C@@H]3Nc2nc3n(n2)CCCC3c2ccc3c(c2)OCO3)sn1]

Chromatography of the racemic 8-(benzo[d][1,3]dioxol-5-yl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (example 15a-c) on Chiralpak AD (isopropanol/heptane=40:60) yielded the title compound as off-white solid (30.9 mg, 28%). MS: m/z=465.3 [M+H]+.

EXAMPLE 15b (−)-8-(Benzo[d][1,3]dioxol-5-yl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

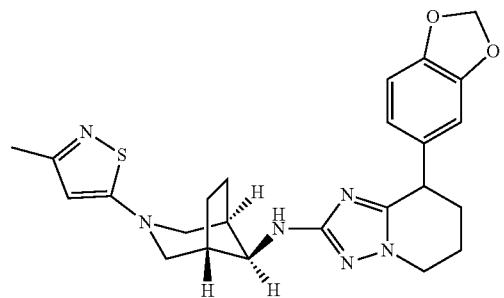 [SMILES: Cc1cc(N2C[C@H]3CC[C@@H](C2)[C@@H]3Nc2nc3n(n2)CCCC3c2ccc3c(c2)OCO3)sn1]

Chromatography of the racemic 8-(benzo[d][1,3]dioxol-5-yl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (example 15a-c) on Chiralpak AD (isopropanol/heptane=40:60) yielded the title compound as off-white solid (19.6 mg, 18%). MS: m/z=465.3 [M+H]+.

EXAMPLE 16a 8-(3-Fluoro-5-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

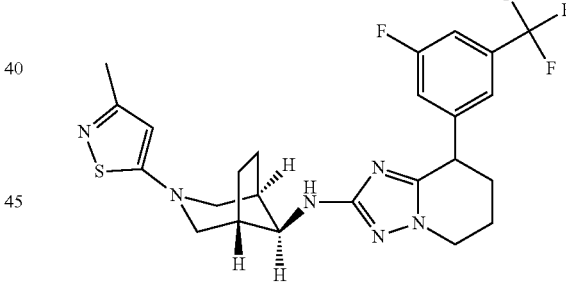

a) 8-(3-Fluoro-5-(trifluoromethyl)phenyl)-[1,2,4]triazolo[1,5-a]pyridin-2-amine

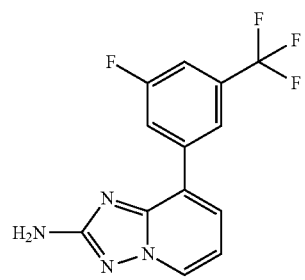 [SMILES: Nc1nc2c(-c3cc(F)cc(C(F)(F)F)c3)cccn2n1]

In a 150 ml round-bottomed flask were combined 8-bromo-[1,2,4]triazolo[1,5-a]pyridin-2-amine (1.50 g, 7.04 mmol), (3-fluoro-5-(trifluoromethyl)phenyl)boronic acid (1.46 g, 7.04 mmol) and cesium carbonate (4.59 g, 14.1 mmol) dioxane (70 ml) and water (7 ml) to give a colorless solution. 1,1′-Bis(diphenylphosphino)ferrocene-palladium (II)dichloride dichloromethane complex (515 mg, 704 μmol) was added. The reaction mixture was stirred for 3 hours at 100° C. Chromatography (silica gel, 70 g, ethyl acetate/heptane=40:60 to 100:0) yielded the title compound as off-white solid (1.69 g, 81%). MS: m/z=297.1 [M+H]⁺.

b) 2-Bromo-8-(3-fluoro-5-(trifluoromethyl)phenyl)-[1,2,4]triazolo[1,5-a]pyridine

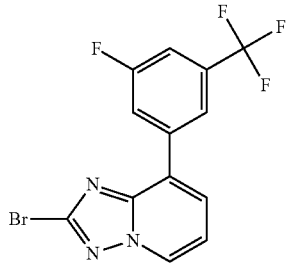 [SMILES: Fc1cc(-c2cccn3nc(Br)nc23)cc(C(F)(F)F)c1]

In a 150 ml round-bottomed flask, tert-butyl nitrite (882 mg, 1.02 ml, 8.56 mmol) and copper (II) bromide (1.91 g, 8.56 mmol) were combined with acetonitrile (60 ml) to give a black solution. The reaction mixture was heated to 60° C., then 8-(3-fluoro-5-(trifluoromethyl)phenyl)-[1,2,4]triazolo[1,5-a]pyridin-2-amine (1.69 g, 5.71 mmol) was added. The reaction was heated at 80° C. for 2 hours. The reaction mixture was cooled to room temperature and concentrated in vacuo. Hydrochloric acid (1 N, 25 ml) was added and the reaction mixture was extracted with ethyl acetate (3×150 ml). Chromatography (silica gel, 70 g, ethyl acetate/heptane=20:80 to 100:0) yielded the title compound as off-white solid (1.84 g, 90%). MS: m/z=362.1 and 362.1 [M+H]⁺.

c) 8-(3-Fluoro-5-(trifluoromethyl)phenyl)-N-((8-endo)-3-(3-methylisothiazol-5-yl)-3-azabicyclo[3.2.1]octan-8-yl)-[1,2,4]triazolo[1,5-a]pyridin-2-amine

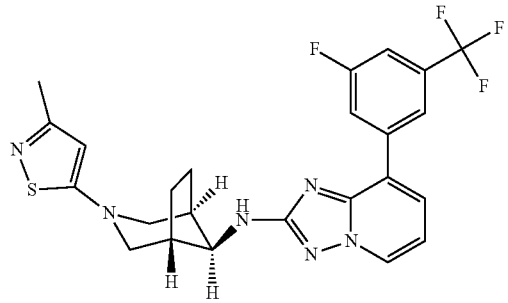 [SMILES: Cc1cc(N2C[C@H]3CC[C@@H](C2)[C@@H]3Nc2nc3c(-c4cc(F)cc(C(F)(F)F)c4)cccn3n2)sn1]

To a microwave vial was added 2-bromo-8-(3-fluoro-5-(trifluoromethyl)phenyl)-[1,2,4]triazolo[1,5-a]pyridine (129 mg, 358 μmol), (8-endo)-3-(3-methylisothiazol-5-yl)-3-azabicyclo[3.2.1]octan-8-amine (80 mg, 358 μmol), sodium tert-butoxide (72.3 mg, 752 μmol), xantphos (34.2 mg, 57.3 μmol) and tris(dibenzylideneacetone)dipalladium (0) chloroform adduct (30.3 mg, 28.7 μmol) in dioxane (4 ml). The vial was capped and heated in the microwave at 150° C. for 30 minutes. Chromatography (silica gel, 20 g, ethyl acetate/heptane=40:60 to 100:0) yielded the title compound as brown solid (120 mg, 67%). MS: m/z=503.3 [M+H]⁺.

d) 8-(3-Fluoro-5-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

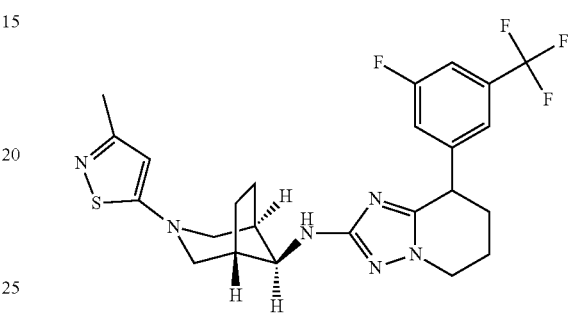

In a 50 ml round-bottomed flask, 8-(3-fluoro-5-(trifluoromethyl)phenyl)-N-((8-endo)-3-(3-methylisothiazol-5-yl)-3-azabicyclo[3.2.1]octan-8-yl)-[1,2,4]triazolo[1,5-a]pyridin-2-amine (120 mg, 239 μmol), iodine (606 μg, 2.39 μmol) and magnesium (46.4 mg, 1.91 mmol) were combined with methanol (12 ml) and tetrahydrofuran (6 ml) to give a light brown solution. The reaction mixture was heated at 80° C. for 14 hours. The mixture was cooled to room temperature and filtered through sintered glass. Chromatography (silica gel, 20 g, ethyl acetate/heptane=60:40 to 100:0) yielded the title compound as yellow solid (80 mg, 66%). MS: m/z=507.3 [M+H]⁺.

EXAMPLE 16b (+)-8-(3-Fluoro-5-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

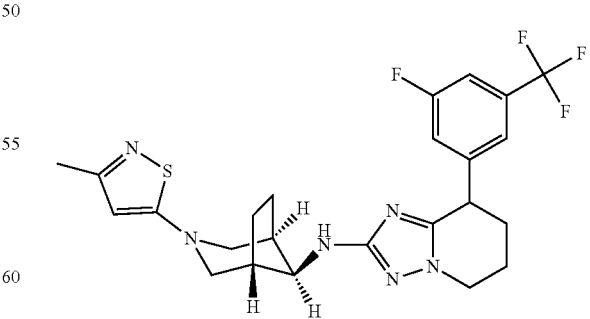

Chromatography of the racemic 8-(3-fluoro-5-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (example 16a) on Reprosil Chiral NR (ethanol/heptane=30:70) yielded the title compound as off-white solid (29.7 mg, 40%). MS: m/z=507.3 [M+H]⁺.

EXAMPLE 16c (−)-8-(3-Fluoro-5-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

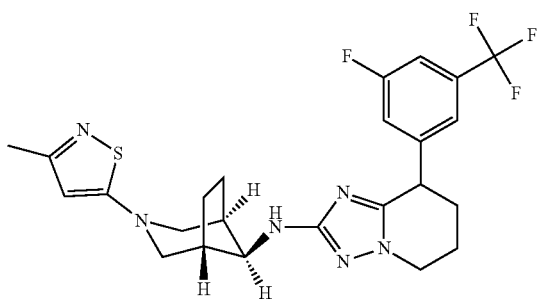 [SMILES: Cc1cc(N2C[C@H]3CC[C@@H](C2)[C@@H]3Nc2nc3n(n2)CCCC3c2cc(F)cc(C(F)(F)F)c2)sn1]

Chromatography of the racemic 8-(3-fluoro-5-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (example 16a) on Reprosil Chiral NR (ethanol/heptane=30:70) yielded the title compound as off-white solid (28.2 mg, 38%). MS: m/z=507.3 [M+H]⁺.

EXAMPLE 17

N-((8-endo)-3-(3-Methylisothiazol-5-yl)-3-azabicyclo[3.2.1]octan-8-yl)-8-(4-(2,2,2-trifluoroethoxy)phenyl)-5,6,7,8-tetrahydro-[1,2,4]triazolo[1,5-a]pyridin-2-amine

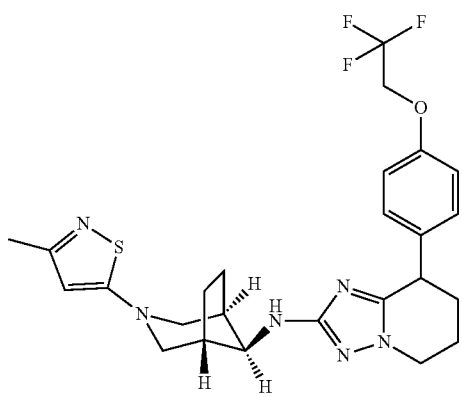 [SMILES: Cc1cc(N2C[C@H]3CC[C@@H](C2)[C@@H]3Nc2nc3n(n2)CCCC3c2ccc(OCC(F)(F)F)cc2)sn1]

a) 8-(4-(2,2,2-Trifluoroethoxy)phenyl)-[1,2,4]triazolo[1,5-a]pyridin-2-amine

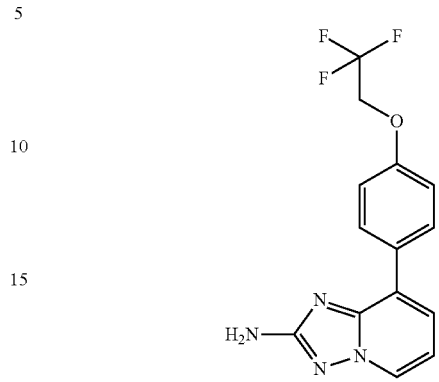

In a 100 mL round-bottomed flask, 8-bromo-[1,2,4]triazolo[1,5-a]pyridin-2-amine (775 mg, 3.64 mmol), cesium carbonate (2.37 g, 7.27 mmol) and (4-(2,2,2-trifluoroethoxy)phenyl)boronic acid (800 mg, 3.64 mmol) were combined with dioxane (45 ml) and water (4.5 ml) to give a light brown solution. 1,1'-Bis(diphenylphosphino)ferrocene-palladium(II)dichloride dichloromethane complex (266 mg, 364 µmol) was added and the reaction mixture was heated at 80° C. for 3 hours. Chromatography (silica gel, 40 g, ethyl acetate/heptane=50:50 to 100:0) yielded the title compound as off-white solid (690 mg, 62%). MS: m/z=309.1 [M+H]⁺.

b) 2-Bromo-8-(4-(2,2,2-trifluoroethoxy)phenyl)-[1,2,4]triazolo[1,5-a]pyridine

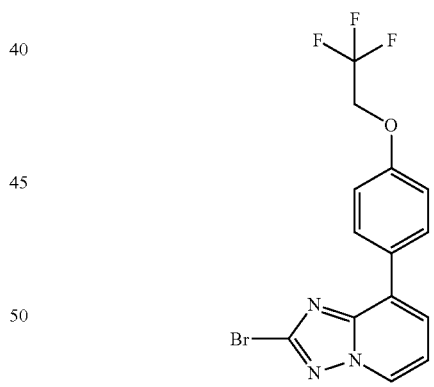

In a 100 mL round-bottomed flask, copper (II) bromide (739 mg, 3.31 mmol) and tert-butyl nitrite (341 mg, 393 µl, 3.31 mmol) were combined with acetonitrile (35 ml) to give a black solution. The reaction mixture was heated to 60° C. and 8-(4-(2,2,2-trifluoroethoxy)phenyl)-[1,2,4]triazolo[1,5-a]pyridin-2-amine (680 mg, 2.21 mmol) was added. The reaction mixture was heated at 80° C. and stirred for 2 hours. The reaction mixture was cooled to room temperature, poured into 25 ml water, acidified with hydrochloric acid (2N) and extracted with ethyl acetate (5×150 ml). Chromatography (silica gel, 40 g, ethyl acetate/heptane=20:80 to 100:0) yielded the title compound as off-white solid (533 mg, 65%). MS: m/z=372.1 and 374.1 [M+H]⁺.

c) N-((8-endo)-3-(3-Methylisothiazol-5-yl)-3-azabi-cyclo[3.2.1]octan-8-yl)-8-(4-(2,2,2-trifluoroethoxy)phenyl)-[1,2,4]triazolo[1,5-a]pyridin-2-amine

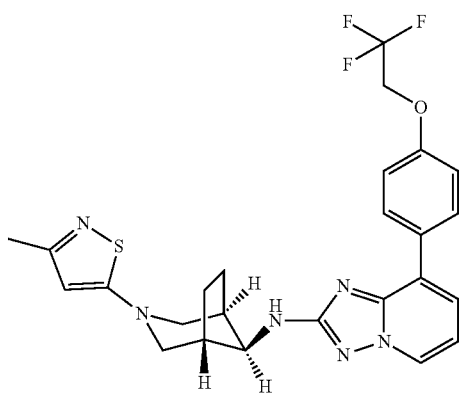 [SMILES: Cc1cc(N2C[C@H]3CC[C@@H](C2)[C@@H]3Nc2nc3c(-c4ccc(OCC(F)(F)F)cc4)cccn3n2)sn1]

To a 10 mL microwave vial was added (8-endo)-3-(3-methylisothiazol-5-yl)-3-azabicyclo[3.2.1]octan-8-amine (100 mg, 448 µmol), 2-bromo-8-(4-(2,2,2-trifluoroethoxy)phenyl)-[1,2,4]triazolo[1,5-a]pyridine (167 mg, 448 µmol), xantphos (41.5 mg, 71.6 µmol), tris(dibenzylideneacetone)dipalladium (0) chloroform adduct (37.1 mg, 35.8 µmol) and sodium tert-butoxide (90.4 mg, 940 µmol) in dioxane (5 ml). The vial was capped and heated in the microwave at 150° C. for 30 minutes. Chromatography (silica gel, 12 g, ethyl acetate/heptane=50:50 to 100:0) yielded the title compound as a light brown solid (35 mg, 15%). MS: m/z=515.3 [M+H]$^+$.

d) N-((8-endo)-3-(3-Methylisothiazol-5-yl)-3-azabi-cyclo[3.2.1]octan-8-yl)-8-(4-(2,2,2-trifluoroethoxy)phenyl)-5,6,7,8-tetrahydro-[1,2,4]triazolo[1,5-a]pyridin-2-amine

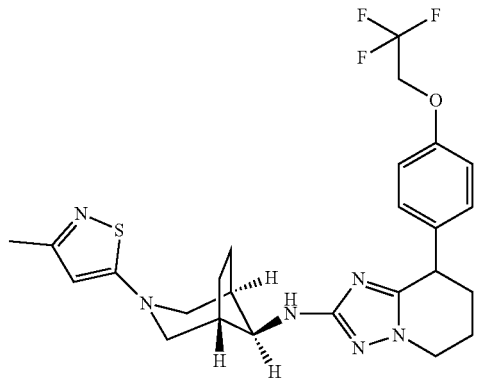 [SMILES: Cc1cc(N2C[C@H]3CC[C@@H](C2)[C@@H]3Nc2nc3n(n2)CCCC3c2ccc(OCC(F)(F)F)cc2)sn1]

In a 10 mL round-bottomed flask, N-((8-endo)-3-(3-methylisothiazol-5-yl)-3-azabicyclo[3.2.1]octan-8-yl)-8-(4-(2,2,2-trifluoroethoxy)phenyl)-[1,2,4]triazolo[1,5-a]pyridin-2-amine (30 mg, 58.3 µmol), magnesium (11.3 mg, 466 µmol) and iodine (148 µg, 0.583 µmol) were combined with methanol (5 ml) and tetrahydrofurane (2.5 ml) to give a dark red suspension. The reaction mixture was heated at 80° C. for 2 hours. Iodine (148 µg, 0.583 µmol) was added again and stirring was continued for 1 hour. Magnesium (11.3 mg, 466 µmol) and iodine (148 µg, 0.583 µmol) were added again and stirring was continued at 80° C. overnight. The reaction mixture was cooled to room temperature, methanol (10 ml) was added and the mixture was filtered through sintered glass. Chromatography (silica gel, 12 g, ethyl acetate/heptane=50:50 to 100:0) and preparative HPLC (Gemini NX 3u, 50×4.6 mm, acetonitril/formic acid (0.05% in water)=90.9:9.1) yielded the title compound as off-white foam (3 mg, 10%). MS: m/z=519.3 (30%) [M+H]$^+$.

EXAMPLE 18a 8-(2-Fluoro-4-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

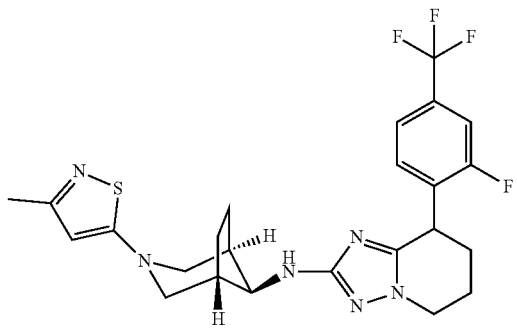 [SMILES: Cc1cc(N2C[C@H]3CC[C@@H](C2)[C@@H]3Nc2nc3n(n2)CCCC3c2ccc(C(F)(F)F)cc2F)sn1]

a) 8-(2-Fluoro-4-(trifluoromethyl)phenyl)-[1,2,4]triazolo[1,5-a]pyridin-2-amine

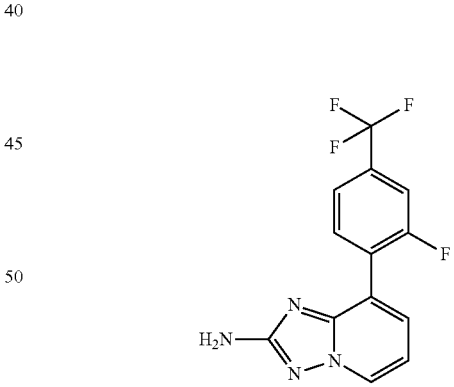

In a 100 mL round-bottomed flask, 8-bromo-[1,2,4]triazolo[1,5-a]pyridin-2-amine (1.02 g, 4.81 mmol), cesium carbonate (3.13 g, 9.62 mmol) and (2-fluoro-4-(trifluoromethyl)phenyl)boronic acid (1.0 g, 4.81 mmol) were combined with dioxane (50 ml) and water (5 ml) to give a light brown solution. 1,1'-Bis(diphenylphosphino)ferrocene-palladium(II)dichloride dichloromethane complex (352 mg, 481 µmol) was added and the reaction mixture was heated at 80° C. for 3 hours. Chromatography (silica gel, 40 g, ethyl acetate/heptane=50:50 to 100:0) yielded the title compound as off-white solid (115 mg, 8.0%). MS: m/z=297.1 [M+H]$^+$.

b) 2-Bromo-8-(2-fluoro-4-(trifluoromethyl)phenyl)-[1,2,4]triazolo[1,5-a]pyridine

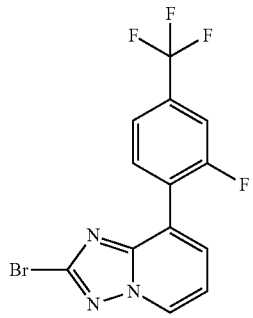 [SMILES: Fc1cc(C(F)(F)F)ccc1-c1cccn2nc(Br)nc12]

In a 25 mL round-bottomed flask, copper (II) bromide (124 mg, 557 μmol) and tert-butyl nitrite (57.4 mg, 66.2 μl, 557 μmol) were combined with acetonitrile (6 ml) to give a black solution. The reaction mixture was heated to 60° C. and 8-(2-fluoro-4-(trifluoromethyl)phenyl)-[1,2,4]triazolo[1,5-a]pyridin-2-amine (110 mg, 371 μmol) was added. The reaction mixture was heated at 80° C. for 2 hours. The reaction mixture was cooled to room temperature, poured into 25 ml water, acidified with hydrochloric acid (2 N) and extracted with ethyl acetate (5×150 ml) Chromatography (silica gel, 40 g, ethyl acetate/heptane=20:80 to 100:0) yielded the title compound as off-white solid (114 mg, 85%). MS: m/z=360.0 and 362.0 [M+H]$^+$.

c) 8-(2-Fluoro-4-(trifluoromethyl)phenyl)-N-((8-endo)-3-(3-methylisothiazol-5-yl)-3-azabicyclo[3.2.1]octan-8-yl)-[1,2,4]triazolo[1,5-a]pyridin-2-amine

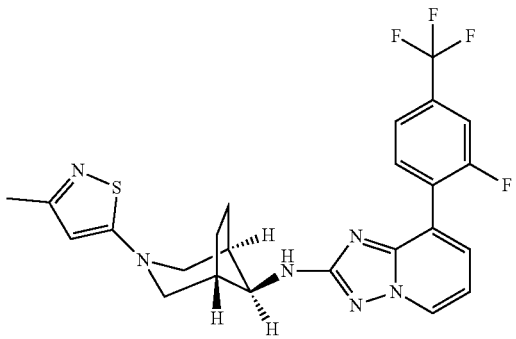 [SMILES: Cc1cc(N2C[C@H]3CC[C@@H](C2)[C@@H]3Nc2nc3c(-c4ccc(C(F)(F)F)cc4F)cccn3n2)sn1]

To a 10 mL microwave vial was added (8-endo)-3-(3-methylisothiazol-5-yl)-3-azabicyclo[3.2.1]octan-8-amine (68.2 mg, 305 μmol), 2-bromo-8-(2-fluoro-4-(trifluoromethyl)phenyl)-[1,2,4]triazolo[1,5-a]pyridine (110 mg, 305 μmol), xantphos (28.3 mg, 48.9 μmol), tris(dibenzylideneacetone)dipalladium (0) chloroform adduct (25.3 mg, 24.4 μmol) and sodium tert-butoxide (61.6 mg, 641 μmol) in dioxane (6 ml). The vial was capped and heated in the microwave at 150° C. for 30 minutes. Chromatography (silica gel, 12 g, ethyl acetate/heptane=50:50 to 100:0) yielded the title compound as light brown solid (61 mg, 40%). MS: m/z=503.2 [M+H]$^+$.

d) 8-(2-Fluoro-4-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

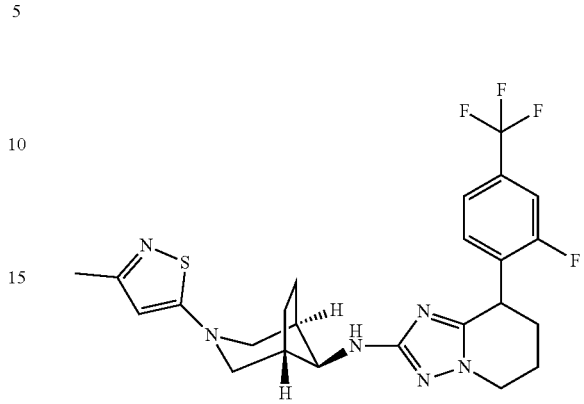

In a 25 mL round-bottomed flask, 8-(2-fluoro-4-(trifluoromethyl)phenyl)-N-((8-endo)-3-(3-methylisothiazol-5-yl)-3-azabicyclo[3.2.1]octan-8-yl)-[1,2,4]triazolo[1,5-a]pyridin-2-amine (56 mg, 111 μmol), magnesium (21.7 mg, 891 μmol) and iodine (283 μg, 1.11 μmol) were combined with methanol (10 ml) and tetrahydrofurane (5 ml) to give a dark red suspension. The reaction mixture was heated to 80° C. and stirred for 2 hours. Iodine (283 μg, 1.11 μmol) was added again and stirring was continued at 80° C. overnight. The reaction mixture was cooled to room temperature, methanol (10 ml) was added and the mixture was filtered through sintered glass. Chromatography (silica gel, 12 g, ethyl acetate/heptane=50:50 to 100:0) yielded the title compound (55 mg, 97%). MS: m/z=505.3 [M+H]$^+$.

EXAMPLE 18b (+)-8-(2-Fluoro-4-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

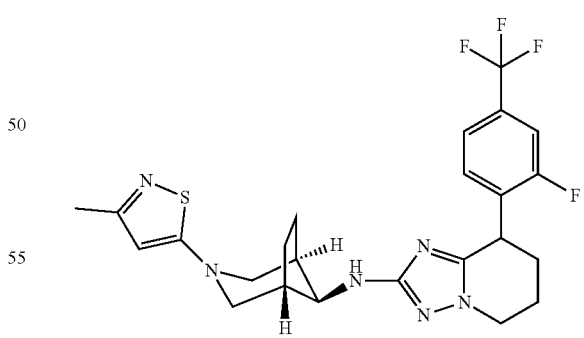

Chromatography of the racemic 8-(2-fluoro-4-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (example 18a) on Reprosil Chiral NR (ethanol/heptane=40:60) and trituration with diethyl ether/pentane (0.5 ml/2 ml) yielded the title compound as off-white solid (10 mg, 18%). MS: m/z=507.2 [M+H]$^+$.

83

EXAMPLE 18c (−)-8-(2-Fluoro-4-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

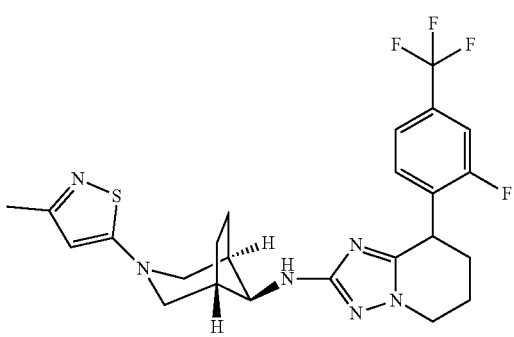 [SMILES: Cc1cc(N2C[C@H]3CC[C@@H](C2)[C@@H]3Nc2nc3n(n2)CCCC3c2ccc(C(F)(F)F)cc2F)sn1]

Chromatography of the racemic 8-(2-fluoro-4-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (example 18a) on Reprosil Chiral NR (ethanol/heptane=40:60) and trituration with diethyl ether/pentane (0.5 ml/2 ml) yielded the title compound as off-white solid (11 mg, 20%). MS: m/z=505.3 [M−H]⁻.

EXAMPLE 19a (+)-8-(4-(Difluoromethoxy)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

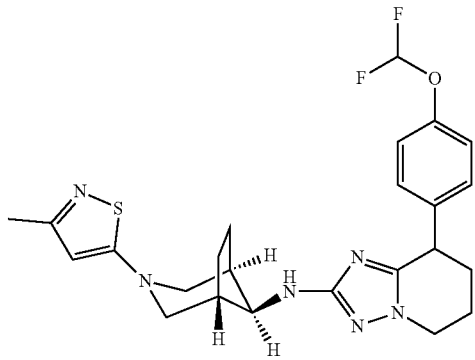 [SMILES: Cc1cc(N2C[C@H]3CC[C@@H](C2)[C@@H]3Nc2nc3n(n2)CCCC3c2ccc(OC(F)F)cc2)sn1]

84 a) 8-(4-(Difluoromethoxy)phenyl)-[1,2,4]triazolo[1,5-a]pyridin-2-amine

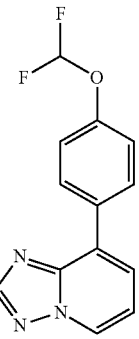

In a 150 ml round-bottomed flask were combined 8-bromo-[1,2,4]triazolo[1,5-a]pyridin-2-amine (1.5 g, 7.04 mmol), 2-(4-(difluoromethoxy)phenyl)-4,4,5,5-tetramethyl-1,3,2-dioxaborolane (1.9 g, 7.04 mmol) and cesium carbonate (4.59 g, 14.1 mmol) in dioxane (70 ml) and water (7 ml) to give a colorless solution. 1,1'-Bis(diphenylphosphino)ferrocene-palladium(II)dichloride dichloromethane complex (515 mg, 704 µmol) was added. The reaction mixture was stirred for 10 hours at 100° C. Chromatography (silica gel, 70 g, ethyl acetate/heptane=50:50 to 100:0) yielded the title compound as light brown solid (1.77 g, 91%). MS: m/z=277.2 [M+H]⁺.

b) 2-Bromo-8-(4-(difluoromethoxy)phenyl)-[1,2,4]triazolo[1,5-a]pyridine

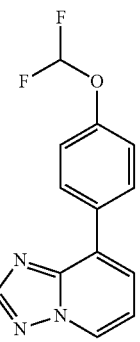

In a 150 ml round-bottomed flask, copper (II) bromide (2.15 g, 9.61 mmol) and tert-butyl nitrite (991 mg, 1.14 ml, 9.61 mmol) were combined with acetonitrile (70 ml) to give a black solution. The reaction mixture was heated to 60° C., then 8-(4-(difluoromethoxy)phenyl)-[1,2,4]triazolo[1,5-a]pyridin-2-amine (1.77 g, 6.41 mmol) was added. The reaction was heated at 80° C. for 2 hours. The reaction mixture was cooled to room temperature and was concentrated in vacuo. Hydrochloric acid (1 N, 25 ml) was added and the reaction mixture was extracted with ethyl acetate (3×150 mlL). Chromatography (silica gel, 70 g, ethyl acetate/heptane=20:80 to 100:0) yielded the title compound as off-white solid (1.70 g, 78%). MS: m/z=340.0 and 342.0 [M+H]⁺.

c) 8-(4-(Difluoromethoxy)phenyl)-N-((8-endo)-3-(3-methylisothiazol-5-yl)-3-azabicyclo[3.2.1]octan-8-yl)-[1,2,4]triazolo[1,5-a]pyridin-2-amine

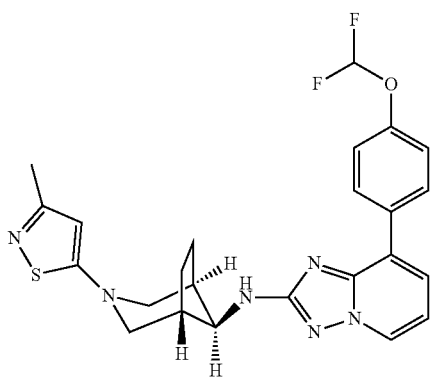 [SMILES: Cc1cc(N2C[C@H]3CC[C@@H](C2)[C@@H]3Nc2nc3c(-c4ccc(OC(F)F)cc4)cccn3n2)sn1]

To a microwave vial was added 2-bromo-8-(4-(difluoromethoxy)phenyl)-[1,2,4]triazolo[1,5-a]pyridine (129 mg, 381 μmol), (8-endo)-3-(3-methylisothiazol-5-yl)-3-azabicyclo[3.2.1]octan-8-amine (85 mg, 381 μmol), sodium tert-butoxide (76.8 mg, 799 μmol), xantphos (36.3 mg, 60.9 mol) and tris(dibenzylideneacetone)dipalladium (0) chloroform adduct (32.2 mg, 30.4 μmol) in dioxane (5 ml). The vial was capped and heated in the microwave at 150° C. for 35 minutes. Chromatography (silica gel, 20 g, ethyl acetate/heptane=40:60 to 100:0) yielded the title compound as light brown solid (89 mg, 49%). MS: m/z=483.2 [M+H]$^+$.

d) 8-(4-(Difluoromethoxy)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

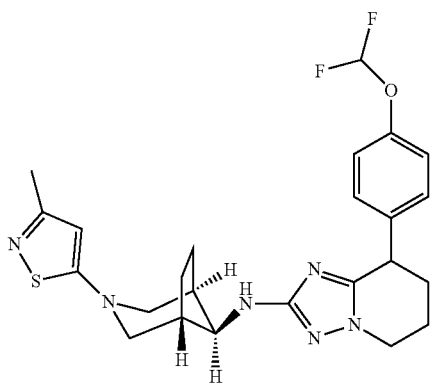 [SMILES: Cc1cc(N2C[C@H]3CC[C@@H](C2)[C@@H]3Nc2nc3n(n2)CCCC3c2ccc(OC(F)F)cc2)sn1]

In a 50 ml round-bottomed flask, 8-(4-(difluoromethoxy)phenyl)-N-((8-endo)-3-(3-methylisothiazol-5-yl)-3-azabicyclo[3.2.1]octan-8-yl)-[1,2,4]triazolo[1,5-a]pyridin-2-amine (84 mg, 174 μmol), iodine (442 μg, 1.74 μmol) and magnesium (33.8 mg, 1.39 mmol) were combined with methanol (10 ml) and tetrahydrofuran (5 ml) to give a light brown solution. The reaction mixture was heated at 80° C. for 14 hours. The reaction mixture was cooled to room temperature and filtered through sintered glass. Chromatography (silica gel, 20 g, ethyl acetate/methanol=100:0 to 80:20) yielded the title compound as yellow solid (63 mg, 67%). MS: m/z=487.3 [M+H]$^+$.

e) (+)-8-(4-(Difluoromethoxy)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

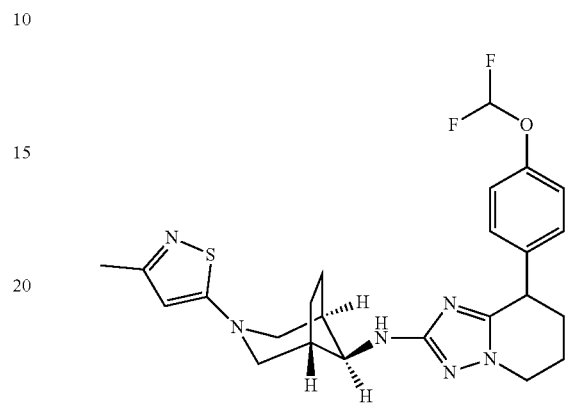

Chromatography of the racemic 8-(4-(difluoromethoxy)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (example 19a-d) on Reprosil Chiral NR (ethanol/heptane=30:70) yielded the title compound as off-white solid (18.5 mg, 33%). MS: m/z=487.3 [M+H]$^+$.

EXAMPLE 19b (−)-8-(4-(Difluoromethoxy)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

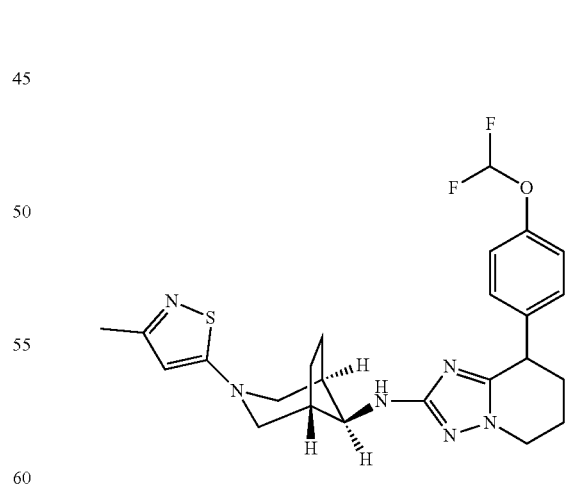

Chromatography of the racemic 8-(4-(difluoromethoxy)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (example 19a-d) on Reprosil Chiral NR (ethanol/heptane=30:70) yielded the title compound as off-white solid (19.5 mg, 34%). MS: m/z=487.3 [M+H]$^+$.

EXAMPLE 20a (−)-N-((8-endo)-3-(3-Methylisothiazol-5-yl)-3-azabicyclo[3.2.1]octan-8-yl)-8-(p-tolyl)-5,6,7,8-tetrahydro-[1,2,4]triazolo[1,5-a]pyridin-2-amine

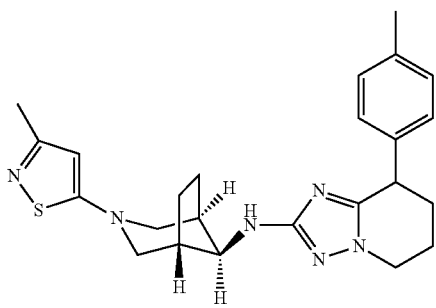 [SMILES: Cc1ccc(C2CCCn3nc(N[C@@H]4[C@@H]5CC[C@H]4CN(c4cc(C)ns4)C5)nc32)cc1]

a) 8-(4-(Difluoromethyl)phenyl)-[1,2,4]triazolo[1,5-a]pyridin-2-amine

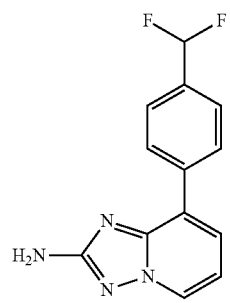 [SMILES: Nc1nc2c(-c3ccc(C(F)F)cc3)cccn2n1]

In a 150 ml round-bottomed flask were combined 8-bromo-[1,2,4]triazolo[1,5-a]pyridin-2-amine (1.12 g, 5.27 mmol), 2-(4-(difluoromethyl)phenyl)-4,4,5,5-tetramethyl-1,3,2-dioxaborolane (1.34 g, 5.27 mmol) and cesium carbonate (3.44 g, 10.5 mmol) dioxane (50 ml) and water (5 ml) to give a colorless solution. 1,1'-Bis(diphenylphosphino)ferrocene-palladium(II)dichloride dichloromethane complex (386 mg, 527 µmol) was added. The reaction mixture was stirred for 10 hours at 100° C. Chromatography (silica gel, 70 g, ethyl acetate/heptane=40:60 to 100:0) yielded the title compound as off-white solid (690 mg, 50%). MS: m/z=261.2 [M+H]$^+$.

b) 2-Bromo-8-(4-(difluoromethyl)phenyl)-[1,2,4]triazolo[1,5-a]pyridine

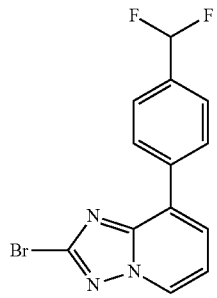 [SMILES: FC(F)c1ccc(-c2cccn3nc(Br)nc23)cc1]

In a 150 ml round-bottomed flask, copper (II) bromide (888 mg, 3.98 mmol) and tert-butyl nitrite (410 mg, 472 µl, 3.98 mmol) were combined with acetonitrile (50 ml). The reaction mixture was heated to 60° C. and 8-(4-(difluoromethyl)phenyl)-[1,2,4]triazolo[1,5-a]pyridin-2-amine (690 mg, 2.65 mmol was added. The reaction was heated at 80° C. for 2 hours. The reaction mixture was cooled to room temperature and was concentrated in vacuo. Hydrochloric acid (1 N, 25 ml) was added and the reaction mixture was extracted with ethyl acetate (3×150 ml). Chromatography (silica gel, 50 g, ethyl acetate/heptane=20:80 to 100:0) yielded the title compound as off-white solid (660 mg, 77%). MS: m/z=324.0 and 326.0 [M+H]$^+$.

c) 8-(4-(Difluoromethyl)phenyl)-N-((8-endo)-3-(3-methylisothiazol-5-yl)-3-azabicyclo[3.2.1]octan-8-yl)-[1,2,4]triazolo[1,5-a]pyridin-2-amine

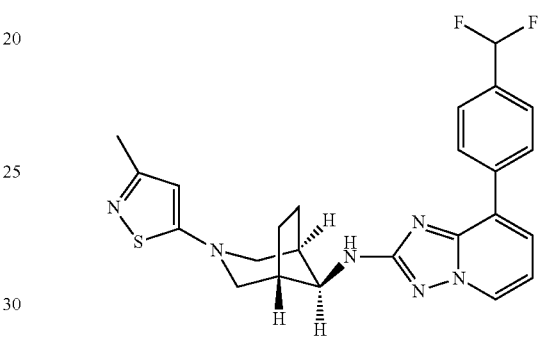

To a microwave vial was added 2-bromo-8-(4-(difluoromethyl)phenyl)-[1,2,4]triazolo[1,5-a]pyridine (123 mg, 381 µmol), (8-endo)-3-(3-methylisothiazol-5-yl)-3-azabicyclo[3.2.1]octan-8-amine (85 mg, 381 µmol), sodium tert-butoxide (76.8 mg, 799 µmol), xantphos (36.3 mg, 60.9 mol) and tris(dibenzylideneacetone)dipalladium (0) chloroform adduct (32.2 mg, 30.4 µmol) in dioxane (5 ml). The vial was capped and heated in the microwave at 150° C. for 35 minutes. Chromatography (silica gel, 20 g, ethyl acetate/heptane=40:60 to 100:0) yielded the title compound as light brown solid (125 mg, 70%). MS: m/z=467.2 [M+H]$^+$.

d) N-((8-endo)-3-(3-Methylisothiazol-5-yl)-3-azabicyclo[3.2.1]octan-8-yl)-8-(p-tolyl)-5,6,7,8-tetrahydro-[1,2,4]triazolo[1,5-a]pyridin-2-amine

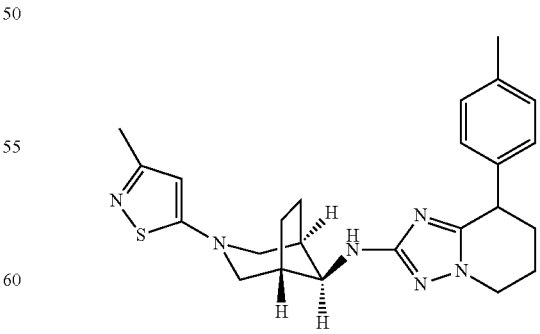

In a 50 ml round-bottomed flask, 8-(4-(difluoromethyl)phenyl)-N-((8-endo)-3-(3-methylisothiazol-5-yl)-3-azabicyclo[3.2.1]octan-8-yl)-[1,2,4]triazolo[1,5-a]pyridin-2-amine (120 mg, 257 µmol), iodine (653 µg, 2.57 µmol) and magnesium (50 mg, 2.06 mmol) were combined with methanol (10 ml) and tetrahydrofuran (5 ml) to give a light brown solution. The reaction mixture was heated at 80° C. for 14 hours. Mass spectroscopy showed that the two fluoro atoma were lost during the reaction. The mixture was cooled to room temperature and filtered through sintered glass. Chromatography (silica gel, 20 g, ethyl acetate/heptane=60:40 to 100:0 yielded the title compound as an orange solid (85 mg, 68%). MS: m/z=435.3 [M+H]$^+$.

e) (−)-N-((8-endo)-3-(3-Methylisothiazol-5-yl)-3-azabicyclo[3.2.1]octan-8-yl)-8-(p-tolyl)-5,6,7,8-tetrahydro-[1,2,4]triazolo[1,5-a]pyridin-2-amine

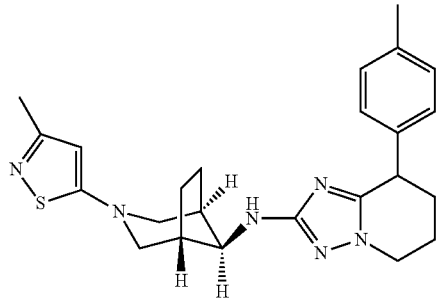 [SMILES: Cc1ccc(C2CCCn3nc(N[C@@H]4[C@@H]5CC[C@H]4CN(c4cc(C)ns4)C5)nc32)cc1]

Chromatography of the racemic N-((8-endo)-3-(3-methylisothiazol-5-yl)-3-azabicyclo[3.2.1]octan-8-yl)-8-(p-tolyl)-5,6,7,8-tetrahydro-[1,2,4]triazolo[1,5-a]pyridin-2-amine (example 20a-d) on Reprosil Chiral NR (ethanol/heptane=40:60) yielded the title compound as off-white solid (26 mg, 31%). MS: m/z=435.3 [M+H]$^+$.

EXAMPLE 20b (+)-N-((8-endo)-3-(3-Methylisothiazol-5-yl)-3-azabicyclo[3.2.1]octan-8-yl)-8-(p-tolyl)-5,6,7,8-tetrahydro-[1,2,4]triazolo[1,5-a]pyridin-2-amine

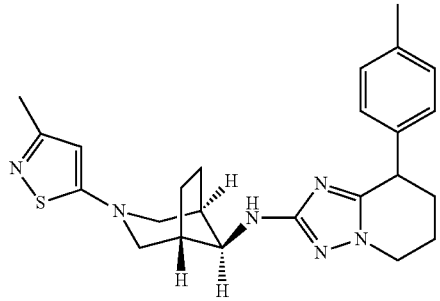 [SMILES: Cc1ccc(C2CCCn3nc(N[C@@H]4[C@@H]5CC[C@H]4CN(c4cc(C)ns4)C5)nc32)cc1]

Chromatography of the racemic N-((8-endo)-3-(3-methylisothiazol-5-yl)-3-azabicyclo[3.2.1]octan-8-yl)-8-(p-tolyl)-5,6,7,8-tetrahydro-[1,2,4]triazolo[1,5-a]pyridin-2-amine (example 20a-d) on Reprosil Chiral NR (ethanol/heptane=40:60) yielded the title compound as off-white solid (22 mg, 23%). MS: m/z=435.3 [M+H]$^+$.

EXAMPLE 21a (−)-8-(2-Methoxy-4-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

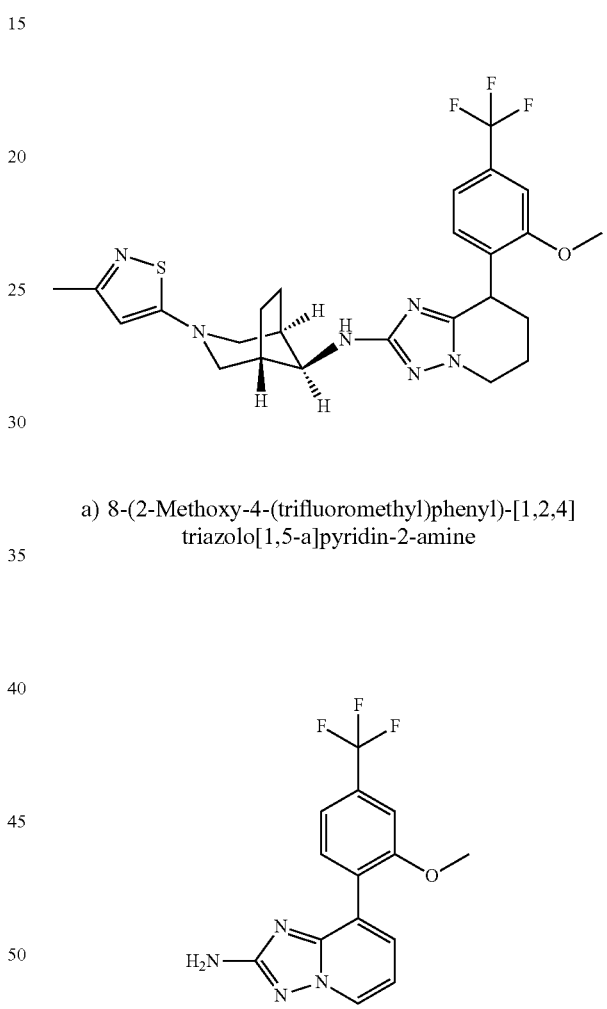

a) 8-(2-Methoxy-4-(trifluoromethyl)phenyl)-[1,2,4]triazolo[1,5-a]pyridin-2-amine In a 100 mL round-bottomed flask, 8-bromo-[1,2,4]triazolo[1,5-a]pyridin-2-amine (1 g, 4.69 mmol), cesium carbonate (3.06 g, 9.39 mmol) and (2-methoxy-4-(trifluoromethyl)phenyl)boronic acid (1.14 g, 5.16 mmol) were combined with dioxane (50 ml) and water (5 ml) to give a light brown solution. 1,1'-Bis(diphenylphosphino)ferrocene-palladium(II)dichloride dichloromethane complex (343 mg, 469 µmol) was added and the reaction mixture was heated to 80° C. and stirred for 3 hours. Chromatography (silica gel, 40 g, ethyl acetate/heptane=50:50 to 100:0 yielded the title compound as off-white solid (1.24 g, 86%). MS: m/z=309.1 [M+H]$^+$.

b) 2-Bromo-8-(2-methoxy-4-(trifluoromethyl)phenyl)-[1,2,4]triazolo[1,5-a]pyridine

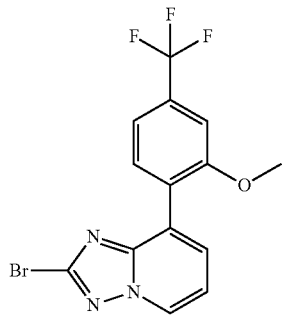 [SMILES: COc1cc(C(F)(F)F)ccc1-c1cccn2nc(Br)nc12]

In a 100 mL round-bottomed flask, copper (II) bromide (1.09 g, 4.87 mmol) and tert-butylnitrite (502 mg, 578 μl, 4.87 mmol) were combined with acetonitrile (50 ml) to give a black solution. The solution was heated to 60° C. Then 8-(2-methoxy-4-(trifluoromethyl)phenyl)-[1,2,4]triazolo[1,5-a]pyridin-2-amine (1.00 g, 3.24 mmol) was added and the reaction mixture was heated at 80° C. for 2 hours. The reaction mixture was cooled to room temperature, poured into 25 ml water, acidified with hydrochloric acid (2N) and extracted with ethyl acetate (3×50 ml). Chromatography (silica gel, 40 g, ethyl acetate/heptane=10:90 to 50:50) yielded the title compound as off-white solid (1.05 g, 87%). MS: m/z=372.0 and 374.0 [M+H]+.

c) 8-(2-Methoxy-4-(trifluoromethyl)phenyl)-N-((8-endo)-3-(3-methylisothiazol-5-yl)-3-azabicyclo[3.2.1]octan-8-yl)-[1,2,4]triazolo[1,5-a]pyridin-2-amine

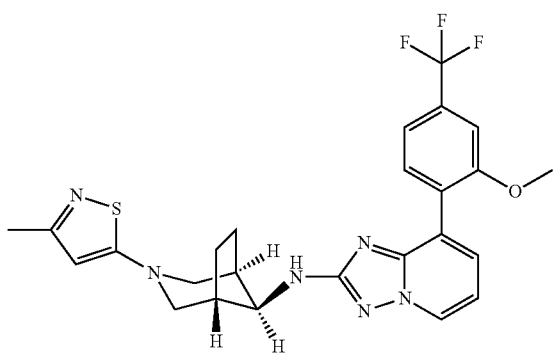

To a microwave vial was added (8-endo)-3-(3-methylisothiazol-5-yl)-3-azabicyclo[3.2.1]octan-8-amine (240 mg, 1.07 mmol), 2-bromo-8-(2-methoxy-4-(trifluoromethyl)phenyl)-[1,2,4]triazolo[1,5-a]pyridine (400 mg, 1.07 mmol), xantphos (99.5 mg, 172 μmol), tris(dibenzylideneacetone) dipalladium (0) chloroform adduct (89 mg, 86 μmol) and sodium tert-butoxide (217 mg, 2.26 mmol) in dioxane (20 ml). The vial was capped and heated in the microwave at 150° C. for 30 minutes. Chromatography (silica gel, 12 g, ethyl acetate/heptane=50:50 to 100:0) yielded the title compound as light brown solid (348 mg, 63%). MS: m/z=515.2 [M+H]+.

d) (−)-8-(2-Methoxy-4-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

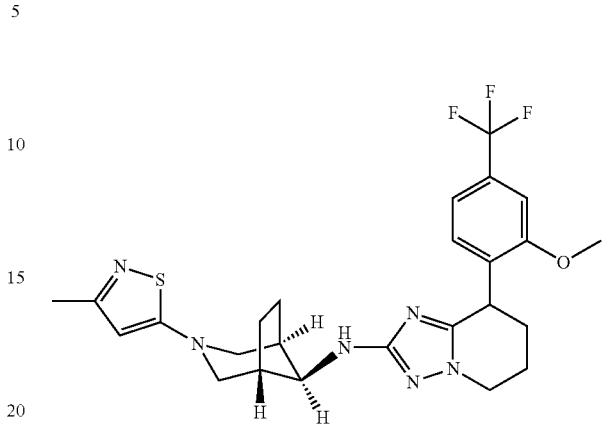

In a 100 mL round-bottomed flask, 8-(2-methoxy-4-(trifluoromethyl)phenyl)-N-((8-endo)-3-(3-methylisothiazol-5-yl)-3-azabicyclo[3.2.1]octan-8-yl)-[1,2,4]triazolo[1,5-a]pyridin-2-amine (310 mg, 602 μmol), magnesium (117 mg, 4.82 mmol) and iodine (1.53 mg, 6.02 μmol) were combined with methanol (50 ml) and tetrahydrofurane (25 ml) to give a light brown suspension. The reaction mixture was heated at 80° C. for 2 hours. Iodine (1.53 mg, 6.02 μmol) was added again and stirring was continued for 1 hour. The reaction mixture was cooled to room temperature, methanol (20 ml) was added and the mixture was filtered through sintered glass. Chromatography (silica gel, 40 g, ethyl acetate/heptane=50:50 to 100:0) and chromatography of the racemic 8-(2-methoxy-4-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (ChiralPak AD, ethanol/heptane=40:60) yielded the title compound as off-white solid (70 mg, 22%). MS: m/z=519.2 [M+H]+.

EXAMPLE 21b (+)-8-(2-Methoxy-4-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

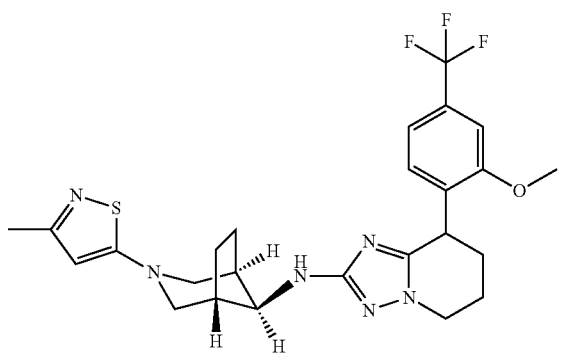

Chromatography of the racemic 8-(2-methoxy-4-(trifluoromethyl)phenyl)-N-((8-endo)-3-(3-methylisothiazol-5-yl)-

3-azabicyclo[3.2.1]octan-8-yl)-5,6,7,8-tetrahydro-[1,2,4]triazolo[1,5-a]pyridin-2-amine (example 21a, ChiralPak AD, ethanol/heptane=40:60) yielded the title compound as off-white solid (64 mg, 21%). MS: m/z=519.2 [M+H]$^+$.

EXAMPLE 22a 8-(5-Fluoro-2-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

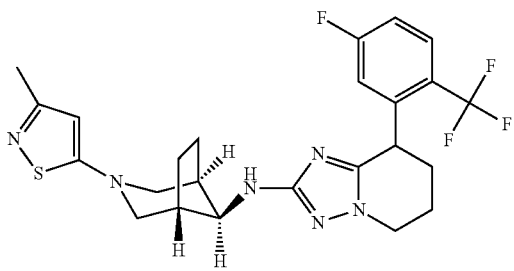 [SMILES: Cc1cc(N2C[C@H]3CC[C@@H](C2)[C@@H]3Nc2nc3n(n2)CCCC3c2cc(F)ccc2C(F)(F)F)sn1]

a) 8-(5-Fluoro-2-(trifluoromethyl)phenyl)-[1,2,4]triazolo[1,5-a]pyridin-2-amine

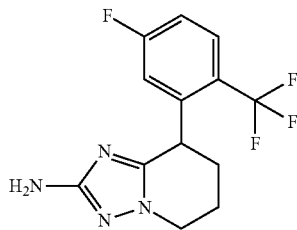 [SMILES: Nc1nc2n(n1)CCCC2c1cc(F)ccc1C(F)(F)F]

In a 150 ml round-bottomed flask were combined 8-bromo-[1,2,4]triazolo[1,5-a]pyridin-2-amine (1.5 g, 7.04 mmol), (5-fluoro-2-(trifluoromethyl)phenyl)boronic acid (2.2 g, 10.6 mmol) and cesium carbonate (4.59 g, 14.1 mmol) in dioxane (70 ml) and water (7 ml) to give a colorless solution. 1,1'-Bis(diphenylphosphino)ferrocenepalladium(II)dichloride dichloromethane complex (515 mg, 704 µmol) was added. The reaction mixture was stirred for 12 hours at 100° C. Chromatography (silica gel, 70 g, ethyl acetate/heptane=40:60 to 100:0) yielded the title compound as off-white solid (600 mg, 29%). MS: m/z=297.1 [M+H]$^+$.

b) 2-Bromo-8-(5-fluoro-2-(trifluoromethyl)phenyl)-[1,2,4]triazolo[1,5-a]pyridine

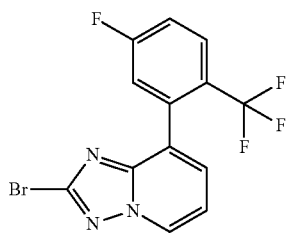 [SMILES: Fc1ccc(C(F)(F)F)c(-c2cccn3nc(Br)nc23)c1]

In a 100 ml round-bottomed flask, tert-butyl nitrite (313 mg, 361 µl, 3.04 mmol) and copper (II) bromide (679 mg, 3.04 mmol) were combined with acetonitrile (30 ml) to give a black solution. The reaction mixture was heated to 60° C., then 8-(5-fluoro-2-(trifluoromethyl)phenyl)-[1,2,4]triazolo[1,5-a]pyridin-2-amine (600 mg, 2.03 mmol) was added. The reaction was heated at 80° C. for 2 hours. The reaction mixture was cooled to room temperature and concentrated in vacuo. Hydrochloric acid (1 N, 25 ml) was added and the reaction mixture was extracted with ethyl acetate (3×150 ml). Chromatography (silica gel, 50 g, ethyl acetate/heptane=0:100 to 100:0) yielded the title compound as white solid (0.66 g, 91%). MS: m/z=360.0 and 362.0 [M+H]$^+$.

c) 8-(5-Fluoro-2-(trifluoromethyl)phenyl)-N-((8-endo)-3-(3-methylisothiazol-5-yl)-3-azabicyclo[3.2.1]octan-8-yl)-[1,2,4]triazolo[1,5-a]pyridin-2-amine

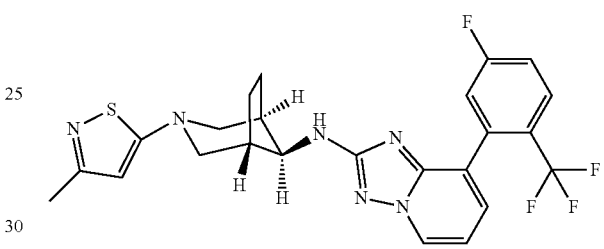

To a 10 mL microwave vial, (8-endo)-3-(3-methylisothiazol-5-yl)-3-azabicyclo[3.2.1]octan-8-amine (150 mg, 672 µmol), 2-bromo-8-(5-fluoro-2-(trifluoromethyl)phenyl)-[1,2,4]triazolo[1,5-a]pyridine (242 mg, 672 µmol), xantphos (62.2 mg, 107 µmol), tris(dibenzylideneacetone)dipalladium (0) chloroform adduct (55.6 mg, 53.7 µmol) and sodium tert-butoxide (136 mg, 1.41 mmol) were combined with dioxane (6 ml) to give a black suspension. The vial was capped and heated in the microwave at 150° C. for 30 minutes. Chromatography (silica gel, 20 g, ethyl acetate/heptane=20:80 to 100:0) yielded the title compound as brown oil (170 mg, 50%). MS: m/z=503.2 [M+H]$^+$.

d) 8-(5-Fluoro-2-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

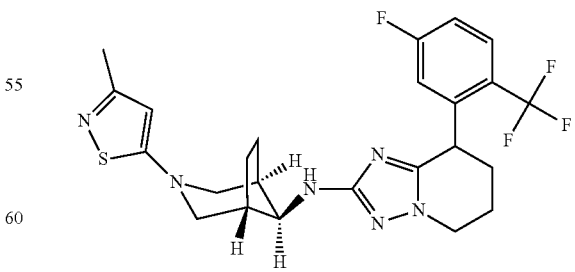

In a 50 ml round-bottomed flask, 8-(5-fluoro-2-(trifluoromethyl)phenyl)-N-((8-endo)-3-(3-methylisothiazol-5-yl)-3-azabicyclo[3.2.1]octan-8-yl)-[1,2,4]triazolo[1,5-a]pyridin-2-amine (165 mg, 328 µmol), iodine (833 µg, 3.28 µmol)

and magnesium (63.8 mg, 2.63 mmol) were combined with methanol (10 ml) and tetrahydrofuran (5 ml) to give a light brown solution. The reaction mixture was heated to 80° C. and stirred for 14 hours. The mixture was cooled to room temperature and filtered through sintered glass. Chromatography (silica gel, 12 g, ethyl acetate/heptane=50:50 to 100:0) yielded the title compound as yellow solid (110 mg, 66%). MS: m/z=507.2 [M+H]$^+$.

EXAMPLE 22b (+)-8-(5-Fluoro-2-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

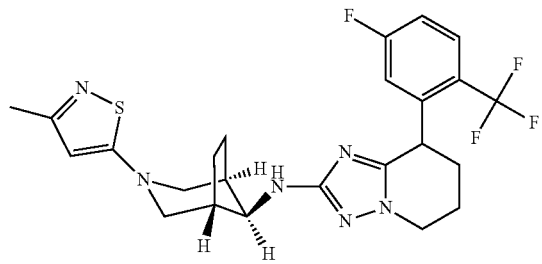 [SMILES: Cc1cc(N2C[C@H]3CC[C@@H](C2)[C@@H]3Nc2nc3n(n2)CCCC3c2cc(F)ccc2C(F)(F)F)sn1]

Chromatography of the racemic 8-(5-fluoro-2-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (example 22a) on Reprosil Chiral NR (ethanol/heptane=40:60) yielded the title compound as white solid (39.2 mg, 38%). MS: m/z=507.2 [M+H]$^+$.

EXAMPLE 22c (−)-8-(5-Fluoro-2-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine

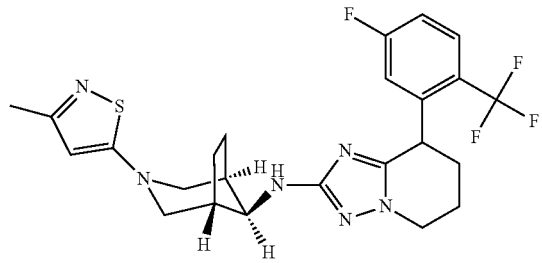 [SMILES: Cc1cc(N2C[C@H]3CC[C@@H](C2)[C@@H]3Nc2nc3n(n2)CCCC3c2cc(F)ccc2C(F)(F)F)sn1]

Chromatography of the racemic 8-(5-fluoro-2-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine (example 22a) on Reprosil Chiral NR (ethanol/heptane=40:60) yielded the title compound as white solid (37.4 mg, 36%). MS: m/z=507.2 [M+H]$^+$.

EXAMPLE 23a 8-(4-Fluoro-2-methylphenyl)-N-[(8-endo)-3-(3-methyl-1,2-thiazol-5-yl)-3-azabicyclo[3.2.1]octan-8-yl]-5,6,7,8-tetrahydro-[1,2,4]triazolo[1,5-a]pyridin-2-amine

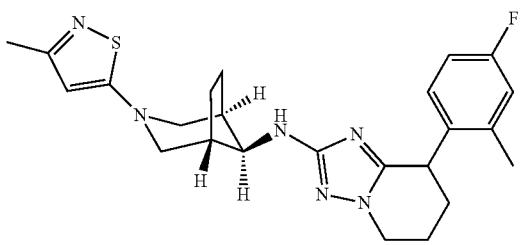

a) 2-Bromo-8-(4-fluoro-2-methylphenyl)-[1,2,4]triazolo[1,5-a]pyridine

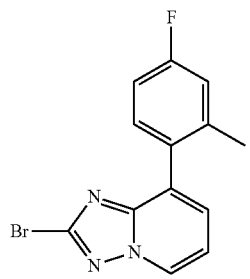 [SMILES: Cc1cc(F)ccc1-c1cccn2nc(Br)nc12]

In a 50 mL round-bottomed flask, tert-butyl nitrite (549 mg, 633 µl, 5.33 mmol) and copper (II) bromide (1.19 g, 5.33 mmol) were combined with acetonitrile (25 ml) to give a dark brown solution. The reaction mixture was heated to 60° C., then 8-(4-fluoro-2-methylphenyl)-[1,2,4]triazolo[1,5-a]pyridine-2-amine (CAS1262197-62-5, 860 mg, 3.55 mmol) was added. The reaction was heated at 80° C. for 2 hours. The mixture was cooled to room temperature and stirred overnight. Chromatography (silica gel, 50 g, ethyl acetate/heptane=30:70 to 100:0) yielded the title compound as off-white solid (943 mg, 87%). MS: m/z=306.0 and 308.0 [M+H]$^+$.

b) 8-(4-Fluoro-2-methylphenyl)-N-((8-endo)-3-(3-methylisothiazol-5-yl)-3-azabicyclo[3.2.1]octan-8-yl)-[1,2,4]triazolo[1,5-a]pyridin-2-amine

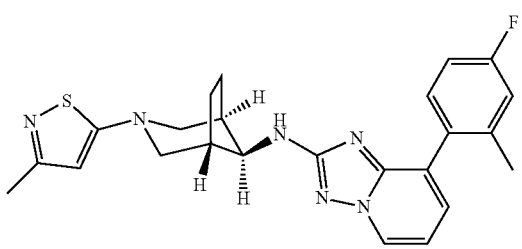

In a 10 ml microwave vial, (8-endo)-3-(3-methylisothiazol-5-yl)-3-azabicyclo[3.2.1]octan-8-amine (200 mg, 896 µmol), 2-bromo-8-(4-fluoro-2-methylphenyl)-[1,2,4]triazolo[1,5-a]pyridine (274 mg, 896 µmol), xantphos (82.9 mg, 143 µmol), tris(dibenzylideneacetone)dipalladium (0) chloroform adduct (74.2 mg, 71.6 µmol) and sodium tert-butoxide (181 mg, 1.88 mmol) were combined with dioxane (20 ml). The vial was capped and heated in the microwave at 150° C. for 30 minutes. Chromatography (silica gel, 12 g, ethyl acetate/heptane=20:80 to 100:0) yielded the title compound as light brown solid (277 mg, 69%). MS: m/z=449.2 [M+H]$^+$.

c) 8-(4-Fluoro-2-methylphenyl)-N-[(8-endo)-3-(3-methyl-1,2-thiazol-5-yl)-3-azabicyclo[3.2.1]octan-8-yl]-5,6,7,8-tetrahydro-[1,2,4]triazolo[1,5-a]pyridin-2-amine

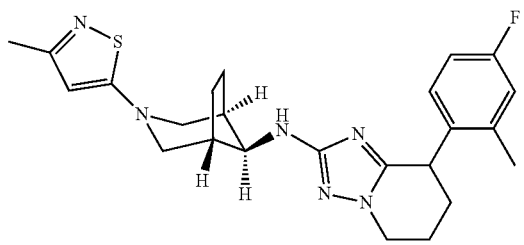

In a 50 mL round-bottomed flask, 8-(4-fluoro-2-methylphenyl)-N-((8-endo)-3-(3-methylisothiazol-5-yl)-3-azabicyclo[3.2.1]octan-8-yl)-[1,2,4]triazolo[1,5-a]pyridin-2-amine (240 mg, 535 µmol), magnesium (104 mg, 4.28 mmol) and iodine (13.6 mg, 53.5 µmol) were combined with methanol (20 ml) and tetrahydrofurane (10 ml) to give a light brown suspension. The reaction mixture was heated at 80° C. for 2 hours. Iodine (13.6 mg, 53.5 µmol) and magnesium (104 mg, 4.28 mmol) were added again and the reaction was stirred for 1 day at 80° C. The mixture was cooled to room temperature and filtered. Magnesium (104 mg, 4.28 mmol) and iodine (13.6 mg, 53.5 µmol) were added again. The reaction was heated to 80° C. and stirred for 1 day. The reaction was cooled to room temperature and filtered. Chromatography (silica gel, 12 g, ethyl acetate/heptane=65:35 to 100:0) yielded the title compound as orange solid (111 mg, 41%). MS: m/z=453.2 [M+H]$^+$.

EXAMPLE 23b (−)-8-(4-Fluoro-2-methylphenyl)-N-[(8-endo)-3-(3-methyl-1,2-thiazol-5-yl)-3-azabicyclo[3.2.1]octan-8-yl]-5,6,7,8-tetrahydro-[1,2,4]triazolo[1,5-a]pyridin-2-amine

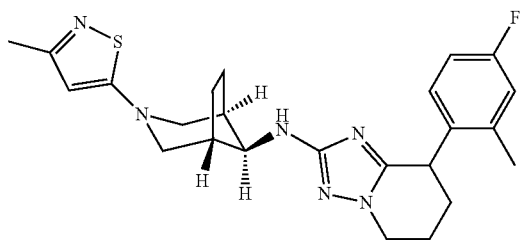

Chromatography of the racemic 8-(4-fluoro-2-methylphenyl)-N-[(8-endo)-3-(3-methyl-1,2-thiazol-5-yl)-3-azabicyclo[3.2.1]octan-8-yl]-5,6,7,8-tetrahydro-[1,2,4]triazolo[1,5-a]pyridin-2-amine (example 23a) on Reprosil Chiral NR (ethanol/heptane=40:60) yielded the title compound as off-white solid (21.3 mg, 43%). MS: m/z=453.3 [M+H]$^+$.

EXAMPLE 23c (+)-8-(4-Fluoro-2-methylphenyl)-N-[(8-endo)-3-(3-methyl-1,2-thiazol-5-yl)-3-azabicyclo[3.2.1]octan-8-yl]-5,6,7,8-tetrahydro-[1,2,4]triazolo[1,5-a]pyridin-2-amine

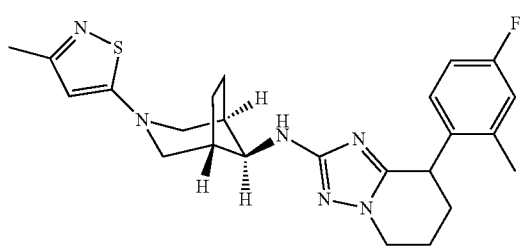

Chromatography of the racemic 8-(4-fluoro-2-methylphenyl)-N-[(8-endo)-3-(3-methyl-1,2-thiazol-5-yl)-3-azabicyclo[3.2.1]octan-8-yl]-5,6,7,8-tetrahydro-[1,2,4]triazolo[1,5-a]pyridin-2-amine (example 23a) on Reprosil Chiral NR (ethanol/heptane=40:60) yielded the title compound as off-white solid (21.3 mg, 43%). MS: m/z=453.3 [M+H]$^+$.

EXAMPLE 24

(−)-N-((8-endo)-3-(3-Methyl-1,2,4-oxadiazol-5-yl)-3-azabicyclo[3.2.1]octan-8-yl)-8-(2,3,4-trifluorophenyl)-5,6,7,8-tetrahydro-[1,2,4]triazolo[1,5-a]pyridin-2-amine

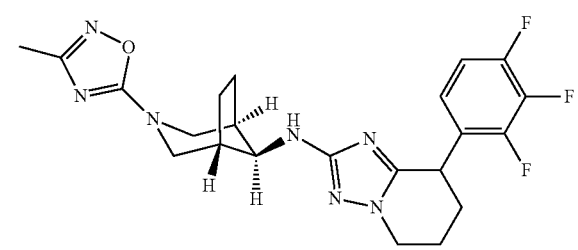 [SMILES: Cc1noc(N2C[C@H]3CC[C@@H](C2)[C@@H]3Nc2nc3n(n2)CCCC3c2ccc(F)c(F)c2F)n1]

a) (8-endo)-tert-Butyl 8-((8-(2,3,4-trifluorophenyl)-[1,2,4]triazolo[1,5-a]pyridin-2-yl)amino)-3-azabicyclo[3.2.1]octane-3-carboxylate

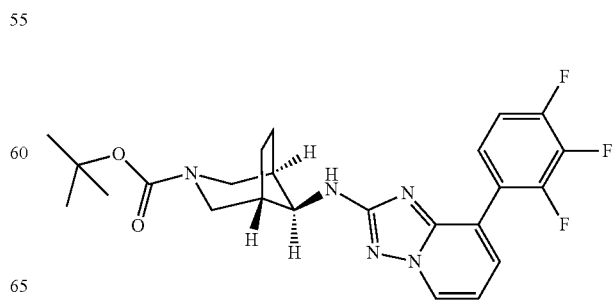

In a microwave vial, (8-endo)-tert-butyl-8-amino-3-azabicyclo[3.2.1]octane-3-carboxylate (CAS1310381-28-2, 1.1 g, 4.88 mmol), 2-bromo-8-(2,3,4-trifluorophenyl)-[1,2,4]triazolo[1,5-a]pyridine (1.6 g, 4.88 mmol), xantphos (451 mg, 780 µmol), tris(dibenzylideneacetone)dipalladium (0) chloroform adduct (404 mg, 390 µmol) and sodium tert-butoxide (984 mg, 10.2 mmol) were combined with dioxane (40 ml) to give a black suspension. The vial was capped and heated in the microwave at 145° C. for 30 minutes. Chromatography (silica gel, 50 g, ethyl acetate/heptane=30:70 to 70:30) yielded the title compound as light brown solid (1.48 g, 64%). MS: m/z=474.2 [M+H]⁺.

b) (8-endo)-tert-Butyl 8-((8-(2,3,4-trifluorophenyl)-5,6,7,8-tetrahydro-[1,2,4]triazolo[1,5-a]pyridin-2-yl)amino)-3-azabicyclo[3.2.1]octane-3-carboxylate

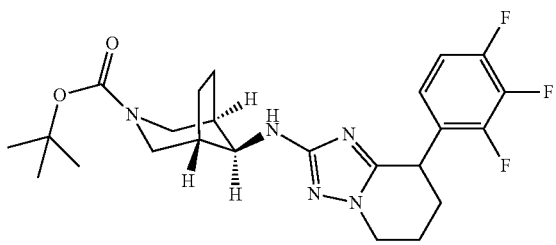 [SMILES: CC(C)(C)OC(=O)N1C[C@H]2CC[C@@H](C1)[C@@H]2Nc1nc2n(n1)CCCC2c1ccc(F)c(F)c1F]

In a 500 mL round-bottomed flask, (8-endo)-tert-butyl 8-((8-(2,3,4-trifluorophenyl)-[1,2,4]triazolo[1,5-a]pyridin-2-yl)amino)-3-azabicyclo[3.2.1]octane-3-carboxylate (1.47 g, 3.1 mmol), magnesium (604 mg, 24.8 mmol) and iodine (7.88 mg, 31 µmol) were combined with methanol (200 ml) and tetrahydrofuran (100 ml) to give a brown suspension. The reaction mixture was heated at 60° C. for 2 hours. Chromatography (Si-amine (Silicycle FLH-R52030B), 12 g, ethyl acetate/heptane=50:50 to 100:0) yielded the title compound as light yellow foam (1.36 g, 92%). MS: m/z=478.3 [M+H]⁺.

c) N-((8-endo)-3-Azabicyclo[3.2.1]octan-8-yl)-8-(2,3,4-trifluorophenyl)-5,6,7,8-tetrahydro-[1,2,4]triazolo[1,5-a]pyridin-2-amine

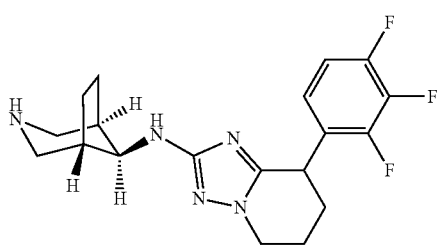 [SMILES: Fc1ccc(C2CCCn3nc(N[C@@H]4[C@@H]5CC[C@H]4CNC5)nc32)c(F)c1F]

In a 150 mL round-bottomed flask, (8-endo)-tert-butyl 8-((8-(2,3,4-trifluorophenyl)-5,6,7,8-tetrahydro-[1,2,4]triazolo[1,5-a]pyridin-2-yl)amino)-3-azabicyclo[3.2.1]octane-3-carboxylate (1.35 g, 2.83 mmol) was combined with dichloromethane (100 ml) to give a light yellow solution. Trifluoroacetic acid (4.64 g, 3.14 ml, 40.7 mmol) was added and stirring was continued at room temperature for 2 hours. The reaction mixture was poured into 15 ml water, basified with aqueous sodium hydroxide (4N) and extracted with dichloromethane (5×100 ml). The organic layers were dried over sodium sulfate and the solvent was removed in vacuo to yield the title compound as light brown solid (915 mg, 86%). MS: m/z=378.2 [M+H]⁺.

d) (8-endo)-8-((8-(2,3,4-Trifluorophenyl)-5,6,7,8-tetrahydro-[1,2,4]triazolo[1,5-a]pyridin-2-yl)amino)-3-azabicyclo[3.2.1]octane-3-carbonitrile

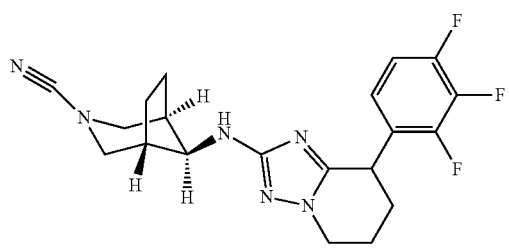 [SMILES: N#CN1C[C@H]2CC[C@@H](C1)[C@@H]2Nc1nc2n(n1)CCCC2c1ccc(F)c(F)c1F]

In a 100 mL round-bottomed flask, N-((8-endo)-3-azabicyclo[3.2.1]octan-8-yl)-8-(2,3,4-trifluorophenyl)-5,6,7,8-tetrahydro-[1,2,4]triazolo[1,5-a]pyridin-2-amine (915 mg, 2.42 mmol) and sodium bicarbonate (224 mg, 2.67 mmol) were combined with ethanol (35 ml) to give a light brown suspension. Cyanic bromide (282 mg, 2.67 mmol) was added and stirring was continued at room temperature overnight. The reaction mixture was filtered through sintered glass, concentrated and dried in vacuo to yield the title compound (MS: m/z=403.2 [M+H]⁺) as light brown solid which was used in the next step without further purification.

e) (−)-N-((8-endo)-3-(3-Methyl-1,2,4-oxadiazol-5-yl)-3-azabicyclo[3.2.1]octan-8-yl)-8-(2,3,4-trifluorophenyl)-5,6,7,8-tetrahydro-[1,2,4]triazolo[1,5-a]pyridin-2-amine

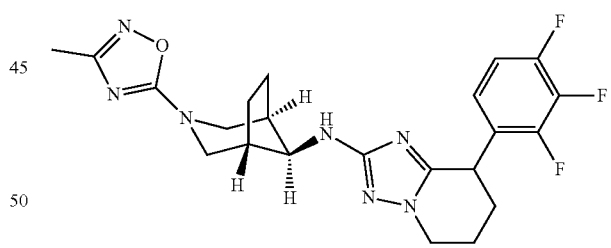

In a 100 mL round-bottomed flask, (8-endo)-8-((8-(2,3,4-trifluorophenyl)-5,6,7,8-tetrahydro-[1,2,4]triazolo[1,5-a]pyridin-2-yl)amino)-3-azabicyclo[3.2.1]octane-3-carbonitrile (976 mg, 2.43 mmol) was combined with ethanol (47 ml) to give a light yellow solution. (E)-N'-hydroxyacetimidamide (216 mg, 2.91 mmol) was added followed by zinc chloride (397 mg, 2.91 mmol, dried in vacuo and heating) in ethanol (5 ml). The reaction mixture was stirred at room temperature for 2 hours and then hydrochloric acid (606 µl, 7.28 mmol) was added. The mixture was heated at 60° C. for 5 hours. The reaction mixture was concentrated in vacuo, poured into 50 ml saturated aqueous sodiumbicarbonate. Extraction with dichloromethane (5×100 ml) and chromatography (Si-amine, 80 g, ethyl acetate/heptane=50:50 to 100:0) yielded the racemic N-((8-endo)-3-(3-methyl-1,2,4-oxadiazol-5-yl)-3-azabicyclo[3.2.1]octan-8-yl)-8-(2,3,4-trifluorophenyl)-5,6,7,8-tetrahydro-[1,2,4]triazolo[1,5-a]pyridin-2-amine. HPLC (Chiralpeak AD. heptane/isopropanol=60:40) and trituration with diethyl ether/pentane (1 ml/2 ml) yielded the title compound as off-white solid (272 mg, 24%), MS: m/z=460.3 [M+H]$^+$ and the corresponding enantiomer (+)-N-((8-endo)-3-(3-methyl-1,2,4-oxadiazol-5-yl)-3-azabicyclo[3.2.1]octan-8-yl)-8-(2,3,4-trifluorophenyl)-5,6,7,8-tetrahydro-[1,2,4]triazolo[1,5-a]pyridin-2-amine (224 mg, 20%) as off-white solid, MS: m/z=460.3 [M+H]$^+$.

EXAMPLE 25a 8-(4-Fluoro-3-(trifluoromethyl)phenyl)-N-((8-endo)-3-(3-methyl-1,2,4-oxadiazol-5-yl)-3-azabicyclo[3.2.1]octan-8-yl)-5,6,7,8-tetrahydro-[1,2,4]triazolo[1,5-a]pyridin-2-amine

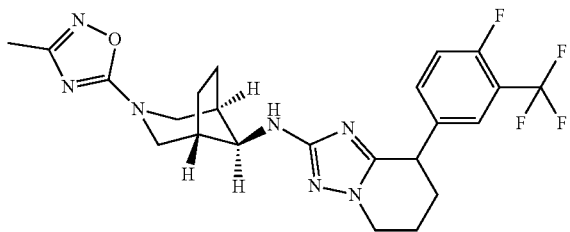 [SMILES: Cc1noc(N2C[C@H]3CC[C@@H](C2)[C@@H]3Nc2nc3n(n2)CCCC3c2ccc(F)c(C(F)(F)F)c2)n1]

a) (8-endo)-tert-Butyl 8-((8-(4-fluoro-3-(trifluoromethyl)phenyl)-[1,2,4]triazolo[1,5-a]pyridin-2-yl)amino)-3-azabicyclo[3.2.1]octane-3-carboxylate

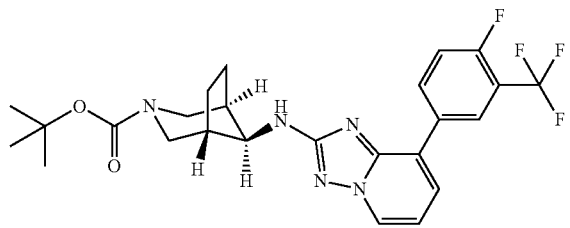 [SMILES: CC(C)(C)OC(=O)N1C[C@H]2CC[C@@H](C1)[C@@H]2Nc1nc2c(-c3ccc(F)c(C(F)(F)F)c3)cccn2n1]

To a 20 ml microwave vial was added (8-endo)-tert-butyl-8-amino-3-azabicyclo[3.2.1]octane-3-carboxylate (250 mg, 1.1 mmol), sodium tert-butoxide (319 mg, 3.31 mmol) and 2-bromo-8-(4-fluoro-3-(trifluoromethyl)phenyl)-[1,2,4]triazolo[1,5-a]pyridine (438 mg, 1.22 mmol) in dioxane (12 ml). Xantphos (102 mg, 177 µmol) and tris(dibenzylideneacetone)dipalladium (0) chloroform adduct (91.5 mg, 88.4 µmol) were added. The reaction mixture was heated in a microwave at 145° C. for 30 minutes. Chromatography (silica gel, 20 g, ethyl acetate/heptane=20:80 to 100:0) yielded the title compound as orange foam (454 mg, 81%). MS: m/z=506.2 [M+H]$^+$.

b) N-((8-endo)-3-Azabicyclo[3.2.1]octan-8-yl)-8-(4-fluoro-3-(trifluoromethyl)phenyl)-[1,2,4]triazolo[1,5-a]pyridin-2-amine

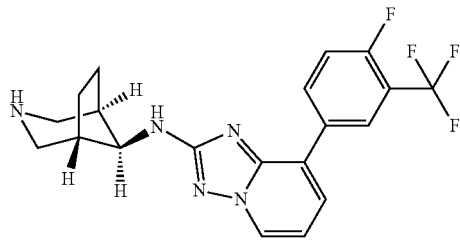 [SMILES: Fc1ccc(-c2cccn3nc(N[C@@H]4[C@@H]5CC[C@H]4CNC5)nc23)cc1C(F)(F)F]

In a 25 ml round-bottomed flask, (8-endo)-tert-butyl 8-((8-(4-fluoro-3-(trifluoromethyl)phenyl)-[1,2,4]triazolo[1,5-a]pyridin-2-yl)amino)-3-azabicyclo[3.2.1]octane-3-carboxylate (456 mg, 902 mol) was combined with dichloromethane (10 ml) to give a light brown solution. Trifluoroacetic acid (1.03 g, 695 µl, 9.02 mmol) was added and stirring was continued at room temperature for 3 hours. The reaction mixture was poured into 15 ml water, basified with aqueous sodium hydroxide (2N) and extracted with dichloromethane (5×25 ml). The organic layers were dried over sodium sulfate, concentrated and dried in vacuo to yield the title compound as light brown solid (365 mg, quant.). MS: m/z=406.2 [M+H]$^+$.

c) (8-endo)-8-((8-(4-Fluoro-3-(trifluoromethyl)phenyl)-[1,2,4]triazolo[1,5-a]pyridin-2-yl)amino)-3-azabicyclo[3.2.1]octane-3-carbonitrile

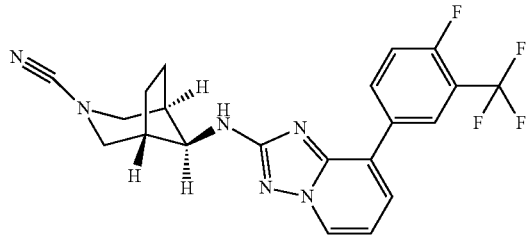 [SMILES: N#CN1C[C@H]2CC[C@@H](C1)[C@@H]2Nc1nc2c(-c3ccc(F)c(C(F)(F)F)c3)cccn2n1]

In a 25 ml round-bottomed flask, N-((8-endo)-3-azabicyclo[3.2.1]octan-8-yl)-8-(4-fluoro-3-(trifluoromethyl)phenyl)-[1,2,4]triazolo[1,5-a]pyridin-2-amine (360 mg, 888 µmol) and sodium bicarbonate (82.1 mg, 977 µmol) were combined with ethanol (10 ml) to give a light brown suspension. Cyanic bromide (103 mg, 977 µmol) was added and stirring was continued at room temperature overnight. The reaction mixture was filtered through sintered glass and the organic phase was concentrated and dried in vacuo to yield the title compound as light brown solid (379 mg, quant.). MS: m/z=431.2 [M+H]$^+$.

d) 8-(4-Fluoro-3-(trifluoromethyl)phenyl)-N-((8-endo)-3-(3-methyl-1,2,4-oxadiazol-5-yl)-3-azabicyclo[3.2.1]octan-8-yl)-[1,2,4]triazolo[1,5-a]pyridin-2-amine

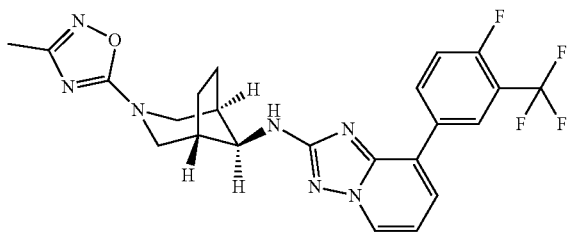 [SMILES: Cc1noc(N2C[C@H]3CC[C@@H](C2)[C@@H]3Nc2nc3c(-c4ccc(F)c(C(F)(F)F)c4)cccn3n2)n1]

In a 25 mL round-bottomed flask, (8-endo)-8-((8-(4-fluoro-3-(trifluoromethyl)phenyl)-[1,2,4]triazolo[1,5-a]pyridin-2-yl)amino)-3-azabicyclo[3.2.1]octane-3-carbonitrile (375 mg, 871 mol) was combined with ethanol (15 ml) to give a light yellow solution. (E)-N'-Hydroxyacetimidamide (77.5 mg, 1.05 mmol) was added followed by zinc chloride (142 mg, 1.05 mmol, dried under HV and heating) in ethanol (1 ml). The reaction mixture was stirred at room temperature overnight and then hydrochloric acid (218 μl, 2.61 mmol) was added. The reaction mixture was heated at 60° C. for 5 hours. The reaction mixture was concentrated in vacuo, poured into 10 ml saturated aqueous bicarbonate and extracted with dichloromethane (5×25 ml). Chromatography (Si-amine, 12 g, ethyl acetate/heptane=50:50 to 100:0) yielded the title compound as light brown solid (276 mg, 65%). MS: m/z=488.2 [M+H]+.

e) 8-(4-Fluoro-3-(trifluoromethyl)phenyl)-N-((8-endo)-3-(3-methyl-1,2,4-oxadiazol-5-yl)-3-azabicyclo[3.2.1]octan-8-yl)-5,6,7,8-tetrahydro-[1,2,4]triazolo[1,5-a]pyridin-2-amine

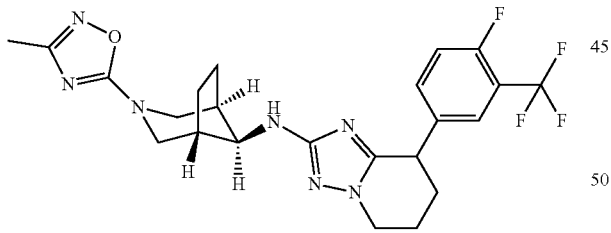

In a 25 ml round-bottomed flask, 8-(4-fluoro-3-(trifluoromethyl)phenyl)-N-((8-endo)-3-(3-methyl-1,2,4-oxadiazol-5-yl)-3-azabicyclo[3.2.1]octan-8-yl)-[1,2,4]triazolo[1,5-a]pyridin-2-amine (265 mg, 544 μmol), magnesium (106 mg, 4.35 mmol) and iodine (1.38 mg, 5.44 μmol) were combined with methanol (10 ml) and tetrahydrofurane (5 ml) to give a dark red suspension. The reaction mixture was heated at 80° C. for 2 hours. Iodine (1.38 mg, 5.44 μmol) was added again and stirring was continued at 80° C. overnight. Chromatography (Si-Amine, 12 g, ethyl acetate/heptane=50:50 to 100:0) yielded the title compound as off-white solid (124 mg, 46%). MS: m/z=492.2 [M+H]+.

EXAMPLE 25b (−)-8-(4-Fluoro-3-(trifluoromethyl)phenyl)-N-((8-endo)-3-(3-methyl-1,2,4-oxadiazol-5-yl)-3-azabicyclo[3.2.1]octan-8-yl)-5,6,7,8-tetrahydro-[1,2,4]triazolo[1,5-a]pyridin-2-amine

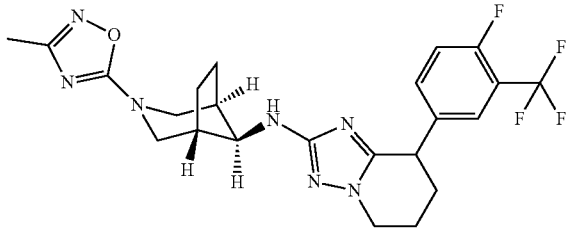 [SMILES: Cc1noc(N2C[C@H]3CC[C@@H](C2)[C@@H]3Nc2nc3n(n2)CCCC3c2ccc(F)c(C(F)(F)F)c2)n1]

Chromatography of the racemic 8-(4-fluoro-3-(trifluoromethyl)phenyl)-N-((8-endo)-3-(3-methyl-1,2,4-oxadiazol-5-yl)-3-azabicyclo[3.2.1]octan-8-yl)-5,6,7,8-tetrahydro-[1,2,4]triazolo[1,5-a]pyridin-2-amine (example 25a) on Reprosil Chiral NR (ethanol/heptane=40:60) and vacuo and trituration with diethyl ether/pentane (0.5 ml/1 ml) yielded the title compound as off-white solid (36 mg, 30%), MS: m/z=492.2 [M+H]+, together with the corresponding enantiomer (+)-8-(4-fluoro-3-(trifluoromethyl)phenyl)-N-((8-endo)-3-(3-methyl-1,2,4-oxadiazol-5-yl)-3-azabicyclo[3.2.1]octan-8-yl)-5,6,7,8-tetrahydro-[1,2,4]triazolo[1,5-a]pyridin-2-amine (44 mg, 37%) as off white solid, MS: m/z=492.3 [M+H]+.

EXAMPLE 26a

N-((8-endo)-3-(3-Methyl-1,2,4-oxadiazol-5-yl)-3-azabicyclo[3.2.1]octan-8-yl)-8-(4-(trifluoromethyl)phenyl)-5,6,7,8-tetrahydro-[1,2,4]triazolo[1,5-a]pyridin-2-amine

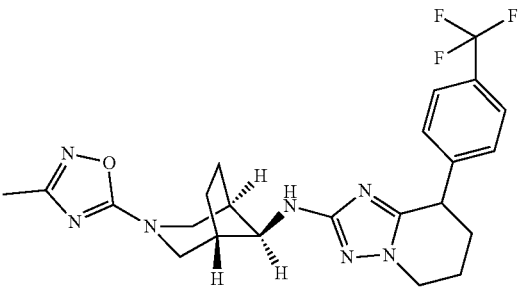 [SMILES: Cc1noc(N2C[C@H]3CC[C@@H](C2)[C@@H]3Nc2nc3n(n2)CCCC3c2ccc(C(F)(F)F)cc2)n1]

a) (8-endo)-tert-Butyl 8-((8-bromo-[1,2,4]triazolo[1,5-a]pyridin-2-yl)amino)-3-azabicyclo[3.2.1]octane-3-carboxylate

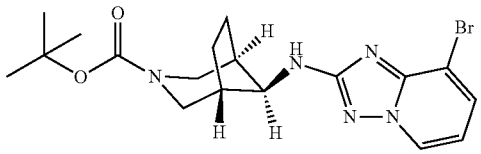 [SMILES: CC(C)(C)OC(=O)N1C[C@H]2CC[C@@H](C1)[C@@H]2Nc1nc2c(Br)cccn2n1]

To a solution of 8-bromo-2-chloro-[1,2,4]triazolo[1,5-a]pyridine (CAS1257705-04-6, 800 mg, 3.44 mmol) and (8-endo)-tert-butyl-8-amino-3-azabicyclo[3.2.1]octane-3-carboxylate (857 mg, 3.79 mmol) in dimethylsulfoxide (20 ml) was added cesium fluoride (4.18 g, 27.5 mmol). The reaction mixture was stirred in a sealed tube at 130° C. for 4 days. Diethyl ether and water were added. The organic layers were separated, dried over magnesium sulfate and evaporated. The crude material was purified by chromatography (silica gel, 40 g, ethyl acetate/heptane=0:100 to 50:50) to yield the title compound as off-white solid (1.73 g, quant.). MS: m/z=422.1 and 424.1 [M+H]$^+$.

b) N-((8-endo)-3-Azabicyclo[3.2.1]octan-8-yl)-8-bromo-[1,2,4]triazolo[1,5-a]pyridin-2-amine

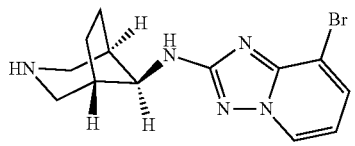 [SMILES: Brc1cccn2nc(N[C@@H]3[C@@H]4CC[C@H]3CNC4)nc12]

In a 250 ml round-bottomed flask, (8-endo)-tert-butyl 8-((8-bromo-[1,2,4]triazolo[1,5-a]pyridin-2-yl)amino)-3-azabicyclo[3.2.1]octane-3-carboxylate (1.73 g, 3.69 mmol) was combined with dichloromethane (100 ml) to give a light yellow solution. Trifluoroacetic acid (4.2 g, 2.84 ml, 36.9 mmol) was added and stirring was continued at room temperature overnight. The reaction mixture was poured into 100 ml water, basified with aqueous sodium hydroxide (4N, 30 ml) and extracted with dichloromethane (3×100 ml). The organic layers were dried over sodium sulfate and concentrated in vacuo to yield the title compound as off-white solid (1.18 g, 99%). MS: m/z=322.0 and 324.0 [M+H]$^+$.

c) (8-endo)-8-((8-Bromo-[1,2,4]triazolo[1,5-a]pyridin-2-yl)amino)-3-azabicyclo[3.2.1]octane-3-carbonitrile

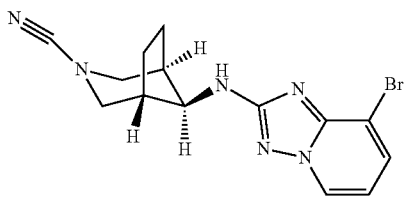 [SMILES: N#CN1C[C@H]2CC[C@@H](C1)[C@@H]2Nc1nc2c(Br)cccn2n1]

In a 50 ml round-bottomed flask, N-((8-endo)-3-azabicyclo[3.2.1]octan-8-yl)-8-bromo-[1,2,4]triazolo[1,5-a]pyridin-2-amine (1.17 g, 3.63 mmol) and sodium bicarbonate (336 mg, 3.99 mmol) were combined with ethanol (27 ml) to give a white suspension. Cyanic bromide (423 mg, 3.99 mmol) was added and stirring was continued at room temperature overnight. Chromatography (Si-Amine, 50 g, ethyl acetate/heptane=60:40 to 100:0) yielded the title compound as white solid (1.12 g, 89%). MS: m/z=347.0 and 349.0 [M+H]$^+$.

d) 8-Bromo-N-((8-endo)-3-(3-methyl-1,2,4-oxadiazol-5-yl)-3-azabicyclo[3.2.1]octan-8-yl)-[1,2,4]triazolo[1,5-a]pyridin-2-amine

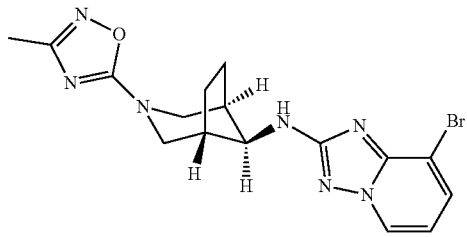 [SMILES: Cc1noc(N2C[C@H]3CC[C@@H](C2)[C@@H]3Nc2nc3c(Br)cccn3n2)n1]

In a 50 round-bottomed flask, (8-endo)-8-((8-bromo-[1,2,4]triazolo[1,5-a]pyridin-2-yl)amino)-3-azabicyclo[3.2.1]octane-3-carbonitrile (1.124 g, 3.24 mmol) was combined with ethanol (25 ml). (E)-N'-Hydroxyacetimidamide (288 mg, 3.88 mmol) was added followed by zinc chloride (529 mg, 3.88 mmol, dried under HV and heating) in ethanol (0.5 ml). The mixture was stirred at room temperature overnight. Hydrochloric acid (809 µl, 9.71 mmol) was added. The reaction mixture was heated at 60° C. for 5 hours and then concentrated in vacuo. The residue was diluted with ethyl acetate (100 ml) and 20 ml saturated aqueous sodium bicarbonate (20 ml) and extracted ethyl acetate. Chromatography (Silica gel, 50 g, ethyl acetate/methanol=90:10 yielded the title compound as off-white solid (1.25 g, 96%). MS: m/z=404.1 and 406.1 [M+H]$^+$.

e) N-((8-endo)-3-(3-Methyl-1,2,4-oxadiazol-5-yl)-3-azabicyclo[3.2.1]octan-8-yl)-8-(4-(trifluoromethyl)phenyl)-[1,2,4]triazolo[1,5-a]pyridin-2-amine

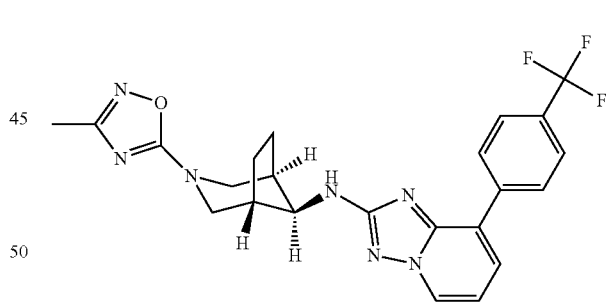

In a 100 ml round-bottomed flask were combined 8-bromo-N-((8-endo)-3-(3-methyl-1,2,4-oxadiazol-5-yl)-3-azabicyclo[3.2.1]octan-8-yl)-[1,2,4]triazolo[1,5-a]pyridin-2-amine (150 mg, 371 µmol), (4-(trifluoromethyl)phenyl)boronic acid (84.6 mg, 445 µmol) and cesium carbonate (242 mg, 742 µmol) in dioxane (40 ml) and water (4 ml) to give a colorless solution. 1,1'-Bis(diphenylphosphino)ferrocene-palladium(II)dichloride dichloromethane complex (27.1 mg, 37.1 µmol) was added. The reaction mixture was stirred for 12 hours at 100° C. Chromatography (silica gel, 20 g, ethyl acetate/heptane=40:60 to 100:0) yielded the title compound as yellow solid (125 mg, 72%). MS: m/z=470.2 [M+H]$^+$.

f) N-((8-endo)-3-(3-Methyl-1,2,4-oxadiazol-5-yl)-3-azabicyclo[3.2.1]octan-8-yl)-8-(4-(trifluoromethyl)phenyl)-5,6,7,8-tetrahydro-[1,2,4]triazolo[1,5-a]pyridin-2-amine

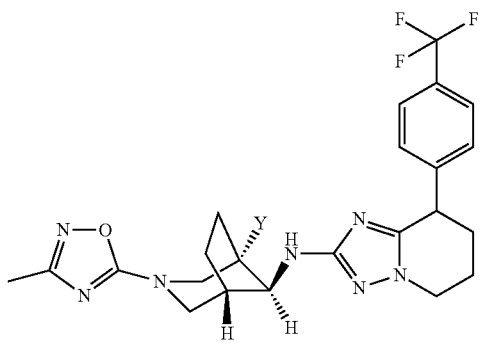

In a 25 ml round-bottomed flask, N-((8-endo)-3-(3-methyl-1,2,4-oxadiazol-5-yl)-3-azabicyclo[3.2.1]octan-8-yl)-8-(4-(trifluoromethyl)phenyl)-[1,2,4]triazolo[1,5-a]pyridin-2-amine (145 mg, 309 µmol), magnesium (60.1 mg, 2.47 mmol) and iodine (784 µg, 3.09 µmol) were combined with methanol (10 ml) and tetrahydrofurane (5 ml) to give a brown suspension. The reaction mixture was heated at 80° C. for 30 minutes. Chromatography (silica gel, 12 g, ethyl acetate/heptane=50:50 to 100:0) yielded the title compound as off-white solid (51 mg, 35%). MS: m/z=474.2 [M+H]$^+$.

Example 26b (−)-N-((8-endo)-3-(3-Methyl-1,2,4-oxadiazol-5-yl)-3-azabicyclo[3.2.1]octan-8-yl)-8-(4-(trifluoromethyl)phenyl)-5,6,7,8-tetrahydro-[1,2,4]triazolo[1,5-a]pyridin-2-amine

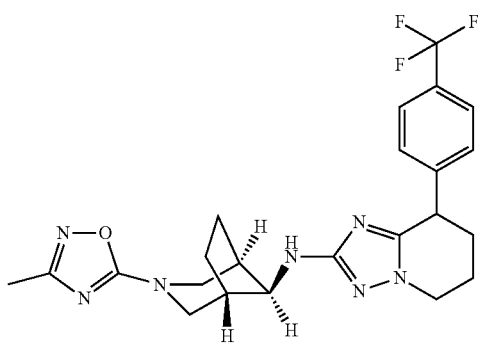 [SMILES: Cc1noc(N2C[C@H]3CC[C@@H](C2)[C@@H]3Nc2nc3n(n2)CCCC3c2ccc(C(F)(F)F)cc2)n1]

Chromatography of the racemic N-((8-endo)-3-(3-methyl-1,2,4-oxadiazol-5-yl)-3-azabicyclo[3.2.1]octan-8-yl)-8-(4-(trifluoromethyl)phenyl)-5,6,7,8-tetrahydro-[1,2,4]triazolo[1,5-a]pyridin-2-amine (example 26a) on Reprosil Chiral NR (ethanol/heptane=40:60) yielded the title compound as off-white solid (12 mg, 26%), MS: m/z=474.2 [M+H]$^+$, and the enantiomer (+)-N-((8-endo)-3-(3-methyl-1,2,4-oxadiazol-5-yl)-3-azabicyclo[3.2.1]octan-8-yl)-8-(4-(trifluoromethyl)phenyl)-5,6,7,8-tetrahydro-[1,2,4]triazolo[1,5-a]pyridin-2-amine as off-white solid (14 mg, 30%), MS: m/z=474.3 [M+H]$^+$.

Example 27a 8-(2-Fluoro-4-(trifluoromethyl)phenyl)-N-((8-endo)-3-(3-methyl-1,2,4-oxadiazol-5-yl)-3-azabicyclo[3.2.1]octan-8-yl)-5,6,7,8-tetrahydro-[1,2,4]triazolo[1,5-a]pyridin-2-amine

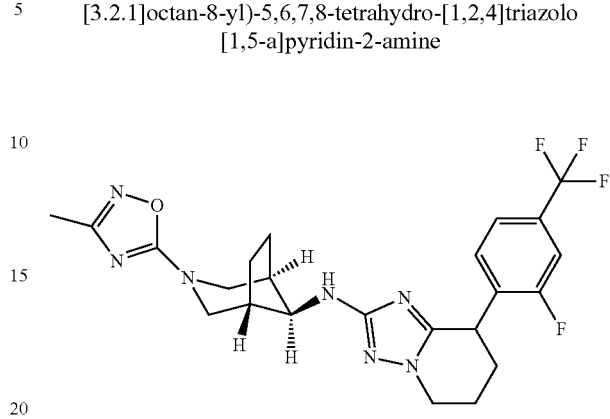

a) (8-endo)-tert-Butyl 8-((8-(2-fluoro-4-(trifluoromethyl)phenyl)-[1,2,4]triazolo[1,5-a]pyridin-2-yl)amino)-3-azabicyclo[3.2.1]octane-3-carboxylate

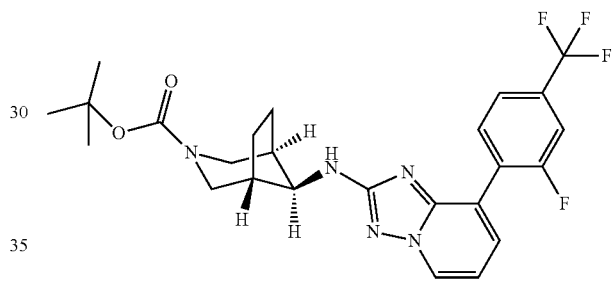

To a solution of (8-endo)-tert-butyl-8-amino-3-azabicyclo[3.2.1]octane-3-carboxylate (240 mg, 1.06 mmol) in dioxane (8 ml) was added 2-bromo-8-(2-fluoro-4-(trifluoromethyl)phenyl)-[1,2,4]triazolo[1,5-a]pyridine (382 mg, 1.06 mmol). Sodium tert-butoxide (306 mg, 3.18 mmol), xantphos (98.2 mg, 170 µmol) and tris(dibenzylideneacetone)dipalladium (0) chloroform adduct (87.8 mg, 84.8 µmol) were added. The vial was capped and heated in the microwave at 145° C. for 30 minutes. Chromatography (silica gel, 70 g, heptane/ethyl acetate=100:0 to 50:50) yielded the title compound as yellow solid (374 mg, 70%). MS: m/z=506.3 [M+H]$^+$.

b) (8-endo)-tert-Butyl 8-((8-(2-fluoro-4-(trifluoromethyl)phenyl)-5,6,7,8-tetrahydro-[1,2,4]triazolo[1,5-a]pyridin-2-yl)amino)-3-azabicyclo[3.2.1]octane-3-carboxylate

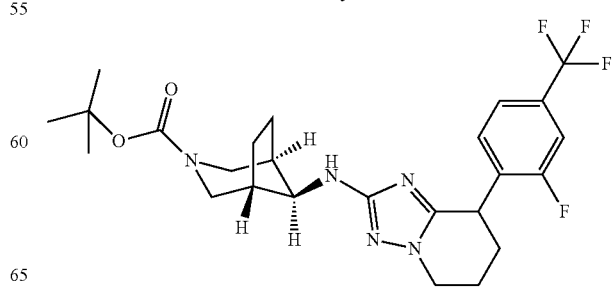

(8-endo)-tert-Butyl 8-((8-(2-fluoro-4-(trifluoromethyl)phenyl)-[1,2,4]triazolo[1,5-a]pyridin-2-yl)amino)-3-azabicyclo[3.2.1]octane-3-carboxylate (371 mg, 734 µmol) was dissolved in methanol (6 ml) and tetrahydrofurane (3 ml) to give a yellow solution. Magnesium (143 mg, 5.87 mmol) and iodine (3.73 mg, 14.7 µmol) were added. The reaction mixture was stirred at 80° C. for 2 hours. Magnesium (70 mg, 2.92 mmol) and iodine (3.73 mg, 14.7 µmol) were added. The reaction mixture was stirred at 80° C. for 4 hours. Again iodine (3.73 mg, 14.7 µmol) was added. The reaction mixture was stirred at 80° C. overnight. Magnesium (30 mg, 1.25 mmol) and iodine (3.73 mg, 14.7 µmol) were added. And stirring was continued at 80° C. for 20 hours. The grey suspension was filtered over dicalite. Chromatography (silica gel, 100 g, heptane/ethyl acetate=100:0 to 0:100) yielded the title compound as yellow solid (177 mg, 47%). MS: m/z=510.4 [M+H]$^+$.

c) N-((8-endo)-3-Azabicyclo[3.2.1]octan-8-yl)-8-(2-fluoro-4-(trifluoromethyl)phenyl)-5,6,7,8-tetrahydro-[1,2,4]triazolo[1,5-a]pyridin-2-amine

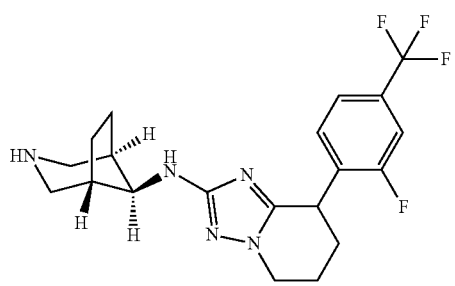 [SMILES: Fc1cc(C(F)(F)F)ccc1C1CCCn2nc(N[C@@H]3[C@@H]4CC[C@H]3CNC4)nc21]

(8-endo)-tert-Butyl 8-((8-(2-fluoro-4-(trifluoromethyl)phenyl)-5,6,7,8-tetrahydro-[1,2,4]triazolo[1,5-a]pyridin-2-yl)amino)-3-azabicyclo[3.2.1]octane-3-carboxylate (177 mg, 347 µmol) was dissolved in dichloromethane (4 ml). Trifluoroacetic acid (396 mg, 268 µl, 3.47 mmol) was added. The reaction mixture was stirred at room temperature overnight. Chromatography (silica gel, 50 g, dichloromethane/methanol=100:0 to 90:10) yielded the title compound as yellow solid (140 mg, 98%). MS: m/z=410.2 [M+H]$^+$.

d) (8-endo)-8-((8-(2-Fluoro-4-(trifluoromethyl)phenyl)-5,6,7,8-tetrahydro-[1,2,4]triazolo[1,5-a]pyridin-2-yl)amino)-3-azabicyclo[3.2.1]octane-3-carbonitrile

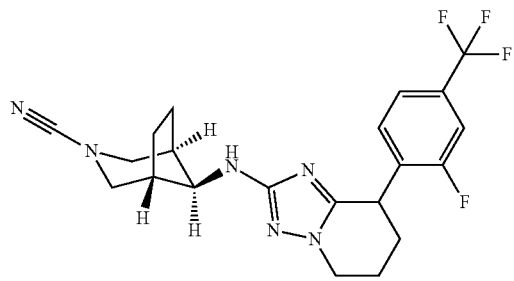 [SMILES: N#CN1C[C@H]2CC[C@@H](C1)[C@@H]2Nc1nc2n(n1)CCCC2c1ccc(C(F)(F)F)cc1F]

To a solution of N-((8-endo)-3-azabicyclo[3.2.1]octan-8-yl)-8-(2-fluoro-4-(trifluoromethyl)phenyl)-5,6,7,8-tetrahydro-[1,2,4]triazolo[1,5-a]pyridin-2-amine (140 mg, 342 mol) in ethanol (3 ml) was added sodium bicarbonate (31.6 mg, 376 µmol) and cyanic bromide (41.1 mg, 376 µmol). The reaction mixture was stirred at room temperature overnight. Chromatography (silica gel, 20 g, heptane/ethyl acetate=100:0 to 0:100) yielded the title compound as yellow oil (130 mg, 88%). MS: m/z=435.3 [M+H]$^+$.

e) 8-(2-Fluoro-4-(trifluoromethyl)phenyl)-N-((8-endo)-3-(3-methyl-1,2,4-oxadiazol-5-yl)-3-azabicyclo[3.2.1]octan-8-yl)-5,6,7,8-tetrahydro-[1,2,4]triazolo[1,5-a]pyridin-2-amine

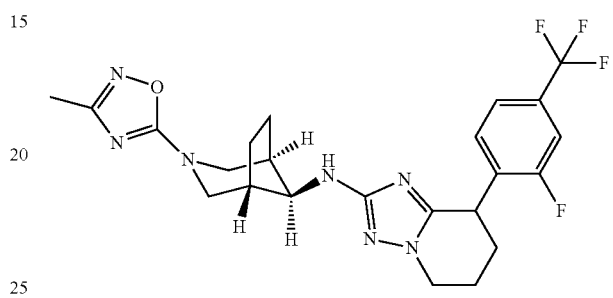

(8-endo)-8-((8-(2-Fluoro-4-(trifluoromethyl)phenyl)-5,6,7,8-tetrahydro-[1,2,4]triazolo[1,5-a]pyridin-2-yl)amino)-3-azabicyclo[3.2.1]octane-3-carbonitrile (130 mg, 299 µmol) was dissolved in ethanol (6 ml), N-hydroxyacetimidamide (27.1 mg, 359 µmol) was added. Then a solution of zinc chloride (49.9 mg, 359 µmol, dried under vacuum and heating) in ethanol (1 ml) was added. The reaction mixture was stirred at room temperature overnight. After 21.5 hours hydrochloric acid (37%, 74.8 µl, 898 µmol) was added. The reaction mixture was stirred at 65° C. The crude reaction mixture was concentrated in vacuo. The residue was taken up in 2 ml saturated aqueous sodium bicarbonate and was extracted with ethyl acetate (3×20 ml). RP-HPLC (Gemini NX 3u, acetonitrile/triethylamine=98:2) yielded the title compound as light yellow waxy solid (54 mg, 95%). MS: m/z=492.2 [M+H]$^+$.

Example 27b (−)-8-(2-Fluoro-4-(trifluoromethyl)phenyl)-N-((8-endo)-3-(3-methyl-1,2,4-oxadiazol-5-yl)-3-azabicyclo[3.2.1]octan-8-yl)-5,6,7,8-tetrahydro-[1,2,4]triazolo[1,5-a]pyridin-2-amine

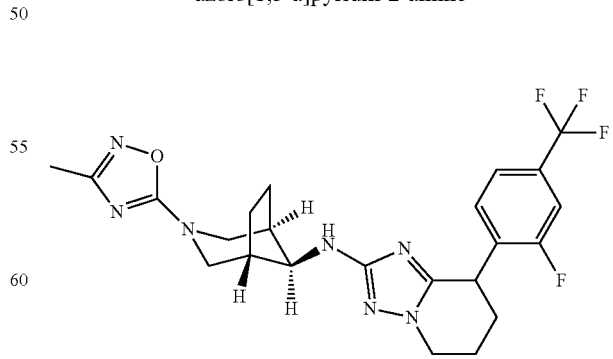

Chromatography of the racemic 8-(2-fluoro-4-(trifluoromethyl)phenyl)-N-((8-endo)-3-(3-methyl-1,2,4-oxadiazol-5-yl)-3-azabicyclo[3.2.1]octan-8-yl)-5,6,7,8-tetrahydro-[1,2,4]triazolo[1,5-a]pyridin-2-amine (example 27a) on Reprosil Chiral NR (ethanol/heptane=20:80) yielded the title compound as white solid (23 mg, 43%). MS: m/z=492.3 [M+H]+, and the corresponding enantiomer (+)-8-(2-fluoro-4-(trifluoromethyl)phenyl)-N-((8-endo)-3-(3-methyl-1,2,4-oxadiazol-5-yl)-3-azabicyclo[3.2.1]octan-8-yl)-5,6,7,8-tetrahydro-[1,2,4]triazolo[1,5-a]pyridin-2-amine as white solid (23 mg, 43%), MS: m/z=492.3 [M+H]+.

Example 28a

N-((8-endo)-3-(3-Methyl-1,2,4-oxadiazol-5-yl)-3-azabicyclo[3.2.1]octan-8-yl)-8-(4-(trifluoromethoxy)phenyl)-5,6,7,8-tetrahydro-[1,2,4]triazolo[1,5-a]pyridin-2-amine

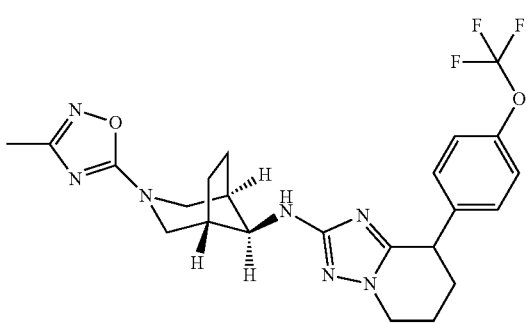 [SMILES: Cc1noc(N2C[C@H]3CC[C@@H](C2)[C@@H]3Nc2nc3n(n2)CCCC3c2ccc(OC(F)(F)F)cc2)n1]

a) (8-endo)-tert-Butyl 8-((8-(4-(trifluoromethoxy)phenyl)-[1,2,4]triazolo[1,5-a]pyridin-2-yl)amino)-3-azabicyclo[3.2.1]octane-3-carboxylate

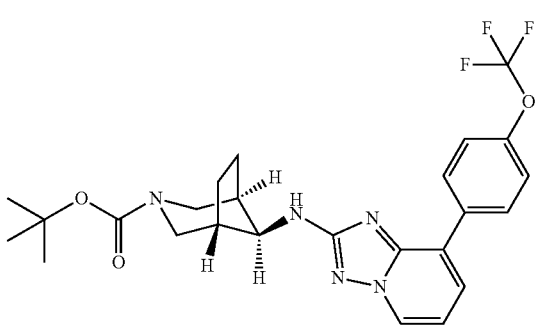 [SMILES: CC(C)(C)OC(=O)N1C[C@H]2CC[C@@H](C1)[C@@H]2Nc1nc2c(-c3ccc(OC(F)(F)F)cc3)cccn2n1]

In a microwave vial, (8-endo)-tert-butyl-8-amino-3-azabicyclo[3.2.1]octane-3-carboxylate (350 mg, 1.55 mmol), 2-bromo-8-(4-(trifluoromethoxy)phenyl)-[1,2,4]triazolo[1,5-a]pyridine (609 mg, 1.7 mmol) and sodium tert-butylate (446 mg, 4.64 mmol) were dissolved in dioxane (12 ml). Xantphos (143 mg, 247 μmol) and tris(dibenzylideneacetone)dipalladium (0) chloroform adduct (128 mg, 124 μmol) were added. The reaction mixture was heated in a microwave at 145° C. for 30 minutes. Chromatography (silica gel, 70 g, heptane/ethyl acetate=100:0 to 60:40) yielded the title compound as yellow solid (547 mg, 70%). MS: m/z=504.3 [M+H]+.

b) N-((8-endo)-3-Azabicyclo[3.2.1]octan-8-yl)-8-(4-(trifluoromethoxy)phenyl)-[1,2,4]triazolo[1,5-a]pyridin-2-amine

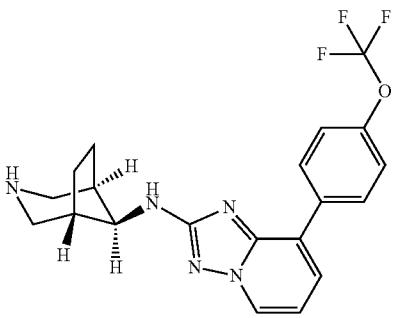 [SMILES: FC(F)(F)Oc1ccc(-c2cccn3nc(N[C@@H]4[C@@H]5CC[C@H]4CNC5)nc23)cc1]

To a yellow solution of (8-endo)-tert-butyl 8-((8-(4-(trifluoromethoxy)phenyl)-[1,2,4]triazolo[1,5-a]pyridin-2-yl)amino)-3-azabicyclo[3.2.1]octane-3-carboxylate (543 mg, 1.08 mmol) in dichloromethane (10 ml) was added trifluoroacetic acid (1.23 g, 831 μl, 10.8 mmol). The reaction mixture was stirred at room temperature for 6 hours. Chromatography (Si-amine, 50 g, heptane/ethyl acetate=100:0 to 40:60) yielded the title compound as light yellow liquid (365 mg, 84%). MS: m/z=404.2 [M+H]+.

c) (8-endo)-8-((8-(4-(Trifluoromethoxy)phenyl)-[1,2,4]triazolo[1,5-a]pyridin-2-yl)amino)-3-azabicyclo[3.2.1]octane-3-carbonitrile N-((8-endo)-3-azabicyclo[3.2.1]octan-8-yl)-8-(4-(trifluoromethoxy)phenyl)-[1,2,4]triazolo[1,5-a]pyridin-2-amine (362 mg, 897 μmol) was dissolved in ethanol (4 ml). Sodium bicarbonate (82.9 mg, 987 μmol1) and cyanic bromide (108 mg, 987 μmol) were added. The reaction mixture was stirred under argon at room temperature overnight. ion). Cyanic bromide (29.5 mg) and sodium bicarbonate (22.6 mg) were added and stirring was continued at room temperature for 2 hours. Chromatography (silica gel, 50 g, heptane/ethyl acetate=100:0 to 50:50) yielded the title compound as white foam (336 mg, 87%). MS: m/z=429.1 [M+H]+.

d) N-((8-endo)-3-(3-Methyl-1,2,4-oxadiazol-5-yl)-3-azabicyclo[3.2.1]octan-8-yl)-8-(4-(trifluoromethoxy)phenyl)-[1,2,4]triazolo[1,5-a]pyridin-2-amine

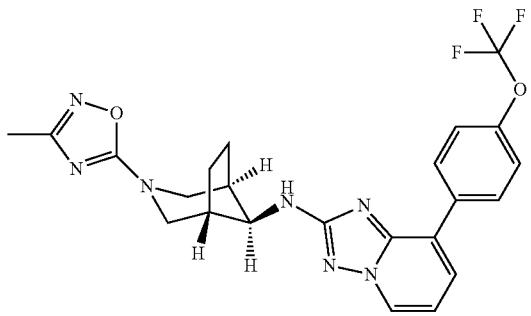 [SMILES: Cc1noc(N2C[C@H]3CC[C@@H](C2)[C@@H]3Nc2nc3c(-c4ccc(OC(F)(F)F)cc4)cccn3n2)n1]

(8-endo)-8-((8-(4-(Trifluoromethoxy)phenyl)-[1,2,4]triazolo[1,5-a]pyridin-2-yl)amino)-3-azabicyclo[3.2.1]octane-3-carbonitrile (274 mg, 640 µmol) was dissolved in ethanol (4 ml). (Z)-N'-Hydroxyacetimidamide (59.8 mg, 767 µmol) was added. Zinc chloride (107 mg, 767 µmol) dissolved in ethanol (1 ml) was added. The reaction mixture was stirred at room temperature overnight. (Z)-N'-Hydroxyacetimidamide (15 mg, 192 µmol, Eq: 0.3) and zink chloride (26.7 mg, 192 µmol) were added. Hydrochloric acid (160 µl, 1.92 mmol) was added. The reaction mixture was stirred at 60° C. for 6 hours. The reaction mixture was concentrated in vacuo. The residue was diluted with 15 ml ethyl acetate and 5 ml saturated aqueous sodium bicarbonate. Extraction with ethyl acetate and chromatography (silica gel, 20 g, heptane/ethyl acetate=100:0 to 30:70) yielded the title compound as white solid (250 mg, 81%). MS: m/z=486.3 [M+H]⁺.

e) N-((8-endo)-3-(3-Methyl-1,2,4-oxadiazol-5-yl)-3-azabicyclo[3.2.1]octan-8-yl)-8-(4-(trifluoromethoxy)phenyl)-5,6,7,8-tetrahydro-[1,2,4]triazolo[1,5-a]pyridin-2-amine

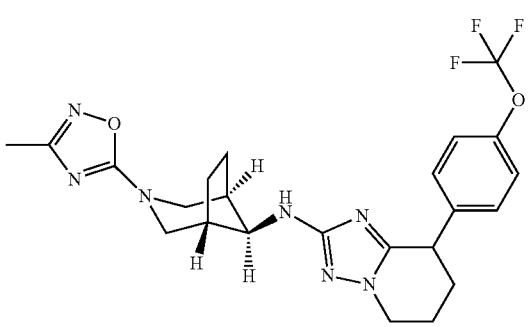 [SMILES: Cc1noc(N2C[C@H]3CC[C@@H](C2)[C@@H]3Nc2nc3n(n2)CCCC3c2ccc(OC(F)(F)F)cc2)n1]

N-((8-endo)-3-(3-Methyl-1,2,4-oxadiazol-5-yl)-3-azabicyclo[3.2.1]octan-8-yl)-8-(4-(trifluoromethoxy)phenyl)-[1,2,4]triazolo[1,5-a]pyridin-2-amine (285 mg, 587 µmol) was dissolved in methanol (8 ml) and tetrahydrofurane (4 ml). Magnesium (114 mg, 4.7 mmol) and iodine (1.49 mg, 5.87 µmol) were added. The light brown reaction mixture was stirred at 80° C. for 4 hours. Magnesium (57 mg) and iodine (2 mg) were added. The reaction mixture was stirred at 80° C. overnight. Chromatogyraphy (Si-amine, 50 g, heptane/ethyl acetate=100:0 to 60:40) yielded the title compound as white solid (220 mg, 77%). MS: m/z=490.4 [M+H]⁺.

Example 28b (−)-N-((8-endo)-3-(3-Methyl-1,2,4-oxadiazol-5-yl)-3-azabicyclo[3.2.1]octan-8-yl)-8-(4-(trifluoromethoxy)phenyl)-5,6,7,8-tetrahydro-[1,2,4]triazolo[1,5-a]pyridin-2-amine

Chromatography of the racemic N-((8-endo)-3-(3-methyl-1,2,4-oxadiazol-5-yl)-3-azabicyclo[3.2.1]octan-8-yl)-8-(4-(trifluoromethoxy)phenyl)-5,6,7,8-tetrahydro-[1,2,4]triazolo[1,5-a]pyridin-2-amine (example 29a) on Chiralpak AD (ethanol/heptane=40:60) yielded the title compound as white solid (57 mg, 26%). MS: m/z=490.3 [M+H]⁺, and the corresponding enantiomer (+)-N-((8-endo)-3-(3-methyl-1,2,4-oxadiazol-5-yl)-3-azabicyclo[3.2.1]octan-8-yl)-8-(4-(trifluoromethoxy)phenyl)-5,6,7,8-tetrahydro-[1,2,4]triazolo[1,5-a]pyridin-2-amine as white solid (80 mg, 36%), MS: m/z=490.3 [M+H]⁺.

Example 29a

N-((8-endo)-3-(3-Methyl-1,2,4-oxadiazol-5-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine

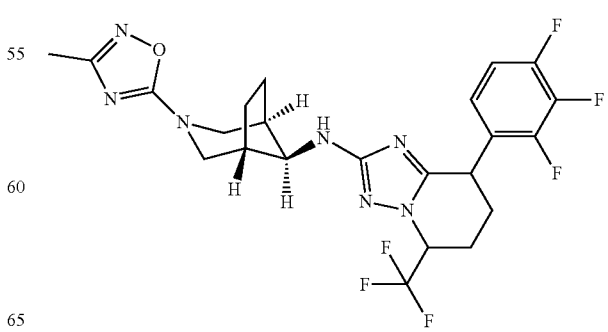

115 a) Ethyl-N-[[3-bromo-6-(trifluoromethyl)pyridin-2-yl]carbamothioyl]carbamate

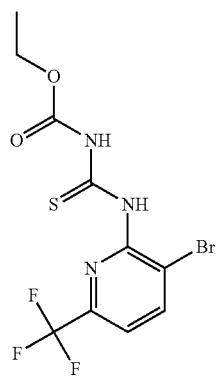 [SMILES: CCOC(=O)NC(=S)Nc1nc(C(F)(F)F)ccc1Br]

In a 100 ml round-bottomed flask, 3-bromo-6-(trifluoromethyl)pyridin-2-amine (CAS1214361-39-3, 5.00 g, 20.7 mmol) and O-ethyl-carbonisothiocyanatidate (2.99 g, 22.8 mmol) were combined with dioxane (55 ml) to give a yellow solution. The reaction mixture was stirred for 5 minutes at room temperature. Then the reaction was heated at 70° C. for 1 hour. Then the reaction was heated to 100° C. and stirred for 3 hours. The reaction was allowed to cool to room temperature while stirring overnight. The crude reaction mixture was concentrated and dried in vacuo to yield the title compound as light yellow solid (5.89 g, 76%). MS: m/z=372.0 and 374.0 [M+H]$^+$.

b) 8-Bromo-5-(trifluoromethyl)-[1,2,4]triazolo[1,5-a]pyridin-2-amine

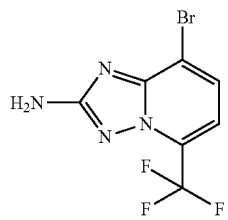 [SMILES: Nc1nc2c(Br)ccc(C(F)(F)F)n2n1]

In a 150 ml round-bottomed flask, hydroxylamine hydrochloride (5.5 g, 79.1 mmol) and diisopropylethylamine (6.14 g, 8.29 ml, 47.5 mmol) were combined with methanol (40 ml) and ethanol (40 ml) to give a white suspension. Ethyl N-[[3-bromo-6-(trifluoromethyl)pyridin-2-yl]carbamothioyl]carbamate (5.89 g, 15.8 mmol) was added and the reaction was stirred for 1.5 hours at room temperature. Then the reaction was heated to 50° C. and stirred overnight. The crude reaction mixture was concentrated in vacuo. The reaction mixture was poured into saturated aqueous sodium bicarbonate (150 ml) and extracted with dichloromethane (3×250 ml). Chromatography (silica gel, 210 g, ethyl acetate/heptane=20:80 to 50:50) yielded the title compound as white solid (3.27 g, 74%). MS: m/z=281.0 and 283.0 [M+H]$^+$.

116 c) 5-(Trifluoromethyl)-8-(2,3,4-trifluorophenyl)-[1,2,4]triazolo[1,5-a]pyridin-2-amine

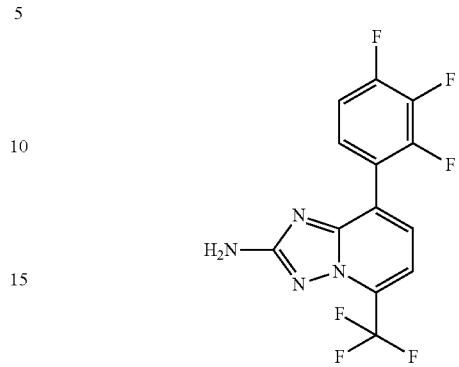

In a 50 ml round-bottomed flask, 8-bromo-5-(trifluoromethyl)-[1,2,4]triazolo[1,5-a]pyridin-2-amine (1.00 g, 3.56 mmol), (2,3,4-trifluorophenyl)boronic acid (626 mg, 3.56 mmol) and cesium carbonate (2.32 g, 7.12 mmol) were combined with dioxane (30 ml) to give a orange suspension. 1,1'-Bis(diphenylphosphino)ferrocene-palladium(II)dichloride dichloromethane complex (260 mg, 356 µmol) was added and the reaction mixture was heated at 80° C. for 15 hours. Chromatography (silica gel, 40 g, ethyl acetate/heptane=30:70 to 100:0) yielded the title compound as light brown solid (629 mg, 53%). MS: m/z=333.1 [M+H]$^+$.

d) 2-Bromo-5-(trifluoromethyl)-8-(2,3,4-trifluorophenyl)-[1,2,4]triazolo[1,5-a]pyridine

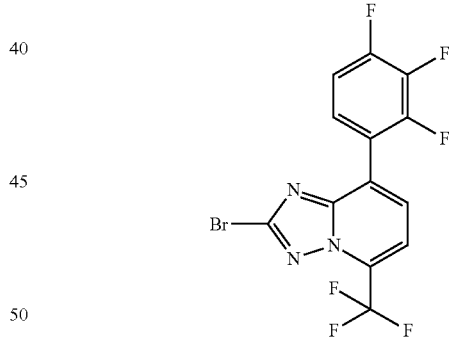

In a 100 ml round-bottomed flask, tert-butyl nitrite (291 mg, 335 µl, 2.82 mmol) and copper (II) bromide (629 mg, 2.82 mmol) were combined with acetonitrile (50 ml) to give a black solution. The reaction mixture was heated to 60° C. and 5-(trifluoromethyl)-8-(2,3,4-trifluorophenyl)-[1,2,4]triazolo[1,5-a]pyridin-2-amine (624 mg, 1.88 mmol) was added. The reaction mixture was heated at 80° C. for 2 hours. The reaction mixture was cooled to room temperature, poured into 25 ml water, acidified with hydrochloric acid (2N) and extracted with ethyl acetate (3×100 ml). Chromatography (silica gel, 40 g, ethyl acetate/heptane=10:90 to 50:50) yielded the title compound as light brown solid (676 mg, 91%). MS: m/z=396.0 and 398.0 [M+H]$^+$.

e) (8-endo)-tert-Butyl 8-((5-(trifluoromethyl)-8-(2,3,4-trifluorophenyl)-[1,2,4]triazolo[1,5-a]pyridin-2-yl)amino)-3-azabicyclo[3.2.1]octane-3-carboxylate

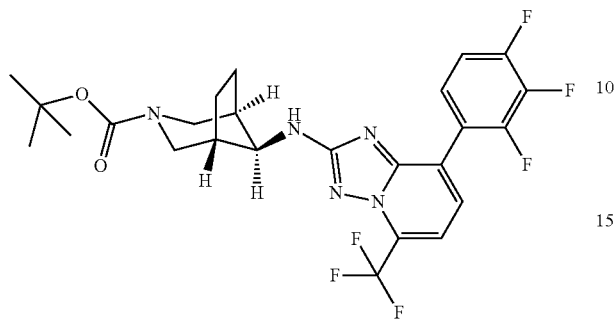

To a 20 ml microwave vial, (8-endo)-tert-butyl-8-amino-3-azabicyclo[3.2.1]octane-3-carboxylate (383 mg, 1.69 mmol), xantphos (157 mg, 271 μmol), tris(dibenzylideneacetone)dipalladium (0) chloroform adduct (140 mg, 135 μmol) and sodium tert-butoxide (341 mg, 3.55 mmol) were combined with dioxane (15 ml) to give a black suspension. The vial was capped and heated in the microwave at 145° C. for 30 minutes. Chromatography (silica gel, 20 g, ethyl acetate/heptane=30:70 to 70:30) yielded the title compound as light brown solid (765 mg, 85%). MS: m/z=540.3 [M−H]⁻.

f) N-((8-endo)-3-Azabicyclo[3.2.1]octan-8-yl)-5-(trifluoromethyl)-8-(2,3,4-trifluorophenyl)-[1,2,4]triazolo[1,5-a]pyridin-2-amine

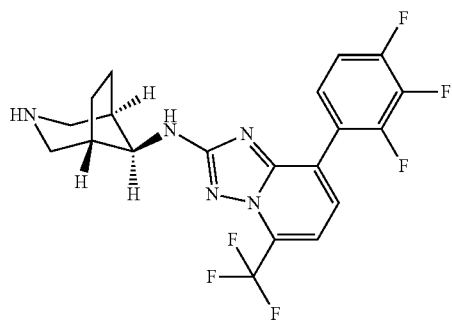 [SMILES: Fc1ccc(-c2ccc(C(F)(F)F)n3nc(N[C@@H]4[C@@H]5CC[C@H]4CNC5)nc23)c(F)c1F]

A suspension of (8-endo)-tert-butyl 8-((5-(trifluoromethyl)-8-(2,3,4-trifluorophenyl)-[1,2,4]triazolo[1,5-a]pyridin-2-yl)amino)-3-azabicyclo[3.2.1]octane-3-carboxylate (758 mg, 1.4 mmol) and Pd/C (41.4 mg, 389 μmol) in ethanol (20 ml) was hydrogenated under hydrogen atmosphere at 80° C. and 80 bar for 18 hours. MS and LCMS showed only SM without BOC. The crude reaction mixture was concentrated and dried in vacuo to yield the title compound as light brown solid (618 mg, quant.). MS: m/z=442.2 [M+H]⁺.

g) N-((8-endo)-3-Azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine

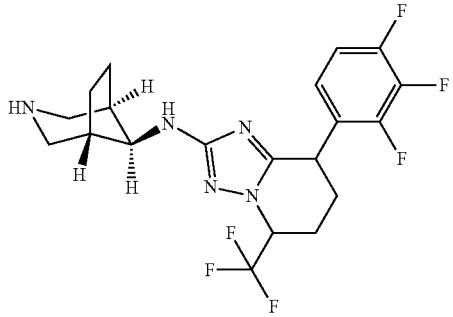 [SMILES: Fc1ccc(C2CCC(C(F)(F)F)n3nc(N[C@@H]4[C@@H]5CC[C@H]4CNC5)nc32)c(F)c1F]

A suspension of N-((8-endo)-3-azabicyclo[3.2.1]octan-8-yl)-5-(trifluoromethyl)-8-(2,3,4-trifluorophenyl)-[1,2,4]triazolo[1,5-a]pyridin-2-amine (486 mg, 1.1 mmol) and Pd/C (117 mg, 1.1 mmol) in ethanol (10 ml) was hydrogenated under hydrogen atmosphere at 80° C. and 80 bar for 18 hours. The catalyst was filtered off and the reaction was repeated with 200 mg Pd/C (200 mg) at 100° C. The catalyst was filtered off and washed with ethanol. Chromatography (Si-amine, 40 g, ethyl acetate/methanol=100:0 to 80:20). The fractions were concentrated and dried in vacuo to yield the title compound as off-white solid (240 mg, 44%). MS: m/z=446.2 [M+H]⁺.

h) (8-endo)-8-((5-(Trifluoromethyl)-8-(2,3,4-trifluorophenyl)-5,6,7,8-tetrahydro-[1,2,4]triazolo[1,5-a]pyridin-2-yl)amino)-3-azabicyclo[3.2.1]octane-3-carbonitrile

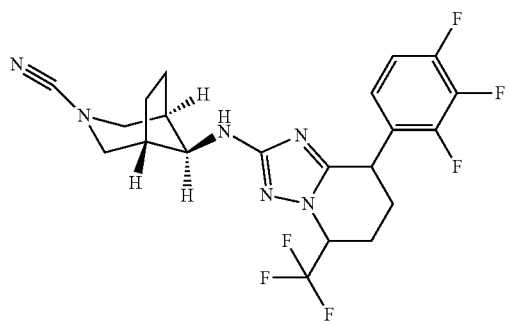 [SMILES: N#CN1C[C@H]2CC[C@@H](C1)[C@@H]2Nc1nc2n(n1)C(C(F)(F)F)CCC2c1ccc(F)c(F)c1F]

In a 25 ml round-bottomed flask, N-((8-endo)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine (236 mg, 530 μmol) and sodium bicarbonate (49 mg, 583 μmol) were combined with ethanol (9 ml) to give a light brown suspension. Cyanic bromide (61.7 mg, 583 μmol) was added and stirring was continued at room temperature for 3 hours. The reaction mixture was filtered through sintered glass and concentrated in vacuo to yield the title compound as off-white solid (249 mg, quant.) which was used in the next step without further purification. MS: m/z=471.2 [M+H]⁺.

i) N-((8-endo)-3-(3-Methyl-1,2,4-oxadiazol-5-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine

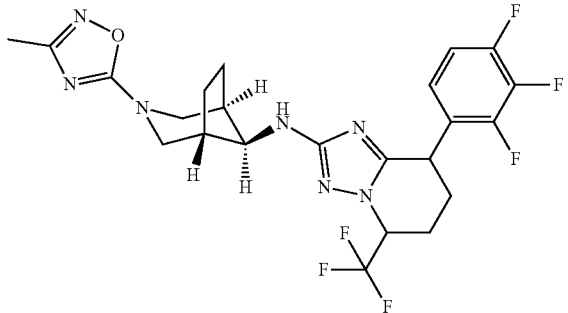 [SMILES: Cc1noc(N2C[C@H]3CC[C@@H](C2)[C@@H]3Nc2nc3n(n2)C(C(F)(F)F)CCC3c2ccc(F)c(F)c2F)n1]

In a 25 ml round-bottomed flask, (8-endo)-8-((5-(trifluoromethyl)-8-(2,3,4-trifluorophenyl)-5,6,7,8-tetrahydro-[1,2,4]triazolo[1,5-a]pyridin-2-yl)amino)-3-azabicyclo[3.2.1]octane-3-carbonitrile (249 mg, 529 μmol) was combined with ethanol (12 ml) to give a light yellow solution. (E)-N'-Hydroxyacetimidamide (39.2 mg, 529 μmol) was added followed by zinc chloride (86.6 mg, 635 μmol, dried under HV and heating) in ethanol (2 ml). The reaction mixture was stirred at room temperature for 2 hours and then hydrochloric acid (132 μl, 1.59 mmol) was added. The reaction mixture was heated at 60° C. for 5 hours. The reaction mixture was concentrated in vacuo, poured into 20 ml saturated aqueous sodium bicarbonate and extracted with dichloromethane (5×50 ml). Chromatography (Si-amine, 80 g, ethyl acetate/heptane=50:50 to 100:0) yielded the title compound as off-white gum (121 mg, 43%). MS: m/z=528.3 [M+H]⁺.

Example 29b (−)-N-((8-endo)-3-(3-Methyl-1,2,4-oxadiazol-5-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine

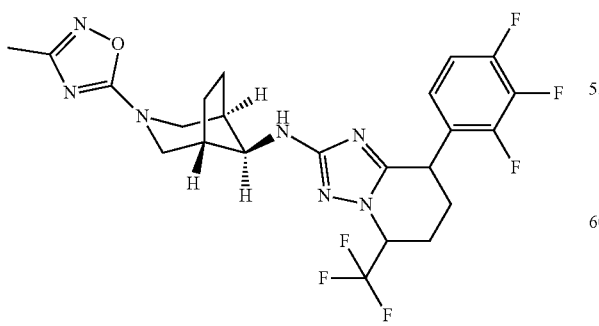

Chromatography of the racemic N-((8-endo)-3-(3-methyl-1,2,4-oxadiazol-5-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine (example 29a) on Reprosil Chiral NR (ethanol/heptane=20:80) yielded the title compound as white solid (19.3 mg, 17%). MS: m/z=528.3 [M+H]⁺.

Example 29c (+)-N-((8-endo)-3-(3-Methyl-1,2,4-oxadiazol-5-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine

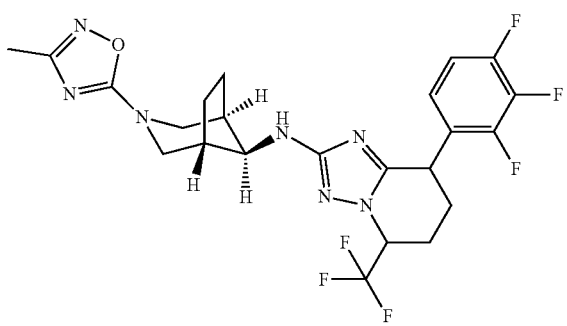 [SMILES: Cc1noc(N2C[C@H]3CC[C@@H](C2)[C@@H]3Nc2nc3n(n2)C(C(F)(F)F)CCC3c2ccc(F)c(F)c2F)n1]

Chromatography of the racemic N-((8-endo)-3-(3-methyl-1,2,4-oxadiazol-5-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine (example 29a) on Reprosil Chiral NR (ethanol/heptane=20:80) yielded the title compound as white solid (17.1 mg, 15%). MS: m/z=528.3 [M+H]⁺.

Example 30

8-(2-Fluoro-4-(trifluoromethyl)phenyl)-N-((8-endo)-3-(5-methyl-1,3,4-oxadiazol-2-yl)-3-azabicyclo[3.2.1]octan-8-yl)-5,6,7,8-tetrahydro-[1,2,4]triazolo[1,5-a]pyridin-2-amine

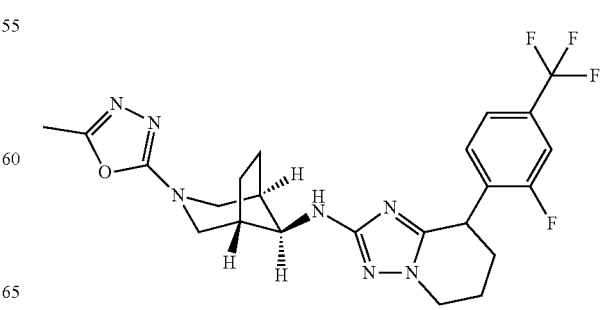

a) (8-endo)-tert-Butyl 8-((8-(2-fluoro-4-(trifluoromethyl)phenyl)-[1,2,4]triazolo[1,5-a]pyridin-2-yl)amino)-3-azabicyclo[3.2.1]octane-3-carboxylate

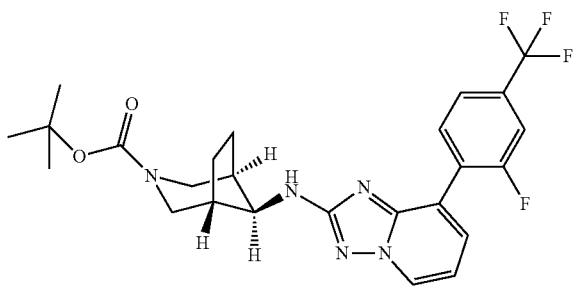 [SMILES: CC(C)(C)OC(=O)N1C[C@H]2CC[C@@H](C1)[C@@H]2Nc1nc2c(-c3ccc(C(F)(F)F)cc3F)cccn2n1]

In a 25 ml microwave vial, to a solution of (8-endo)-tert-butyl 8-amino-3-azabicyclo[3.2.1]octane-3-carboxylate (240 mg, 1.06 mmol) in dioxane (8 ml) was added 2-bromo-8-(2-fluoro-4-(trifluoromethyl)phenyl)-[1,2,4]triazolo[1,5-a]pyridine (382 mg, 1.06 mmol). Sodium tert-butoxide (306 mg, 3.18 mmol), xantphos (98.2 mg, 170 µmol) and tris(dibenzylideneacetone)dipalladium (0) chloroform adduct (87.8 mg, 84.8 µmol) were added. The vial was capped and heated in the microwave at 145° C. for 30 minutes. Chromatography (silica gel, 70 g, heptane/ethyl acetate=100:0 to 50:30) yielded the title compound as yellow solid (374 mg, 70%). MS: m/z=506.3 [M+H]$^+$.

b) (8-endo)-tert-Butyl 8-((8-(2-fluoro-4-(trifluoromethyl)phenyl)-5,6,7,8-tetrahydro-[1,2,4]triazolo[1,5-a]pyridin-2-yl)amino)-3-azabicyclo[3.2.1]octane-3-carboxylate

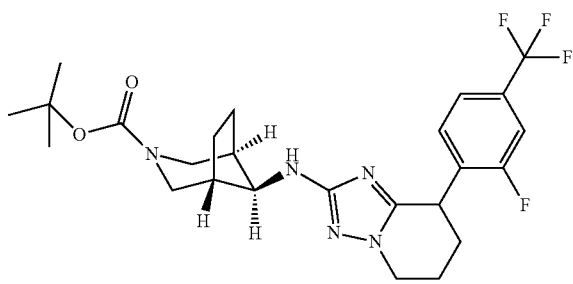 [SMILES: CC(C)(C)OC(=O)N1C[C@H]2CC[C@@H](C1)[C@@H]2Nc1nc2n(n1)CCCC2c1ccc(C(F)(F)F)cc1F]

(8-endo)-tert-Butyl 8-((8-(2-fluoro-4-(trifluoromethyl)phenyl)-[1,2,4]triazolo[1,5-a]pyridin-2-yl)amino)-3-azabicyclo[3.2.1]octane-3-carboxylate (371 mg, 734 µmol) was dissolved in methanol (6 ml) and tetrahydrofurane (3 ml) to give a yellow solution. Magnesium (143 mg, 5.87 mmol) and iodine (3.73 mg, 14.7 µmol) were added. The reaction mixture was stirred at 80° C. for 2 hours. Magnesium (70 mg) and iodine (3.73 mg, 14.7 µmol) were added. The reaction mixture was stirred at 80° C. for 4 hours. Iodine (3.73 mg, 14.7 µmol) was added. The reaction mixture was stirred at 80° C. overnight. Magnesium (30 mg) and iodine (3.73 mg, 14.7 µmol) were added. The reaction mixture was stirred at 80° C. for 20 hours. The grey suspension was filtered over dicalite. Chromatography (silica gel, 100 g, heptane/ethyl acetate=100:0 to 0:100) yielded the title compound as yellow solid (177 mg, 47%). MS: m/z=510.4 [M+H]$^+$.

c) N-((8-endo)-3-Azabicyclo[3.2.1]octan-8-yl)-8-(2-fluoro-4-(trifluoromethyl)phenyl)-5,6,7,8-tetrahydro-[1,2,4]triazolo[1,5-a]pyridin-2-amine

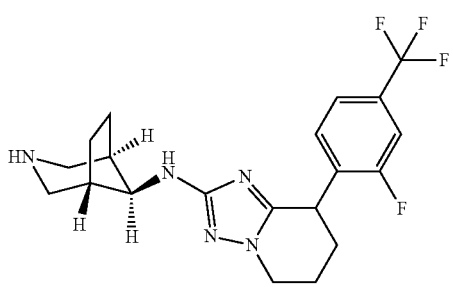 [SMILES: Fc1cc(C(F)(F)F)ccc1C1CCCn2nc(N[C@@H]3[C@@H]4CC[C@H]3CNC4)nc21]

(8-endo)-tert-Butyl 8-((8-(2-fluoro-4-(trifluoromethyl)phenyl)-5,6,7,8-tetrahydro-[1,2,4]triazolo[1,5-a]pyridin-2-yl)amino)-3-azabicyclo[3.2.1]octane-3-carboxylate (17 mg, 33.4 mol) was dissolved in dichloromethane (0.3 ml). Trifluoroacetic acid (38 mg, 25.7 µl, 334 mol) was added. The reaction mixture was stirred at for 15 hours and then concentrated in vacuo to yield the title compound as colorless oil (17 mg, 17%), MS: m/z=410.3 [M+H]$^+$. The crude product was used for the next step without purification.

d) 8-(2-Fluoro-4-(trifluoromethyl)phenyl)-N-((8-endo)-3-(5-methyl-1,3,4-oxadiazol-2-yl)-3-azabicyclo[3.2.1]octan-8-yl)-5,6,7,8-tetrahydro-[1,2,4]triazolo[1,5-a]pyridin-2-amine

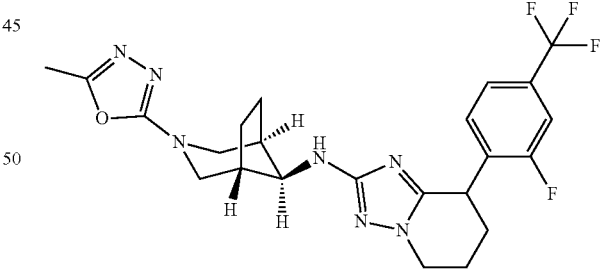

N-((8-endo)-3-azabicyclo[3.2.1]octan-8-yl)-8-(2-fluoro-4-(trifluoromethyl)phenyl)-5,6,7,8-tetrahydro-[1,2,4]triazolo[1,5-a]pyridin-2-amine (13 mg, 31.8 µmol) was dissolved in ethanol (0.7 ml). Triethylamine (16.1 mg, 22.1 µl, 159 µmol) and 2-bromo-5-methyl-1,3,4-oxadiazole (6.21 mg, 38.1 µmol) were added. The reaction mixture was stirred in a sealed tube at 130° C. for 5 hours. Chromatography (Si-amine, 80 g, heptane/ethyl acetate=100:0 to 40:60) yielded the title compound as white solid (11 mg, 71%). MS: m/z=492.4 [M+H]$^+$.

Example 31a

N-[(8-endo)-3-(5-Methyl-1,3,4-oxadiazol-2-yl)-3-azabicyclo[3.2.1]octan-8-yl]-5-(trifluoromethyl)-8-(2,3,4-trifluorophenyl)-5,6,7,8-tetrahydro-[1,2,4]triazolo[1,5-a]pyridin-2-amine (Diastereomer A)

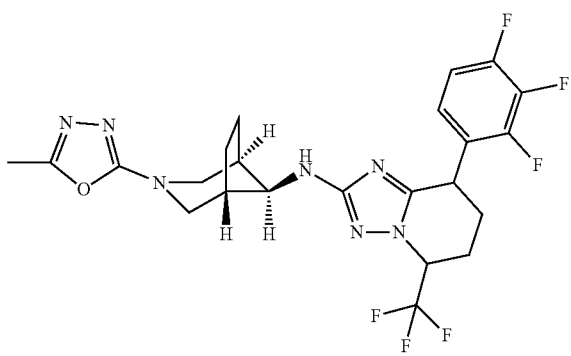 [SMILES: Cc1nnc(N2C[C@H]3CC[C@@H](C2)[C@@H]3Nc2nc3n(n2)C(C(F)(F)F)CCC3c2ccc(F)c(F)c2F)o1]

a) 5-(Trifluoromethyl)-8-(2,3,4-trifluorophenyl)-5,6,7,8-tetrahydro-[1,2,4]triazolo[1,5-a]pyridin-2-amine

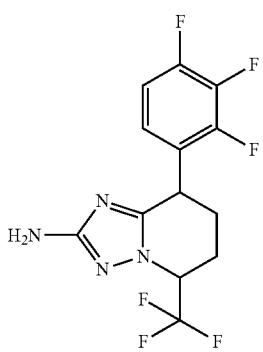 [SMILES: Nc1nc2n(n1)C(C(F)(F)F)CCC2c1ccc(F)c(F)c1F]

A suspension of 5-(trifluoromethyl)-8-(2,3,4-trifluorophenyl)-[1,2,4]triazolo[1,5-a]pyridin-2-amine (2.03 g, 6.11 mmol), hydrochloric acid (6.11 ml, 6.11 mmol) and Pd/C (181 mg, 1.7 mmol) in ethanol (30 ml) was hydrogenated under hydrogen atmosphere at 80° C. and 80 bar for 18 hours. The catalyst was filtered off and the reaction was repeated under the same conditions with Pd/C (500 mg). The catalyst was filtered off. The reaction mixture was poured into 25 ml saturated aqueous sodium bicarbonate and extracted with ethyl acetate (3×100 ml). The organic layers were dried over sodium sulfate, concentrated and dried in vacuo to yield the title compound as light brown solid (1.02 g, 50%). MS: m/z=337.1 [M+H]$^+$.

b) 2-Bromo-5-(trifluoromethyl)-8-(2,3,4-trifluorophenyl)-5,6,7,8-tetrahydro-[1,2,4]triazolo[1,5-a]pyridine

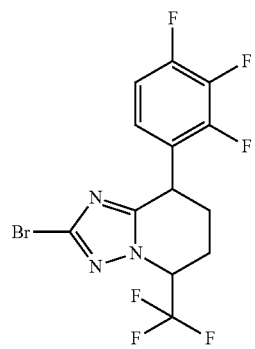 [SMILES: Fc1ccc(C2CCC(C(F)(F)F)n3nc(Br)nc32)c(F)c1F]

To a black solution of tert-butyl nitrite (469 mg, 541 µl, 4.55 mmol) and copper (II) bromide (1.02 g, 4.55 mmol) in acetonitrile (100 ml) at 60° C. 5-(trifluoromethyl)-8-(2,3,4-trifluorophenyl)-5,6,7,8-tetrahydro-[1,2,4]triazolo[1,5-a]pyridin-2-amine (1.02 g, 3.03 mmol) was added portionwise. After addition the reaction mixture was heated at 75° C. for 1 hour. The reaction mixture was concentrated in vacuo, diluted with hydrochloric acid (1 M, 20 ml) and extracted with ethyl acetate (3×100 ml). Chromatography (silica gel, 10 g, ethyl acetate/heptane=20:80 to 80:20) yielded the title compound as light yellow waxy solid (900 mg, 74%). MS: m/z=400.1 and 398.1 [M−H]$^-$.

c) (8-endo)-tert-Butyl 8-((5-(trifluoromethyl)-8-(2,3,4-trifluorophenyl)-5,6,7,8-tetrahydro-[1,2,4]triazolo[1,5-a]pyridin-2-yl)amino)-3-azabicyclo[3.2.1]octane-3-carboxylate

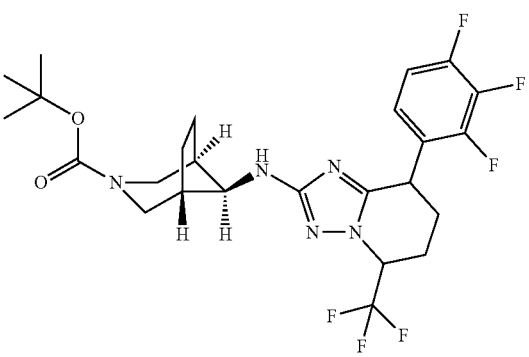 [SMILES: CC(C)(C)OC(=O)N1C[C@H]2CC[C@@H](C1)[C@@H]2Nc1nc2n(n1)C(C(F)(F)F)CCC2c1ccc(F)c(F)c1F]

To a solution of (8-endo)-tert-butyl-8-amino-3-azabicyclo[3.2.1]octane-3-carboxylate (100 mg, 442 µmol) in dioxane (5 ml) was added 2-bromo-5-(trifluoromethyl)-8-(2,3,4-trifluorophenyl)-5,6,7,8-tetrahydro-[1,2,4]triazolo[1,5-a]pyridine (177 mg, 442 µmol). Dibromo-bis-(tritert-butyl)-phosphine-palladium (34.3 mg, 44.2 µmol) and sodium tert-butoxide (87.1 mg, 906 µmol) were added. The reaction mixture was heated in the microwave at 150° C. for 30 minutes. Chromatography (silica gel, 12 g, ethyl acetate/heptane=50:50 to 100:0) yielded the title compound as light yellow gum (51 mg, 21%). MS: m/z=546.2 [M+H]$^+$.

d) N-[(8-endo)-3-(5-Methyl-1,3,4-oxadiazol-2-yl)-3-azabicyclo[3.2.1]octan-8-yl]-5-(trifluoromethyl)-8-(2,3,4-trifluorophenyl)-5,6,7,8-tetrahydro-[1,2,4]triazolo[1,5-a]pyridin-2-amine (Diastereomer A)

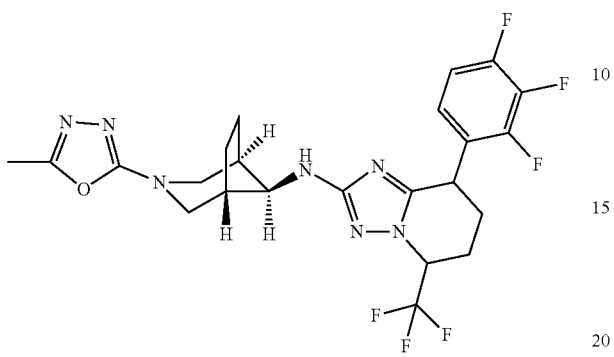

In a 25 ml round-bottomed flask, (8-endo)-tert-butyl 8-((5-(trifluoromethyl)-8-(2,3,4-trifluorophenyl)-5,6,7,8-tetrahydro-[1,2,4]triazolo[1,5-a]pyridin-2-yl)amino)-3-azabicyclo[3.2.1]octane-3-carboxylate (51 mg, 93.5 µmol) was combined with dichloromethane (5 ml) to give a light yellow solution. Trifluoroacetic acid (107 mg, 72 µl, 935 µmol) was added and stirring was continued for 1 hour. The crude reaction mixture was poured into 5 ml water, basified with aqueous sodium hydroxide (4N) and extracted with dichloromethane (4×20 ml). The organic layers were dried over sodium sulfate and concentrated in vacuo. The residue was taken up in ethanol (5 ml) and 2-bromo-5-methyl-1,3,4-oxadiazole (15.2 mg, 93.5 µmol) and triethylamine (37.8 mg, 52.1 µl, 374 µmol) were added. The reaction mixture was heated to 130° C. and stirred overnight. Chromatography (Si-amine, 12 g, ethyl acetate/heptane=50:50 to 100:0) yielded the title compound, one single diastereoisomer (peak A), as off-white solid (9 mg, 18%). MS: m/z=528.3 [M+H]⁺.

Example 31b

N-((8-endo)-3-(5-Methyl-1,3,4-oxadiazol-2-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine (Diastreomer B)

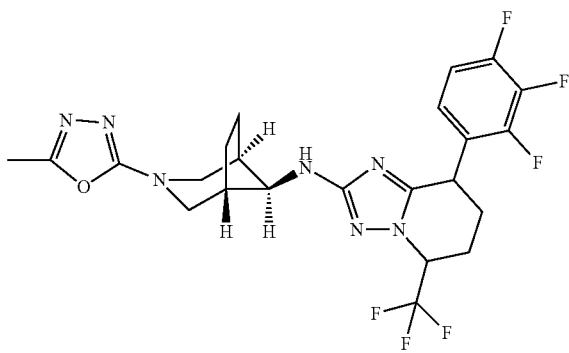 [SMILES: Cc1nnc(N2C[C@H]3CC[C@@H](C2)[C@@H]3Nc2nc3n(n2)C(C(F)(F)F)CCC3c2ccc(F)c(F)c2F)o1]

The chromatography (Si-amine, 12 g, ethyl acetate/heptane=50:50 to 100:0) in example 31a yielded as well the title compound, one single diastereoisomer (peak B), as off-white solid (9 mg, 18%). MS: m/z=528.3 [M+H]⁺.

Example 31c (+)-N-((8-endo)-3-(5-Methyl-1,3,4-oxadiazol-2-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine

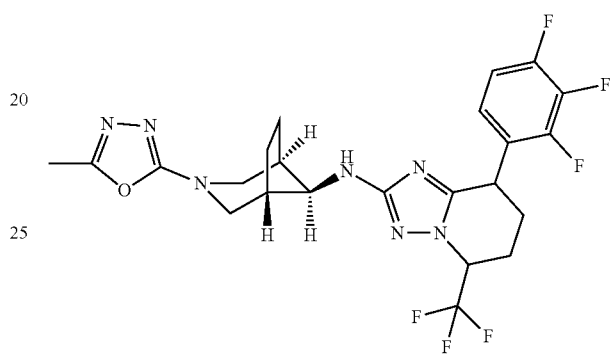

a) N-((8-endo)-3-(5-Methyl-1,3,4-oxadiazol-2-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine

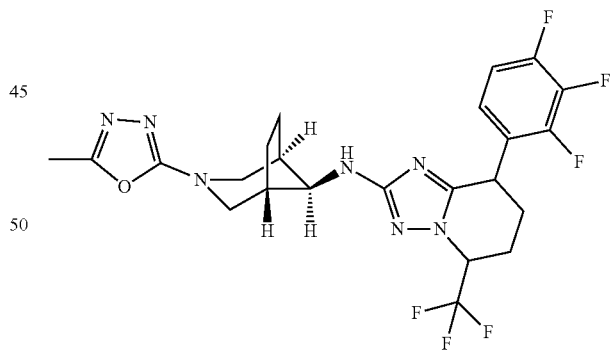

In a sealed tube N-((8-endo)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine (206 mg, 463 µmol), 2-bromo-5-methyl-1,3,4-oxadiazole (75.4 mg, 463 µmol) and triethylamine (187 mg, 258 µl, 1.85 mmol) were combined with ethanol (20 ml) to give a brown solution. The reaction mixture was heated to 130° C. and stirred overnight. Chromatography (Si-amine, 12 g, ethyl acetate/heptane=50:50 to 100:0) yielded the title compound as off-white solid (198 mg, 81%). MS: m/z=528.3 [M+H]⁺.

b) (+)-N-((8-endo)-3-(5-Methyl-1,3,4-oxadiazol-2-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine

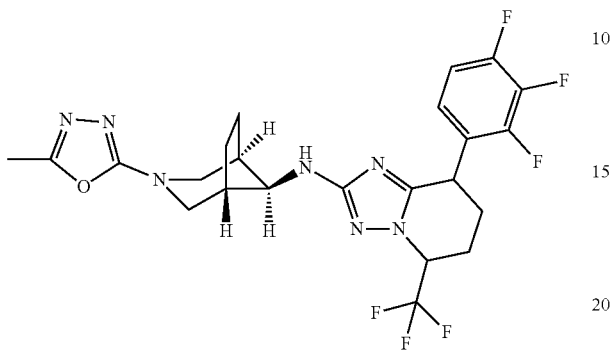

Chromatography of the racemic N-((8-endo)-3-(5-methyl-1,3,4-oxadiazol-2-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine (example 31c-a) on Reprosil Chiral NR (ethanol/heptane=20:80) yielded the title compound as off-white solid (51 mg, 27%). MS: m/z=528.3 [M+H]$^+$.

Example 31d (−)-N-((8-endo)-3-(5-Methyl-1,3,4-oxadiazol-2-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine

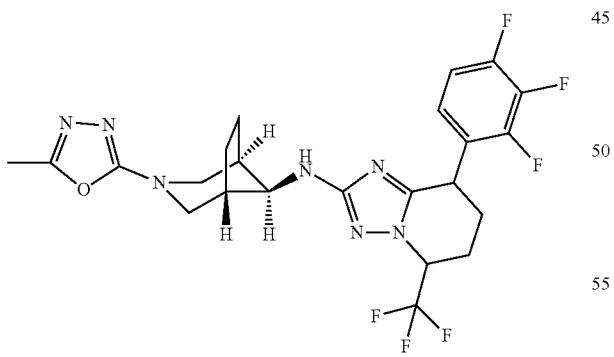

Chromatography of the racemic N-((8-endo)-3-(5-methyl-1,3,4-oxadiazol-2-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine (example 31c-a) on Reprosil Chiral NR (ethanol/heptane=20:80) yielded the title compound as off-white solid (55 mg, 29%). MS: m/z=528.3 [M+H]$^+$.

Example 32a

N-[(8-endo)-3-(5-Methyl-1,3,4-oxadiazol-2-yl)-3-azabicyclo[3.2.1]octan-8-yl]-5-(trifluoromethyl)-8-[4-(trifluoromethyl)phenyl]-5,6,7,8-tetrahydro-[1,2,4]triazolo[1,5-a]pyridin-2-amine

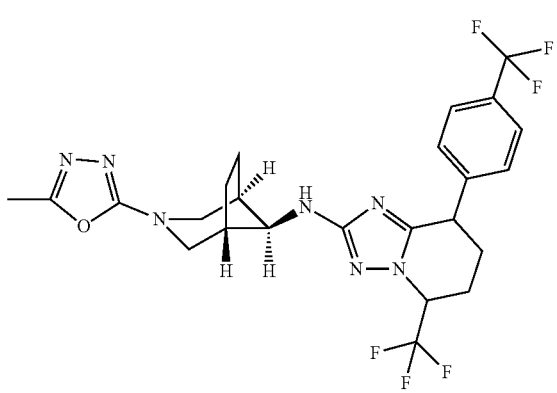 [SMILES: Cc1nnc(N2C[C@H]3CC[C@@H](C2)[C@@H]3Nc2nc3n(n2)C(C(F)(F)F)CCC3c2ccc(C(F)(F)F)cc2)o1]

a) 5-(Trifluoromethyl)-8-(4-(trifluoromethyl)phenyl)-[1,2,4]triazolo[1,5-a]pyridin-2-amine

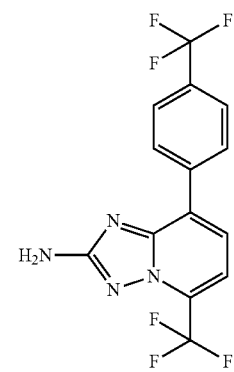 [SMILES: Nc1nc2c(-c3ccc(C(F)(F)F)cc3)ccc(C(F)(F)F)n2n1]

In a 100 ml round-bottomed flask, 8-bromo-5-(trifluoromethyl)-[1,2,4]triazolo[1,5-a]pyridin-2-amine (1.00 g, 3.56 mmol), (4-(trifluoromethyl)phenyl)boronic acid (676 mg, 3.56 mmol) and cesium carbonate (2.32 g, 7.12 mmol) were combined with dioxane (30 ml) and water (3 ml) to give a light brown solution. Under argon 1,1'-bis(diphenylphosphino)ferrocene-palladium(II)dichloride dichloromethane complex (260 mg, 356 µmol) was added. The reaction mixture was heated at 80° C. overnight. (4-(Trifluoromethyl)phenyl)boronic acid (676 mg, 3.56 mmol) was added again and stirring was continued for 1 hour. Chromatography (silica gel, 1 kg, ethyl acetate/heptane=20:80 to 80:20) yielded the title compound as light brown solid (1.18 g, 99%). MS: m/z=347.2 [M+H]$^+$.

b) 2-Bromo-5-(trifluoromethyl)-8-(4-(trifluoromethyl)phenyl)-[1,2,4]triazolo[1,5-a]pyridine

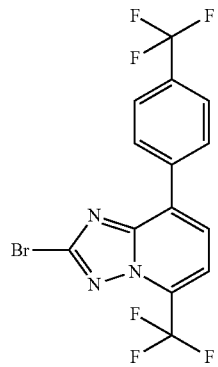 [SMILES: FC(F)(F)c1ccc(-c2ccc(C(F)(F)F)n3nc(Br)nc23)cc1]

In a 25 ml round-bottomed flask, copper (II) bromide (1.17 g, 5.25 mmol) and tert-butyl nitrite (541 mg, 623 µl, 5.25 mmol) were combined with acetonitrile (15 ml) to give a black solution. The reaction mixture was heated to 60° C. and then 5-(trifluoromethyl)-8-(4-(trifluoromethyl)phenyl)-[1,2,4]triazolo[1,5-a]pyridin-2-amine (1.275 g, 3.5 mmol) was added. The reaction mixture was heated at 80° C. for 1 hour. Chromatography (silica gel, 40 g, ethyl acetate/heptane=20:80 to 50:50) yielded the title compound as light brown viscous oil (1.30 g, 90%). MS: m/z=410.1 and 412.1 [M+H]+.

c) (8-endo)-tert-Butyl 8-((5-(trifluoromethyl)-8-(4-(trifluoromethyl)phenyl)-[1,2,4]triazolo[1,5-a]pyridin-2-yl)amino)-3-azabicyclo[3.2.1]octane-3-carboxylate

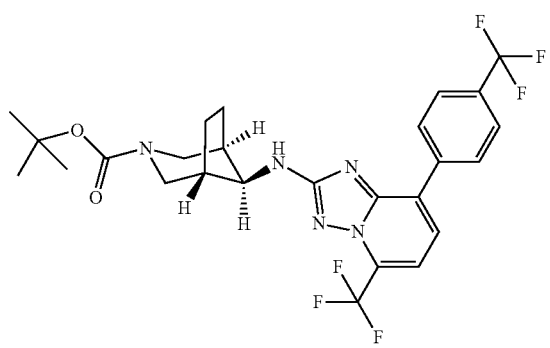 [SMILES: CC(C)(C)OC(=O)N1C[C@H]2CC[C@@H](C1)[C@@H]2Nc1nc2c(-c3ccc(C(F)(F)F)cc3)ccc(C(F)(F)F)n2n1]

In a microwave vial, (8-endo)-tert-butyl 8-amino-3-azabicyclo[3.2.1]octane-3-carboxylate (712 mg, 3.15 mmol), 2-bromo-5-(trifluoromethyl)-8-(4-(trifluoromethyl)phenyl)-[1,2,4]triazolo[1,5-a]pyridine (1.29 g, 3.15 mmol), xantphos (291 mg, 503 µmol), tris(dibenzylideneacetone)dipalladium (0) chloroform adduct (260 mg, 252 µmol) and sodium tert-butoxide (635 mg, 6.61 mmol) were combined with dioxan (25 ml) to give a black suspension. The vial was heated in the microwave at 145° C. for 30 minutes. Chromatography (silica gel, 40 g, ethyl acetate/heptan=30:70 to 70:30) yielded the title compound as light brown solid (1.01 g, 58%). MS: m/z=554.6 [M+H]+.

d) N-((8-endo)-3-Azabicyclo[3.2.1]octan-8-yl)-5-(trifluoromethyl)-8-(4-(trifluoromethyl)phenyl)-5,6,7,8-tetrahydro-[1,2,4]triazolo[1,5-a]pyridin-2-amine

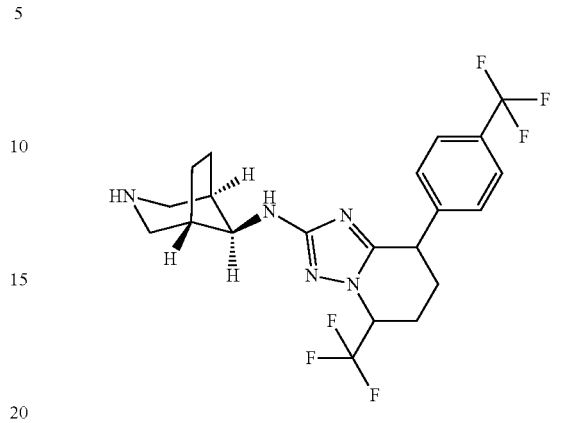

A degassed suspension of (8-endo)-tert-butyl 8-((5-(trifluoromethyl)-8-(4-(trifluoromethyl)phenyl)-[1,2,4]triazolo[1,5-a]pyridin-2-yl)amino)-3-azabicyclo[3.2.1]octane-3-carboxylate (1.01 g, 1.82 mmol), Pd—C (193 mg, 1.82 mmol) and aqueous hydrochloric acid (1N, 1.82 ml, 1.82 mmol) was hydrogenated under hydrogen atmosphere at 100° C. and 80 bar for 18 hours. To the reaction mixture was added again Pd—C (423 mg, 3.98 mmol) and hydrogenation was continued at 100° C. and 80 bar for 20 hours. The catalyst was filtered off and the mother liquor was concentrated in vacuo. The reaction mixture was poured into aqueous sodium hydroxide (1N, 25 ml) and extracted with dichloromethane (4×100 ml). The organic layers were dried over sodium sulfate, concentrated and dried in vacuo to yield the title compound as off-white solid (759 mg, 91%). MS: m/z=458.5 [M−H]−.

e) N-[(8-endo)-3-(5-Methyl-1,3,4-oxadiazol-2-yl)-3-azabicyclo[3.2.1]octan-8-yl]-5-(trifluoromethyl)-8-[4-(trifluoromethyl)phenyl]-5,6,7,8-tetrahydro-[1,2,4]triazolo[1,5-a]pyridin-2-amine

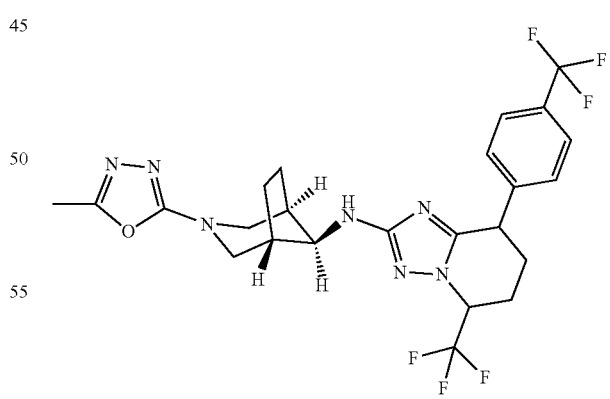

In a sealed tube N-((8-endo)-3-azabicyclo[3.2.1]octan-8-yl)-5-(trifluoromethyl)-8-(4-(trifluoromethyl)phenyl)-5,6,7,8-tetrahydro-[1,2,4]triazolo[1,5-a]pyridin-2-amine (530 mg, 1.15 mmol), 2-bromo-5-methyl-1,3,4-oxadiazole (188 mg, 1.15 mmol) and triethylamine (467 mg, 643 µl, 4.61 mmol) were combined with ethanol (25 ml) to give a brown solution. The reaction mixture was heated at 130° C. overnight. Chromatography (silica gel-NH2, 40 g, ethyl acetate/heptane=0:100 to 50:50) yielded the title compound (diastereomer 1) as light yellow solid (111 mg, 18%), MS: m/z=542.4 [M+H]⁺. (In addition a small amount of the second diastereomer was isolated, 15 mg, 3%, MS: m/z=542.2 [M+H]⁺).

Example 32b (−)-N-((8-endo)-3-(5-Methyl-1,3,4-oxadiazol-2-yl)-3-azabicyclo[3.2.1]octan-8-yl)-5-(trifluoromethyl)-8-(4-(trifluoromethyl)phenyl)-5,6,7,8-tetrahydro-[1,2,4]triazolo[1,5-a]pyridin-2-amine

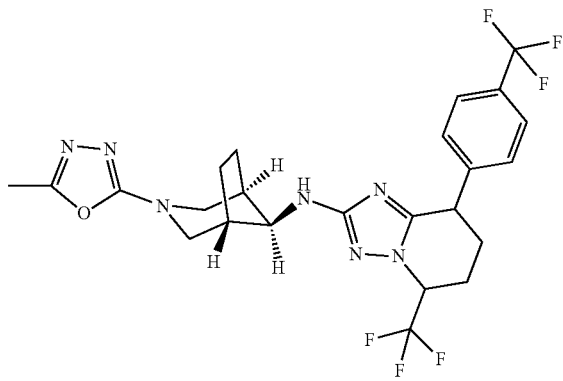 [SMILES: Cc1nnc(N2C[C@H]3CC[C@@H](C2)[C@@H]3Nc2nc3n(n2)C(C(F)(F)F)CCC3c2ccc(C(F)(F)F)cc2)o1]

Chromatography of the racemic N-((8-endo)-3-(5-methyl-1,3,4-oxadiazol-2-yl)-3-azabicyclo[3.2.1]octan-8-yl)-5-(trifluoromethyl)-8-(4-(trifluoromethyl)phenyl)-5,6,7,8-tetrahydro-[1,2,4]triazolo[1,5-a]pyridin-2-amine (example 32a) on Chiralpak AD (heptane/ethanol=60:40) yielded the title compound as white solid (36.5 mg, 35%). MS: m/z=542.5 [M+H]⁺.

Example 32c (+)-N-((8-endo)-3-(5-Methyl-1,3,4-oxadiazol-2-yl)-3-azabicyclo[3.2.1]octan-8-yl)-5-(trifluoromethyl)-8-(4-(trifluoromethyl)phenyl)-5,6,7,8-tetrahydro-[1,2,4]triazolo[1,5-a]pyridin-2-amine

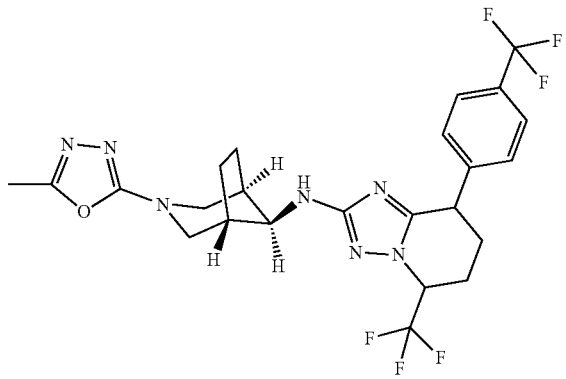 [SMILES: Cc1nnc(N2C[C@H]3CC[C@@H](C2)[C@@H]3Nc2nc3n(n2)C(C(F)(F)F)CCC3c2ccc(C(F)(F)F)cc2)o1]

Chromatography of the racemic N-((8-endo)-3-(5-methyl-1,3,4-oxadiazol-2-yl)-3-azabicyclo[3.2.1]octan-8-yl)-5-(trifluoromethyl)-8-(4-(trifluoromethyl)phenyl)-5,6,7, 8-tetrahydro-[1,2,4]triazolo[1,5-a]pyridin-2-amine (example 32a) on Chiralpak AD (heptane/ethanol=60:40) yielded the title compound as light brown oil (27.8 mg, 27%). MS: m/z=542.5 [M+H]⁺.

Example 33

(−)-8-(3,5-Bis(trifluoromethyl)phenyl)-N-((8-endo)-3-(5-methyl-1,3,4-oxadiazol-2-yl)-3-azabicyclo[3.2.1]octan-8-yl)-5,6,7,8-tetrahydro-[1,2,4]triazolo[1,5-a]pyridin-2-amine

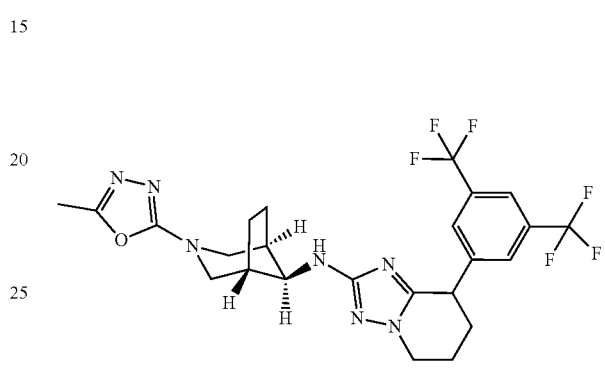

a) Ethyl 2-(3,5-bis(trifluoromethyl)phenyl)-5-((tetrahydro-2H-pyran-2-yl)oxy)pentanoate

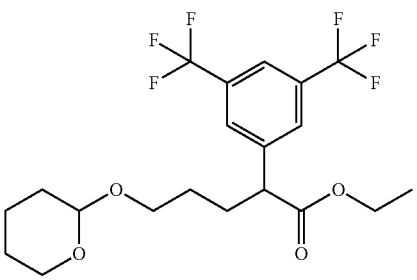 [SMILES: CCOC(=O)C(CCCOC1CCCCO1)c1cc(C(F)(F)F)cc(C(F)(F)F)c1]

In a 150 ml round-bottomed flask, ethyl 2-(3,5-bis(trifluoromethyl)phenyl)acetate (CAS144632-97-3, 5.30 g, 17.7 mmol) was combined with dimethylformamide (45 ml) to give a colorless solution. The reaction mixture was cooled to 0° C. and sodium hydride (770 mg, 17.7 mmol) was added in small portions. The reaction mixture was stirred at 0° C. for 20 minutes and then at room temperature for 20 minutes. Then 2-(3-bromopropoxy)tetrahydro-2H-pyran (3.94 g, 2.99 ml, 17.7 mmol) in dimethylformamide (45 ml) was added dropwise at room temperature and stirring was continued for 3 hours. The reaction mixture was poured into 50 ml saturated aqueous ammonium chloride and extracted with ethyl acetate. The organic layers were dried over sodium sulfate, concentrated and dried in vacuo to yield the title compound as light yellow liquid (8.31 g, quant.). MS: m/z=443.2 [M+H]⁺.

b) 2-(3,5-Bis(trifluoromethyl)phenyl)-5-((tetrahydro-2H-pyran-2-yl)oxy)pentanehydrazide

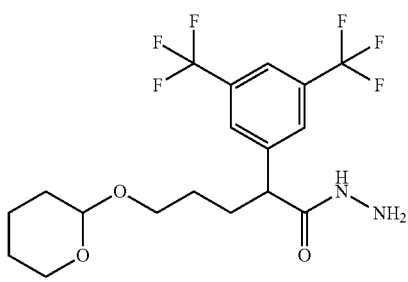 [SMILES: NNC(=O)C(CCCOC1CCCCO1)c1cc(C(F)(F)F)cc(C(F)(F)F)c1]

In a 150 ml round-bottomed flask, ethyl 2-(3,5-bis(trifluoromethyl)phenyl)-5-((tetrahydro-2H-pyran-2-yl)oxy) pentanoate (8.2 g, 18.5 mmol) and hydrazine hydrate (12.1 g, 11.9 ml, 371 mmol) were combined with methanol (50 ml) to give a light yellow solution. The mixture was heated to 80° C. overnight. The crude reaction mixture was concentrated in vacuo, poured into water (25 ml) and extracted with ethyl acetate. The organic layers were dried over sodium sulfate, concentrated and dried in vacuo to yield the title compound as light yellow viscous oil (7.53 g, 95%). MS: m/z=429.2 [M+H]$^+$.

c) 5-(1-(3,5-Bis(trifluoromethyl)phenyl)-4-((tetrahydro-2H-pyran-2-yl)oxy)butyl)-1H-1,2,4-triazol-3-amine

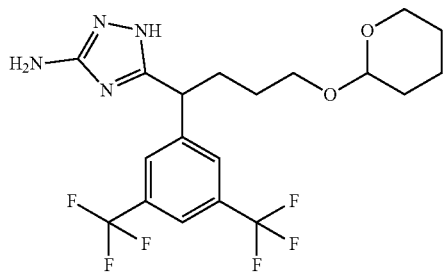 [SMILES: Nc1n[nH]c(C(CCCOC2CCCCO2)c2cc(C(F)(F)F)cc(C(F)(F)F)c2)n1]

In a microwave tube were combined 2-(3,5-bis(trifluoromethyl)phenyl)-5-((tetrahydro-2H-pyran-2-yl)oxy)pentanehydrazide (2.00 g, 4.67 mmol), methyl carbamimidothioate hemisulfate (650 mg, 2.33 mmol) and triethylamine (1.42 g, 1.95 ml, 14 mmol) in 2-propanol (12 ml). The mixture was stirred at 130° C. for 16 hours in an oil bath. The reaction mixture was poured into 100 ml water and extracted with dichloromethane. The organic layers were dried over sodium sulfate, concentrated in vacuo and purified by chromatography (silica gel, 40 g, dichloromethane/methanol=100:0 to 90:10). The title compound was obtained as yellow viscous oil (1.91 g, 90%). MS: m/z=453.1 [M+H]$^+$.

d) 4-(3,5-Bis(trifluoromethyl)phenyl)-4-(3-bromo-1H-1,2,4-triazol-5-yl)butan-1-ol

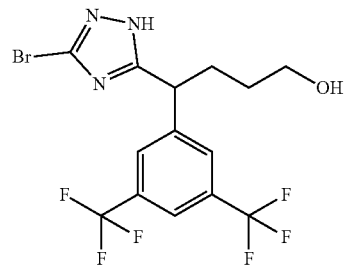 [SMILES: OCCCC(c1cc(C(F)(F)F)cc(C(F)(F)F)c1)c1nc(Br)n[nH]1]

In a 250 ml round-bottomed flask, tert-butyl nitrite (380 mg, 438 µl, 3.32 mmol) and copper (II) bromide (741 mg, 3.32 mmol) were combined with acetonitrile (100 ml) to give a black solution. The reaction mixture was heated to 60° C. and then 5-(1-(3,5-bis(trifluoromethyl)phenyl)-4-((tetrahydro-2H-pyran-2-yl)oxy)butyl)-1H-1,2,4-triazol-3-amine (1.00 g, 2.21 mmol) in acetonitrile (5 ml) was added. The reaction mixture was heated at 80° C. for 1 hour. Aqueous hydrochloric acid (2N, 5 ml) was added and stirring was continued for 30 minutes. The crude reaction mixture was concentrated in vacuo, poured into aqueous hydrochloric acid (1N, 15 ml) and extracted with ethyl acetate. Chromatography (silica gel, 40 g, ethyl acetate/heptane=10:90 to 100:0) yielded the title compound as yellow viscous oil (451 mg, 47%). MS: m/z=432.0 and 433.9 [M+H]$^+$.

e) 8-(3,5-Bis(trifluoromethyl)phenyl)-2-bromo-5,6,7,8-tetrahydro-[1,2,4]triazolo[1,5-a]pyridine

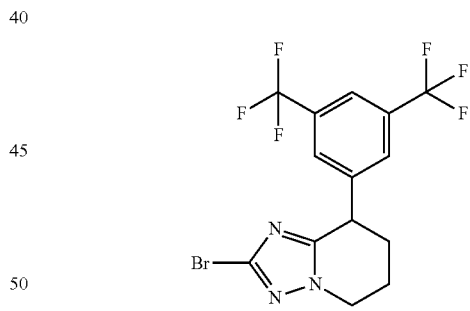

In a 25 ml round-bottomed flask, 4-(3,5-bis(trifluoromethyl)phenyl)-4-(3-bromo-1H-1,2,4-triazol-5-yl)butan-1-ol (440 mg, 1.02 mmol) was combined with tetrahydrofurane (15 ml) to give a light yellow solution. 2-(Trimethylphosphoranylidene)acetonitrile (0.5 M in tetrahydrofuran, 2.44 ml, 1.22 mmol) was added and stirring was continued at room temperature overnight. 2-(Trimethylphosphoranylidene)acetonitrile (0.5 M in tetrahydrofurane, 2.44 ml, 1.22 mmol) was added again and the reaction mixture was heated at 60° C. for 5 hours. The reaction mixture was poured into water (20 ml) and extracted with ethyl acetate. Chromatography (silica gel, 40 g, ethyl acetate/heptane=10:90 to 50:50) yielded the title compound as off-white solid (74 mg, 18%). MS: m/z=414.9+415.9 [M+H]$^+$.

f) (8-endo)-tert-Butyl 8-((8-(3,5-bis(trifluoromethyl)phenyl)-5,6,7,8-tetrahydro-[1,2,4]triazolo[1,5-a]pyridin-2-yl)amino)-3-azabicyclo[3.2.1]octane-3-carboxylate

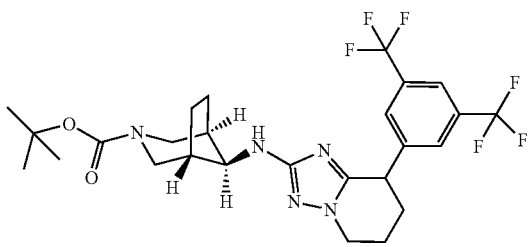 [SMILES: CC(C)(C)OC(=O)N1C[C@H]2CC[C@@H](C1)[C@@H]2Nc1nc2n(n1)CCCC2c1cc(C(F)(F)F)cc(C(F)(F)F)c1]

In a microwave vial under argon, were combined (8-endo)-tert-butyl 8-amino-3-azabicyclo[3.2.1]octane-3-carboxylate (40.2 mg, 177 µmol), 8-(3,5-bis(trifluoromethyl)phenyl)-2-bromo-5,6,7,8-tetrahydro-[1,2,4]triazolo[1,5-a]pyridine (70 mg, 169 µmol), 1,2,3,4,5-pentaphenyl-1'-(di-tert-butylphosphino)ferrocene (Q-Phos, 19.2 mg, 27 µmol), tris(dibenzylideneacetone)dipalladium (0) chloroform adduct (14 mg, 13.5 µmol) and sodium tert-butoxide (34.1 mg, 355 µmol) in dioxane (4 ml) to give a black suspension. The vial was capped and heated in the microwave at 145° C. for 75 minutes. Chromatography (silica gel-NH2, 12 g, ethyl acetate/heptane=0:100 to 50:50) yielded the title compound as light brown solid (55 mg, 58%). MS: m/z=560.4 [M+H]+.

g) 8-(3,5-Bis(trifluoromethyl)phenyl)-N-((8-endo)-3-(5-methyl-1,3,4-oxadiazol-2-yl)-3-azabicyclo[3.2.1]octan-8-yl)-5,6,7,8-tetrahydro-[1,2,4]triazolo[1,5-a]pyridin-2-amine

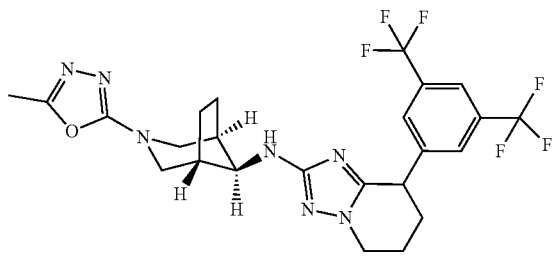 [SMILES: Cc1nnc(N2C[C@H]3CC[C@@H](C2)[C@@H]3Nc2nc3n(n2)CCCC3c2cc(C(F)(F)F)cc(C(F)(F)F)c2)o1]

rac

In a 25 ml round-bottomed flask, (8-endo)-tert-butyl 8-((8-(3,5-bis(trifluoromethyl)phenyl)-5,6,7,8-tetrahydro-[1,2,4]triazolo[1,5-a]pyridin-2-yl)amino)-3-azabicyclo[3.2.1]octane-3-carboxylate (55 mg, 98.3 µmol) was combined with dichloromethane (5 ml) to give a colorless solution. Trifluoroacetic acid (112 mg, 75.7 µl, 983 µmol) was added and stirring was continued for 3 hours. The crude reaction mixture was concentrated in vacuo and taken up in ethanol (5 ml). 2-Bromo-5-methyl-1,3,4-oxadiazole (17.6 mg, 108 µmol) and triethylamine (49.7 mg, 68.5 µl, 491 µmol) were added and the mixture was stirred over the weekend in a closed microwave vial at 130° C. Chromatography (silica gel-NH2, 12 g, ethyl acetate/heptane=50:50 to 100:0) yielded the title compound as off-white solid (38 mg, 71%). MS: m/z=542.2 [M+H]+.

(−)-8-(3,5-Bis(trifluoromethyl)phenyl)-N-((8-endo)-3-(5-methyl-1,3,4-oxadiazol-2-yl)-3-azabicyclo[3.2.1]octan-8-yl)-5,6,7,8-tetrahydro-[1,2,4]triazolo[1,5-a]pyridin-2-amine

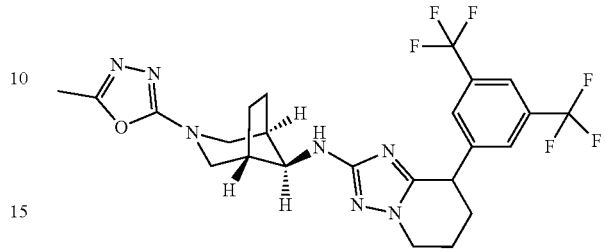

Chromatography of the racemic 8-(3,5-bis(trifluoromethyl)phenyl)-N-((8-endo)-3-(5-methyl-1,3,4-oxadiazol-2-yl)-3-azabicyclo[3.2.1]octan-8-yl)-5,6,7,8-tetrahydro-[1,2,4]triazolo[1,5-a]pyridin-2-amine (example 33g) on Reprosil Chiral NR (heptane/ethanol=60:40) yielded the title compound as off-white solid (8.0 mg, 24%). MS: m/z=540.3 [M+H]+. (In addition the corresponding (+)-enantiomer was isolated, 8 mg, 24%, MS: m/z=540.3 [M+H]+).

Example 34a

N-((8-endo)-3-(5-Methyl-1,3,4-oxadiazol-2-yl)-3-azabicyclo[3.2.1]octan-8-yl)-5-(trifluoromethyl)-8-(3-(trifluoromethyl)phenyl)-5,6,7,8-tetrahydro-[1,2,4]triazolo[1,5-a]pyridin-2-amine

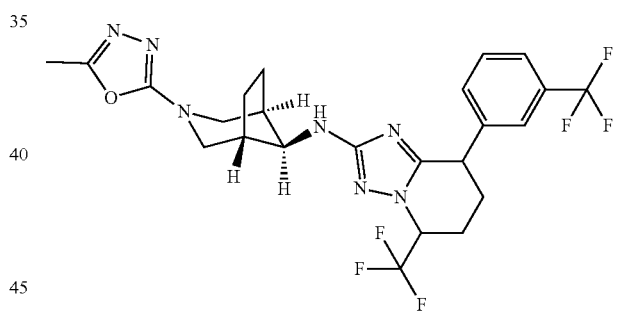

a) 5-(Trifluoromethyl)-8-(3-(trifluoromethyl)phenyl)-[1,2,4]triazolo[1,5-a]pyridin-2-amine

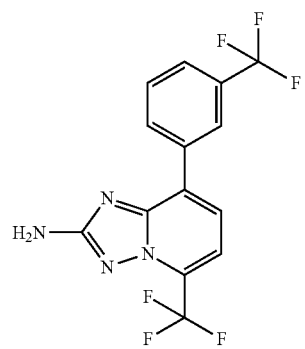 [SMILES: Nc1nc2c(-c3cccc(C(F)(F)F)c3)ccc(C(F)(F)F)n2n1]

In a 100 ml round-bottomed flask, 8-bromo-5-(trifluoromethyl)-[1,2,4]triazolo[1,5-a]pyridin-2-amine (2.00 g, 7.12 mmol), (3-(trifluoromethyl)phenyl)boronic acid (1.35 g, 7.12 mmol) and cesium carbonate (4.64 g, 14.2 mmol) were combined with dioxane (40 ml) and water (4 ml) to give a light brown solution. Under argon 1,1'-bis(diphenylphosphino)ferrocene-palladium(II)dichloride dichloromethane complex (521 mg, 712 µmol) was added. The reaction mixture was heated at 80° C. for 2 hours. Chromatography (silica gel, 40 g, ethyl acetate/heptan=10:90 to 50:50) yielded the title compound as off-white solid (2.4 g, 97%). MS: m/z=347.0 [M+H]$^+$.

b) 2-Bromo-5-(trifluoromethyl)-8-(3-(trifluoromethyl)phenyl)-[1,2,4]triazolo[1,5-a]pyridine

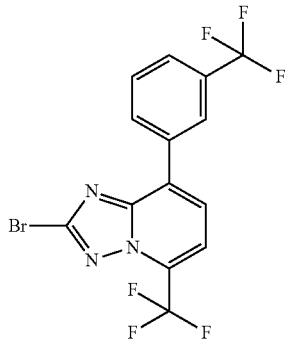 [SMILES: FC(F)(F)c1cccc(-c2ccc(C(F)(F)F)n3nc(Br)nc23)c1]

In a 100 ml round-bottomed flask, copper (II) bromide (2.32 g, 10.4 mmol) and tert-butyl nitrite (1.07 g, 1.24 ml, 10.4 mmol) were combined with acetonitrile (30 ml) to give a black solution. The reaction mixture was heated to 60° C. and then 5-(trifluoromethyl)-8-(3-(trifluoromethyl)phenyl)-[1,2,4]triazolo[1,5-a]pyridin-2-amine (2.40 g, 6.93 mmol) was added. The reaction mixture was heated at 80° C. for 1 hour. Chromatography (silica gel, 40 g, ethyl acetate/heptane=20:80 to 50:50) yielded the title compound as light brown oil (2.48 g, 87%). MS: m/z=410.0 and 412.0 [M+H]$^+$.

c) (8-endo)-tert-Butyl 8-((5-(trifluoromethyl)-8-(3-(trifluoromethyl)phenyl)-[1,2,4]triazolo[1,5-a]pyridin-2-yl)amino)-3-azabicyclo[3.2.1]octane-3-carboxylate

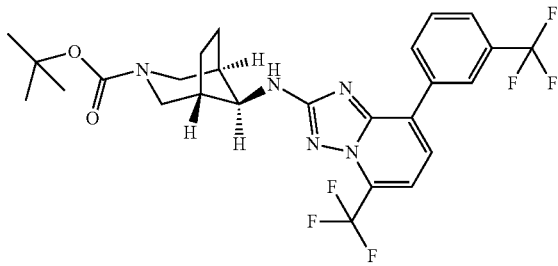 [SMILES: CC(C)(C)OC(=O)N1C[C@H]2CC[C@@H](C1)[C@@H]2Nc1nc2c(-c3cccc(C(F)(F)F)c3)ccc(C(F)(F)F)n2n1]

In a microwave vial, (8-endo)-tert-butyl 8-amino-3-azabicyclo[3.2.1]octane-3-carboxylate (1.35 g, 5.97 mmol), 2-bromo-5-(trifluoromethyl)-8-(3-(trifluoromethyl)phenyl)-[1,2,4]triazolo[1,5-a]pyridine (2.45 g, 5.97 mmol), xantphos (553 mg, 956 µmol), tris(dibenzylideneacetone)dipalladium (0) chloroform adduct (495 mg, 478 µmol) and sodium tert-butoxide (1.21 g, 12.5 mmol) were combined with dioxane (47 ml) to give a black suspension. The vial was capped and heated in the microwave at 145° C. for 30 minutes. Chromatography (silica gel, 40 g, ethyl acetate/heptan=30:70 to 70:30) yielded the title compound as light brown solid (1.85 g, 56%). MS: m/z=554.3 [M–H]$^-$.

e) N-((8-endo)-3-Azabicyclo[3.2.1]octan-8-yl)-5-(trifluoromethyl)-8-(3-(trifluoromethyl)phenyl)-[1,2,4]triazolo[1,5-a]pyridin-2-amine

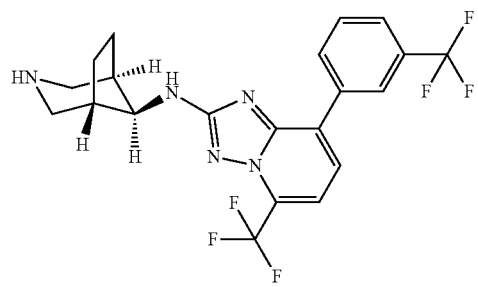 [SMILES: FC(F)(F)c1cccc(-c2ccc(C(F)(F)F)n3nc(N[C@@H]4[C@@H]5CC[C@H]4CNC5)nc23)c1]

In a 100 ml round-bottomed flask, (8-endo)-tert-butyl 8-((5-(trifluoromethyl)-8-(3-(trifluoromethyl)phenyl)-[1,2,4]triazolo[1,5-a]pyridin-2-yl)amino)-3-azabicyclo[3.2.1]octane-3-carboxylate (1.80 g, 3.24 mmol) was combined with dichloromethane (30 ml) to give a light brown solution. Trifluoroacetic acid (3.69 g, 2.5 ml, 32.4 mmol) was added and stirring was continued at room temperature for 3 hours. The reaction mixture was poured into water (20 ml), basified with aqueous sodium hydroxide (4N) and extracted with dichloromethane. Chromatography (silica gel-NH2, 40 g, ethyl acetate/heptane=50:50 to 100:0) yielded the title compound as light yellow solid (1.23 g, 83%). MS: m/z=456.2 [M+H]$^+$.

f) N-((8-endo)-3-Azabicyclo[3.2.1]octan-8-yl)-5-(trifluoromethyl)-8-(3-(trifluoromethyl)phenyl)-5,6,7,8-tetrahydro-[1,2,4]triazolo[1,5-a]pyridin-2-amine

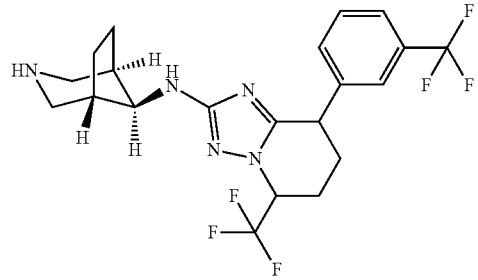 [SMILES: FC(F)(F)c1cccc(C2CCC(C(F)(F)F)n3nc(N[C@@H]4[C@@H]5CC[C@H]4CNC5)nc32)c1]

A degassed suspension of N-((8-endo)-3-azabicyclo[3.2.1]octan-8-yl)-5-(trifluoromethyl)-8-(3-(trifluoromethyl)phenyl)-[1,2,4]triazolo[1,5-a]pyridin-2-amine (1.23 g, 2.7 mmol), Pd—C (287 mg, 2.7 mmol) and hydrochloric acid (1N, 2.7 ml, 2.7 mmol) was hydrogenated under hydrogen atmosphere at 60° C. and 80 bar over the weekend. The catalyst was filtered off through glass fiber paper and the organic phase was concentrated in vacuo. The reaction mixture was poured into aqueous sodium hydroxide (4M, 25 ml) and extracted with ethyl acetate. The organic layers were dried over sodium sulfate, concentrated and dried in vacuo to yield the title compound as off-white solid (1.19 g, 86%). MS: m/z=460.2 [M+H]⁺.

g) N-((8-endo)-3-(5-Methyl-1,3,4-oxadiazol-2-yl)-3-azabicyclo[3.2.1]octan-8-yl)-5-(trifluoromethyl)-8-(3-(trifluoromethyl)phenyl)-5,6,7,8-tetrahydro-[1,2,4]triazolo[1,5-a]pyridin-2-amine

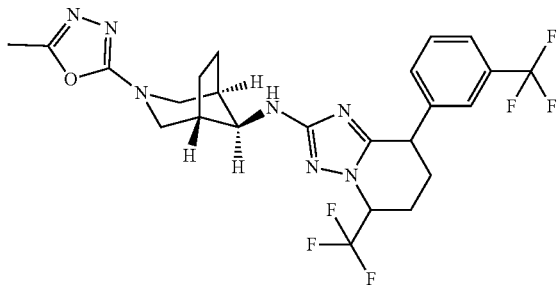 [SMILES: Cc1nnc(N2C[C@H]3CC[C@@H](C2)[C@@H]3Nc2nc3n(n2)C(C(F)(F)F)CCC3c2cccc(C(F)(F)F)c2)o1]

To a microwave vial was added N-((8-endo)-3-azabicyclo[3.2.1]octan-8-yl)-5-(trifluoromethyl)-8-(3-(trifluoromethyl)phenyl)-5,6,7,8-tetrahydro-[1,2,4]triazolo[1,5-a]pyridin-2-amine (120 mg, 261 µmol), triethylamine (132 mg, 182 µl, 1.31 mmol) and 2-bromo-5-methyl-1,3,4-oxadiazole (46.8 mg, 287 µmol) in ethanol (7 ml). The vial was capped and heated in the oilbath at 130° C. for 3 hours. Chromatography (silica gel-NH2, 4 g, ethyl acetate/heptane=50:50 to 100:0) yielded the title compound as off-white solid (130 mg, 92%). MS: m/z=542.3 [M+H]⁺.

Example 34b (+)-N-((8-endo)-3-(5-Methyl-1,3,4-oxadiazol-2-yl)-3-azabicyclo[3.2.1]octan-8-yl)-5-(trifluoromethyl)-8-(3-(trifluoromethyl)phenyl)-5,6,7,8-tetrahydro-[1,2,4]triazolo[1,5-a]pyridin-2-amine

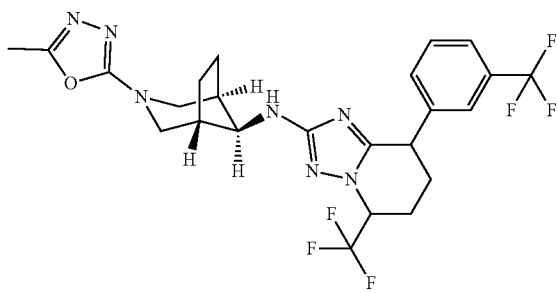 [SMILES: Cc1nnc(N2C[C@H]3CC[C@@H](C2)[C@@H]3Nc2nc3n(n2)C(C(F)(F)F)CCC3c2cccc(C(F)(F)F)c2)o1]

Chromatography of the racemic N-((8-endo)-3-(5-methyl-1,3,4-oxadiazol-2-yl)-3-azabicyclo[3.2.1]octan-8-yl)-5-(trifluoromethyl)-8-(3-(trifluoromethyl)phenyl)-5,6,7,8-tetrahydro-[1,2,4]triazolo[1,5-a]pyridin-2-amine (example 34a, 130 mg, 240 µmol) on Reprosil Chiral NR (heptane/ethanol=70:30) yielded the title compound as off-white solid (48 mg, 37%). MS: m/z=542.2 [M+H]⁺.

Example 34c (−)-N-((8-endo)-3-(5-Methyl-1,3,4-oxadiazol-2-yl)-3-azabicyclo[3.2.1]octan-8-yl)-5-(trifluoromethyl)-8-(3-(trifluoromethyl)phenyl)-5,6,7,8-tetrahydro-[1,2,4]triazolo[1,5-a]pyridin-2-amine

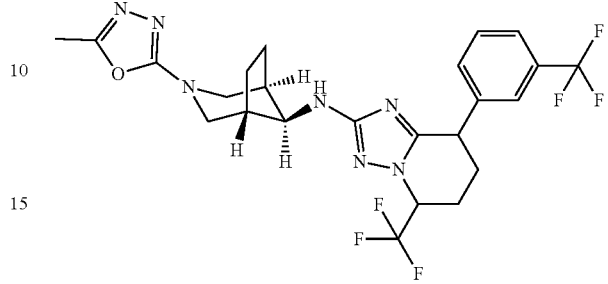

Chromatography of the racemic N-((8-endo)-3-(5-methyl-1,3,4-oxadiazol-2-yl)-3-azabicyclo[3.2.1]octan-8-yl)-5-(trifluoromethyl)-8-(3-(trifluoromethyl)phenyl)-5,6,7,8-tetrahydro-[1,2,4]triazolo[1,5-a]pyridin-2-amine (example 34a, 130 mg, 240 µmol) on Reprosil Chiral NR (heptane/ethanol=70:30) yielded the title compound as off-white solid (31 mg, 24%). MS: m/z=542.2 [M+H]⁺.

Example 35a

N-((8-endo)-3-(3-Methyl-1,2,4-oxadiazol-5-yl)-3-azabicyclo[3.2.1]octan-8-yl)-5-(trifluoromethyl)-8-(2-(trifluoromethyl)phenyl)-5,6,7,8-tetrahydro-[1,2,4]triazolo[1,5-a]pyridin-2-amine

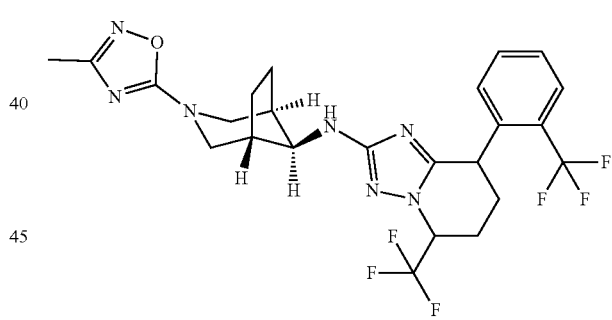

a) 5-(Trifluoromethyl)-8-(2-(trifluoromethyl)phenyl)-[1,2,4]triazolo[1,5-a]pyridin-2-amine

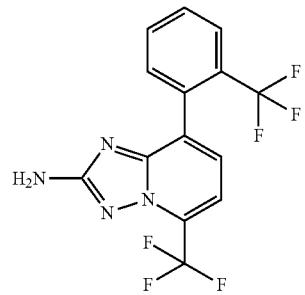 [SMILES: Nc1nc2c(-c3ccccc3C(F)(F)F)ccc(C(F)(F)F)n2n1]

In a 25 ml round-bottomed flask, 8-bromo-5-(trifluoromethyl)-[1,2,4]triazolo[1,5-a]pyridin-2-amine (400 mg, 1.42 mmol), (2-(trifluoromethyl)phenyl)boronic acid (270 mg, 1.42 mmol) and cesium carbonate (927 mg, 2.85 mmol) were combined with dioxane (10 ml) and water (1 ml) to give a light brown solution. Under argon 1,1'-bis(diphenylphosphino)ferrocene-palladium(II)dichloride dichloromethane complex (104 mg, 142 µmol) was added. The reaction mixture was heated at 80° C. for 2 hours. (2-(Trifluoromethyl)phenyl)boronic acid (270 mg, 1.42 mmol) was added again and stirring was continued overnight. (2-(Trifluoromethyl)phenyl)boronic acid (270 mg, 1.42 mmol) was added once again and stirring continued for another 3 hours. Chromatography (silica gel, 40 g, ethyl acetate/heptane=10:90 to 50:50) yielded the title compound as light brown oil (286 mg, 55%). MS: m/z=347.2 [M+H]⁺.

b) 2-Bromo-5-(trifluoromethyl)-8-(2-(trifluoromethyl)phenyl)-[1,2,4]triazolo[1,5-a]pyridine

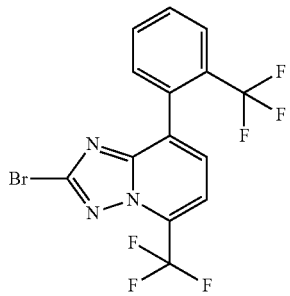 [SMILES: FC(F)(F)c1ccccc1-c1ccc(C(F)(F)F)n2nc(Br)nc12]

In a 25 ml round-bottomed flask, copper (II) bromide (277 mg, 1.24 mmol) and tert-butyl nitrite (128 mg, 147 µl, 1.24 mmol) were combined with acetonitrile (5 ml) to give a black solution. The reaction mixture was heated to 60° C. and then 5-(trifluoromethyl)-8-(2-(trifluoromethyl)phenyl)-[1,2,4]triazolo[1,5-a]pyridin-2-amine (286 mg, 826 µmol) was added. The reaction mixture was heated at 80° C. for 1 hour. Chromatography (silica gel, 40 g, ethyl acetate/heptane=20:80 to 50:50) yielded the title compound as a solid (399 mg, quant., purity 85%). MS: m/z=410.1 and 412.1 [M+H]⁺.

c) (8-endo)-tert-Butyl 8-((5-(trifluoromethyl)-8-(2-(trifluoromethyl)phenyl)-[1,2,4]triazolo[1,5-a]pyridin-2-yl)amino)-3-azabicyclo[3.2.1]octane-3-carboxylate

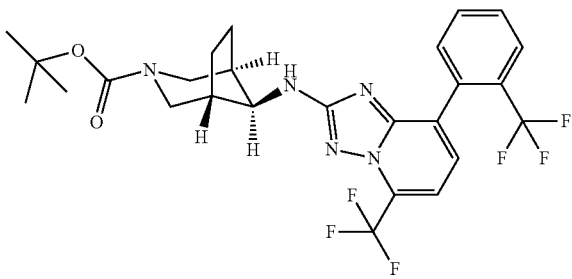 [SMILES: CC(C)(C)OC(=O)N1C[C@H]2CC[C@@H](C1)[C@@H]2Nc1nc2c(-c3ccccc3C(F)(F)F)ccc(C(F)(F)F)n2n1]

To a microwave vial, (8-endo)-tert-butyl 8-amino-3-azabicyclo[3.2.1]octane-3-carboxylate (220 mg, 973 µmol), 2-bromo-5-(trifluoromethyl)-8-(2-(trifluoromethyl)phenyl)-[1,2,4]triazolo[1,5-a]pyridine (399 mg, 973 µmol), xantphos (90.1 mg, 156 µmol), tris(dibenzylideneacetone)dipalladium (0) chloroform adduct (80.6 mg, 77.8 µmol) and sodium tert-butoxide (196 mg, 2.04 mmol) were combined with dioxane (8 ml) to give a black suspension. The vial was capped and heated in the microwave at 145° C. for 30 minutes. Chromatography (silica gel, 20 g, ethyl acetate/heptan=30:70 to 70:30) yielded the title compound as brown solid (339 mg, 63%). MS: m/z=556.5 [M+H]⁺.

d) N-((8-endo)-3-Azabicyclo[3.2.1]octan-8-yl)-5-(trifluoromethyl)-8-(2-(trifluoromethyl)phenyl)-[1,2,4]triazolo[1,5-a]pyridin-2-amine

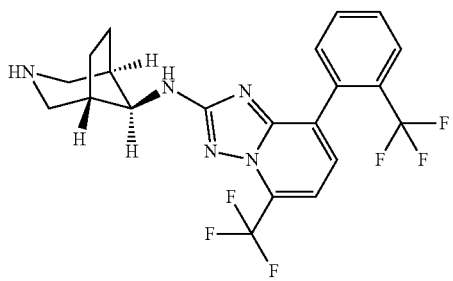 [SMILES: FC(F)(F)c1ccccc1-c1ccc(C(F)(F)F)n2nc(N[C@@H]3[C@@H]4CC[C@H]3CNC4)nc12]

In a 25 ml round-bottomed flask, (8-endo)-tert-butyl 8-((5-(trifluoromethyl)-8-(2-(trifluoromethyl)phenyl)-[1,2,4]triazolo[1,5-a]pyridin-2-yl)amino)-3-azabicyclo[3.2.1]octane-3-carboxylate (300 mg, 540 µmol) was combined with dichloromethane (10 ml) to give a light yellow solution. Trifluoroacetic acid (1.48 g, 1 ml, 13 mmol) was added and stirring continued at room temperature overnight. The reaction mixture was poured into water (5 ml), basified with aqueous sodium hydroxide (4N) and extracted with dichloromethane. Chromatography (silica gel-NH2, 12 g, ethyl acetate/heptane=50:50 to 100:0) yielded the title compound as light yellow solid (129 mg, 53%). MS: m/z=456.2 [M+H]⁺.

e) N-((8-endo)-3-Azabicyclo[3.2.1]octan-8-yl)-5-(trifluoromethyl)-8-(2-(trifluoromethyl)phenyl)-5,6,7,8-tetrahydro-[1,2,4]triazolo[1,5-a]pyridin-2-amine

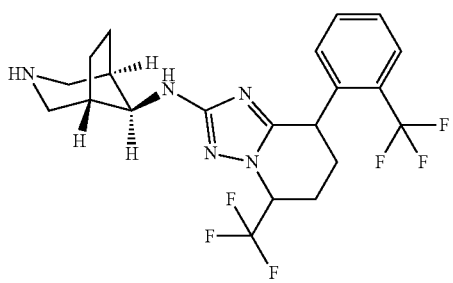 [SMILES: FC(F)(F)c1ccccc1C1CCC(C(F)(F)F)n2nc(N[C@@H]3[C@@H]4CC[C@H]3CNC4)nc21]

A degassed suspension of N-((8-endo)-3-azabicyclo[3.2.1]octan-8-yl)-5-(trifluoromethyl)-8-(2-(trifluoromethyl)phenyl)-[1,2,4]triazolo[1,5-a]pyridin-2-amine (100 mg, 220 µmol), Pd—C (23.4 mg, 220 µmol) and hydrochloric acid (1N, 220 µl, 220 µmol) was hydrogenated under hydrogen atmosphere at 60° C. and 80 bar for 18 hours. Then Pd—C (51.4 mg, 483 µmol) was added again and hydrogenation continued at 80° C. and 80 bar for 20 hours. The catalyst was filtered off through glass fiber paper and the organic phase was concentrated in vacuo. The reaction mixture was poured into aqueous sodium hydroxide (4M, 2 ml) and extracted with ethyl acetate. The organic layers were dried over sodium sulfate, concentrated and dried in vacuo to yield the title compound as off-white solid (93 mg, 92%). MS: m/z=460.2 [M+H]$^+$.

f) N-((8-endo)-3-(3-Methyl-1,2,4-oxadiazol-5-yl)-3-azabicyclo[3.2.1]octan-8-yl)-5-(trifluoromethyl)-8-(2-(trifluoromethyl)phenyl)-5,6,7,8-tetrahydro-[1,2,4]triazolo[1,5-a]pyridin-2-amine

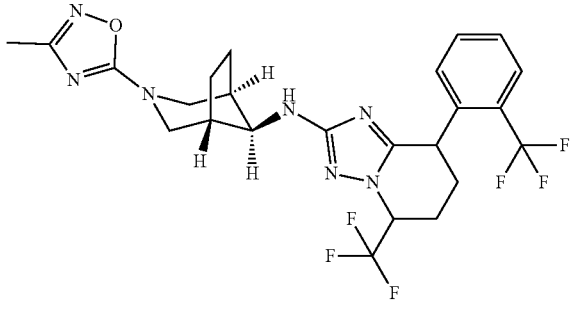 [SMILES: Cc1noc(N2C[C@H]3CC[C@@H](C2)[C@@H]3Nc2nc3n(n2)C(C(F)(F)F)CCC3c2ccccc2C(F)(F)F)n1]

In a 25 ml round-bottomed flask, N-((8-endo)-3-azabicyclo[3.2.1]octan-8-yl)-5-(trifluoromethyl)-8-(2-(trifluoromethyl)phenyl)-5,6,7,8-tetrahydro-[1,2,4]triazolo[1,5-a]pyridin-2-amine (100 mg, 218 µmol) and sodium bicarbonate (20.1 mg, 239 µmol) were combined with ethanol (5 ml) to give an off-white suspension. Cyanic bromide (25.4 mg, 239 µmol) was added and the mixture was stirred for 4 hours at room temperature. The reaction mixture was filtered through sintered glass, dried in vacuo and taken up in ethanol (5 ml). (E)-N'-Hydroxyacetimidamide (19.3 mg, 261 µmol) followed by zinc chloride (35.6 mg, 261 µmol) were added and stirring was continued at room temperature overnight. Aqueous hydrochloric acid (37%, 54.4 µl, 653 µmol) was added and the reaction mixture was heated at 60° C. for 15 hours. The crude reaction mixture was concentrated in vacuo, poured into saturated aqueous sodium bicarbonate (25 ml) and extracted with dichloromethane. Chromatography (silica gel-NH2, 12 g, ethyl acetate/heptane=30:70 to 100:0) yielded the title compound as light brown solid (67 mg, 57%). MS: m/z=542.4 [M+H]$^+$.

Example 35b (+)-N-((8-endo)-3-(3-Methyl-1,2,4-oxadiazol-5-yl)-3-azabicyclo[3.2.1]octan-8-yl)-5-(trifluoromethyl)-8-(2-(trifluoromethyl)phenyl)-5,6,7,8-tetrahydro-[1,2,4]triazolo[1,5-a]pyridin-2-amine

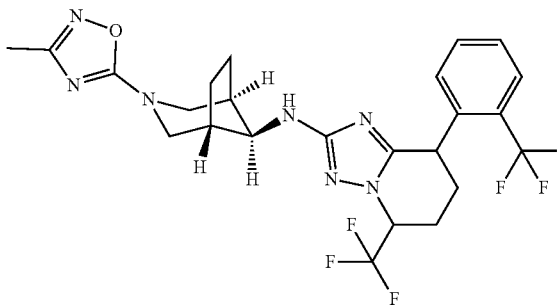

Chromatography of the racemic N-((8-endo)-3-(3-methyl-1,2,4-oxadiazol-5-yl)-3-azabicyclo[3.2.1]octan-8-yl)-5-(trifluoromethyl)-8-(2-(trifluoromethyl)phenyl)-5,6,7,8-tetrahydro-[1,2,4]triazolo[1,5-a]pyridin-2-amine (example 35a, 62 mg, 114 µmol) on Reprosil Chiral NR (heptane/ethanol=80:20) yielded the title compound as off-white solid (20 mg, 32%). MS: m/z=542.3 [M+H]$^+$.

Example 35c (−)-N-((8-endo)-3-(3-Methyl-1,2,4-oxadiazol-5-yl)-3-azabicyclo[3.2.1]octan-8-yl)-5-(trifluoromethyl)-8-(2-(trifluoromethyl)phenyl)-5,6,7,8-tetrahydro-[1,2,4]triazolo[1,5-a]pyridin-2-amine

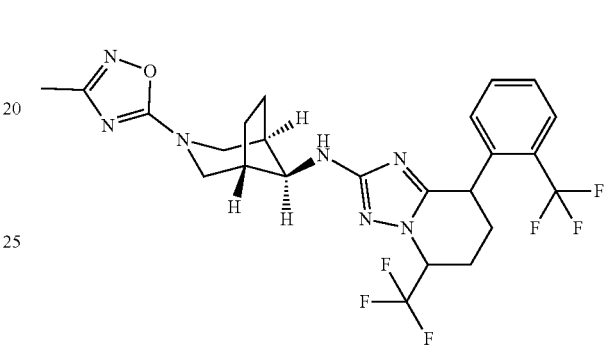

Chromatography of the racemic N-((8-endo)-3-(3-methyl-1,2,4-oxadiazol-5-yl)-3-azabicyclo[3.2.1]octan-8-yl)-5-(trifluoromethyl)-8-(2-(trifluoromethyl)phenyl)-5,6,7,8-tetrahydro-[1,2,4]triazolo[1,5-a]pyridin-2-amine (example 35a, 62 mg, 114 µmol) on Reprosil Chiral NR (heptane/ethanol=80:20) yielded the title compound as off-white solid (20 mg, 32%). MS: m/z=542.2 [M+H]$^+$.

Example 36a

N-((8-endo)-3-(3-Methyl-1,2,4-oxadiazol-5-yl)-3-azabicyclo[3.2.1]octan-8-yl)-5-(trifluoromethyl)-8-(3-(trifluoromethyl)phenyl)-5,6,7,8-tetrahydro-[1,2,4]triazolo[1,5-a]pyridin-2-amine

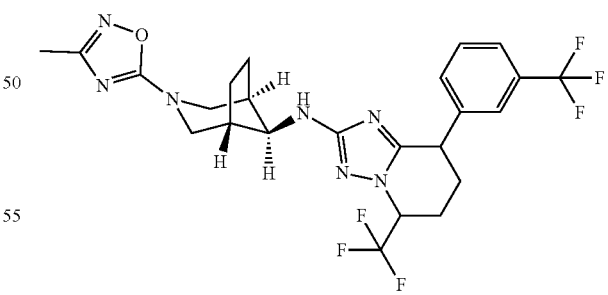

In a 25 mL round-bottomed flask, N-((8-endo)-3-azabicyclo[3.2.1]octan-8-yl)-5-(trifluoromethyl)-8-(3-(trifluoromethyl)phenyl)-5,6,7,8-tetrahydro-[1,2,4]triazolo[1,5-a]pyridin-2-amine (200 mg, 435 µmol) and sodium bicarbonate (40.2 mg, 479 µmol) were combined with ethanol (10 ml) to give an off-white suspension. Cyanic bromide (50.7 mg, 479 µmol) was added and stirring was continued for 4 hours at room temperature. The reaction mixture was filtered through sintered glass, dried in vacuo and taken up in ethanol (10 ml). (E)-N'-Hydroxyacetimidamide (38.7 mg, 522 µmol) followed by zinc chloride (71.2 mg, 522 µmol) were added and stirring was continued at room temperature overnight. Aqueous hydrochloric acid (37%, 109 µl, 1.31 mmol) was added and the reaction mixture was heated at 60° C. for 5 hours. The crude reaction mixture was concentrated in vacuo, poured into saturated aqueous sodiumbicarbonate (25 ml) and extracted with dichloromethane. Chromatography (silica gel-NH2, 12 g, ethyl acetate/heptane=30:70 to 100:0) yielded the title compound as off-white solid (153 mg, 65%). MS: m/z=542.4 [M+H]$^+$.

Example 36b (+)-N-((8-endo)-3-(3-Methyl-1,2,4-oxadiazol-5-yl)-3-azabicyclo[3.2.1]octan-8-yl)-5-(trifluoromethyl)-8-(3-(trifluoromethyl)phenyl)-5,6,7,8-tetrahydro-[1,2,4]triazolo[1,5-a]pyridin-2-amine

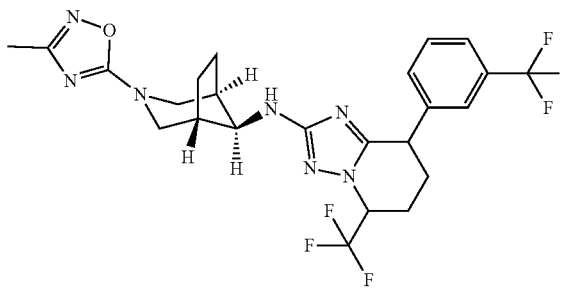

Chromatography of the racemic N-((8-endo)-3-(3-methyl-1,2,4-oxadiazol-5-yl)-3-azabicyclo[3.2.1]octan-8-yl)-5-(trifluoromethyl)-8-(3-(trifluoromethyl)phenyl)-5,6,7,8-tetrahydro-[1,2,4]triazolo[1,5-a]pyridin-2-amine (example 36a, 147 mg, 271 µmol) on Reprosil Chiral NR (heptane/ethanol=80:20) yielded the title compound as off-white solid (61 mg, 42%). MS: m/z=542.4 [M+H]$^+$.

Example 36c (−)-N-((8-endo)-3-(3-Methyl-1,2,4-oxadiazol-5-yl)-3-azabicyclo[3.2.1]octan-8-yl)-5-(trifluoromethyl)-8-(3-(trifluoromethyl)phenyl)-5,6,7,8-tetrahydro-[1,2,4]triazolo[1,5-a]pyridin-2-amine

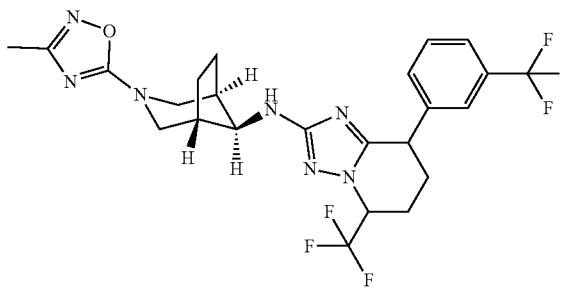

Chromatography of the racemic N-((8-endo)-3-(3-methyl-1,2,4-oxadiazol-5-yl)-3-azabicyclo[3.2.1]octan-8-yl)-5-(trifluoromethyl)-8-(3-(trifluoromethyl)phenyl)-5,6,7, 8-tetrahydro-[1,2,4]triazolo[1,5-a]pyridin-2-amine (example 36a, 147 mg, 271 µmol) on Reprosil Chiral NR (heptane/ethanol=80:20) yielded the title compound as off-white solid (48 mg, 33%). MS: m/z=542.4 [M+H]$^+$.

Example 37

(−)-N-((8-endo)-3-(3-Methyl-1,2,4-oxadiazol-5-yl)-3-azabicyclo[3.2.1]octan-8-yl)-6-(trifluoromethyl)-8-(2,3,4-trifluorophenyl)-5,6,7,8-tetrahydro-[1,2,4]triazolo[1,5-a]pyridin-2-amine

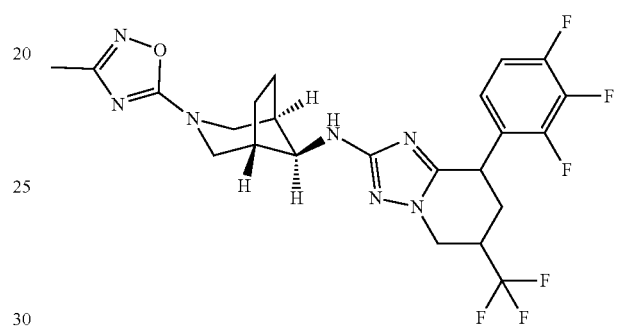

a) 6-(Trifluoromethyl)-8-(2,3,4-trifluorophenyl)-[1,2,4]triazolo[1,5-a]pyridin-2-amine

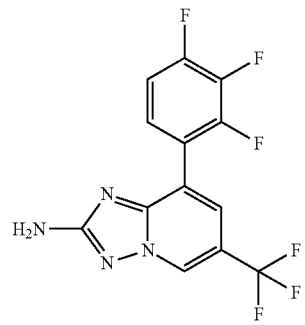 [SMILES: Nc1nc2c(-c3ccc(F)c(F)c3F)cc(C(F)(F)F)cn2n1]

In a 250 ml round-bottomed flask, 8-bromo-6-(trifluoromethyl)-[1,2,4]triazolo[1,5-a]pyridin-2-amine (CAS1257705-46-6, 2.05 g, 7.29 mmol), (2,3,4-trifluorophenyl)boronic acid (1.28 g, 7.29 mmol) and cesiumcarbonate (4.75 g, 14.6 mmol) were combined with dioxane (150 ml) and water (15 ml) to give a light brown suspension. 1,1'-bis(diphenylphosphino)ferrocene-palladium(II)dichloride dichloromethane complex (534 mg, 729 µmol) was added. The reaction mixture was heated at 80° C. overnight. Chromatography (silica gel, 40 g, ethyl acetate/heptane=50:50 to 100:0) yielded the title compound as light brown solid (1.98 g, 74%). MS: m/z=333.0 [M+H]$^+$.

b) 2-Bromo-6-(trifluoromethyl)-8-(2,3,4-trifluorophenyl)-[1,2,4]triazolo[1,5-a]pyridine

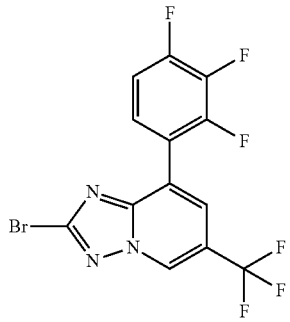 [SMILES: Fc1ccc(-c2cc(C(F)(F)F)cn3nc(Br)nc23)c(F)c1F]

In a 100 ml round-bottomed flask, copper (II) bromide (1.8 g, 8.05 mmol) and tert-butyl nitrite (830 mg, 957 µl, 8.05 mmol) were combined with acetonitrile (200 ml) to give a black solution. The reaction mixture was heated to 60° C. and 6-(trifluoromethyl)-8-(2,3,4-trifluorophenyl)-[1,2,4]triazolo[1,5-a]pyridin-2-amine (1.98 g, 5.36 mmol) was added portionwise. The reaction mixture was heated at 80° C. for 2 hours. Chromatography (silica gel, 40 g, ethyl acetate/heptane=10:90 to 50:50) yielded the title compound as off-white solid (1.71 g, 81%). MS: m/z=395.9 and 397.9 [M+H]$^+$.

c) (endo)-tert-Butyl-8-((6-(trifluoromethyl)-8-(2,3,4-trifluorophenyl)-[1,2,4]triazolo[1,5-a]pyridin-2-yl)amino)-3-azabicyclo[3.2.1]octane-3-carboxylate

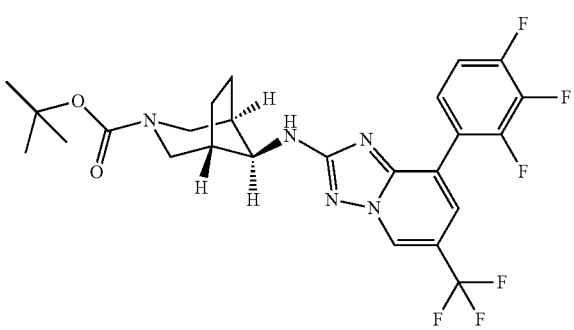 [SMILES: CC(C)(C)OC(=O)N1C[C@H]2CC[C@@H](C1)[C@@H]2Nc1nc2c(-c3ccc(F)c(F)c3F)cc(C(F)(F)F)cn2n1]

In a microwave vial, (endo)-tert-butyl-8-amino-3-azabicyclo[3.2.1]octane-3-carboxylate (868 mg, 3.84 mmol), 2-bromo-6-(trifluoromethyl)-8-(2,3,4-trifluorophenyl)-[1,2,4]triazolo[1,5-a]pyridine (1.52 g, 3.84 mmol), xantphos (355 mg, 614 µmol), tris(dibenzylideneacetone)dipalladium (0) chloroform adduct (318 mg, 307 µmol) and sodium tert-butoxide (774 mg, 8.06 mmol) were combined with dioxane (30 ml) to give a black suspension. The vial was capped and heated in the microwave at 145° C. for 30 minutes. Chromatography (silica gel, 12 g, ethyl acetate/heptane=10:90 to 100:0) yielded the title compound as light brown solid (729 mg, 35%). MS: m/z=540.2 [M−H]$^-$.

d) (endo)-tert-Butyl-8-((6-(trifluoromethyl)-8-(2,3,4-trifluorophenyl)-5,6,7,8-tetrahydro-[1,2,4]triazolo[1,5-a]pyridin-2-yl)amino)-3-azabicyclo[3.2.1]octane-3-carboxylate

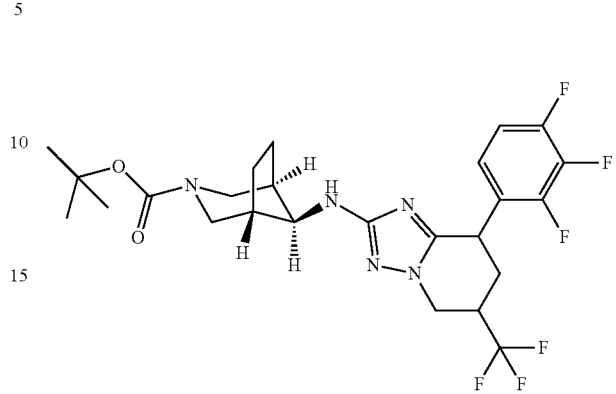

In a 250 ml round-bottomed flask, (endo)-tert-butyl-8-((6-(trifluoromethyl)-8-(2,3,4-trifluorophenyl)-[1,2,4]triazolo[1,5-a]pyridin-2-yl)amino)-3-azabicyclo[3.2.1]octane-3-carboxylate (520 mg, 960 µmol), magnesium (187 mg, 7.68 mmol) and iodine (2.44 mg, 9.6 mol) were combined with methanol (90 ml) and tetrahydrofuran (45 ml) to give a brown suspension. The reaction mixture was heated at 60° C. overnight. Iodine (2.44 mg, 9.6 µmol) was added again and stirring was continued at 60° C. for 1 hour. Chromatography (silica gel-NH2, 40 g, ethyl acetate/heptane=10:90 to 50:50) yielded the title compound as light yellow solid (338 mg, 65%). MS: m/z=546.3 [M+H]$^+$.

e) N-((endo)-3-Azabicyclo[3.2.1]octan-8-yl)-6-(trifluoromethyl)-8-(2,3,4-trifluorophenyl)-5,6,7,8-tetrahydro-[1,2,4]triazolo[1,5-a]pyridin-2-amine

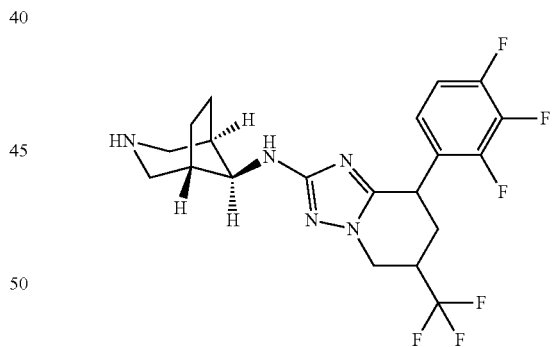

In a 50 ml round-bottomed flask, (endo)-tert-butyl-8-((6-(trifluoromethyl)-8-(2,3,4-trifluorophenyl)-5,6,7,8-tetrahydro-[1,2,4]triazolo[1,5-a]pyridin-2-yl)amino)-3-azabicyclo[3.2.1]octane-3-carboxylate (335 mg, 614 µmol) was combined with dichloromethane (23 ml) to give a light yellow solution. Trifluoroacetic acid (1.40 g, 946 µl, 12.3 mmol) was added and stirring was continued at room temperature for 3 hours. The reaction mixture was poured into water (5 ml), basified with aqueous sodium hydroxide (4N) and extracted with dichloromethane. The organic layers were dried over sodiumsulfate, concentrated and dried in vacuo to yield the title compound as light brown solid (200 mg, 74%). MS: m/z=446.2 [M+H]$^+$.

f) N-((endo)-3-(3-Methyl-1,2,4-oxadiazol-5-yl)-3-azabicyclo[3.2.1]octan-8-yl)-6-(trifluoromethyl)-8-(2,3,4-trifluorophenyl)-5,6,7,8-tetrahydro-[1,2,4]triazolo[1,5-a]pyridin-2-amine

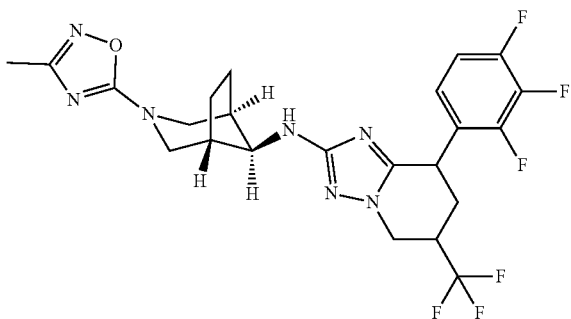 [SMILES: Cc1noc(N2C[C@H]3CC[C@@H](C2)[C@@H]3Nc2nc3n(n2)CC(C(F)(F)F)CC3c2ccc(F)c(F)c2F)n1]

In a 25 ml round-bottomed flask, N-((endo)-3-azabicyclo[3.2.1]octan-8-yl)-6-(trifluoromethyl)-8-(2,3,4-trifluorophenyl)-5,6,7,8-tetrahydro-[1,2,4]triazolo[1,5-a]pyridin-2-amine (200 mg, 449 mol) and sodium bicarbonate (41.5 mg, 494 µmol) were combined with ethanol (10 ml) to give an off-white suspension. Cyanic bromide (52.3 mg, 494 µmol) was added and the mixture was stirred for 4 hours at room temperature. The reaction mixture was filtered through sintered glass, dried in vacuo and taken up in ethanol (10 ml). (E)-N'-Hydroxyacetimidamide (39.9 mg, 539 mol) followed by zinc chloride (73.4 mg, 539 µmol) were added and stirring was continued at room temperature overnight. Aqueous hydrochloric acid (37%, 112 µl, 1.35 mmol) was added and the reaction mixture was heated at 60° C. for 15 hours. The crude reaction mixture was concentrated in vacuo, poured into aqueous sodiumbicarbonate (25 ml) and extracted with dichloromethane. Chromatography (silica gel-NH2, 12 g, ethyl acetate/heptane=30:70 to 100:0) yielded the title compound as off-white solid (115 mg, 49%). MS: m/z=528.2 [M+H]+.

(−)-N-((8-endo)-3-(3-Methyl-1,2,4-oxadiazol-5-yl)-3-azabicyclo[3.2.1]octan-8-yl)-6-(trifluoromethyl)-8-(2,3,4-trifluorophenyl)-5,6,7,8-tetrahydro-[1,2,4]triazolo[1,5-a]pyridin-2-amine

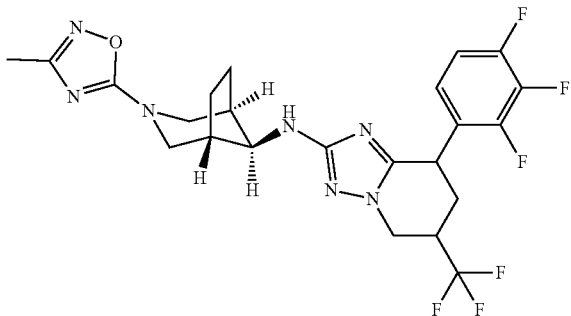 [SMILES: Cc1noc(N2C[C@H]3CC[C@@H](C2)[C@@H]3Nc2nc3n(n2)CC(C(F)(F)F)CC3c2ccc(F)c(F)c2F)n1]

Chromatography of the diasteremeric mixture of N-((endo)-3-(3-methyl-1,2,4-oxadiazol-5-yl)-3-azabicyclo[3.2.1]octan-8-yl)-6-(trifluoromethyl)-8-(2,3,4-trifluorophenyl)-5,6,7,8-tetrahydro-[1,2,4]triazolo[1,5-a]pyridin-2-amine (example 37f, 109 mg, 207 µmol) on Reprosil Chiral NR (heptane/ethanol=70:30) yielded the title compound as off-white solid (19 mg, 17%). MS: m/z=528.3 [M+H]+. [In addition the (+)-enantiomer of the title compound (24 mg, 22%, MS: m/z=528.3 [M+H]+) as well as the (−)-enantiomer (10 mg, 9%, MS: m/z=528.3 [M+H]+) and (+)-enantiomer (12 mg, 11%, MS: m/z=528.3 [M+H]+) of the second diastereoisomer were obtained as off-white solids].

Example 38

(−)-N-((endo)-3-(3-Methylisoxazol-5-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine

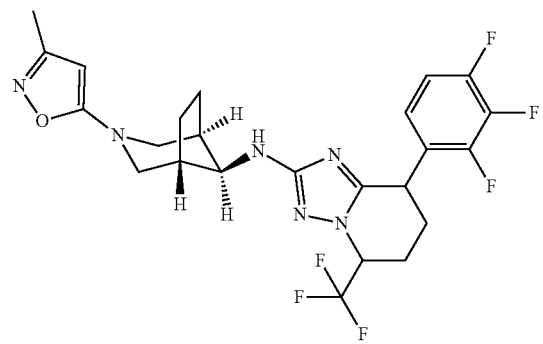 [SMILES: Cc1cc(N2C[C@H]3CC[C@@H](C2)[C@@H]3Nc2nc3n(n2)C(C(F)(F)F)CCC3c2ccc(F)c(F)c2F)on1]

a) N-((endo)-3-(3-Methylisoxazol-5-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine

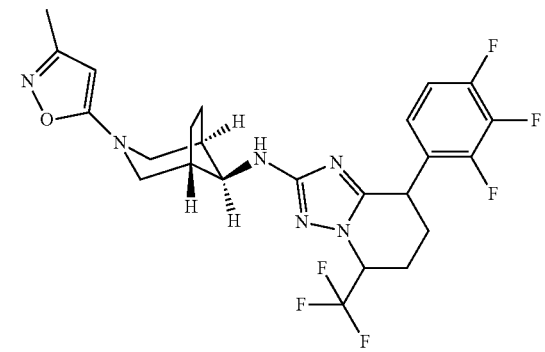 [SMILES: Cc1cc(N2C[C@H]3CC[C@@H](C2)[C@@H]3Nc2nc3n(n2)C(C(F)(F)F)CCC3c2ccc(F)c(F)c2F)on1]

In a 25 ml three-necked flask, N-((endo)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine (example 29g, 1.00 g, 2.25 mmol), copper (I) iodide (42.8 mg, 225 µmol), tripotassium phosphate (953 mg, 4.49 mmol) and N,N-diethylsalicylamide (130 mg, 674 µmol) were combined with dimethylformamide (20 ml) to give a light green solution. The reaction mixture was cooled to −20° C., 5-iodo-3-methylisoxazole (563 mg, 2.69 mmol) was added and the mixture was stirred at −20° C. for 4 hours. The reaction mixture was poured into saturated aqueous sodiumbicarbonate and extracted with ethyl acetate. Chromatography (silica gel-NH2, 40 g, ethyl acetate/heptane=10:

90 to 100:0) yielded the title compound (81 mg, 7%) as light yellow oil. MS: m/z=527.5 [M+H]⁺.

b) (−)-N-((endo)-3-(3-Methylisoxazol-5-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine

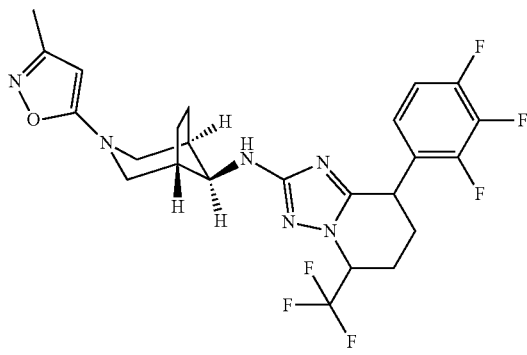 [SMILES: Cc1cc(N2C[C@H]3CC[C@@H](C2)[C@@H]3Nc2nc3n(n2)C(C(F)(F)F)CCC3c2ccc(F)c(F)c2F)on1]

Chromatography of the racemic N-((endo)-3-(3-methylisoxazol-5-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine (example 38a) on Reprosil Chiral NR (ethanol/heptane=20:80) yielded the title compound as off-white solid (20 mg, 26%). MS: m/z=527.6 [M+H]⁺. In addition the (+)-enantiomer of the title compound (20 mg, 26%, MS: m/z=527.6 [M+H]⁺) was obtained as off-white solid.

The invention claimed is:

1. A compound of formula I

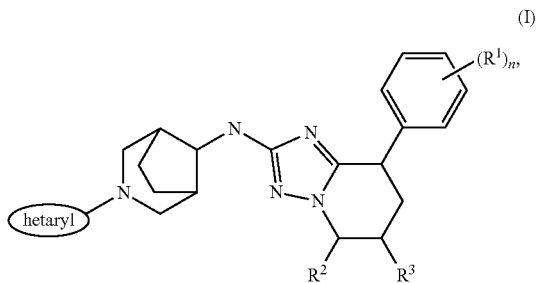

or a pharmaceutically acceptable salt thereof,
wherein:
hetaryl is a five membered heteroaryl group selected from the group consisting of

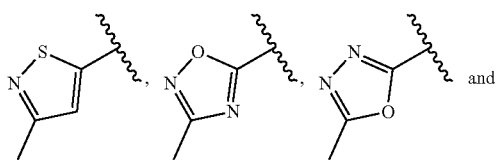

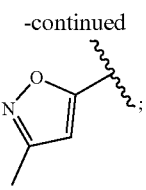

$R^1$ is hydrogen, halogen, lower alkyl, lower alkoxy, lower alkyl substituted by halogen, S-lower alkyl substituted by halogen or lower alkoxy substituted by halogen, or two adjacent le groups may together form an additional ring containing
—O—CH₂—O—;
n is an integer selected from 1 to 5;
$R^2$ is hydrogen or lower alkyl substituted by halogen; and
$R^3$ is hydrogen or lower alkyl substituted by halogen.

2. A compound of formula Ia according to claim 1

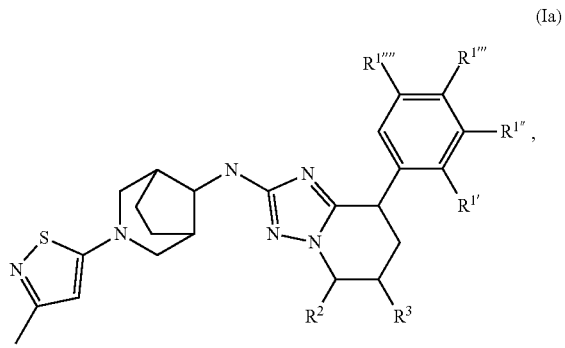

or a pharmaceutically acceptable salt thereof,
wherein:
$R^{1'}$ is hydrogen, halogen, lower alkyl, lower alkoxy, lower alkyl substituted by halogen or lower alkoxy substituted by halogen;
$R^{1''}$ is hydrogen, halogen, lower alkyl substituted by halogen or lower alkoxy substituted by halogen;
$R^{1'''}$ is hydrogen, halogen, lower alkyl, lower alkyl substituted by halogen, lower alkoxy, lower alkoxy substituted by halogen, S-lower alkyl substituted by halogen;
or $R^2$ and $R^3$, together with the carbon atoms to which they are attached, form a ring, containing —O—CH₂—O—;
$R^{1''''}$ is hydrogen or halogen;
$R^2$ is hydrogen or lower alkyl substituted by halogen; and
$R^3$ is hydrogen or lower alkyl substituted by halogen.

3. A compound of formula Ia according to claim 2, wherein the compound is selected from the group consisting of:
N-((8-endo)-3-(3-Methylisothiazol-5-yl)-3-azabicyclo[3.2.1]octan-8-yl)-8-(4-(trifluoromethyl)phenyl)-5,6,7,8-tetrahydro-[1,2,4]triazolo[1,5-a]pyridin-2-amine;
(+)-N-((8-endo)-3-(3-Methylisothiazol-5-yl)-3-azabicyclo[3.2.1]octan-8-yl)-8-(4-(trifluoromethyl)phenyl)-5,6,7,8-tetrahydro-[1,2,4]triazolo[1,5-a]pyridin-2-amine;
(−)-N-((8-endo)-3-(3-Methylisothiazol-5-yl)-3-azabicyclo[3.2.1]octan-8-yl)-8-(4-(trifluoromethyl)phenyl)-5,6,7,8-tetrahydro-[1,2,4]triazolo[1,5-a]pyridin-2-amine;
(−)-N-[(8-endo)-3-(3-Methyl-1,2-thiazol-5-yl)-3-azabicyclo[3.2.1]octan-8-yl]-8-(2,3,4-trifluorophenyl)-5,6,7,8-tetrahydro-[1,2,4]triazolo[1,5-a]pyridin-2-amine;

(+)-N-[(8-endo)-3-(3-Methyl-1,2-thiazol-5-yl)-3-azabicyclo[3.2.1]octan-8-yl]-8-(2,3,4-trifluorophenyl)-5,6,7,8-tetrahydro-[1,2,4]triazolo[1,5-a]pyridin-2-amine;

N-((8-endo)-3-(3-Methylisothiazol-5-yl)-3-azabicyclo[3.2.1]octan-8-yl)-8-(4-(trifluoromethoxy)phenyl)-5,6,7,8-tetrahydro-[1,2,4]triazolo[1,5-a]pyridin-2-amine;

(+)-N-[(8-endo)-3-(3-Methyl-1,2-thiazol-5-yl)-3-azabicyclo[3.2.1]octan-8-yl]-8-[4-(trifluoromethoxy)phenyl]-5,6,7,8-tetrahydro-[1,2,4]triazolo[1,5-a]pyridin-2-amine;

(−)-N-[(8-endo)-3-(3-Methyl-1,2-thiazol-5-yl)-3-azabicyclo[3.2.1]octan-8-yl]-8-[4-(trifluoromethoxy)phenyl]-5,6,7,8-tetrahydro-[1,2,4]triazolo[1,5-a]pyridin-2-amine;

8-(2-Chloro-4-fluorophenyl)-N-[(8-endo)-3-(3-methyl-1,2-thiazol-5-yl)-3-azabicyclo[3.2.1]octan-8-yl]-5,6,7,8-tetrahydro-[1,2,4]triazolo[1,5-a]pyridin-2-amine;

N-[(8-endo)-3-(3-Methyl-1,2-thiazol-5-yl)-3-azabicyclo[3.2.1]octan-8-yl]-8-[4-(trifluoromethylsulfanyl)phenyl]-5,6,7,8-tetrahydro-[1,2,4]triazolo[1,5-a]pyridin-2-amine;

(+)-N-((8-endo)-3-(3-Methylisothiazol-5-yl)-3-azabicyclo[3.2.1]octan-8-yl)-8-(4-((trifluoromethyl)thio)phenyl)-5,6,7,8-tetrahydro-[1,2,4]triazolo[1,5-a]pyridin-2-amine;

(−)-N-((8-endo)-3-(3-Methylisothiazol-5-yl)-3-azabicyclo[3.2.1]octan-8-yl)-8-(4-((trifluoromethyl)thio)phenyl)-5,6,7,8-tetrahydro-[1,2,4]triazolo[1,5-a]pyridin-2-amine;

(+)-N-((8-endo)-3-(3-Methylisothiazol-5-yl)-3-azabicyclo[3.2.1]octan-8-yl)-8-(4-(2,2,2-trifluoroethyl)phenyl)-5,6,7,8-tetrahydro-[1,2,4]triazolo[1,5-a]pyridin-2-amine;

(−)-N-((8-endo)-3-(3-Methylisothiazol-5-yl)-3-azabicyclo[3.2.1]octan-8-yl)-8-(4-(2,2,2-trifluoroethyl)phenyl)-5,6,7,8-tetrahydro-[1,2,4]triazolo[1,5-a]pyridin-2-amine;

N-((8-endo)-3-(3-Methylisothiazol-5-yl)-3-azabicyclo[3.2.1]octan-8-yl)-8-(2-(trifluoromethyl)phenyl)-5,6,7,8-tetrahydro-[1,2,4]triazolo[1,5-a]pyridin-2-amine;

N-((8-endo)-3-(3-Methylisothiazol-5-yl)-3-azabicyclo[3.2.1]octan-8-yl)-8-(2-(trifluoromethyl)phenyl)-5,6,7,8-tetrahydro-[1,2,4]triazolo[1,5-a]pyridin-2-amine (enantiomer A);

N-((8-endo)-3-(3-Methylisothiazol-5-yl)-3-azabicyclo[3.2.1]octan-8-yl)-8-(2-(trifluoromethyl)phenyl)-5,6,7,8-tetrahydro-[1,2,4]triazolo[1,5-a]pyridin-2-amine (enantiomer B);

(+)-N-((8-endo)-3-(3-Methylisothiazol-5-yl)-3-azabicyclo[3.2.1]octan-8-yl)-8-(3-(trifluoromethyl)phenyl)-5,6,7,8-tetrahydro-[1,2,4]triazolo[1,5-a]pyridin-2-amine;

(−)-N-((8-endo)-3-(3-Methylisothiazol-5-yl)-3-azabicyclo[3.2.1]octan-8-yl)-8-(3-(trifluoromethyl)phenyl)-5,6,7,8-tetrahydro-[1,2,4]triazolo[1,5-a]pyridin-2-amine;

(+)-N-((8-endo)-3-(3-Methylisothiazol-5-yl)-3-azabicyclo[3.2.1]octan-8-yl)-8-(2-(trifluoromethoxy)phenyl)-5,6,7,8-tetrahydro-[1,2,4]triazolo[1,5-a]pyridin-2-amine;

(−)-N-((8-endo)-3-(3-Methylisothiazol-5-yl)-3-azabicyclo[3.2.1]octan-8-yl)-8-(2-(trifluoromethoxy)phenyl)-5,6,7,8-tetrahydro-[1,2,4]triazolo[1,5-a]pyridin-2-amine;

(+)-N-((8-endo)-3-(3-Methylisothiazol-5-yl)-3-azabicyclo[3.2.1]octan-8-yl)-8-(3-(trifluoromethoxy)phenyl)-5,6,7,8-tetrahydro-[1,2,4]triazolo[1,5-a]pyridin-2-amine;

(−)-N-((8-endo)-3-(3-Methylisothiazol-5-yl)-3-azabicyclo[3.2.1]octan-8-yl)-8-(3-(trifluoromethoxy)phenyl)-5,6,7,8-tetrahydro-[1,2,4]triazolo[1,5-a]pyridin-2-amine;

8-(4-Methoxyphenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine;

(+)-8-(4-Methoxyphenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine;

(−)-8-(4-Methoxyphenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine;

(+)-8-(4-Fluoro-2-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine;

(−)-8-(4-Fluoro-2-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine;

(−)-N-((8-endo)-3-(3-Methylisothiazol-5-yl)-3-azabicyclo[3.2.1]octan-8-yl)-8-(3,4,5-trifluorophenyl)-5,6,7,8-tetrahydro-[1,2,4]triazolo[1,5-a]pyridin-2-amine;

(+)-(N-((8-endo)-3-(3-Methylisothiazol-5-yl)-3-azabicyclo[3.2.1]octan-8-yl)-8-(3,4,5-trifluorophenyl)-5,6,7,8-tetrahydro-[1,2,4]triazolo[1,5-a]pyridin-2-amine;

(+)-8-(4-Fluoro-3-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine;

(−)8-(4-Fluoro-3-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine;

(+)-8-(Benzo[d][1,3]dioxol-5-yl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine;

(−)-8-(Benzo[d][1,3]dioxol-5-yl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine;

8-(3-Fluoro-5-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine;

(+)-8-(3-Fluoro-5-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine;

(−)-8-(3-Fluoro-5-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine;

N-((8-endo)-3-(3-Methylisothiazol-5-yl)-3-azabicyclo[3.2.1]octan-8-yl)-8-(4-(2,2,2-trifluoroethoxy)phenyl)-5,6,7,8-tetrahydro-[1,2,4]triazolo[1,5-a]pyridin-2-amine;

8-(2-Fluoro-4-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine;

(+)-8-(2-Fluoro-4-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine;

(−)-8-(2-Fluoro-4-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine;

(+)-8-(4-(Difluoromethoxy)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine;

(−)-8-(4-(Difluoromethoxy)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine;

(−)-N-((8-endo)-3-(3-Methylisothiazol-5-yl)-3-azabicyclo[3.2.1]octan-8-yl)-8-(p-tolyl)-5,6,7,8-tetrahydro-[1,2,4]triazolo[1,5-a]pyridin-2-amine;

(+)-N-((8-endo)-3-(3-Methylisothiazol-5-yl)-3-azabicyclo[3.2.1]octan-8-yl)-8-(p-tolyl)-5,6,7,8-tetrahydro-[1,2,4]triazolo[1,5-a]pyridin-2-amine;

(−)-8-(2-Methoxy-4-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine;

(+)-8-(2-Methoxy-4-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine;

8-(5-Fluoro-2-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine;

(+)-8-(5-Fluoro-2-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine;

(−)-8-(5-Fluoro-2-(trifluoromethyl)phenyl)-N-((8-endo)-3-(3-methylisothiazol-5-yl)-3-azabicyclo[3.2.1]octan-8-yl)-5,6,7,8-tetrahydro-[1,2,4]triazolo[1,5-a]pyridin-2-amine;

8-(4-Fluoro-2-methylphenyl)-N-[(8-endo)-3-(3-methyl-1,2-thiazol-5-yl)-3-azabicyclo[3.2.1]octan-8-yl]-5,6,7,8-tetrahydro-[1,2,4]triazolo[1,5-a]pyridin-2-amine;

(−)-8-(4-Fluoro-2-methylphenyl)-N-[(8-endo)-3-(3-methyl-1,2-thiazol-5-yl)-3-azabicyclo[3.2.1]octan-8-yl]-5,6,7,8-tetrahydro-[1,2,4]triazolo[1,5-a]pyridin-2-amine; and (+)-8-(4-Fluoro-2-methylphenyl)-N-[(8-endo)-3-(3-methyl- 1,2-thiazol-5-yl)-3-azabicyclo[3.2.1]octan-8-yl]-5,6,7,8-tetrahydro-[1,2,4]triazolo[1,5-a]pyridin-2-amine; or a pharmaceutically acceptable salt thereof.

4. A compound of formula Ib according to claim 1

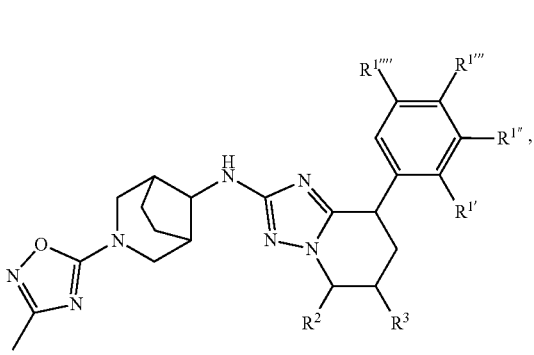

Ib or a pharmaceutically acceptable salt thereof,
wherein:
R$^{1'}$ is hydrogen, halogen, lower alkyl, lower alkoxy, lower alkyl substituted by halogen or lower alkoxy substituted by halogen;

R$^{1''}$ is hydrogen, halogen, lower alkyl substituted by halogen or lower alkoxy substituted by halogen;

R$^{1'''}$ is hydrogen, halogen, lower alkyl, lower alkyl substituted by halogen, lower alkoxy, lower alkoxy substituted by halogen, S-lower alkyl substituted by halogen;

or R$^2$ and R$^3$ form together with the carbon atoms, to which they are attached a ring, containing —O—CH$_2$—O—;

R$^{1''''}$ is hydrogen or halogen;
R$^2$ is hydrogen or lower alkyl substituted by halogen; and
R$^3$ is hydrogen or lower alkyl substituted by halogen.

5. A compound of formula Ib according to claim 4, wherein the compound is selected from the group consisting of:

(−)-N-((8-endo)-3-(3-Methyl-1,2,4-oxadiazol-5-yl)-3-azabicyclo[3.2.1]octan-8-yl)-8-(2,3,4-trifluorophenyl)-5,6,7,8-tetrahydro-[1,2,4]triazolo[1,5-a]pyridin-2-amine;

8-(4-Fluoro-3-(trifluoromethyl)phenyl)-N-((8-endo)-3-(3-methyl-1,2,4-oxadiazol-5-yl)-3-azabicyclo[3.2.1]octan-8-yl)-5,6,7,8-tetrahydro-[1,2,4]triazolo[1,5-a]pyridin-2-amine;

(−)-8-(4-Fluoro-3-(trifluoromethyl)phenyl)-N-((8-endo)-3-(3-methyl-1,2,4-oxadiazol-5-yl)-3-azabicyclo[3.2.1]octan-8-yl)-5,6,7,8-tetrahydro-[1,2,4]triazolo[1,5-a]pyridin-2-amine;

N-((8-endo)-3-(3-Methyl-1,2,4-oxadiazol-5-yl)-3-azabicyclo[3.2.1]octan-8-yl)-8-(4-(trifluoromethyl)phenyl)-5,6,7,8-tetrahydro-[1,2,4]triazolo[1,5-a]pyridin-2-amine;

(−)-N-((8-endo)-3-(3-Methyl-1,2,4-oxadiazol-5-yl)-3-azabicyclo[3.2.1]octan-8-yl)-8-(4-(trifluoromethyl)phenyl)-5,6,7,8-tetrahydro-[1,2,4]triazolo[1,5-a]pyridin-2-amine;

8-(2-Fluoro-4-(trifluoromethyl)phenyl)-N-((8-endo)-3-(3-methyl-1,2,4-oxadiazol-5-yl)-3-azabicyclo[3.2.1]octan-8-yl)-5,6,7,8-tetrahydro-[1,2,4]triazolo[1,5-a]pyridin-2-amine;

(−)-8-(2-Fluoro-4-(trifluoromethyl)phenyl)-N-((8-endo)-3-(3-methyl-1,2,4-oxadiazol-5-yl)-3-azabicyclo[3.2.1]octan-8-yl)-5,6,7,8-tetrahydro-[1,2,4]triazolo[1,5-a]pyridin-2-amine;

N-((8-endo)-3-(3-Methyl-1,2,4-oxadiazol-5-yl)-3-azabicyclo[3.2.1]octan-8-yl)-8-(4-(trifluoromethoxy)phenyl)-5,6,7,8-tetrahydro-[1,2,4]triazolo[1,5-a]pyridin-2-amine;

(−)-N-((8-endo)-3-(3-Methyl-1,2,4-oxadiazol-5-yl)-3-azabicyclo[3.2.1]octan-8-yl)-8-(4-(trifluoromethoxy)phenyl)-5,6,7,8-tetrahydro-[1,2,4]triazolo[1,5-a]pyridin-2-amine;

N-((8-endo)-3-(3-Methyl-1,2,4-oxadiazol-5-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine;

(−)-N-((8-endo)-3-(3-Methyl-1,2,4-oxadiazol-5-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine;

(+)-N-((8-endo)-3-(3-Methyl-1,2,4-oxadiazol-5-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine;

N-((8-endo)-3-(3-Methyl-1,2,4-oxadiazol-5-yl)-3-azabicyclo[3.2.1]octan-8-yl)-5-(trifluoromethyl)-8-(2-(trifluoromethyl)phenyl)-5,6,7,8-tetrahydro-[1,2,4]triazolo[1,5-a]pyridin-2-amine;

(+)-N-((8-endo)-3-(3-Methyl-1,2,4-oxadiazol-5-yl)-3-azabicyclo[3.2.1]octan-8-yl)-5-(trifluoromethyl)-8-(2-(trifluoromethyl)phenyl)-5,6,7,8-tetrahydro-[1,2,4]triazolo[1,5-a]pyridin-2-amine;

(−)-N-((8-endo)-3-(3-Methyl-1,2,4-oxadiazol-5-yl)-3-azabicyclo[3.2.1]octan-8-yl)-5-(trifluoromethyl)-8-(2-(trifluoromethyl)phenyl)-5,6,7,8-tetrahydro-[1,2,4]triazolo[1,5-a]pyridin-2-amine;

N-((8-endo)-3-(3-Methyl-1,2,4-oxadiazol-5-yl)-3-azabicyclo[3.2.1]octan-8-yl)-5-(trifluoromethyl)-8-(3-(trifluoromethyl)phenyl)-5,6,7,8-tetrahydro-[1,2,4]triazolo[1,5-a]pyridin-2-amine;

(+)-N-((8-endo)-3-(3-Methyl-1,2,4-oxadiazol-5-yl)-3-azabicyclo[3.2.1]octan-8-yl)-5-(trifluoromethyl)-8-(3-(trifluoromethyl)phenyl)-5,6,7,8-tetrahydro-[1,2,4]triazolo[1,5-a]pyridin-2-amine;

(−)-N-((8-endo)-3-(3-Methyl-1,2,4-oxadiazol-5-yl)-3-azabicyclo[3.2.1]octan-8-yl)-5-(trifluoromethyl)-8-(3-(trifluoromethyl)phenyl)-5,6,7,8-tetrahydro-[1,2,4]triazolo[1,5-a]pyridin-2-amine; and (−)-N-((8-endo)-3-(3-Methyl-1,2,4-oxadiazol-5-yl)-3-azabicyclo[3.2.1]octan-8-yl)-6-(trifluoromethyl)-8-(2,3,4-trifluorophenyl)-5,6,7,8-tetrahydro-[1,2,4]triazolo[1,5-a]pyridin-2-amine, or a pharmaceutically acceptable salt thereof.

6. A compound of formula Ic according to claim 1,

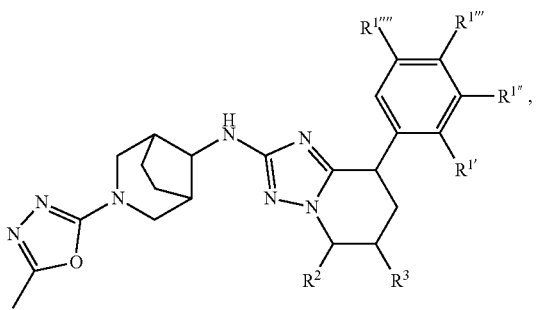

Ic or a pharmaceutically acceptable salt thereof,
wherein:
$R^{1'}$ is hydrogen, halogen, lower alkyl, lower alkoxy, lower alkyl substituted by halogen or lower alkoxy substituted by halogen;

$R^{1''}$ is hydrogen, halogen, lower alkyl substituted by halogen or lower alkoxy substituted by halogen;

$R^{1'''}$ is hydrogen, halogen, lower alkyl, lower alkyl substituted by halogen, lower alkoxy, lower alkoxy substituted by halogen, S-lower alkyl substituted by halogen;

or $R^2$ and $R^3$ form together with the carbon atoms, to which they are attached a ring, containing —O—CH$_2$—O—;

$R^{1''''}$ is hydrogen or halogen;

$R^2$ is hydrogen or lower alkyl substituted by halogen; and $R^3$ is hydrogen or lower alkyl substituted by halogen.

7. A compound of formula Ic according to claim 6, wherein the compound is selected from the group consisting of:

8-(2-Fluoro-4-(trifluoromethyl)phenyl)-N-((8-endo)-3-(5-methyl-1,3,4-oxadiazol-2-yl)-3-azabicyclo[3.2.1]octan-8-yl)-5,6,7,8-tetrahydro-[1,2,4]triazolo[1,5-a]pyridin-2-amine;

N-[(8-endo)-3-(5-Methyl-1,3,4-oxadiazol-2-yl)-3-azabicyclo[3.2.1]octan-8-yl]-5-(trifluoromethyl)-8-(2,3,4-trifluorophenyl)-5,6,7,8-tetrahydro-[1,2,4]triazolo[1,5-a]pyridin-2-amine (diastereomer A);

N-((8-endo)-3-(5-Methyl-1,3,4-oxadiazol-2-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine (diastereomer B);

(+)-N-((8-endo)-3-(5-Methyl-1,3,4-oxadiazol-2-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine;

N-((8-endo)-3-(5-Methyl-1,3,4-oxadiazol-2-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine;

(+)-N-((8-endo)-3-(5-Methyl-1,3,4-oxadiazol-2-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine;

(−)-N-((8-endo)-3-(5-Methyl-1,3,4-oxadiazol-2-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine;

N-[(8-endo)-3-(5-Methyl-1,3,4-oxadiazol-2-yl)-3-azabicyclo[3.2.1]octan-8-yl]-5-(trifluoromethyl)-8-[4-(trifluoromethyl)phenyl]-5,6,7,8-tetrahydro-[1,2,4]triazolo[1,5-a]pyridin-2-amine;

(−)-N-((8-endo)-3-(5-Methyl-1,3,4-oxadiazol-2-yl)-3-azabicyclo[3.2.1]octan-8-yl)-5-(trifluoromethyl)-8-(4-(trifluoromethyl)phenyl)-5,6,7,8-tetrahydro-[1,2,4]triazolo[1,5-a]pyridin-2-amine;

(+)-N-((8-endo)-3-(5-Methyl-1,3,4-oxadiazol-2-yl)-3-azabicyclo[3.2.1]octan-8-yl)-5-(trifluoromethyl)-8-(4-(trifluoromethyl)phenyl)-5,6,7,8-tetrahydro-[1,2,4]triazolo[1,5-a]pyridin-2-amine;

(−)-8-(3,5-Bis(trifluoromethyl)phenyl)-N-((8-endo)-3-(5-methyl-1,3,4-oxadiazol-2-yl)-3-azabicyclo[3.2.1]octan-8-yl)-5,6,7,8-tetrahydro-[1,2,4]triazolo[1,5-a]pyridin-2-amine;

N-((8-endo)-3-(5-Methyl-1,3,4-oxadiazol-2-yl)-3-azabicyclo[3.2.1]octan-8-yl)-5-(trifluoromethyl)-8-(3-(trifluoromethyl)phenyl)-5,6,7,8-tetrahydro-[1,2,4]triazolo[1,5-a]pyridin-2-amine;

(+)-N-((8-endo)-3-(5-Methyl-1,3,4-oxadiazol-2-yl)-3-azabicyclo[3.2.1]octan-8-yl)-5-(trifluoromethyl)-8-(3-(trifluoromethyl)phenyl)-5,6,7,8-tetrahydro-[1,2,4]triazolo[1,5-a]pyridin-2-amine; and (−)-N-((8-endo)-3-(5-Methyl-1,3,4-oxadiazol-2-yl)-3-azabicyclo[3.2.1]octan-8-yl)-5-(trifluoromethyl)-8-(3-(trifluoromethyl)phenyl)-5,6,7,8-tetrahydro-[1,2,4]triazolo[1,5-a]pyridin-2-amine, or a pharmaceutically acceptable salt thereof.

8. A compound of formula Id according to claim 1,

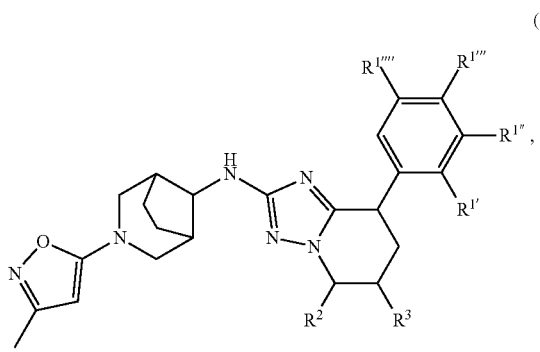
(Id)

or a pharmaceutically acceptable salt thereof,
wherein:

$R^1$ is hydrogen, halogen, lower alkyl, lower alkoxy, lower alkyl substituted by halogen or lower alkoxy substituted by halogen;

$R^{1'''}$ is hydrogen, halogen, lower alkyl substituted by halogen or lower alkoxy substituted by halogen;

$R^{1''''}$ is hydrogen, halogen, lower alkyl, lower alkyl substituted by halogen, lower alkoxy, lower alkoxy substituted by halogen, S-lower alkyl substituted by halogen;

or $R^2$ and $R^3$ form together with the carbon atoms, to which they are attached a ring, containing —O—CH$_2$—O—;

$R^{1''''}$ is hydrogen or halogen;

$R^2$ is hydrogen or lower alkyl substituted by halogen; and $R^3$ is hydrogen or lower alkyl substituted by halogen.

9. A compound of formula Id according to claim 8, wherein the compound is:

(−)-N-((endo)-3-(3-Methylisoxazol-5-yl)-3-azabicyclo[3.2.1]octan-8-yl)-5-(trifluoromethyl)-8-(2,3,4-trifluorophenyl)-5,6,7,8-tetrahydro-[1,2,4]triazolo[1,5-a]pyridin-2-amine, or a pharmaceutically acceptable salt thereof.

10. A process for preparing a compound of formula I of claim 1, or a pharmaceutically acceptable salt thereof, wherein the process comprises:

reducing a compound of formula

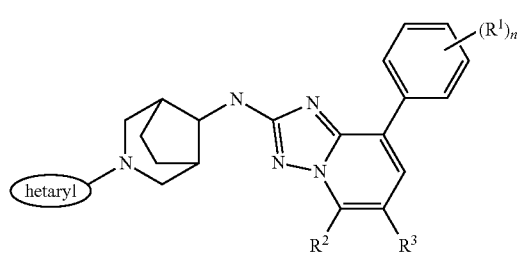

by catalytic hydrogenation or with Mg in methanol in the presence of iodine to a compound of formula I

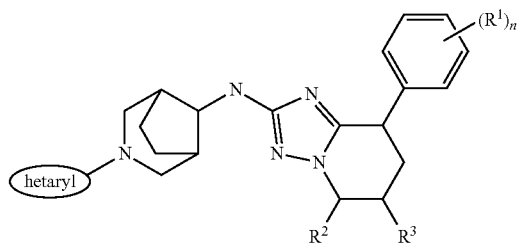
I wherein $R^1$, $R^2$, and $R^3$ are as in claim 1, and optionally converting the compounds obtained into pharmaceutically acceptable acid addition salts.

11. The process of claim 10 further comprising the steps:

b) reacting a compound of formula

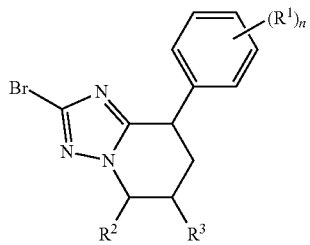

with a compound of formula

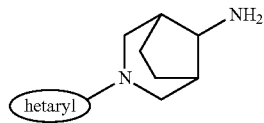

to give a compound of formula

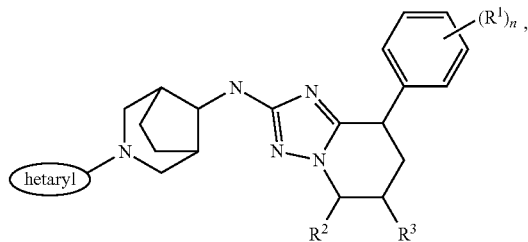

and c) reacting a compound of formula

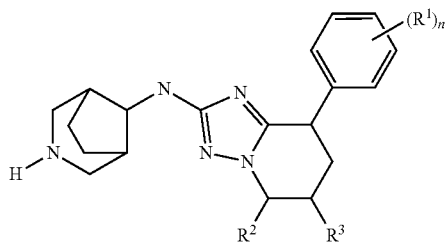

with a compound of formula

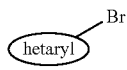

to give a compound of formula I:

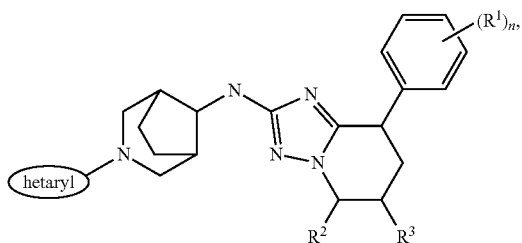

(I)

12. A pharmaceutical composition comprising a compound of claim 1, or a pharmaceutically acceptable salt thereof, wherein the pharmaceutical composition further comprises one or more pharmaceutically acceptable excipients.

13. A method of treating a disease selected from the group consisting of Alzheimer's disease, cerebral amyloid angiopathy, hereditary cerebral hemorrhage with amyloidosis, Dutch-type (HCHWA-D), multi-infarct dementia, dementia pugilistica and Down syndrome in a human, wherein the method comprises the administration of a therapeutically effective amount of a compound of claim 1, or a pharmaceutically acceptable salt thereof.

* * * * *